(12) United States Patent
Ishikawa et al.

(10) Patent No.: US 6,987,008 B1
(45) Date of Patent: Jan. 17, 2006

(54) VARIANT NUCLEOSIDE-5'-PHOSPHATE PRODUCING ENZYME

(75) Inventors: Kohki Ishikawa, Kawasaki (JP); Ei-ichiro Suzuki, Kawasaki (JP); Keiko Gondoh, Kawasaki (JP); Nobuhisa Shimba, Kawasaki (JP); Yasuhiro Mihara, Kawasaki (JP); Hisashi Kawasaki, Kawasaki (JP); Osamu Kurahashi, Kawasaki (JP); Tohru Kouda, Kawasaki (JP); Megumi Shimaoka, Kawasaki (JP); Rie Kozutsumi, Kawasaki (JP); Yasuhisa Asano, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 520 days.

(21) Appl. No.: 09/807,990

(22) PCT Filed: Sep. 1, 2000

(86) PCT No.: PCT/JP00/05973

§ 371 (c)(1),
(2), (4) Date: May 3, 2001

(87) PCT Pub. No.: WO01/18184

PCT Pub. Date: Mar. 15, 2001

(30) Foreign Application Priority Data

Sep. 3, 1999 (JP) ................................. 11-249545

(51) Int. Cl.
*C12P 19/30* (2006.01)
*C12N 9/14* (2006.01)
*C07H 21/04* (2006.01)

(52) U.S. Cl. .................. 435/89; 435/195; 435/196; 435/252.33; 435/320.1; 536/23.1; 536/23.2

(58) Field of Classification Search ........ 435/193–196, 435/252.33, 320.1, 40, 92, 89; 536/23.1, 536/23.2
See application file for complete search history.

(56) References Cited

U.S. PATENT DOCUMENTS

| 6,010,851 A | 1/2000 | Mihara et al. ............ 435/6 |
| 6,015,697 A | 1/2000 | Mihara et al. ............ 435/87 |
| 6,207,435 B1 | 3/2001 | Mihara et al. ............ 435/196 |

FOREIGN PATENT DOCUMENTS

| EP | 0 832 970 | 4/1998 |
| EP | 0 857 788 | 8/1998 |
| WO | WO 96/37603 | 11/1996 |

*Primary Examiner*—Nashaat T. Nashed
(74) *Attorney, Agent, or Firm*—Oblon, Spivak, McClelland, Maier & Neustadt, P.C.

(57) ABSTRACT

There is provided a mutant nucleoside-5'-phosphate producing enzyme with improved nucleoside-5'-phosphate producing ability of a nucleoside-5'-phosphate producing enzyme that has transphosphorylation activity and/or phosphatase activity and has one Lys residue, two Arg residues and two His residues with distances between their Cα's within a particular range and a space around them allowing a binding of a nucleoside, of which mutation is designed by using the crystal structure of EB-AP.

25 Claims, 47 Drawing Sheets

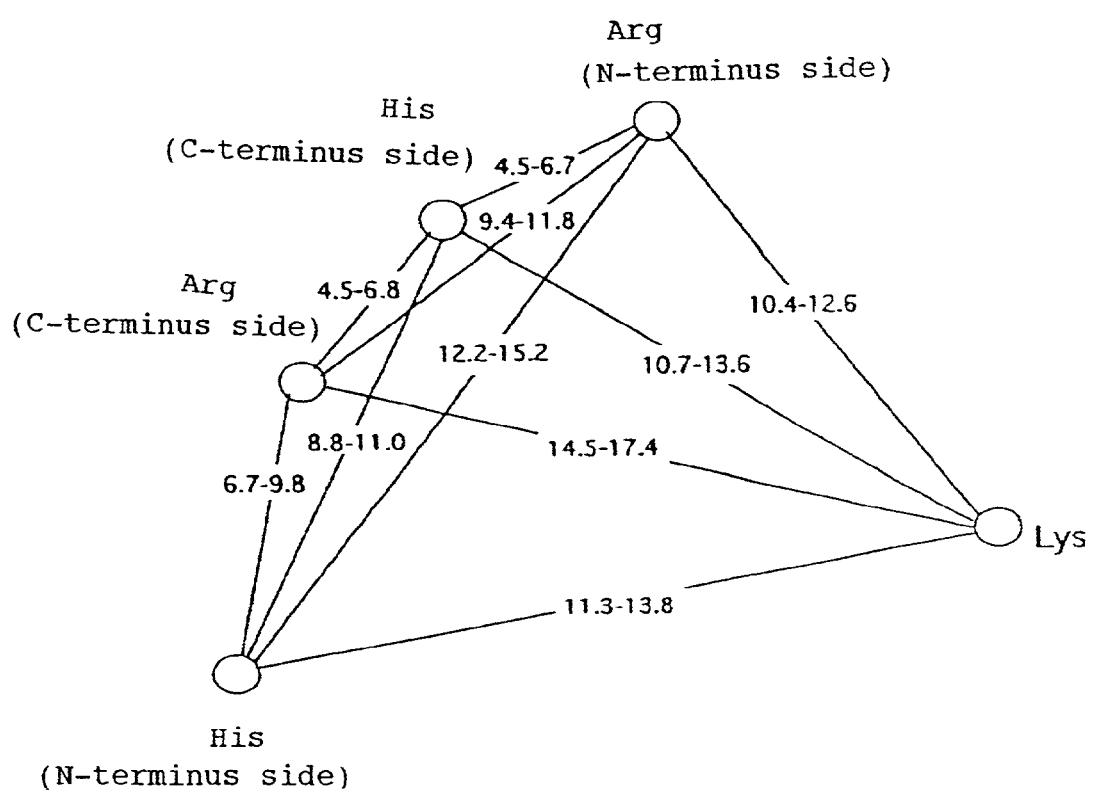
F I G. 1

```
              α1                                α2                                α3
E.blattae    :LALVATGNDT TTKPDLYYLK NSEAINSLAL LPPPPAVGSI AFLNDQAMYE QGRLLRNTER GKLAAEDANL  70
M.morganii   :  AIPAGNDA TTKPDLYYLK NEQAIDSLKL LPPPEVGSI  QFLNDQAMYE KGRMLRNTER GKQAQADADL
S.typhimurium:       KYT SAETVQPFHS PEESVNSQFY LPPPPGNDDP AYRYDKEAYF KGYAILGSPR WKQAAEDADV
Z.mobilis    :ASGLSQSVSA HTEKSEPSST YHFHSDPLLY LAPPPTSGSP LQAHDDQTFN STRQLKGSTR WALATQDADL
                                   *    ***   *         *
              α4       α5                       α6              α7
E.blattae    :SSGGVANAFS GAFGSPITEK DAPALHKLLT NMIEDAGDLA TRSAKDHYMR IRPFAFYGVS TCNTTEQDKL 140
M.morganii   :AAGGVATAFS GAFGYPITEK DSPELYKLLT NMIEDAGDLA TRSAKEHYMR IRPFAFYGTE TCNTKDQKKL
S.typhimurium:SVENIARIFS PVVGAKINPK DTPETWNMLK NLLTMGGYYA TASAKYYMR  TRPFVLFNHS TCRPEDENTL
Z.mobilis    :HLASVLKDYA CAAGMNLDIA QLPHLANLIK RALRTEYDDI GR-AKNNWNR  KRPFVDTDQP ICTEKDREGL
                                  *                    *    **         *  **    *
                     α8        α9                          α11                  α12
E.blattae    :SKNGSYPSGH TSIGWATALV LAEINPQRQN EILKRGYELG QSRVICGYHW QSDVDAARVV GSAVVATLHT 210
M.morganii   :STNGSYPSGH TSIGWATALV LAEVNPANQD AILERGYQLG QSRVICGYHW QSDVDAARIV GSAAVATLHS
S.typhimurium:RKNGSYPSGH TAYGTLLALV LSEARPERAQ ELARRGWEFG QSLWICGAHW QSDVDAGRYV GAVEFARLQT
Z.mobilis    :GKQGSLPSGH TTIGWSVALI LAELIPDHAA NILQRGQIFG LSRIVQGAHW ESDVQAGYIM ASGEIAALHG
              *     ****  *    * *   *              *   *     * *   *              *
              α13
E.blattae    :NPAFQQQLQK AKAEFAQHQK K
M.morganii   :DPAFQAQLAK AKQEFAQKSQ K
S.typhimurium:IPAFQKSLAK VREELNDKNN LLSKEDHPKL NY
Z.mobilis    :DADFRRDMEL ARKELEKART SAHTPDDLLC KIEQSAR
              *
```

```
S72F(s)   5'-CA-AAC-CTG-AGC-TTT-GGC-GAT-GTG-GC-3'(SEQ ID NO:11)
S72F(as)  3'-GT-TTG-GAC-TCG-AAA-CCG-CTA-CAC-CG-5'(SEQ ID NO:12)
              N   L   S  F72  G   D   V         (SEQ ID NO:13)

S72Y(s)   5'-CA-AAC-CTG-AGC-TAC-GGC-GAT-GTG-GC-3'(SEQ ID NO:14)
S72Y(as)  3'-GT-TTG-GAC-TCG-ATG-CCG-CTA-CAC-CG-5'(SEQ ID NO:15)
              N   L   S  Y72  G   D   V         (SEQ ID NO:16)

S72W(s)   5'-CA-AAC-CTG-AGC-TGG-GGC-GAT-GTG-GC-3'(SEQ ID NO:17)
S72W(as)  3'-GT-TTG-GAC-TCG-ACC-CCG-CTA-CAC-CG-5'(SEQ ID NO:18)
              N   L   S  W72  G   D   V         (SEQ ID NO:19)

S72D(s)   5'-CA-AAC-CTG-AGC-GAC-GGC-GAT-GTG-GC-3'(SEQ ID NO:20)
S72D(as)  3'-GT-TTG-GAC-TCG-CTG-CCG-CTA-CAC-CG-5'(SEQ ID NO:21)
              N   L   S  D72  G   D   V         (SEQ ID NO:22)

S72V(s)   5'-CA-AAC-CTG-AGC-GTT-GGC-GAT-GTG-GC-3'(SEQ ID NO:23)
S72V(as)  3'-GT-TTG-GAC-TCG-CAA-CCG-CTA-CAC-CG-5'(SEQ ID NO:24)
              N   L   S  V72  G   D   V         (SEQ ID NO:25)

S72E(s)   5'-CA-AAC-CTG-AGC-GAA-GGC-GAT-GTG-GC-3'(SEQ ID NO:26)
S72E(as)  3'-GT-TTG-GAC-TCG-CTT-CCG-CTA-CAC-CG-5'(SEQ ID NO:27)
              N   L   S  E72  G   D   V         (SEQ ID NO:28)

S72M(s)   5'-CA-AAC-CTG-AGC-ATG-GGC-GAT-GTG-GC-3'(SEQ ID NO:29)
S72M(as)  3'-GT-TTG-GAC-TCG-TAC-CCG-CTA-CAC-CG-5'(SEQ ID NO:30)
              N   L   S  M72  G   D   V         (SEQ ID NO:31)

S72T(s)   5'-CA-AAC-CTG-AGC-ACC-GGC-GAT-GTG-GC-3'(SEQ ID NO:32)
S72T(as)  3'-GT-TTG-GAC-TCG-TGG-CCG-CTA-CAC-CG-5'(SEQ ID NO:33)
              N   L   S  T72  G   D   V         (SEQ ID NO:34)

S72L(s)   5'-CA-AAC-CTG-AGC-CTG-GGC-GAT-GTG-GC-3'(SEQ ID NO:35)
S72L(as)  3'-GT-TTG-GAC-TCG-GAC-CCG-CTA-CAC-CG-5'(SEQ ID NO:36)
              N   L   S  L72  G   D   V         (SEQ ID NO:37)

S72R(s)   5'-CA-AAC-CTG-AGC-CGT-GGC-GAT-GTG-GC-3'(SEQ ID NO:38)
S72R(as)  3'-GT-TTG-GAC-TCG-GCA-CCG-CTA-CAC-CG-5'(SEQ ID NO:39)
              N   L   S  R72  G   D   V         (SEQ ID NO:40)

S72Q(s)   5'-CA-AAC-CTG-AGC-CAG-GGC-GAT-GTG-GC-3'(SEQ ID NO:41)
S72Q(as)  3'-GT-TTG-GAC-TCG-GTC-CCG-CTA-CAC-CG-5'(SEQ ID NO:42)
              N   L   S  Q72  G   D   V         (SEQ ID NO:43)
```

```
S72K(s)    5'-CA-AAC-CTG-AGC-AAA-GGC-GAT-GTG-GC-3' (SEQ ID NO:44)
S72K(as)   3'-GT-TTG-GAC-TCG-TTT-CCG-CTA-CAC-CG-5' (SEQ ID NO:45)
              N   L   S   K72 G   D   V            (SEQ ID NO:46)

S72P(s)    5'-CA-AAC-CTG-AGC-CCG-GGC-GAT-GTG-GC-3' (SEQ ID NO:47)
S72P(as)   3'-GT-TTG-GAC-TCG-GGC-CCG-CTA-CAC-CG-5' (SEQ ID NO:48)
              N   L   S   P72 G   D   V            (SEQ ID NO:49)

S72A(s)    5'-CA-AAC-CTG-AGC-GCG-GGC-GAT-GTG-GC-3' (SEQ ID NO:50)
S72A(as)   3'-GT-TTG-GAC-TCG-CGC-CCG-CTA-CAC-CG-5' (SEQ ID NO:51)
              N   L   S   A72 G   D   V            (SEQ ID NO:52)

S72N(s)    5'-CA-AAC-CTG-AGC-AAC-GGC-GAT-GTG-GC-3' (SEQ ID NO:53)
S72N(as)   3'-GT-TTG-GAC-TCG-TTG-CCG-CTA-CAC-CG-5' (SEQ ID NO:54)
              N   L   S   N72 G   D   V            (SEQ ID NO:55)

S72G(s)    5'-CA-AAC-CTG-AGC-GGT-GGC-GAT-GTG-GC-3' (SEQ ID NO:56)
S72G(as)   3'-GT-TTG-GAC-TCG-CCA-CCG-CTA-CAC-CG-5' (SEQ ID NO:57)
              N   L   S   G72 G   D   V            (SEQ ID NO:58)

S72H(s)    5'-CA-AAC-CTG-AGC-CAC-GGC-GAT-GTG-GC-3' (SEQ ID NO:59)
S72H(as)   3'-GT-TTG-GAC-TCG-GTG-CCG-CTA-CAC-CG-5' (SEQ ID NO:60)
              N   L   S   H72 G   D   V            (SEQ ID NO:61)
```

FIG. 7

```
L16W(s)    5'-CG-AAA-CCG-GAT-TGG-TAC-TAC-CTC-AA-3' (SEQ ID NO:62)
L16W(as)   3'-GC-TTT-GGC-CTA-ACC-ATG-ATG-GAG-TT-5' (SEQ ID NO:63)
              K   P   D  W16  Y   Y   L           (SEQ ID NO:64)

S71W(s)    5'-AT-GCA-AAC-CTG-TGG-AGT-GGC-GAT-GT-3' (SEQ ID NO:65)
S71W(as)   3'-TA-CGT-TTG-GAC-ACC-TCA-CCG-CTA-CA-5' (SEQ ID NO:66)
              A   N   L  W71  S   G   D           (SEQ ID NO:67)

S73W(s)    5'-AC-CTG-AGC-AGT-TGG-GAT-GTG-GCG-AA-3' (SEQ ID NO:68)
S73W(as)   3'-TG-GAC-TCG-TCA-ACC-CTA-CAC-CGC-TT-5' (SEQ ID NO:69)
              L   S   S  W73  D   V   A           (SEQ ID NO:70)

E104F(s)   5'-CC-AAT-ATG-ATT-TTT-GAC-GCC-GGG-GA-3' (SEQ ID NO:71)
E104F(as)  3'-GG-TTA-TAC-TAA-AAA-CTG-CGG-CCC-CT-5' (SEQ ID NO:72)
              N   M   I  F104 D   A   G           (SEQ ID NO:73)

E104W(s)   5'-CC-AAT-ATG-ATT-TGG-GAC-GCC-GGG-GA-3' (SEQ ID NO:74)
E104W(as)  3'-GG-TTA-TAC-TAA-ACC-CTG-CGG-CCC-CT-5' (SEQ ID NO:75)
              N   M   I  W104 D   A   G           (SEQ ID NO:76)
```

FIG. 8A

```
A72F(s)    5'-CA-GAC-CTG-GCC-TTT-GGC-GAT-GTG-GC-3' (SEQ ID NO:77)
A72F(as)   3'-GT-CTG-GAC-CGG-AAA-CCG-CTA-CAC-CG-5' (SEQ ID NO:78)
              D    L    A   F72   G    D    V       (SEQ ID NO:79)

A72E(s)    5'-CA-GAC-CTG-GCC-GAA-GGC-GAT-GTG-GC-3' (SEQ ID NO:80)
A72E(as)   3'-GT-CTG-GAC-CGG-CTT-CCG-CTA-CAC-CG-5' (SEQ ID NO:81)
              D    L    A   E72   G    D    V       (SEQ ID NO:82)
```

FIG. 8B

```
I103D(s)   5'-TG-ACC-AAT-ATG-GAC-GAG-GAC-GCC-GG-3' (SEQ ID NO:83)
I103D(as)  3'-AC-TGG-TTA-TAC-CTG-CTC-CTG-CGG-CC-5' (SEQ ID NO:84)
              T    N    M  D103   E    D    A       (SEQ ID NO:85)

T153N(s)   5'-GG-CAT-ACC-TCT-AAC-GGC-TGG-GCT-AC-3' (SEQ ID NO:86)
T153N(as)  3'-CC-GTA-TGG-AGA-TTG-CCG-ACC-CGA-TG-5' (SEQ ID NO:87)
              H    T    S  N153   G    W    A       (SEQ ID NO:88)
```

FIG. 8C

```
L140F(s)   5'-AC-CAG-GAC-AAA-TTC-TCC-AAA-AAT-GG-3' (SEQ ID NO:89)
L140F(as)  3'-TG-GTC-CTG-TTT-AAG-AGG-TTT-TTA-CC-5' (SEQ ID NO:90)
              Q    D    K  F140   S    K    N       (SEQ ID NO:91)

L140K(s)   5'-AC-CAG-GAC-AAA-AAA-TCC-AAA-AAT-GG-3' (SEQ ID NO:92)
L140K(as)  3'-TG-GTC-CTG-TTT-TTT-AGG-TTT-TTA-CC-5' (SEQ ID NO:93)
              Q    D    K  K140   S    K    N       (SEQ ID NO:94)

L140E(s)   5'-AC-CAG-GAC-AAA-GAA-TCC-AAA-AAT-GG-3' (SEQ ID NO:95)
L140E(as)  3'-TG-GTC-CTG-TTT-CTT-AGG-TTT-TTA-CC-5' (SEQ ID NO:96)
              Q    D    K  E140   S    K    N       (SEQ ID NO:97)
```

FIG. 8D

```
EB-AP:   LALVATGNDTTTKPDLYYLKNSEAINSLALLPPPPAVGSIAFLNDQAMYEQGRLLRNTER
           V  GND TTKPDLYYLKN++AI+SLALLPPPP VGSIAFLNDQAMYE+GRLLRNTER
EA-AP:    LVPAGNDATTKPDLYYLKNAQAIDSLALLPPPPEVGSIAFLNDQAMYEKGRLLRNTER

[72]
EB-AP:   GKLAAEDANLSSGGVANAFSGAFGSPITEKDAPALHKLLTNMIEDAGDLATRSAKDHYMR
         GKLAAEDANLS+GGVANAFS AFGSPITEKDAP LHKLLTNMIEDAGDLATRSAK+ YMR
EA-AP:   GKLAAEDANLSAGGVANAFSSAFGSPITEKDAPQLHKLLTNMIEDAGDLATRSAKEKYMR
              [70]

EB-AP:   IRPFAFYGVSTCNTTEQDKLSKNGSYPSGHTSIGWATALVLAEINPQRQNEILKRGYELG
         IRPFAFYGVSTCNTTEQDKLSKNGSYPSGHTSIGWATALVLAEINPQRQNEILKRGYELG
EA-AP:   IRPFAFYGVSTCNTTEQDKLSKNGSYPSGHTSIGWATALVLAEINPQRQNEILKRGYELG

EB-AP:   QSRVICGYHWQSDVDAARVVGSAVVATLHTNPAFQQQLQKAKAEFAQHQKK
         +SRVICGYHWQSDVDAAR+VGSAVVATLHTNPAFQQQLQKAK EFA+ QK
EA-AP:   ESRVICGYHWQSDVDAARIVGSAVVATLHTNPAFQQQLQKAKDEFAKTQK
```

```
ATOM      1  N   GLY A   7      35.965  71.208  89.712  1.00 36.57
ATOM      2  CA  GLY A   7      37.459  71.295  89.574  1.00 31.92
ATOM      3  C   GLY A   7      38.160  69.982  89.872  1.00 29.76
ATOM      4  O   GLY A   7      39.301  69.858  89.492  1.00 31.81
ATOM      5  N   ASN A   8      37.485  68.990  90.532  1.00 26.40
ATOM      6  CA  ASN A   8      38.284  67.775  90.697  1.00 26.63
ATOM      7  C   ASN A   8      38.466  67.018  89.396  1.00 29.21
ATOM      8  O   ASN A   8      37.736  67.238  88.431  1.00 30.52
ATOM      9  CB  ASN A   8      37.677  66.810  91.702  1.00 27.01
ATOM     10  CG  ASN A   8      37.725  67.396  93.104  1.00 32.45
ATOM     11  OD1 ASN A   8      38.751  67.744  93.636  1.00 30.02
ATOM     12  ND2 ASN A   8      36.545  67.536  93.707  1.00 31.60
ATOM     13  N   ASP A   9      39.455  66.154  89.463  1.00 29.14
ATOM     14  CA  ASP A   9      39.787  65.216  88.391  1.00 30.47
ATOM     15  C   ASP A   9      40.661  64.081  88.901  1.00 31.02
ATOM     16  O   ASP A   9      40.804  63.931  90.110  1.00 31.00
ATOM     17  CB  ASP A   9      40.394  65.960  87.195  1.00 30.92
ATOM     18  CG  ASP A   9      41.802  66.484  87.429  1.00 32.66
ATOM     19  OD1 ASP A   9      42.307  66.333  88.532  1.00 35.03
ATOM     20  OD2 ASP A   9      42.400  67.018  86.493  1.00 31.63
ATOM     21  N   THR A  10      41.272  63.298  87.998  1.00 28.72
ATOM     22  CA  THR A  10      42.188  62.228  88.430  1.00 28.53
ATOM     23  C   THR A  10      43.408  62.655  89.259  1.00 30.10
ATOM     24  O   THR A  10      43.946  61.944  90.095  1.00 29.06
ATOM     25  CB  THR A  10      42.692  61.405  87.235  1.00 26.05
ATOM     26  OG1 THR A  10      43.272  60.172  87.655  1.00 27.75
ATOM     27  CG2 THR A  10      43.670  62.174  86.313  1.00 23.76
ATOM     28  N   THR A  11      43.814  63.900  88.996  1.00 30.82
ATOM     29  CA  THR A  11      44.932  64.389  89.799  1.00 32.79
ATOM     30  C   THR A  11      44.605  64.736  91.267  1.00 36.32
ATOM     31  O   THR A  11      45.435  64.658  92.162  1.00 37.21
ATOM     32  CB  THR A  11      45.588  65.591  89.143  1.00 30.53
ATOM     33  OG1 THR A  11      44.845  66.781  89.359  1.00 27.79
ATOM     34  CG2 THR A  11      45.899  65.362  87.656  1.00 32.16
ATOM     35  N   THR A  12      43.317  65.076  91.495  1.00 34.81
ATOM     36  CA  THR A  12      42.910  65.213  92.900  1.00 32.91
ATOM     37  C   THR A  12      42.265  63.992  93.549  1.00 33.08
ATOM     38  O   THR A  12      42.350  63.742  94.736  1.00 32.49
ATOM     39  CB  THR A  12      41.963  66.395  93.077  1.00 30.92
ATOM     40  OG1 THR A  12      40.719  66.162  92.409  1.00 32.04
ATOM     41  CG2 THR A  12      42.599  67.667  92.543  1.00 29.75
ATOM     42  N   LYS A  13      41.565  63.229  92.703  1.00 31.17
ATOM     43  CA  LYS A  13      40.791  62.064  93.174  1.00 30.27
ATOM     44  C   LYS A  13      40.904  60.812  92.287  1.00 31.40
ATOM     45  O   LYS A  13      39.981  60.348  91.605  1.00 33.05
ATOM     46  CB  LYS A  13      39.294  62.395  93.331  1.00 29.09
ATOM     47  CG  LYS A  13      39.001  63.747  93.965  1.00 32.97
ATOM     48  CD  LYS A  13      37.536  64.076  94.166  1.00 37.86
ATOM     49  CE  LYS A  13      36.767  62.909  94.772  1.00 47.28
ATOM     50  NZ  LYS A  13      35.340  63.270  94.947  1.00 52.08
ATOM     51  N   PRO A  14      42.138  60.283  92.279  1.00 33.01
ATOM     52  CA  PRO A  14      42.516  59.249  91.290  1.00 32.06
ATOM     53  C   PRO A  14      41.823  57.907  91.452  1.00 30.98
ATOM     54  O   PRO A  14      41.961  56.989  90.668  1.00 32.57
```

FIG. 11

| ATOM | 55 | CB | PRO | A | 14 | 44.035 | 59.145 | 91.468 | 1.00 | 34.46 |
| ATOM | 56 | CG | PRO | A | 14 | 44.283 | 59.564 | 92.920 | 1.00 | 33.02 |
| ATOM | 57 | CD | PRO | A | 14 | 43.225 | 60.638 | 93.181 | 1.00 | 34.46 |
| ATOM | 58 | N | ASP | A | 15 | 41.046 | 57.815 | 92.513 | 1.00 | 29.27 |
| ATOM | 59 | CA | ASP | A | 15 | 40.204 | 56.655 | 92.809 | 1.00 | 28.89 |
| ATOM | 60 | C | ASP | A | 15 | 38.810 | 56.684 | 92.146 | 1.00 | 21.76 |
| ATOM | 61 | O | ASP | A | 15 | 38.078 | 55.706 | 92.030 | 1.00 | 20.59 |
| ATOM | 62 | CB | ASP | A | 15 | 40.125 | 56.599 | 94.368 | 1.00 | 37.60 |
| ATOM | 63 | CG | ASP | A | 15 | 39.589 | 57.903 | 95.080 | 1.00 | 45.11 |
| ATOM | 64 | OD1 | ASP | A | 15 | 40.062 | 59.044 | 94.817 | 1.00 | 45.67 |
| ATOM | 65 | OD2 | ASP | A | 15 | 38.687 | 57.751 | 95.922 | 1.00 | 49.07 |
| ATOM | 66 | N | LEU | A | 16 | 38.495 | 57.910 | 91.726 | 1.00 | 20.49 |
| ATOM | 67 | CA | LEU | A | 16 | 37.182 | 58.179 | 91.135 | 1.00 | 23.90 |
| ATOM | 68 | C | LEU | A | 16 | 37.156 | 58.814 | 89.727 | 1.00 | 22.23 |
| ATOM | 69 | O | LEU | A | 16 | 36.109 | 59.011 | 89.134 | 1.00 | 23.21 |
| ATOM | 70 | CB | LEU | A | 16 | 36.354 | 59.099 | 92.029 | 1.00 | 23.35 |
| ATOM | 71 | CG | LEU | A | 16 | 35.814 | 58.432 | 93.297 | 1.00 | 25.48 |
| ATOM | 72 | CD1 | LEU | A | 16 | 34.876 | 57.253 | 93.075 | 1.00 | 24.05 |
| ATOM | 73 | CD2 | LEU | A | 16 | 35.092 | 59.477 | 94.104 | 1.00 | 25.22 |
| ATOM | 74 | N | TYR | A | 17 | 38.343 | 59.175 | 89.273 | 1.00 | 20.96 |
| ATOM | 75 | CA | TYR | A | 17 | 38.555 | 59.605 | 87.889 | 1.00 | 22.04 |
| ATOM | 76 | C | TYR | A | 17 | 39.780 | 58.903 | 87.334 | 1.00 | 22.80 |
| ATOM | 77 | O | TYR | A | 17 | 40.790 | 58.799 | 88.021 | 1.00 | 23.48 |
| ATOM | 78 | CB | TYR | A | 17 | 38.856 | 61.095 | 87.711 | 1.00 | 18.01 |
| ATOM | 79 | CG | TYR | A | 17 | 37.928 | 62.099 | 88.371 | 1.00 | 24.78 |
| ATOM | 80 | CD1 | TYR | A | 17 | 37.129 | 62.916 | 87.542 | 1.00 | 22.78 |
| ATOM | 81 | CD2 | TYR | A | 17 | 37.905 | 62.248 | 89.781 | 1.00 | 23.58 |
| ATOM | 82 | CE1 | TYR | A | 17 | 36.317 | 63.919 | 88.113 | 1.00 | 26.51 |
| ATOM | 83 | CE2 | TYR | A | 17 | 37.090 | 63.240 | 90.349 | 1.00 | 22.88 |
| ATOM | 84 | CZ | TYR | A | 17 | 36.303 | 64.059 | 89.517 | 1.00 | 24.63 |
| ATOM | 85 | OH | TYR | A | 17 | 35.482 | 65.023 | 90.066 | 1.00 | 22.92 |
| ATOM | 86 | N | TYR | A | 18 | 39.670 | 58.482 | 86.053 | 1.00 | 26.17 |
| ATOM | 87 | CA | TYR | A | 18 | 40.838 | 58.209 | 85.191 | 1.00 | 21.13 |
| ATOM | 88 | C | TYR | A | 18 | 41.332 | 59.414 | 84.464 | 1.00 | 19.92 |
| ATOM | 89 | O | TYR | A | 18 | 42.490 | 59.511 | 84.083 | 1.00 | 22.64 |
| ATOM | 90 | CB | TYR | A | 18 | 40.563 | 57.195 | 84.080 | 1.00 | 17.53 |
| ATOM | 91 | CG | TYR | A | 18 | 40.312 | 55.826 | 84.610 | 1.00 | 16.91 |
| ATOM | 92 | CD1 | TYR | A | 18 | 41.425 | 55.028 | 84.916 | 1.00 | 19.86 |
| ATOM | 93 | CD2 | TYR | A | 18 | 38.985 | 55.372 | 84.771 | 1.00 | 16.65 |
| ATOM | 94 | CE1 | TYR | A | 18 | 41.218 | 53.725 | 85.383 | 1.00 | 18.64 |
| ATOM | 95 | CE2 | TYR | A | 18 | 38.765 | 54.053 | 85.213 | 1.00 | 17.52 |
| ATOM | 96 | CZ | TYR | A | 18 | 39.892 | 53.262 | 85.515 | 1.00 | 21.18 |
| ATOM | 97 | OH | TYR | A | 18 | 39.734 | 51.974 | 85.977 | 1.00 | 26.15 |
| ATOM | 98 | N | LEU | A | 19 | 40.412 | 60.336 | 84.236 | 1.00 | 21.49 |
| ATOM | 99 | CA | LEU | A | 19 | 40.788 | 61.462 | 83.366 | 1.00 | 22.71 |
| ATOM | 100 | C | LEU | A | 19 | 41.094 | 62.812 | 84.021 | 1.00 | 25.01 |
| ATOM | 101 | O | LEU | A | 19 | 40.771 | 63.125 | 85.159 | 1.00 | 25.24 |
| ATOM | 102 | CB | LEU | A | 19 | 39.708 | 61.669 | 82.290 | 1.00 | 21.68 |
| ATOM | 103 | CG | LEU | A | 19 | 39.301 | 60.442 | 81.432 | 1.00 | 22.88 |
| ATOM | 104 | CD1 | LEU | A | 19 | 40.430 | 59.842 | 80.583 | 1.00 | 20.39 |
| ATOM | 105 | CD2 | LEU | A | 19 | 38.078 | 60.812 | 80.608 | 1.00 | 18.83 |
| ATOM | 106 | N | LYS | A | 20 | 41.736 | 63.667 | 83.246 | 1.00 | 26.44 |
| ATOM | 107 | CA | LYS | A | 20 | 41.947 | 65.032 | 83.717 | 1.00 | 26.77 |
| ATOM | 108 | C | LYS | A | 20 | 40.935 | 66.034 | 83.292 | 1.00 | 26.42 |

FIG. 12

| ATOM | 109 | O   | LYS A | 20 | 40.182 | 65.870 | 82.341 | 1.00 | 29.05 |
| ATOM | 110 | CB  | LYS A | 20 | 43.239 | 65.608 | 83.187 | 1.00 | 30.61 |
| ATOM | 111 | CG  | LYS A | 20 | 44.400 | 64.791 | 83.648 | 1.00 | 32.90 |
| ATOM | 112 | CD  | LYS A | 20 | 45.633 | 65.326 | 82.963 | 1.00 | 39.72 |
| ATOM | 113 | CE  | LYS A | 20 | 46.698 | 64.259 | 83.113 | 1.00 | 50.27 |
| ATOM | 114 | NZ  | LYS A | 20 | 46.148 | 62.977 | 82.610 | 1.00 | 62.00 |
| ATOM | 115 | N   | ASN A | 21 | 41.050 | 67.184 | 83.943 | 1.00 | 24.09 |
| ATOM | 116 | CA  | ASN A | 21 | 40.154 | 68.246 | 83.530 | 1.00 | 23.98 |
| ATOM | 117 | C   | ASN A | 21 | 40.177 | 68.539 | 82.032 | 1.00 | 25.08 |
| ATOM | 118 | O   | ASN A | 21 | 39.134 | 68.722 | 81.427 | 1.00 | 25.36 |
| ATOM | 119 | CB  | ASN A | 21 | 40.310 | 69.512 | 84.371 | 1.00 | 23.81 |
| ATOM | 120 | CG  | ASN A | 21 | 39.601 | 69.311 | 85.697 | 1.00 | 26.97 |
| ATOM | 121 | OD1 | ASN A | 21 | 38.392 | 69.175 | 85.836 | 1.00 | 26.36 |
| ATOM | 122 | ND2 | ASN A | 21 | 40.403 | 69.303 | 86.744 | 1.00 | 32.00 |
| ATOM | 123 | N   | SER A | 22 | 41.378 | 68.486 | 81.450 | 1.00 | 23.72 |
| ATOM | 124 | CA  | SER A | 22 | 41.592 | 68.804 | 80.008 | 1.00 | 25.53 |
| ATOM | 125 | C   | SER A | 22 | 40.992 | 67.752 | 79.068 | 1.00 | 25.77 |
| ATOM | 126 | O   | SER A | 22 | 40.524 | 68.007 | 77.966 | 1.00 | 27.65 |
| ATOM | 127 | CB  | SER A | 22 | 43.079 | 68.868 | 79.699 | 1.00 | 23.34 |
| ATOM | 128 | OG  | SER A | 22 | 43.719 | 67.716 | 80.303 | 1.00 | 33.30 |
| ATOM | 129 | N   | GLU A | 23 | 40.957 | 66.529 | 79.624 | 1.00 | 22.35 |
| ATOM | 130 | CA  | GLU A | 23 | 40.320 | 65.466 | 78.899 | 1.00 | 21.87 |
| ATOM | 131 | C   | GLU A | 23 | 38.811 | 65.375 | 78.974 | 1.00 | 23.18 |
| ATOM | 132 | O   | GLU A | 23 | 38.197 | 64.451 | 78.471 | 1.00 | 25.83 |
| ATOM | 133 | CB  | GLU A | 23 | 40.923 | 64.165 | 79.337 | 1.00 | 22.13 |
| ATOM | 134 | CG  | GLU A | 23 | 42.451 | 64.215 | 79.214 | 1.00 | 26.78 |
| ATOM | 135 | CD  | GLU A | 23 | 43.021 | 62.908 | 79.718 | 1.00 | 30.40 |
| ATOM | 136 | OE1 | GLU A | 23 | 42.946 | 62.648 | 80.900 | 1.00 | 31.10 |
| ATOM | 137 | OE2 | GLU A | 23 | 43.544 | 62.118 | 78.957 | 1.00 | 32.35 |
| ATOM | 138 | N   | ALA A | 24 | 38.196 | 66.359 | 79.610 | 1.00 | 21.49 |
| ATOM | 139 | CA  | ALA A | 24 | 36.751 | 66.165 | 79.738 | 1.00 | 22.48 |
| ATOM | 140 | C   | ALA A | 24 | 35.973 | 66.420 | 78.438 | 1.00 | 22.81 |
| ATOM | 141 | O   | ALA A | 24 | 36.325 | 67.333 | 77.704 | 1.00 | 23.36 |
| ATOM | 142 | CB  | ALA A | 24 | 36.188 | 67.183 | 80.734 | 1.00 | 21.43 |
| ATOM | 143 | N   | ILE A | 25 | 34.859 | 65.694 | 78.228 | 1.00 | 23.46 |
| ATOM | 144 | CA  | ILE A | 25 | 33.845 | 66.149 | 77.243 | 1.00 | 23.60 |
| ATOM | 145 | C   | ILE A | 25 | 33.312 | 67.535 | 77.530 | 1.00 | 24.71 |
| ATOM | 146 | O   | ILE A | 25 | 32.788 | 67.809 | 78.603 | 1.00 | 25.03 |
| ATOM | 147 | CB  | ILE A | 25 | 32.684 | 65.160 | 77.096 | 1.00 | 20.26 |
| ATOM | 148 | CG1 | ILE A | 25 | 33.237 | 63.749 | 76.838 | 1.00 | 23.14 |
| ATOM | 149 | CG2 | ILE A | 25 | 31.739 | 65.555 | 75.954 | 1.00 | 21.26 |
| ATOM | 150 | CD1 | ILE A | 25 | 34.298 | 63.551 | 75.722 | 1.00 | 16.94 |
| ATOM | 151 | N   | ASN A | 26 | 33.485 | 68.431 | 76.562 | 1.00 | 22.50 |
| ATOM | 152 | CA  | ASN A | 26 | 32.797 | 69.706 | 76.751 | 1.00 | 22.04 |
| ATOM | 153 | C   | ASN A | 26 | 31.295 | 69.680 | 76.533 | 1.00 | 22.52 |
| ATOM | 154 | O   | ASN A | 26 | 30.731 | 70.042 | 75.509 | 1.00 | 22.34 |
| ATOM | 155 | CB  | ASN A | 26 | 33.474 | 70.744 | 75.900 | 1.00 | 20.15 |
| ATOM | 156 | CG  | ASN A | 26 | 32.982 | 72.133 | 76.217 | 1.00 | 24.94 |
| ATOM | 157 | OD1 | ASN A | 26 | 31.923 | 72.459 | 76.732 | 1.00 | 29.46 |
| ATOM | 158 | ND2 | ASN A | 26 | 33.827 | 73.032 | 75.809 | 1.00 | 25.76 |
| ATOM | 159 | N   | SER A | 27 | 30.627 | 69.289 | 77.622 | 1.00 | 19.77 |
| ATOM | 160 | CA  | SER A | 27 | 29.166 | 69.168 | 77.549 | 1.00 | 18.88 |
| ATOM | 161 | C   | SER A | 27 | 28.412 | 70.423 | 77.177 | 1.00 | 18.74 |
| ATOM | 162 | O   | SER A | 27 | 27.390 | 70.393 | 76.517 | 1.00 | 21.73 |

FIG. 13

```
ATOM    163  CB   SER A  27      28.606  68.619  78.870  1.00 19.35
ATOM    164  OG   SER A  27      28.967  69.518  79.940  1.00 19.36
ATOM    165  N    LEU A  28      28.961  71.564  77.588  1.00 18.08
ATOM    166  CA   LEU A  28      28.271  72.815  77.262  1.00 20.15
ATOM    167  C    LEU A  28      28.283  73.062  75.761  1.00 23.12
ATOM    168  O    LEU A  28      27.303  73.485  75.165  1.00 22.25
ATOM    169  CB   LEU A  28      28.990  74.042  77.798  1.00 17.00
ATOM    170  CG   LEU A  28      28.159  75.188  78.376  1.00 18.01
ATOM    171  CD1  LEU A  28      26.847  75.547  77.733  1.00 14.28
ATOM    172  CD2  LEU A  28      29.053  76.394  78.592  1.00 16.45
ATOM    173  N    ALA A  29      29.478  72.767  75.193  1.00 23.87
ATOM    174  CA   ALA A  29      29.598  72.827  73.707  1.00 22.62
ATOM    175  C    ALA A  29      28.773  71.847  72.837  1.00 20.86
ATOM    176  O    ALA A  29      28.192  72.239  71.830  1.00 25.89
ATOM    177  CB   ALA A  29      31.065  72.692  73.326  1.00 20.24
ATOM    178  N    LEU A  30      28.733  70.580  73.267  1.00 15.78
ATOM    179  CA   LEU A  30      28.079  69.497  72.519  1.00 18.05
ATOM    180  C    LEU A  30      26.557  69.416  72.559  1.00 22.38
ATOM    181  O    LEU A  30      25.845  69.251  71.566  1.00 23.63
ATOM    182  CB   LEU A  30      28.732  68.194  72.977  1.00 16.47
ATOM    183  CG   LEU A  30      28.234  66.887  72.360  1.00 17.59
ATOM    184  CD1  LEU A  30      28.812  65.706  73.120  1.00 12.95
ATOM    185  CD2  LEU A  30      28.456  66.775  70.850  1.00 13.89
ATOM    186  N    LEU A  31      26.075  69.533  73.812  1.00 22.39
ATOM    187  CA   LEU A  31      24.633  69.430  74.049  1.00 18.84
ATOM    188  C    LEU A  31      23.817  70.624  73.538  1.00 16.30
ATOM    189  O    LEU A  31      24.260  71.763  73.576  1.00 19.93
ATOM    190  CB   LEU A  31      24.381  69.199  75.556  1.00 16.94
ATOM    191  CG   LEU A  31      24.923  67.873  76.095  1.00 17.95
ATOM    192  CD1  LEU A  31      24.177  66.669  75.553  1.00 11.60
ATOM    193  CD2  LEU A  31      24.823  67.878  77.628  1.00 18.77
ATOM    194  N    PRO A  32      22.581  70.333  73.105  1.00 14.80
ATOM    195  CA   PRO A  32      21.589  71.404  72.910  1.00 18.31
ATOM    196  C    PRO A  32      21.228  72.028  74.278  1.00 22.24
ATOM    197  O    PRO A  32      21.453  71.442  75.327  1.00 22.27
ATOM    198  CB   PRO A  32      20.402  70.621  72.348  1.00 15.94
ATOM    199  CG   PRO A  32      20.545  69.184  72.847  1.00 16.93
ATOM    200  CD   PRO A  32      22.038  68.972  72.954  1.00 15.56
ATOM    201  N    PRO A  33      20.657  73.249  74.287  1.00 23.41
ATOM    202  CA   PRO A  33      20.190  73.780  75.586  1.00 20.34
ATOM    203  C    PRO A  33      19.059  72.945  76.084  1.00 19.93
ATOM    204  O    PRO A  33      18.409  72.292  75.285  1.00 18.67
ATOM    205  CB   PRO A  33      19.659  75.158  75.224  1.00 18.52
ATOM    206  CG   PRO A  33      20.267  75.499  73.877  1.00 21.71
ATOM    207  CD   PRO A  33      20.406  74.146  73.177  1.00 21.12
ATOM    208  N    PRO A  34      18.785  72.950  77.411  1.00 19.36
ATOM    209  CA   PRO A  34      17.645  72.138  77.863  1.00 13.70
ATOM    210  C    PRO A  34      16.348  72.759  77.351  1.00 11.77
ATOM    211  O    PRO A  34      16.280  73.937  77.090  1.00 14.58
ATOM    212  CB   PRO A  34      17.760  72.358  79.389  1.00 13.66
ATOM    213  CG   PRO A  34      18.471  73.698  79.571  1.00 14.81
ATOM    214  CD   PRO A  34      19.499  73.679  78.464  1.00 16.49
ATOM    215  N    PRO A  35      15.257  72.007  77.284  1.00 12.52
ATOM    216  CA   PRO A  35      14.011  72.710  76.973  1.00 13.71
```

F I G. 14

```
ATOM    217  C    PRO A  35      13.665  73.842  77.945  1.00  20.26
ATOM    218  O    PRO A  35      13.728  73.715  79.159  1.00  20.52
ATOM    219  CB   PRO A  35      12.997  71.579  76.991  1.00  11.74
ATOM    220  CG   PRO A  35      13.723  70.243  77.051  1.00  12.04
ATOM    221  CD   PRO A  35      15.140  70.581  77.482  1.00  11.57
ATOM    222  N    ALA A  36      13.311  74.962  77.356  1.00  19.25
ATOM    223  CA   ALA A  36      12.919  76.136  78.122  1.00  18.78
ATOM    224  C    ALA A  36      11.457  76.120  78.497  1.00  18.25
ATOM    225  O    ALA A  36      10.582  75.579  77.847  1.00  18.88
ATOM    226  CB   ALA A  36      13.152  77.414  77.304  1.00  17.95
ATOM    227  N    VAL A  37      11.182  76.753  79.609  1.00  18.03
ATOM    228  CA   VAL A  37       9.803  77.005  79.965  1.00  16.78
ATOM    229  C    VAL A  37       9.135  77.993  78.998  1.00  17.18
ATOM    230  O    VAL A  37       9.640  79.048  78.650  1.00  19.89
ATOM    231  CB   VAL A  37       9.740  77.500  81.436  1.00  18.33
ATOM    232  CG1  VAL A  37      10.381  76.501  82.418  1.00  13.83
ATOM    233  CG2  VAL A  37       8.300  77.825  81.832  1.00  14.21
ATOM    234  N    GLY A  38       7.952  77.616  78.561  1.00  18.34
ATOM    235  CA   GLY A  38       7.422  78.249  77.343  1.00  22.06
ATOM    236  C    GLY A  38       7.538  77.398  76.043  1.00  21.25
ATOM    237  O    GLY A  38       6.851  77.623  75.068  1.00  22.09
ATOM    238  N    SER A  39       8.422  76.401  76.060  1.00  21.73
ATOM    239  CA   SER A  39       8.520  75.487  74.905  1.00  20.30
ATOM    240  C    SER A  39       7.604  74.277  74.964  1.00  21.10
ATOM    241  O    SER A  39       7.217  73.736  76.002  1.00  19.55
ATOM    242  CB   SER A  39       9.946  74.998  74.748  1.00  15.45
ATOM    243  OG   SER A  39      10.197  73.967  75.704  1.00  15.38
ATOM    244  N    ILE A  40       7.287  73.796  73.772  1.00  17.17
ATOM    245  CA   ILE A  40       6.618  72.485  73.702  1.00  14.71
ATOM    246  C    ILE A  40       7.475  71.311  74.225  1.00  10.81
ATOM    247  O    ILE A  40       6.998  70.315  74.782  1.00  15.23
ATOM    248  CB   ILE A  40       6.102  72.235  72.219  1.00  15.78
ATOM    249  CG1  ILE A  40       5.162  73.368  71.791  1.00  15.41
ATOM    250  CG2  ILE A  40       5.406  70.863  72.091  1.00  14.54
ATOM    251  CD1  ILE A  40       4.812  73.332  70.307  1.00  18.26
ATOM    252  N    ALA A  41       8.790  71.443  74.040  1.00  10.69
ATOM    253  CA   ALA A  41       9.633  70.373  74.530  1.00  13.79
ATOM    254  C    ALA A  41       9.566  70.300  76.091  1.00  15.36
ATOM    255  O    ALA A  41       9.369  69.245  76.683  1.00  20.02
ATOM    256  CB   ALA A  41      11.046  70.610  74.065  1.00  11.61
ATOM    257  N    PHE A  42       9.547  71.495  76.702  1.00  16.94
ATOM    258  CA   PHE A  42       9.200  71.480  78.151  1.00  15.75
ATOM    259  C    PHE A  42       7.818  70.970  78.533  1.00  16.07
ATOM    260  O    PHE A  42       7.652  70.182  79.448  1.00  19.72
ATOM    261  CB   PHE A  42       9.513  72.819  78.819  1.00  17.93
ATOM    262  CG   PHE A  42       9.380  72.700  80.338  1.00  20.96
ATOM    263  CD1  PHE A  42      10.297  71.904  81.056  1.00  19.46
ATOM    264  CD2  PHE A  42       8.324  73.370  80.997  1.00  20.99
ATOM    265  CE1  PHE A  42      10.148  71.763  82.450  1.00  17.30
ATOM    266  CE2  PHE A  42       8.190  73.248  82.402  1.00  19.79
ATOM    267  CZ   PHE A  42       9.111  72.443  83.100  1.00  13.36
ATOM    268  N    LEU A  43       6.790  71.375  77.765  1.00  19.00
ATOM    269  CA   LEU A  43       5.507  70.643  77.917  1.00  19.22
ATOM    270  C    LEU A  43       5.573  69.103  77.945  1.00  19.39
```

FIG. 15

| ATOM | 271 | O | LEU | A | 43 | 4.957 | 68.410 | 78.749 | 1.00 | 17.69 |
|---|---|---|---|---|---|---|---|---|---|---|
| ATOM | 272 | CB | LEU | A | 43 | 4.472 | 71.003 | 76.826 | 1.00 | 21.60 |
| ATOM | 273 | CG | LEU | A | 43 | 3.213 | 71.850 | 77.034 | 1.00 | 24.67 |
| ATOM | 274 | CD1 | LEU | A | 43 | 2.597 | 71.800 | 78.433 | 1.00 | 17.68 |
| ATOM | 275 | CD2 | LEU | A | 43 | 2.172 | 71.549 | 75.953 | 1.00 | 21.72 |
| ATOM | 276 | N | ASN | A | 44 | 6.392 | 68.588 | 77.023 | 1.00 | 19.47 |
| ATOM | 277 | CA | ASN | A | 44 | 6.653 | 67.176 | 77.076 | 1.00 | 19.82 |
| ATOM | 278 | C | ASN | A | 44 | 7.419 | 66.619 | 78.312 | 1.00 | 17.44 |
| ATOM | 279 | O | ASN | A | 44 | 7.018 | 65.604 | 78.855 | 1.00 | 15.52 |
| ATOM | 280 | CB | ASN | A | 44 | 7.259 | 66.847 | 75.747 | 1.00 | 19.07 |
| ATOM | 281 | CG | ASN | A | 44 | 7.491 | 65.366 | 75.643 | 1.00 | 22.97 |
| ATOM | 282 | OD1 | ASN | A | 44 | 8.605 | 64.906 | 75.468 | 1.00 | 30.35 |
| ATOM | 283 | ND2 | ASN | A | 44 | 6.444 | 64.588 | 75.862 | 1.00 | 22.13 |
| ATOM | 284 | N | ASP | A | 45 | 8.482 | 67.324 | 78.726 | 1.00 | 19.71 |
| ATOM | 285 | CA | ASP | A | 45 | 9.175 | 67.050 | 80.020 | 1.00 | 19.87 |
| ATOM | 286 | C | ASP | A | 45 | 8.192 | 66.977 | 81.213 | 1.00 | 19.30 |
| ATOM | 287 | O | ASP | A | 45 | 8.103 | 66.009 | 81.956 | 1.00 | 21.00 |
| ATOM | 288 | CB | ASP | A | 45 | 10.225 | 68.119 | 80.273 | 1.00 | 13.57 |
| ATOM | 289 | CG | ASP | A | 45 | 11.563 | 67.769 | 79.706 | 1.00 | 12.64 |
| ATOM | 290 | OD1 | ASP | A | 45 | 12.408 | 68.656 | 79.625 | 1.00 | 15.68 |
| ATOM | 291 | OD2 | ASP | A | 45 | 11.823 | 66.611 | 79.414 | 1.00 | 14.57 |
| ATOM | 292 | N | GLN | A | 46 | 7.347 | 68.007 | 81.299 | 1.00 | 19.62 |
| ATOM | 293 | CA | GLN | A | 46 | 6.199 | 67.904 | 82.220 | 1.00 | 19.44 |
| ATOM | 294 | C | GLN | A | 46 | 5.259 | 66.702 | 82.166 | 1.00 | 22.23 |
| ATOM | 295 | O | GLN | A | 46 | 4.960 | 66.057 | 83.175 | 1.00 | 21.67 |
| ATOM | 296 | CB | GLN | A | 46 | 5.353 | 69.153 | 82.218 | 1.00 | 16.35 |
| ATOM | 297 | CG | GLN | A | 46 | 6.282 | 70.333 | 82.395 | 1.00 | 18.35 |
| ATOM | 298 | CD | GLN | A | 46 | 5.398 | 71.519 | 82.591 | 1.00 | 26.07 |
| ATOM | 299 | OE1 | GLN | A | 46 | 5.334 | 72.143 | 83.629 | 1.00 | 31.83 |
| ATOM | 300 | NE2 | GLN | A | 46 | 4.622 | 71.823 | 81.591 | 1.00 | 22.82 |
| ATOM | 301 | N | ALA | A | 47 | 4.838 | 66.364 | 80.935 | 1.00 | 19.12 |
| ATOM | 302 | CA | ALA | A | 47 | 3.979 | 65.187 | 80.813 | 1.00 | 17.83 |
| ATOM | 303 | C | ALA | A | 47 | 4.661 | 63.871 | 81.172 | 1.00 | 15.90 |
| ATOM | 304 | O | ALA | A | 47 | 4.065 | 62.940 | 81.701 | 1.00 | 18.55 |
| ATOM | 305 | CB | ALA | A | 47 | 3.441 | 65.066 | 79.367 | 1.00 | 17.11 |
| ATOM | 306 | N | MET | A | 48 | 5.970 | 63.818 | 80.841 | 1.00 | 18.16 |
| ATOM | 307 | CA | MET | A | 48 | 6.799 | 62.644 | 81.235 | 1.00 | 19.52 |
| ATOM | 308 | C | MET | A | 48 | 7.012 | 62.460 | 82.765 | 1.00 | 21.38 |
| ATOM | 309 | O | MET | A | 48 | 6.996 | 61.358 | 83.316 | 1.00 | 20.83 |
| ATOM | 310 | CB | MET | A | 48 | 8.173 | 62.667 | 80.539 | 1.00 | 21.42 |
| ATOM | 311 | CG | MET | A | 48 | 8.150 | 62.603 | 78.984 | 1.00 | 29.81 |
| ATOM | 312 | SD | MET | A | 48 | 7.330 | 61.126 | 78.308 | 1.00 | 36.20 |
| ATOM | 313 | CE | MET | A | 48 | 5.582 | 61.633 | 78.280 | 1.00 | 33.60 |
| ATOM | 314 | N | TYR | A | 49 | 7.139 | 63.655 | 83.414 | 1.00 | 21.32 |
| ATOM | 315 | CA | TYR | A | 49 | 7.066 | 63.807 | 84.885 | 1.00 | 21.30 |
| ATOM | 316 | C | TYR | A | 49 | 5.773 | 63.244 | 85.515 | 1.00 | 22.58 |
| ATOM | 317 | O | TYR | A | 49 | 5.797 | 62.383 | 86.390 | 1.00 | 24.04 |
| ATOM | 318 | CB | TYR | A | 49 | 7.304 | 65.282 | 85.217 | 1.00 | 20.61 |
| ATOM | 319 | CG | TYR | A | 49 | 7.034 | 65.494 | 86.692 | 1.00 | 23.57 |
| ATOM | 320 | CD1 | TYR | A | 49 | 5.755 | 65.931 | 87.109 | 1.00 | 23.57 |
| ATOM | 321 | CD2 | TYR | A | 49 | 8.080 | 65.194 | 87.574 | 1.00 | 21.83 |
| ATOM | 322 | CE1 | TYR | A | 49 | 5.524 | 66.097 | 88.481 | 1.00 | 26.09 |
| ATOM | 323 | CE2 | TYR | A | 49 | 7.844 | 65.349 | 88.943 | 1.00 | 23.18 |
| ATOM | 324 | CZ | TYR | A | 49 | 6.591 | 65.842 | 89.377 | 1.00 | 26.31 |

FIG. 16

| ATOM | 325 | OH | TYR A | 49 | 6.444 | 66.124 | 90.726 | 1.00 | 29.46 |
|---|---|---|---|---|---|---|---|---|---|
| ATOM | 326 | N | GLU A | 50 | 4.639 | 63.731 | 84.994 | 1.00 | 22.09 |
| ATOM | 327 | CA | GLU A | 50 | 3.336 | 63.234 | 85.472 | 1.00 | 21.48 |
| ATOM | 328 | C | GLU A | 50 | 3.052 | 61.776 | 85.230 | 1.00 | 23.20 |
| ATOM | 329 | O | GLU A | 50 | 2.548 | 61.050 | 86.081 | 1.00 | 24.23 |
| ATOM | 330 | CB | GLU A | 50 | 2.190 | 64.023 | 84.862 | 1.00 | 21.88 |
| ATOM | 331 | CG | GLU A | 50 | 2.304 | 65.537 | 84.986 | 1.00 | 21.13 |
| ATOM | 332 | CD | GLU A | 50 | 2.054 | 65.976 | 86.417 | 1.00 | 25.41 |
| ATOM | 333 | OE1 | GLU A | 50 | 1.887 | 65.138 | 87.287 | 1.00 | 24.65 |
| ATOM | 334 | OE2 | GLU A | 50 | 2.004 | 67.162 | 86.679 | 1.00 | 25.05 |
| ATOM | 335 | N | GLN A | 51 | 3.479 | 61.343 | 84.032 | 1.00 | 23.02 |
| ATOM | 336 | CA | GLN A | 51 | 3.427 | 59.907 | 83.812 | 1.00 | 24.72 |
| ATOM | 337 | C | GLN A | 51 | 4.275 | 59.006 | 84.728 | 1.00 | 26.23 |
| ATOM | 338 | O | GLN A | 51 | 3.804 | 57.996 | 85.253 | 1.00 | 25.10 |
| ATOM | 339 | CB | GLN A | 51 | 3.680 | 59.545 | 82.355 | 1.00 | 24.41 |
| ATOM | 340 | CG | GLN A | 51 | 3.461 | 58.028 | 82.141 | 1.00 | 38.05 |
| ATOM | 341 | CD | GLN A | 51 | 2.115 | 57.435 | 82.657 | 1.00 | 53.15 |
| ATOM | 342 | OE1 | GLN A | 51 | 1.093 | 58.076 | 82.867 | 1.00 | 61.03 |
| ATOM | 343 | NE2 | GLN A | 51 | 2.098 | 56.123 | 82.834 | 1.00 | 55.24 |
| ATOM | 344 | N | GLY A | 52 | 5.556 | 59.414 | 84.922 | 1.00 | 26.76 |
| ATOM | 345 | CA | GLY A | 52 | 6.400 | 58.689 | 85.876 | 1.00 | 26.91 |
| ATOM | 346 | C | GLY A | 52 | 5.793 | 58.681 | 87.286 | 1.00 | 25.60 |
| ATOM | 347 | O | GLY A | 52 | 5.666 | 57.699 | 87.997 | 1.00 | 24.37 |
| ATOM | 348 | N | ARG A | 53 | 5.321 | 59.874 | 87.621 | 1.00 | 28.09 |
| ATOM | 349 | CA | ARG A | 53 | 4.527 | 60.032 | 88.834 | 1.00 | 29.75 |
| ATOM | 350 | C | ARG A | 53 | 3.384 | 59.049 | 89.067 | 1.00 | 32.01 |
| ATOM | 351 | O | ARG A | 53 | 3.284 | 58.437 | 90.115 | 1.00 | 34.69 |
| ATOM | 352 | CB | ARG A | 53 | 4.128 | 61.494 | 88.965 | 1.00 | 30.41 |
| ATOM | 353 | CG | ARG A | 53 | 3.857 | 61.919 | 90.389 | 1.00 | 29.15 |
| ATOM | 354 | CD | ARG A | 53 | 3.519 | 63.393 | 90.461 | 1.00 | 29.38 |
| ATOM | 355 | NE | ARG A | 53 | 2.385 | 63.740 | 89.609 | 1.00 | 31.35 |
| ATOM | 356 | CZ | ARG A | 53 | 1.088 | 63.593 | 89.886 | 1.00 | 32.29 |
| ATOM | 357 | NH1 | ARG A | 53 | 0.187 | 64.144 | 89.125 | 1.00 | 32.06 |
| ATOM | 358 | NH2 | ARG A | 53 | 0.661 | 62.938 | 90.931 | 1.00 | 32.66 |
| ATOM | 359 | N | LEU A | 54 | 2.575 | 58.839 | 88.033 | 1.00 | 32.47 |
| ATOM | 360 | CA | LEU A | 54 | 1.588 | 57.735 | 88.076 | 1.00 | 31.67 |
| ATOM | 361 | C | LEU A | 54 | 2.114 | 56.273 | 88.119 | 1.00 | 33.30 |
| ATOM | 362 | O | LEU A | 54 | 1.452 | 55.329 | 88.568 | 1.00 | 35.90 |
| ATOM | 363 | CB | LEU A | 54 | 0.603 | 57.880 | 86.901 | 1.00 | 33.52 |
| ATOM | 364 | CG | LEU A | 54 | -0.599 | 58.822 | 87.055 | 1.00 | 32.85 |
| ATOM | 365 | CD1 | LEU A | 54 | -1.298 | 59.020 | 85.709 | 1.00 | 30.53 |
| ATOM | 366 | CD2 | LEU A | 54 | -0.286 | 60.130 | 87.777 | 1.00 | 36.56 |
| ATOM | 367 | N | LEU A | 55 | 3.374 | 56.117 | 87.657 | 1.00 | 31.95 |
| ATOM | 368 | CA | LEU A | 55 | 4.016 | 54.784 | 87.735 | 1.00 | 32.70 |
| ATOM | 369 | C | LEU A | 55 | 4.577 | 54.392 | 89.091 | 1.00 | 33.98 |
| ATOM | 370 | O | LEU A | 55 | 4.842 | 53.224 | 89.386 | 1.00 | 32.73 |
| ATOM | 371 | CB | LEU A | 55 | 5.194 | 54.646 | 86.790 | 1.00 | 31.04 |
| ATOM | 372 | CG | LEU A | 55 | 4.832 | 54.514 | 85.343 | 1.00 | 28.60 |
| ATOM | 373 | CD1 | LEU A | 55 | 3.960 | 53.287 | 85.101 | 1.00 | 27.88 |
| ATOM | 374 | CD2 | LEU A | 55 | 6.118 | 54.471 | 84.539 | 1.00 | 28.33 |
| ATOM | 375 | N | ARG A | 56 | 4.732 | 55.458 | 89.911 | 1.00 | 36.20 |
| ATOM | 376 | CA | ARG A | 56 | 5.257 | 55.308 | 91.281 | 1.00 | 37.04 |
| ATOM | 377 | C | ARG A | 56 | 4.616 | 54.240 | 92.164 | 1.00 | 40.28 |
| ATOM | 378 | O | ARG A | 56 | 5.260 | 53.518 | 92.907 | 1.00 | 41.22 |

F I G. 1 7

| ATOM | 379 | CB | ARG | A | 56 | 5.249 | 56.643 | 91.993 | 1.00 | 32.58 |
|---|---|---|---|---|---|---|---|---|---|---|
| ATOM | 380 | CG | ARG | A | 56 | 6.368 | 57.502 | 91.476 | 1.00 | 22.04 |
| ATOM | 381 | CD | ARG | A | 56 | 6.142 | 58.874 | 92.049 | 1.00 | 21.74 |
| ATOM | 382 | NE | ARG | A | 56 | 7.073 | 59.804 | 91.447 | 1.00 | 23.56 |
| ATOM | 383 | CZ | ARG | A | 56 | 7.062 | 61.074 | 91.750 | 1.00 | 25.56 |
| ATOM | 384 | NH1 | ARG | A | 56 | 6.401 | 61.444 | 92.790 | 1.00 | 30.94 |
| ATOM | 385 | NH2 | ARG | A | 56 | 7.688 | 61.979 | 91.035 | 1.00 | 22.33 |
| ATOM | 386 | N | ASN | A | 57 | 3.306 | 54.120 | 91.997 | 1.00 | 44.42 |
| ATOM | 387 | CA | ASN | A | 57 | 2.602 | 53.027 | 92.680 | 1.00 | 48.62 |
| ATOM | 388 | C | ASN | A | 57 | 2.786 | 51.585 | 92.169 | 1.00 | 47.46 |
| ATOM | 389 | O | ASN | A | 57 | 2.316 | 50.630 | 92.759 | 1.00 | 51.15 |
| ATOM | 390 | CB | ASN | A | 57 | 1.124 | 53.435 | 92.726 | 1.00 | 59.30 |
| ATOM | 391 | CG | ASN | A | 57 | 0.389 | 53.137 | 94.049 | 1.00 | 68.98 |
| ATOM | 392 | OD1 | ASN | A | 57 | -0.829 | 53.335 | 94.164 | 1.00 | 75.09 |
| ATOM | 393 | ND2 | ASN | A | 57 | 1.140 | 52.692 | 95.058 | 1.00 | 71.68 |
| ATOM | 394 | N | THR | A | 58 | 3.461 | 51.442 | 91.036 | 1.00 | 42.68 |
| ATOM | 395 | CA | THR | A | 58 | 3.555 | 50.086 | 90.475 | 1.00 | 36.64 |
| ATOM | 396 | C | THR | A | 58 | 4.821 | 49.318 | 90.871 | 1.00 | 33.64 |
| ATOM | 397 | O | THR | A | 58 | 5.721 | 49.876 | 91.477 | 1.00 | 31.69 |
| ATOM | 398 | CB | THR | A | 58 | 3.492 | 50.189 | 88.948 | 1.00 | 36.81 |
| ATOM | 399 | OG1 | THR | A | 58 | 4.774 | 50.576 | 88.447 | 1.00 | 37.64 |
| ATOM | 400 | CG2 | THR | A | 58 | 2.432 | 51.203 | 88.507 | 1.00 | 35.36 |
| ATOM | 401 | N | GLU | A | 59 | 4.937 | 48.068 | 90.409 | 1.00 | 33.08 |
| ATOM | 402 | CA | GLU | A | 59 | 6.238 | 47.410 | 90.581 | 1.00 | 34.80 |
| ATOM | 403 | C | GLU | A | 59 | 7.487 | 48.104 | 89.944 | 1.00 | 33.45 |
| ATOM | 404 | O | GLU | A | 59 | 8.607 | 48.153 | 90.463 | 1.00 | 34.28 |
| ATOM | 405 | CB | GLU | A | 59 | 6.067 | 45.933 | 90.191 | 1.00 | 43.43 |
| ATOM | 406 | CG | GLU | A | 59 | 7.242 | 45.007 | 90.614 | 1.00 | 59.74 |
| ATOM | 407 | CD | GLU | A | 59 | 7.519 | 44.933 | 92.159 | 1.00 | 69.61 |
| ATOM | 408 | OE1 | GLU | A | 59 | 6.582 | 45.064 | 92.960 | 1.00 | 74.78 |
| ATOM | 409 | OE2 | GLU | A | 59 | 8.686 | 44.751 | 92.589 | 1.00 | 74.97 |
| ATOM | 410 | N | ARG | A | 60 | 7.229 | 48.734 | 88.768 | 1.00 | 27.61 |
| ATOM | 411 | CA | ARG | A | 60 | 8.251 | 49.599 | 88.158 | 1.00 | 25.02 |
| ATOM | 412 | C | ARG | A | 60 | 8.614 | 50.851 | 88.958 | 1.00 | 22.94 |
| ATOM | 413 | O | ARG | A | 60 | 9.772 | 51.257 | 89.002 | 1.00 | 24.63 |
| ATOM | 414 | CB | ARG | A | 60 | 7.874 | 49.966 | 86.690 | 1.00 | 26.16 |
| ATOM | 415 | CG | ARG | A | 60 | 8.877 | 50.860 | 85.900 | 1.00 | 24.47 |
| ATOM | 416 | CD | ARG | A | 60 | 10.268 | 50.249 | 85.758 | 1.00 | 23.96 |
| ATOM | 417 | NE | ARG | A | 60 | 11.285 | 51.161 | 85.217 | 1.00 | 25.64 |
| ATOM | 418 | CZ | ARG | A | 60 | 12.214 | 51.778 | 85.945 | 1.00 | 24.77 |
| ATOM | 419 | NH1 | ARG | A | 60 | 12.159 | 51.805 | 87.261 | 1.00 | 24.78 |
| ATOM | 420 | NH2 | ARG | A | 60 | 13.227 | 52.294 | 85.325 | 1.00 | 19.79 |
| ATOM | 421 | N | GLY | A | 61 | 7.562 | 51.411 | 89.587 | 1.00 | 21.94 |
| ATOM | 422 | CA | GLY | A | 61 | 7.623 | 52.443 | 90.620 | 1.00 | 22.33 |
| ATOM | 423 | C | GLY | A | 61 | 8.468 | 52.051 | 91.824 | 1.00 | 24.44 |
| ATOM | 424 | O | GLY | A | 61 | 9.350 | 52.773 | 92.253 | 1.00 | 25.22 |
| ATOM | 425 | N | LYS | A | 62 | 8.248 | 50.821 | 92.307 | 1.00 | 26.95 |
| ATOM | 426 | CA | LYS | A | 62 | 9.102 | 50.251 | 93.350 | 1.00 | 26.24 |
| ATOM | 427 | C | LYS | A | 62 | 10.590 | 50.158 | 93.045 | 1.00 | 24.89 |
| ATOM | 428 | O | LYS | A | 62 | 11.443 | 50.668 | 93.756 | 1.00 | 23.23 |
| ATOM | 429 | CB | LYS | A | 62 | 8.519 | 48.900 | 93.723 | 1.00 | 29.90 |
| ATOM | 430 | CG | LYS | A | 62 | 9.379 | 48.296 | 94.835 | 1.00 | 38.76 |
| ATOM | 431 | CD | LYS | A | 62 | 8.847 | 46.904 | 95.222 | 1.00 | 47.47 |
| ATOM | 432 | CE | LYS | A | 62 | 9.944 | 45.971 | 95.773 | 1.00 | 53.72 |

F I G. 18

| ATOM | 433 | NZ  | LYS | A | 62 | 10.167 | 44.857 | 94.832 | 1.00 | 60.22 |
| ATOM | 434 | N   | LEU | A | 63 | 10.866 | 49.560 | 91.882 | 1.00 | 24.67 |
| ATOM | 435 | CA  | LEU | A | 63 | 12.239 | 49.634 | 91.346 | 1.00 | 23.65 |
| ATOM | 436 | C   | LEU | A | 63 | 12.805 | 51.043 | 91.186 | 1.00 | 22.74 |
| ATOM | 437 | O   | LEU | A | 63 | 13.927 | 51.359 | 91.517 | 1.00 | 25.19 |
| ATOM | 438 | CB  | LEU | A | 63 | 12.232 | 48.973 | 89.981 | 1.00 | 27.11 |
| ATOM | 439 | CG  | LEU | A | 63 | 13.477 | 48.298 | 89.403 | 1.00 | 31.83 |
| ATOM | 440 | CD1 | LEU | A | 63 | 14.808 | 48.658 | 90.077 | 1.00 | 33.84 |
| ATOM | 441 | CD2 | LEU | A | 63 | 13.440 | 48.410 | 87.874 | 1.00 | 26.95 |
| ATOM | 442 | N   | ALA | A | 64 | 11.979 | 51.940 | 90.642 | 1.00 | 21.62 |
| ATOM | 443 | CA  | ALA | A | 64 | 12.492 | 53.308 | 90.539 | 1.00 | 20.51 |
| ATOM | 444 | C   | ALA | A | 64 | 12.862 | 53.971 | 91.863 | 1.00 | 21.79 |
| ATOM | 445 | O   | ALA | A | 64 | 13.890 | 54.636 | 91.984 | 1.00 | 21.21 |
| ATOM | 446 | CB  | ALA | A | 64 | 11.456 | 54.196 | 89.862 | 1.00 | 19.01 |
| ATOM | 447 | N   | ALA | A | 65 | 11.984 | 53.747 | 92.870 | 1.00 | 23.25 |
| ATOM | 448 | CA  | ALA | A | 65 | 12.374 | 54.212 | 94.235 | 1.00 | 24.88 |
| ATOM | 449 | C   | ALA | A | 65 | 13.684 | 53.619 | 94.784 | 1.00 | 22.62 |
| ATOM | 450 | O   | ALA | A | 65 | 14.551 | 54.328 | 95.268 | 1.00 | 22.95 |
| ATOM | 451 | CB  | ALA | A | 65 | 11.249 | 54.013 | 95.265 | 1.00 | 25.38 |
| ATOM | 452 | N   | GLU | A | 66 | 13.848 | 52.295 | 94.572 | 1.00 | 23.38 |
| ATOM | 453 | CA  | GLU | A | 66 | 15.116 | 51.632 | 94.878 | 1.00 | 23.41 |
| ATOM | 454 | C   | GLU | A | 66 | 16.332 | 52.188 | 94.152 | 1.00 | 26.06 |
| ATOM | 455 | O   | GLU | A | 66 | 17.321 | 52.604 | 94.744 | 1.00 | 25.12 |
| ATOM | 456 | CB  | GLU | A | 66 | 14.968 | 50.136 | 94.665 | 1.00 | 25.85 |
| ATOM | 457 | CG  | GLU | A | 66 | 13.818 | 49.616 | 95.533 | 1.00 | 31.94 |
| ATOM | 458 | CD  | GLU | A | 66 | 13.546 | 48.142 | 95.293 | 1.00 | 37.59 |
| ATOM | 459 | OE1 | GLU | A | 66 | 13.147 | 47.430 | 96.220 | 1.00 | 40.33 |
| ATOM | 460 | OE2 | GLU | A | 66 | 13.721 | 47.673 | 94.176 | 1.00 | 40.79 |
| ATOM | 461 | N   | ASP | A | 67 | 16.204 | 52.276 | 92.817 | 1.00 | 24.01 |
| ATOM | 462 | CA  | ASP | A | 67 | 17.222 | 52.928 | 91.986 | 1.00 | 19.72 |
| ATOM | 463 | C   | ASP | A | 67 | 17.549 | 54.333 | 92.402 | 1.00 | 16.72 |
| ATOM | 464 | O   | ASP | A | 67 | 18.694 | 54.767 | 92.414 | 1.00 | 18.91 |
| ATOM | 465 | CB  | ASP | A | 67 | 16.787 | 52.944 | 90.495 | 1.00 | 21.68 |
| ATOM | 466 | CG  | ASP | A | 67 | 16.824 | 51.580 | 89.801 | 1.00 | 25.22 |
| ATOM | 467 | OD1 | ASP | A | 67 | 17.340 | 50.629 | 90.370 | 1.00 | 23.32 |
| ATOM | 468 | OD2 | ASP | A | 67 | 16.349 | 51.434 | 88.666 | 1.00 | 26.83 |
| ATOM | 469 | N   | ALA | A | 68 | 16.485 | 55.059 | 92.773 | 1.00 | 16.48 |
| ATOM | 470 | CA  | ALA | A | 68 | 16.685 | 56.425 | 93.250 | 1.00 | 19.28 |
| ATOM | 471 | C   | ALA | A | 68 | 17.489 | 56.510 | 94.569 | 1.00 | 20.86 |
| ATOM | 472 | O   | ALA | A | 68 | 18.165 | 57.494 | 94.837 | 1.00 | 22.07 |
| ATOM | 473 | CB  | ALA | A | 68 | 15.330 | 57.134 | 93.419 | 1.00 | 19.81 |
| ATOM | 474 | N   | ASN | A | 69 | 17.472 | 55.371 | 95.299 | 1.00 | 23.11 |
| ATOM | 475 | CA  | ASN | A | 69 | 18.330 | 55.262 | 96.514 | 1.00 | 27.41 |
| ATOM | 476 | C   | ASN | A | 69 | 19.816 | 55.042 | 96.273 | 1.00 | 29.49 |
| ATOM | 477 | O   | ASN | A | 69 | 20.646 | 55.304 | 97.140 | 1.00 | 28.64 |
| ATOM | 478 | CB  | ASN | A | 69 | 17.933 | 54.145 | 97.466 | 1.00 | 24.19 |
| ATOM | 479 | CG  | ASN | A | 69 | 16.632 | 54.425 | 98.142 | 1.00 | 25.79 |
| ATOM | 480 | OD1 | ASN | A | 69 | 16.298 | 55.549 | 98.445 | 1.00 | 26.84 |
| ATOM | 481 | ND2 | ASN | A | 69 | 15.894 | 53.359 | 98.410 | 1.00 | 30.16 |
| ATOM | 482 | N   | LEU | A | 70 | 20.104 | 54.574 | 95.034 | 1.00 | 25.30 |
| ATOM | 483 | CA  | LEU | A | 70 | 21.514 | 54.442 | 94.627 | 1.00 | 23.20 |
| ATOM | 484 | C   | LEU | A | 70 | 22.329 | 55.691 | 94.640 | 1.00 | 21.41 |
| ATOM | 485 | O   | LEU | A | 70 | 22.013 | 56.696 | 94.028 | 1.00 | 23.50 |
| ATOM | 486 | CB  | LEU | A | 70 | 21.672 | 53.890 | 93.225 | 1.00 | 22.19 |

FIG. 19

```
ATOM    487  CG   LEU A  70      21.078  52.512  93.095  1.00  22.16
ATOM    488  CD1  LEU A  70      21.830  51.459  93.896  1.00  20.70
ATOM    489  CD2  LEU A  70      21.016  52.154  91.624  1.00  23.47
ATOM    490  N    SER A  71      23.450  55.563  95.304  1.00  21.73
ATOM    491  CA   SER A  71      24.527  56.515  95.119  1.00  22.25
ATOM    492  C    SER A  71      25.355  56.171  93.888  1.00  20.52
ATOM    493  O    SER A  71      25.269  55.081  93.357  1.00  23.70
ATOM    494  CB   SER A  71      25.453  56.521  96.349  1.00  22.74
ATOM    495  OG   SER A  71      26.232  55.303  96.432  1.00  28.68
ATOM    496  N    SER A  72      26.220  57.079  93.445  1.00  20.02
ATOM    497  CA   SER A  72      27.096  56.747  92.294  1.00  20.88
ATOM    498  C    SER A  72      27.860  55.479  92.410  1.00  22.52
ATOM    499  O    SER A  72      27.979  54.663  91.518  1.00  21.65
ATOM    500  CB   SER A  72      28.113  57.834  92.083  1.00  19.05
ATOM    501  OG   SER A  72      27.352  58.966  91.735  1.00  22.00
ATOM    502  N    GLY A  73      28.336  55.318  93.640  1.00  20.71
ATOM    503  CA   GLY A  73      28.979  54.068  94.006  1.00  16.81
ATOM    504  C    GLY A  73      28.146  52.783  93.939  1.00  15.97
ATOM    505  O    GLY A  73      28.697  51.705  93.753  1.00  20.02
ATOM    506  N    GLY A  74      26.818  52.915  94.046  1.00  16.07
ATOM    507  CA   GLY A  74      26.090  51.649  93.967  1.00  18.17
ATOM    508  C    GLY A  74      25.671  51.260  92.526  1.00  21.98
ATOM    509  O    GLY A  74      25.202  50.164  92.238  1.00  21.28
ATOM    510  N    VAL A  75      25.887  52.210  91.567  1.00  22.48
ATOM    511  CA   VAL A  75      25.521  51.777  90.174  1.00  22.71
ATOM    512  C    VAL A  75      26.174  50.493  89.628  1.00  18.50
ATOM    513  O    VAL A  75      25.497  49.573  89.210  1.00  20.32
ATOM    514  CB   VAL A  75      25.820  52.946  89.218  1.00  23.52
ATOM    515  CG1  VAL A  75      25.719  52.707  87.712  1.00  21.49
ATOM    516  CG2  VAL A  75      25.153  54.265  89.560  1.00  17.54
ATOM    517  N    ALA A  76      27.517  50.394  89.738  1.00  21.05
ATOM    518  CA   ALA A  76      28.149  49.125  89.372  1.00  20.51
ATOM    519  C    ALA A  76      27.414  47.875  89.826  1.00  24.64
ATOM    520  O    ALA A  76      27.033  47.028  89.015  1.00  24.90
ATOM    521  CB   ALA A  76      29.612  49.071  89.810  1.00  19.14
ATOM    522  N    ASN A  77      27.131  47.820  91.145  1.00  20.97
ATOM    523  CA   ASN A  77      26.463  46.601  91.622  1.00  17.62
ATOM    524  C    ASN A  77      25.019  46.464  91.205  1.00  16.57
ATOM    525  O    ASN A  77      24.536  45.350  91.024  1.00  19.24
ATOM    526  CB   ASN A  77      26.615  46.509  93.137  1.00  23.52
ATOM    527  CG   ASN A  77      25.817  45.362  93.677  1.00  21.57
ATOM    528  OD1  ASN A  77      24.672  45.508  94.079  1.00  26.66
ATOM    529  ND2  ASN A  77      26.435  44.202  93.627  1.00  24.64
ATOM    530  N    ALA A  78      24.377  47.638  91.017  1.00  17.23
ATOM    531  CA   ALA A  78      23.060  47.710  90.339  1.00  18.62
ATOM    532  C    ALA A  78      22.874  47.025  88.941  1.00  19.92
ATOM    533  O    ALA A  78      21.767  46.705  88.517  1.00  21.04
ATOM    534  CB   ALA A  78      22.636  49.160  90.208  1.00  13.62
ATOM    535  N    PHE A  79      24.025  46.748  88.292  1.00  19.22
ATOM    536  CA   PHE A  79      24.019  45.921  87.070  1.00  20.71
ATOM    537  C    PHE A  79      24.117  44.420  87.238  1.00  23.30
ATOM    538  O    PHE A  79      24.161  43.662  86.273  1.00  23.64
ATOM    539  CB   PHE A  79      25.116  46.352  86.082  1.00  18.00
ATOM    540  CG   PHE A  79      24.821  47.683  85.382  1.00  19.59
```

FIG. 20

```
ATOM    541  CD1 PHE A   79      25.181  48.903  85.984  1.00 17.05
ATOM    542  CD2 PHE A   79      24.214  47.687  84.104  1.00 18.56
ATOM    543  CE1 PHE A   79      25.026  50.119  85.298  1.00 19.06
ATOM    544  CE2 PHE A   79      24.040  48.906  83.419  1.00 15.97
ATOM    545  CZ  PHE A   79      24.500  50.104  83.989  1.00 17.87
ATOM    546  N   SER A   80      24.150  43.947  88.488  1.00 19.74
ATOM    547  CA  SER A   80      24.500  42.511  88.632  1.00 17.29
ATOM    548  C   SER A   80      23.601  41.501  87.944  1.00 18.57
ATOM    549  O   SER A   80      23.977  40.494  87.339  1.00 22.38
ATOM    550  CB  SER A   80      24.608  42.106  90.125  1.00 15.17
ATOM    551  OG  SER A   80      25.646  42.920  90.700  1.00 17.32
ATOM    552  N   GLY A   81      22.309  41.852  88.041  1.00 19.68
ATOM    553  CA  GLY A   81      21.271  41.005  87.413  1.00 22.50
ATOM    554  C   GLY A   81      21.293  40.977  85.855  1.00 24.85
ATOM    555  O   GLY A   81      21.318  39.939  85.211  1.00 23.46
ATOM    556  N   ALA A   82      21.380  42.197  85.279  1.00 24.60
ATOM    557  CA  ALA A   82      21.686  42.339  83.855  1.00 24.50
ATOM    558  C   ALA A   82      22.985  41.643  83.417  1.00 25.22
ATOM    559  O   ALA A   82      23.000  40.873  82.468  1.00 23.42
ATOM    560  CB  ALA A   82      21.649  43.819  83.470  1.00 20.35
ATOM    561  N   PHE A   83      24.050  41.874  84.197  1.00 23.76
ATOM    562  CA  PHE A   83      25.319  41.242  83.894  1.00 21.76
ATOM    563  C   PHE A   83      25.325  39.726  83.974  1.00 22.85
ATOM    564  O   PHE A   83      26.090  39.052  83.322  1.00 25.72
ATOM    565  CB  PHE A   83      26.349  41.867  84.792  1.00 20.01
ATOM    566  CG  PHE A   83      27.770  41.527  84.394  1.00 20.95
ATOM    567  CD1 PHE A   83      28.486  40.587  85.152  1.00 16.94
ATOM    568  CD2 PHE A   83      28.391  42.208  83.307  1.00 23.09
ATOM    569  CE1 PHE A   83      29.841  40.355  84.843  1.00 18.79
ATOM    570  CE2 PHE A   83      29.751  41.991  83.001  1.00 20.95
ATOM    571  CZ  PHE A   83      30.474  41.069  83.795  1.00 21.43
ATOM    572  N   GLY A   84      24.409  39.187  84.768  1.00 22.31
ATOM    573  CA  GLY A   84      24.478  37.740  84.865  1.00 24.39
ATOM    574  C   GLY A   84      25.199  37.163  86.093  1.00 29.49
ATOM    575  O   GLY A   84      25.158  35.963  86.362  1.00 32.27
ATOM    576  N   SER A   85      25.873  38.058  86.843  1.00 30.33
ATOM    577  CA  SER A   85      26.685  37.625  88.001  1.00 28.46
ATOM    578  C   SER A   85      27.047  38.788  88.936  1.00 29.06
ATOM    579  O   SER A   85      26.915  39.945  88.556  1.00 29.00
ATOM    580  CB  SER A   85      27.915  36.861  87.536  1.00 24.04
ATOM    581  OG  SER A   85      28.903  37.746  87.028  1.00 28.11
ATOM    582  N   PRO A   86      27.436  38.518  90.216  1.00 29.45
ATOM    583  CA  PRO A   86      27.599  39.650  91.122  1.00 26.27
ATOM    584  C   PRO A   86      28.721  40.513  90.733  1.00 22.75
ATOM    585  O   PRO A   86      29.830  40.064  90.530  1.00 22.43
ATOM    586  CB  PRO A   86      27.873  39.029  92.493  1.00 27.52
ATOM    587  CG  PRO A   86      27.284  37.627  92.399  1.00 27.61
ATOM    588  CD  PRO A   86      27.591  37.258  90.945  1.00 31.08
ATOM    589  N   ILE A   87      28.350  41.776  90.659  1.00 22.99
ATOM    590  CA  ILE A   87      29.363  42.816  90.469  1.00 24.80
ATOM    591  C   ILE A   87      29.642  43.494  91.811  1.00 25.76
ATOM    592  O   ILE A   87      28.956  44.424  92.220  1.00 24.68
ATOM    593  CB  ILE A   87      28.908  43.860  89.427  1.00 24.26
ATOM    594  CG1 ILE A   87      28.626  43.165  88.076  1.00 23.29
```

FIG. 21

```
ATOM    595  CG2  ILE A   87      29.997  44.923  89.306  1.00  23.62
ATOM    596  CD1  ILE A   87      27.925  44.100  87.092  1.00  21.95
ATOM    597  N    THR A   88      30.655  42.914  92.481  1.00  25.86
ATOM    598  CA   THR A   88      30.925  43.247  93.903  1.00  25.48
ATOM    599  C    THR A   88      32.418  43.249  94.166  1.00  25.25
ATOM    600  O    THR A   88      33.131  42.561  93.445  1.00  24.26
ATOM    601  CB   THR A   88      30.332  42.211  94.859  1.00  22.31
ATOM    602  OG1  THR A   88      31.102  41.029  94.702  1.00  25.42
ATOM    603  CG2  THR A   88      28.833  41.943  94.710  1.00  19.45
ATOM    604  N    GLU A   89      32.891  43.970  95.204  1.00  26.63
ATOM    605  CA   GLU A   89      34.322  43.845  95.577  1.00  25.29
ATOM    606  C    GLU A   89      34.810  42.429  95.889  1.00  25.30
ATOM    607  O    GLU A   89      35.924  41.999  95.611  1.00  26.30
ATOM    608  CB   GLU A   89      34.652  44.773  96.741  1.00  25.64
ATOM    609  CG   GLU A   89      34.334  46.193  96.340  1.00  26.52
ATOM    610  CD   GLU A   89      34.551  47.228  97.414  1.00  29.70
ATOM    611  OE1  GLU A   89      35.136  48.245  97.123  1.00  33.05
ATOM    612  OE2  GLU A   89      34.138  47.077  98.540  1.00  27.59
ATOM    613  N    LYS A   90      33.860  41.697  96.459  1.00  26.25
ATOM    614  CA   LYS A   90      34.095  40.310  96.883  1.00  28.81
ATOM    615  C    LYS A   90      34.285  39.313  95.780  1.00  28.19
ATOM    616  O    LYS A   90      35.206  38.518  95.773  1.00  30.49
ATOM    617  CB   LYS A   90      32.889  39.869  97.672  1.00  31.00
ATOM    618  CG   LYS A   90      32.956  38.478  98.228  1.00  37.00
ATOM    619  CD   LYS A   90      31.536  38.026  98.583  1.00  43.53
ATOM    620  CE   LYS A   90      31.386  36.504  98.712  1.00  50.17
ATOM    621  NZ   LYS A   90      32.257  35.875  97.701  1.00  60.80
ATOM    622  N    ASP A   91      33.324  39.416  94.870  1.00  28.68
ATOM    623  CA   ASP A   91      33.271  38.504  93.738  1.00  29.34
ATOM    624  C    ASP A   91      33.911  38.947  92.420  1.00  29.37
ATOM    625  O    ASP A   91      34.429  38.173  91.635  1.00  31.54
ATOM    626  CB   ASP A   91      31.827  38.162  93.438  1.00  30.91
ATOM    627  CG   ASP A   91      31.087  37.722  94.674  1.00  31.69
ATOM    628  OD1  ASP A   91      31.395  36.657  95.212  1.00  35.66
ATOM    629  OD2  ASP A   91      30.186  38.438  95.088  1.00  29.63
ATOM    630  N    ALA A   92      33.830  40.240  92.165  1.00  28.62
ATOM    631  CA   ALA A   92      34.443  40.713  90.919  1.00  26.75
ATOM    632  C    ALA A   92      35.255  41.981  91.131  1.00  26.94
ATOM    633  O    ALA A   92      34.937  43.081  90.690  1.00  26.94
ATOM    634  CB   ALA A   92      33.390  40.934  89.817  1.00  23.93
ATOM    635  N    PRO A   93      36.336  41.826  91.930  1.00  27.16
ATOM    636  CA   PRO A   93      37.151  43.015  92.274  1.00  25.78
ATOM    637  C    PRO A   93      37.832  43.865  91.160  1.00  24.62
ATOM    638  O    PRO A   93      37.844  45.098  91.178  1.00  22.75
ATOM    639  CB   PRO A   93      38.120  42.411  93.292  1.00  25.31
ATOM    640  CG   PRO A   93      38.219  40.926  92.945  1.00  23.54
ATOM    641  CD   PRO A   93      36.817  40.578  92.534  1.00  25.29
ATOM    642  N    ALA A   94      38.409  43.174  90.170  1.00  25.16
ATOM    643  CA   ALA A   94      38.954  43.886  89.005  1.00  23.77
ATOM    644  C    ALA A   94      37.923  44.715  88.249  1.00  17.72
ATOM    645  O    ALA A   94      38.116  45.897  88.005  1.00  19.91
ATOM    646  CB   ALA A   94      39.676  42.931  88.058  1.00  21.52
ATOM    647  N    LEU A   95      36.787  44.081  88.026  1.00  19.68
ATOM    648  CA   LEU A   95      35.577  44.770  87.539  1.00  20.23
```

FIG. 22

| ATOM | 649 | C | LEU | A | 95 | 35.001 | 45.902 | 88.385 | 1.00 | 21.85 |
| --- | --- | --- | --- | --- | --- | --- | --- | --- | --- | --- |
| ATOM | 650 | O | LEU | A | 95 | 34.809 | 47.026 | 87.943 | 1.00 | 21.66 |
| ATOM | 651 | CB | LEU | A | 95 | 34.466 | 43.755 | 87.271 | 1.00 | 20.70 |
| ATOM | 652 | CG | LEU | A | 95 | 33.250 | 44.285 | 86.467 | 1.00 | 21.32 |
| ATOM | 653 | CD1 | LEU | A | 95 | 32.299 | 43.149 | 86.063 | 1.00 | 20.10 |
| ATOM | 654 | CD2 | LEU | A | 95 | 33.698 | 45.111 | 85.240 | 1.00 | 20.93 |
| ATOM | 655 | N | HIS | A | 96 | 34.755 | 45.606 | 89.667 | 1.00 | 21.70 |
| ATOM | 656 | CA | HIS | A | 96 | 34.313 | 46.691 | 90.543 | 1.00 | 17.84 |
| ATOM | 657 | C | HIS | A | 96 | 35.214 | 47.924 | 90.580 | 1.00 | 17.76 |
| ATOM | 658 | O | HIS | A | 96 | 34.767 | 49.069 | 90.496 | 1.00 | 19.44 |
| ATOM | 659 | CB | HIS | A | 96 | 34.042 | 46.116 | 91.937 | 1.00 | 20.62 |
| ATOM | 660 | CG | HIS | A | 96 | 32.934 | 46.893 | 92.613 | 1.00 | 21.96 |
| ATOM | 661 | ND1 | HIS | A | 96 | 33.021 | 48.094 | 93.229 | 1.00 | 21.34 |
| ATOM | 662 | CD2 | HIS | A | 96 | 31.614 | 46.470 | 92.680 | 1.00 | 24.62 |
| ATOM | 663 | CE1 | HIS | A | 96 | 31.790 | 48.442 | 93.690 | 1.00 | 18.16 |
| ATOM | 664 | NE2 | HIS | A | 96 | 30.923 | 47.437 | 93.338 | 1.00 | 23.59 |
| ATOM | 665 | N | LYS | A | 97 | 36.539 | 47.639 | 90.629 | 1.00 | 18.11 |
| ATOM | 666 | CA | LYS | A | 97 | 37.544 | 48.713 | 90.581 | 1.00 | 18.50 |
| ATOM | 667 | C | LYS | A | 97 | 37.519 | 49.564 | 89.317 | 1.00 | 20.80 |
| ATOM | 668 | O | LYS | A | 97 | 37.452 | 50.781 | 89.373 | 1.00 | 21.08 |
| ATOM | 669 | CB | LYS | A | 97 | 38.924 | 48.085 | 90.766 | 1.00 | 17.26 |
| ATOM | 670 | CG | LYS | A | 97 | 40.125 | 49.014 | 90.594 | 1.00 | 21.24 |
| ATOM | 671 | CD | LYS | A | 97 | 40.283 | 50.213 | 91.525 | 1.00 | 30.10 |
| ATOM | 672 | CE | LYS | A | 97 | 41.482 | 51.160 | 91.164 | 1.00 | 33.55 |
| ATOM | 673 | NZ | LYS | A | 97 | 41.557 | 52.449 | 91.915 | 1.00 | 29.55 |
| ATOM | 674 | N | LEU | A | 98 | 37.532 | 48.857 | 88.155 | 1.00 | 22.36 |
| ATOM | 675 | CA | LEU | A | 98 | 37.291 | 49.555 | 86.851 | 1.00 | 22.04 |
| ATOM | 676 | C | LEU | A | 98 | 36.128 | 50.581 | 86.806 | 1.00 | 17.59 |
| ATOM | 677 | O | LEU | A | 98 | 36.223 | 51.763 | 86.522 | 1.00 | 18.13 |
| ATOM | 678 | CB | LEU | A | 98 | 37.025 | 48.477 | 85.780 | 1.00 | 21.44 |
| ATOM | 679 | CG | LEU | A | 98 | 36.766 | 49.042 | 84.375 | 1.00 | 20.93 |
| ATOM | 680 | CD1 | LEU | A | 98 | 36.265 | 47.902 | 83.493 | 1.00 | 22.92 |
| ATOM | 681 | CD2 | LEU | A | 98 | 37.963 | 49.801 | 83.811 | 1.00 | 18.27 |
| ATOM | 682 | N | LEU | A | 99 | 34.977 | 50.024 | 87.188 | 1.00 | 19.16 |
| ATOM | 683 | CA | LEU | A | 99 | 33.753 | 50.802 | 87.186 | 1.00 | 18.37 |
| ATOM | 684 | C | LEU | A | 99 | 33.644 | 51.930 | 88.169 | 1.00 | 20.61 |
| ATOM | 685 | O | LEU | A | 99 | 33.068 | 52.964 | 87.883 | 1.00 | 18.31 |
| ATOM | 686 | CB | LEU | A | 99 | 32.545 | 49.874 | 87.263 | 1.00 | 18.90 |
| ATOM | 687 | CG | LEU | A | 99 | 32.428 | 48.860 | 86.191 | 1.00 | 20.87 |
| ATOM | 688 | CD1 | LEU | A | 99 | 32.464 | 49.503 | 84.841 | 1.00 | 14.73 |
| ATOM | 689 | CD2 | LEU | A | 99 | 31.190 | 48.099 | 86.497 | 1.00 | 19.82 |
| ATOM | 690 | N | THR | A | 100 | 34.252 | 51.692 | 89.359 | 1.00 | 22.03 |
| ATOM | 691 | CA | THR | A | 100 | 34.357 | 52.777 | 90.360 | 1.00 | 19.41 |
| ATOM | 692 | C | THR | A | 100 | 35.259 | 53.938 | 89.957 | 1.00 | 16.72 |
| ATOM | 693 | O | THR | A | 100 | 34.984 | 55.118 | 90.136 | 1.00 | 16.55 |
| ATOM | 694 | CB | THR | A | 100 | 34.889 | 52.174 | 91.674 | 1.00 | 19.50 |
| ATOM | 695 | OG1 | THR | A | 100 | 34.030 | 51.113 | 92.091 | 1.00 | 19.99 |
| ATOM | 696 | CG2 | THR | A | 100 | 35.092 | 53.221 | 92.758 | 1.00 | 21.12 |
| ATOM | 697 | N | ASN | A | 101 | 36.397 | 53.537 | 89.358 | 1.00 | 20.56 |
| ATOM | 698 | CA | ASN | A | 101 | 37.415 | 54.515 | 88.998 | 1.00 | 19.91 |
| ATOM | 699 | C | ASN | A | 101 | 37.022 | 55.479 | 87.873 | 1.00 | 21.88 |
| ATOM | 700 | O | ASN | A | 101 | 37.610 | 56.546 | 87.711 | 1.00 | 22.38 |
| ATOM | 701 | CB | ASN | A | 101 | 38.692 | 53.763 | 88.716 | 1.00 | 20.98 |
| ATOM | 702 | CG | ASN | A | 101 | 39.950 | 54.556 | 89.041 | 1.00 | 22.36 |

FIG. 23

```
ATOM    703  OD1 ASN A 101      40.938  53.978  89.459  1.00 30.43
ATOM    704  ND2 ASN A 101      39.964  55.868  88.889  1.00 23.45
ATOM    705  N   MET A 102      35.952  55.090  87.154  1.00 21.94
ATOM    706  CA  MET A 102      35.407  55.984  86.103  1.00 22.28
ATOM    707  C   MET A 102      34.142  56.755  86.455  1.00 22.36
ATOM    708  O   MET A 102      33.571  57.482  85.638  1.00 23.37
ATOM    709  CB  MET A 102      35.162  55.213  84.781  1.00 19.03
ATOM    710  CG  MET A 102      34.239  54.001  84.972  1.00 18.05
ATOM    711  SD  MET A 102      33.744  53.082  83.481  1.00 20.07
ATOM    712  CE  MET A 102      32.429  54.165  83.010  1.00 16.04
ATOM    713  N   ILE A 103      33.681  56.555  87.724  1.00 21.00
ATOM    714  CA  ILE A 103      32.441  57.221  88.180  1.00 18.78
ATOM    715  C   ILE A 103      32.371  58.697  87.833  1.00 17.38
ATOM    716  O   ILE A 103      31.413  59.152  87.245  1.00 18.08
ATOM    717  CB  ILE A 103      32.174  57.025  89.732  1.00 16.18
ATOM    718  CG1 ILE A 103      31.696  55.603  90.031  1.00 19.21
ATOM    719  CG2 ILE A 103      31.135  58.037  90.272  1.00 12.63
ATOM    720  CD1 ILE A 103      31.708  55.185  91.522  1.00 17.58
ATOM    721  N   GLU A 104      33.426  59.429  88.218  1.00 18.81
ATOM    722  CA  GLU A 104      33.369  60.900  88.092  1.00 18.36
ATOM    723  C   GLU A 104      33.828  61.520  86.772  1.00 19.60
ATOM    724  O   GLU A 104      33.420  62.606  86.365  1.00 19.13
ATOM    725  CB  GLU A 104      34.092  61.600  89.241  1.00 18.56
ATOM    726  CG  GLU A 104      33.446  61.448  90.617  1.00 19.21
ATOM    727  CD  GLU A 104      31.994  61.944  90.665  1.00 23.36
ATOM    728  OE1 GLU A 104      31.225  61.359  91.382  1.00 26.94
ATOM    729  OE2 GLU A 104      31.574  62.888  90.013  1.00 28.46
ATOM    730  N   ASP A 105      34.606  60.713  86.049  1.00 18.95
ATOM    731  CA  ASP A 105      34.743  60.936  84.587  1.00 17.40
ATOM    732  C   ASP A 105      33.378  61.099  83.886  1.00 15.12
ATOM    733  O   ASP A 105      33.104  62.102  83.234  1.00 18.61
ATOM    734  CB  ASP A 105      35.429  59.743  83.951  1.00 16.81
ATOM    735  CG  ASP A 105      36.831  59.545  84.440  1.00 15.10
ATOM    736  OD1 ASP A 105      37.573  60.520  84.573  1.00 19.01
ATOM    737  OD2 ASP A 105      37.177  58.402  84.685  1.00 15.56
ATOM    738  N   ALA A 106      32.500  60.091  84.096  1.00 15.05
ATOM    739  CA  ALA A 106      31.111  60.157  83.607  1.00 15.61
ATOM    740  C   ALA A 106      30.166  61.126  84.315  1.00 19.62
ATOM    741  O   ALA A 106      29.409  61.881  83.720  1.00 18.83
ATOM    742  CB  ALA A 106      30.467  58.782  83.682  1.00 11.73
ATOM    743  N   GLY A 107      30.263  61.102  85.674  1.00 21.49
ATOM    744  CA  GLY A 107      29.323  61.899  86.503  1.00 16.83
ATOM    745  C   GLY A 107      29.599  63.356  86.594  1.00 14.80
ATOM    746  O   GLY A 107      28.714  64.204  86.575  1.00 17.67
ATOM    747  N   ASP A 108      30.899  63.611  86.662  1.00 16.37
ATOM    748  CA  ASP A 108      31.305  65.002  86.772  1.00 17.18
ATOM    749  C   ASP A 108      31.877  65.572  85.485  1.00 18.56
ATOM    750  O   ASP A 108      31.324  66.472  84.877  1.00 18.77
ATOM    751  CB  ASP A 108      32.282  65.144  87.947  1.00 16.92
ATOM    752  CG  ASP A 108      32.862  66.530  88.143  1.00 21.34
ATOM    753  OD1 ASP A 108      32.247  67.528  87.812  1.00 23.69
ATOM    754  OD2 ASP A 108      33.983  66.642  88.614  1.00 27.32
ATOM    755  N   LEU A 109      33.049  65.065  85.107  1.00 18.48
ATOM    756  CA  LEU A 109      33.814  65.703  84.005  1.00 20.77
```

FIG. 24

```
ATOM    757  C    LEU A 109      32.954  65.922  82.752  1.00 21.46
ATOM    758  O    LEU A 109      32.905  67.026  82.199  1.00 23.24
ATOM    759  CB   LEU A 109      35.024  64.826  83.679  1.00 20.60
ATOM    760  CG   LEU A 109      36.393  65.285  84.113  1.00 21.65
ATOM    761  CD1  LEU A 109      37.408  64.213  84.096  1.00 17.20
ATOM    762  CD2  LEU A 109      36.469  66.186  85.254  1.00 20.25
ATOM    763  N    ALA A 110      32.206  64.812  82.422  1.00 21.81
ATOM    764  CA   ALA A 110      31.336  64.771  81.215  1.00 20.79
ATOM    765  C    ALA A 110      30.074  65.608  81.232  1.00 23.23
ATOM    766  O    ALA A 110      29.504  65.885  80.182  1.00 23.66
ATOM    767  CB   ALA A 110      30.921  63.333  80.868  1.00 20.49
ATOM    768  N    THR A 111      29.672  66.038  82.465  1.00 20.15
ATOM    769  CA   THR A 111      28.453  66.863  82.653  1.00 19.21
ATOM    770  C    THR A 111      28.654  68.292  83.132  1.00 18.58
ATOM    771  O    THR A 111      27.754  69.106  83.131  1.00 18.77
ATOM    772  CB   THR A 111      27.469  66.257  83.628  1.00 18.46
ATOM    773  OG1  THR A 111      28.011  66.399  84.949  1.00 23.25
ATOM    774  CG2  THR A 111      27.094  64.802  83.347  1.00 15.78
ATOM    775  N    ARG A 112      29.870  68.595  83.547  1.00 20.94
ATOM    776  CA   ARG A 112      30.068  69.805  84.369  1.00 22.62
ATOM    777  C    ARG A 112      29.745  71.185  83.786  1.00 23.68
ATOM    778  O    ARG A 112      29.035  72.025  84.325  1.00 21.09
ATOM    779  CB   ARG A 112      31.512  69.782  84.911  1.00 22.88
ATOM    780  CG   ARG A 112      31.847  70.852  85.952  1.00 22.67
ATOM    781  CD   ARG A 112      33.319  70.922  86.319  1.00 18.55
ATOM    782  NE   ARG A 112      33.831  69.709  86.930  1.00 22.11
ATOM    783  CZ   ARG A 112      35.138  69.496  86.853  1.00 21.99
ATOM    784  NH1  ARG A 112      35.949  70.322  86.227  1.00 23.29
ATOM    785  NH2  ARG A 112      35.623  68.436  87.414  1.00 23.83
ATOM    786  N    SER A 113      30.323  71.398  82.583  1.00 21.66
ATOM    787  CA   SER A 113      30.146  72.736  81.981  1.00 19.14
ATOM    788  C    SER A 113      28.721  73.124  81.629  1.00 20.09
ATOM    789  O    SER A 113      28.288  74.263  81.806  1.00 23.06
ATOM    790  CB   SER A 113      31.029  72.919  80.732  1.00 24.64
ATOM    791  OG   SER A 113      30.812  71.854  79.778  1.00 25.18
ATOM    792  N    ALA A 114      27.955  72.094  81.186  1.00 19.43
ATOM    793  CA   ALA A 114      26.510  72.272  80.944  1.00 17.15
ATOM    794  C    ALA A 114      25.695  72.377  82.247  1.00 16.95
ATOM    795  O    ALA A 114      24.890  73.293  82.402  1.00 17.79
ATOM    796  CB   ALA A 114      25.935  71.096  80.117  1.00 15.05
ATOM    797  N    LYS A 115      25.993  71.462  83.200  1.00 18.76
ATOM    798  CA   LYS A 115      25.431  71.618  84.559  1.00 20.52
ATOM    799  C    LYS A 115      25.524  73.029  85.143  1.00 18.24
ATOM    800  O    LYS A 115      24.535  73.710  85.429  1.00 19.61
ATOM    801  CB   LYS A 115      26.048  70.606  85.508  1.00 17.41
ATOM    802  CG   LYS A 115      25.304  69.294  85.482  1.00 22.93
ATOM    803  CD   LYS A 115      25.867  68.477  86.654  1.00 26.73
ATOM    804  CE   LYS A 115      25.353  67.039  86.850  1.00 26.14
ATOM    805  NZ   LYS A 115      23.888  67.023  87.009  1.00 26.36
ATOM    806  N    ASP A 116      26.784  73.454  85.203  1.00 19.25
ATOM    807  CA   ASP A 116      27.073  74.739  85.832  1.00 20.02
ATOM    808  C    ASP A 116      26.589  75.938  85.076  1.00 23.51
ATOM    809  O    ASP A 116      26.208  76.967  85.612  1.00 24.69
ATOM    810  CB   ASP A 116      28.573  74.896  86.053  1.00 22.26
```

F I G. 25

```
ATOM    811  CG   ASP A 116      29.203  73.871  87.029  1.00 25.80
ATOM    812  OD1  ASP A 116      28.502  73.085  87.657  1.00 27.77
ATOM    813  OD2  ASP A 116      30.431  73.847  87.166  1.00 28.44
ATOM    814  N    HIS A 117      26.596  75.793  83.741  1.00 23.53
ATOM    815  CA   HIS A 117      26.022  76.894  82.957  1.00 21.71
ATOM    816  C    HIS A 117      24.496  77.044  83.026  1.00 20.75
ATOM    817  O    HIS A 117      23.932  78.108  83.223  1.00 20.51
ATOM    818  CB   HIS A 117      26.536  76.787  81.501  1.00 22.93
ATOM    819  CG   HIS A 117      25.987  77.909  80.635  1.00 22.08
ATOM    820  ND1  HIS A 117      26.531  79.128  80.459  1.00 23.33
ATOM    821  CD2  HIS A 117      24.824  77.852  79.881  1.00 22.30
ATOM    822  CE1  HIS A 117      25.741  79.836  79.615  1.00 23.49
ATOM    823  NE2  HIS A 117      24.693  79.041  79.262  1.00 23.57
ATOM    824  N    TYR A 118      23.825  75.906  82.825  1.00 19.95
ATOM    825  CA   TYR A 118      22.363  76.013  82.795  1.00 19.91
ATOM    826  C    TYR A 118      21.711  76.075  84.159  1.00 22.89
ATOM    827  O    TYR A 118      20.615  76.596  84.278  1.00 22.53
ATOM    828  CB   TYR A 118      21.702  74.869  82.020  1.00 18.70
ATOM    829  CG   TYR A 118      22.112  74.964  80.550  1.00 19.86
ATOM    830  CD1  TYR A 118      21.604  76.030  79.775  1.00 20.81
ATOM    831  CD2  TYR A 118      22.998  74.004  80.005  1.00 20.19
ATOM    832  CE1  TYR A 118      21.964  76.104  78.410  1.00 24.18
ATOM    833  CE2  TYR A 118      23.393  74.097  78.652  1.00 22.07
ATOM    834  CZ   TYR A 118      22.841  75.133  77.869  1.00 24.85
ATOM    835  OH   TYR A 118      23.138  75.231  76.525  1.00 25.02
ATOM    836  N    MET A 119      22.385  75.453  85.158  1.00 22.72
ATOM    837  CA   MET A 119      21.795  75.408  86.516  1.00 25.49
ATOM    838  C    MET A 119      20.328  75.033  86.619  1.00 22.79
ATOM    839  O    MET A 119      19.526  75.639  87.309  1.00 23.65
ATOM    840  CB   MET A 119      22.009  76.758  87.200  1.00 31.90
ATOM    841  CG   MET A 119      23.479  77.200  87.296  1.00 41.79
ATOM    842  SD   MET A 119      23.683  78.779  88.163  1.00 50.25
ATOM    843  CE   MET A 119      22.932  79.838  86.910  1.00 48.37
ATOM    844  N    ARG A 120      19.958  74.021  85.840  1.00 21.05
ATOM    845  CA   ARG A 120      18.529  73.782  85.704  1.00 19.45
ATOM    846  C    ARG A 120      17.877  73.247  86.989  1.00 16.34
ATOM    847  O    ARG A 120      18.483  72.369  87.587  1.00 17.21
ATOM    848  CB   ARG A 120      18.345  72.757  84.558  1.00 16.25
ATOM    849  CG   ARG A 120      16.913  72.517  84.063  1.00 17.39
ATOM    850  CD   ARG A 120      16.775  71.558  82.842  1.00 19.83
ATOM    851  NE   ARG A 120      15.450  71.636  82.189  1.00 20.39
ATOM    852  CZ   ARG A 120      14.929  70.642  81.479  1.00 12.14
ATOM    853  NH1  ARG A 120      15.600  69.574  81.259  1.00 12.74
ATOM    854  NH2  ARG A 120      13.724  70.767  81.007  1.00 15.75
ATOM    855  N    ILE A 121      16.676  73.723  87.290  1.00 16.46
ATOM    856  CA   ILE A 121      15.807  73.186  88.360  1.00 22.91
ATOM    857  C    ILE A 121      15.258  71.795  88.080  1.00 23.50
ATOM    858  O    ILE A 121      14.648  71.571  87.043  1.00 26.14
ATOM    859  CB   ILE A 121      14.594  74.134  88.686  1.00 25.98
ATOM    860  CG1  ILE A 121      14.986  75.592  88.783  1.00 29.16
ATOM    861  CG2  ILE A 121      13.793  73.870  89.982  1.00 23.20
ATOM    862  CD1  ILE A 121      16.075  75.914  89.785  1.00 29.73
ATOM    863  N    ARG A 122      15.463  70.877  89.036  1.00 21.01
ATOM    864  CA   ARG A 122      14.883  69.534  88.976  1.00 19.80
```

FIG. 26

| ATOM | 865 | C | ARG A 122 | 13.372 | 69.532 | 89.091 | 1.00 | 17.61 |
|---|---|---|---|---|---|---|---|---|
| ATOM | 866 | O | ARG A 122 | 12.805 | 70.488 | 89.613 | 1.00 | 18.79 |
| ATOM | 867 | CB | ARG A 122 | 15.533 | 68.653 | 90.033 | 1.00 | 17.47 |
| ATOM | 868 | CG | ARG A 122 | 17.023 | 68.706 | 89.841 | 1.00 | 18.78 |
| ATOM | 869 | CD | ARG A 122 | 17.721 | 67.861 | 90.852 | 1.00 | 21.00 |
| ATOM | 870 | NE | ARG A 122 | 19.141 | 68.121 | 90.748 | 1.00 | 28.80 |
| ATOM | 871 | CZ | ARG A 122 | 19.914 | 67.081 | 90.491 | 1.00 | 34.31 |
| ATOM | 872 | NH1 | ARG A 122 | 19.401 | 65.871 | 90.426 | 1.00 | 40.28 |
| ATOM | 873 | NH2 | ARG A 122 | 21.196 | 67.257 | 90.289 | 1.00 | 32.47 |
| ATOM | 874 | N | PRO A 123 | 12.700 | 68.460 | 88.577 | 1.00 | 17.64 |
| ATOM | 875 | CA | PRO A 123 | 11.243 | 68.461 | 88.684 | 1.00 | 18.56 |
| ATOM | 876 | C | PRO A 123 | 10.668 | 68.630 | 90.118 | 1.00 | 20.86 |
| ATOM | 877 | O | PRO A 123 | 9.881 | 69.536 | 90.331 | 1.00 | 20.65 |
| ATOM | 878 | CB | PRO A 123 | 10.808 | 67.150 | 88.004 | 1.00 | 16.86 |
| ATOM | 879 | CG | PRO A 123 | 12.028 | 66.572 | 87.296 | 1.00 | 15.55 |
| ATOM | 880 | CD | PRO A 123 | 13.235 | 67.291 | 87.881 | 1.00 | 15.48 |
| ATOM | 881 | N | PHE A 124 | 11.077 | 67.771 | 91.105 | 1.00 | 21.82 |
| ATOM | 882 | CA | PHE A 124 | 10.489 | 67.948 | 92.468 | 1.00 | 20.01 |
| ATOM | 883 | C | PHE A 124 | 10.541 | 69.394 | 93.016 | 1.00 | 16.73 |
| ATOM | 884 | O | PHE A 124 | 9.581 | 69.970 | 93.486 | 1.00 | 17.82 |
| ATOM | 885 | CB | PHE A 124 | 11.044 | 66.869 | 93.422 | 1.00 | 17.84 |
| ATOM | 886 | CG | PHE A 124 | 12.484 | 67.199 | 93.795 | 1.00 | 19.87 |
| ATOM | 887 | CD1 | PHE A 124 | 12.748 | 68.117 | 94.850 | 1.00 | 20.96 |
| ATOM | 888 | CD2 | PHE A 124 | 13.554 | 66.632 | 93.075 | 1.00 | 19.87 |
| ATOM | 889 | CE1 | PHE A 124 | 14.068 | 68.524 | 95.134 | 1.00 | 21.78 |
| ATOM | 890 | CE2 | PHE A 124 | 14.881 | 67.014 | 93.381 | 1.00 | 21.98 |
| ATOM | 891 | CZ | PHE A 124 | 15.129 | 67.975 | 94.386 | 1.00 | 23.27 |
| ATOM | 892 | N | ALA A 125 | 11.681 | 70.039 | 92.775 | 1.00 | 18.30 |
| ATOM | 893 | CA | ALA A 125 | 11.866 | 71.464 | 93.089 | 1.00 | 20.06 |
| ATOM | 894 | C | ALA A 125 | 11.033 | 72.481 | 92.291 | 1.00 | 24.90 |
| ATOM | 895 | O | ALA A 125 | 10.455 | 73.445 | 92.789 | 1.00 | 24.77 |
| ATOM | 896 | CB | ALA A 125 | 13.358 | 71.840 | 92.990 | 1.00 | 16.96 |
| ATOM | 897 | N | PHE A 126 | 10.941 | 72.202 | 90.977 | 1.00 | 23.91 |
| ATOM | 898 | CA | PHE A 126 | 10.017 | 72.958 | 90.145 | 1.00 | 22.66 |
| ATOM | 899 | C | PHE A 126 | 8.590 | 72.919 | 90.692 | 1.00 | 20.74 |
| ATOM | 900 | O | PHE A 126 | 7.910 | 73.945 | 90.785 | 1.00 | 21.66 |
| ATOM | 901 | CB | PHE A 126 | 10.051 | 72.379 | 88.705 | 1.00 | 19.61 |
| ATOM | 902 | CG | PHE A 126 | 9.147 | 73.140 | 87.765 | 1.00 | 16.99 |
| ATOM | 903 | CD1 | PHE A 126 | 9.669 | 74.211 | 87.022 | 1.00 | 15.15 |
| ATOM | 904 | CD2 | PHE A 126 | 7.794 | 72.757 | 87.656 | 1.00 | 17.75 |
| ATOM | 905 | CE1 | PHE A 126 | 8.824 | 74.913 | 86.144 | 1.00 | 14.16 |
| ATOM | 906 | CE2 | PHE A 126 | 6.940 | 73.472 | 86.799 | 1.00 | 17.56 |
| ATOM | 907 | CZ | PHE A 126 | 7.471 | 74.538 | 86.048 | 1.00 | 12.93 |
| ATOM | 908 | N | TYR A 127 | 8.183 | 71.664 | 91.002 | 1.00 | 20.13 |
| ATOM | 909 | CA | TYR A 127 | 6.843 | 71.414 | 91.525 | 1.00 | 20.41 |
| ATOM | 910 | C | TYR A 127 | 6.642 | 71.689 | 93.032 | 1.00 | 24.41 |
| ATOM | 911 | O | TYR A 127 | 5.525 | 71.665 | 93.532 | 1.00 | 23.70 |
| ATOM | 912 | CB | TYR A 127 | 6.370 | 69.994 | 91.207 | 1.00 | 20.85 |
| ATOM | 913 | CG | TYR A 127 | 6.198 | 69.850 | 89.697 | 1.00 | 25.51 |
| ATOM | 914 | CD1 | TYR A 127 | 7.200 | 69.185 | 88.947 | 1.00 | 27.02 |
| ATOM | 915 | CD2 | TYR A 127 | 5.064 | 70.407 | 89.065 | 1.00 | 25.24 |
| ATOM | 916 | CE1 | TYR A 127 | 7.057 | 69.037 | 87.552 | 1.00 | 28.75 |
| ATOM | 917 | CE2 | TYR A 127 | 4.907 | 70.261 | 87.663 | 1.00 | 28.24 |
| ATOM | 918 | CZ | TYR A 127 | 5.891 | 69.543 | 86.936 | 1.00 | 28.76 |

FIG. 27

```
ATOM    919  OH   TYR A 127       5.716  69.314  85.588  1.00 27.53
ATOM    920  N    GLY A 128       7.764  71.960  93.723  1.00 23.74
ATOM    921  CA   GLY A 128       7.675  72.217  95.170  1.00 24.88
ATOM    922  C    GLY A 128       7.138  71.011  95.924  1.00 24.57
ATOM    923  O    GLY A 128       6.383  71.095  96.866  1.00 29.82
ATOM    924  N    VAL A 129       7.527  69.854  95.426  1.00 24.16
ATOM    925  CA   VAL A 129       7.144  68.604  96.044  1.00 23.21
ATOM    926  C    VAL A 129       8.377  67.802  96.358  1.00 24.99
ATOM    927  O    VAL A 129       9.529  68.188  96.189  1.00 25.90
ATOM    928  CB   VAL A 129       6.193  67.776  95.187  1.00 22.38
ATOM    929  CG1  VAL A 129       6.738  67.390  93.815  1.00 17.75
ATOM    930  CG2  VAL A 129       4.895  68.549  95.125  1.00 24.52
ATOM    931  N    SER A 130       8.089  66.617  96.832  1.00 25.98
ATOM    932  CA   SER A 130       9.242  65.724  96.973  1.00 29.71
ATOM    933  C    SER A 130       9.322  64.672  95.895  1.00 29.73
ATOM    934  O    SER A 130       8.403  64.485  95.103  1.00 30.28
ATOM    935  CB   SER A 130       9.183  64.999  98.309  1.00 35.36
ATOM    936  OG   SER A 130       7.964  64.244  98.427  1.00 41.61
ATOM    937  N    THR A 131      10.440  63.952  95.934  1.00 30.35
ATOM    938  CA   THR A 131      10.533  62.819  94.996  1.00 27.90
ATOM    939  C    THR A 131       9.733  61.569  95.361  1.00 28.80
ATOM    940  O    THR A 131       9.051  61.508  96.366  1.00 30.16
ATOM    941  CB   THR A 131      11.996  62.471  94.783  1.00 26.62
ATOM    942  OG1  THR A 131      12.500  61.841  95.953  1.00 29.21
ATOM    943  CG2  THR A 131      12.839  63.682  94.446  1.00 19.32
ATOM    944  N    CYS A 132       9.835  60.528  94.551  1.00 27.12
ATOM    945  CA   CYS A 132       9.203  59.271  94.996  1.00 27.75
ATOM    946  C    CYS A 132       9.911  58.540  96.137  1.00 28.96
ATOM    947  O    CYS A 132       9.556  57.487  96.634  1.00 28.80
ATOM    948  CB   CYS A 132       9.081  58.274  93.831  1.00 24.68
ATOM    949  SG   CYS A 132      10.538  57.273  93.459  1.00 24.12
ATOM    950  N    ASN A 133      11.021  59.158  96.447  1.00 33.31
ATOM    951  CA   ASN A 133      12.012  58.492  97.236  1.00 39.44
ATOM    952  C    ASN A 133      12.008  58.776  98.750  1.00 45.19
ATOM    953  O    ASN A 133      12.269  57.928  99.583  1.00 50.38
ATOM    954  CB   ASN A 133      13.285  58.876  96.522  1.00 35.83
ATOM    955  CG   ASN A 133      14.294  57.823  96.731  1.00 37.18
ATOM    956  OD1  ASN A 133      15.478  58.059  96.663  1.00 38.83
ATOM    957  ND2  ASN A 133      13.815  56.623  97.017  1.00 42.51
ATOM    958  N    THR A 134      11.642  59.993  99.118  1.00 48.69
ATOM    959  CA   THR A 134      12.585  61.110  98.925  1.00 56.17
ATOM    960  C    THR A 134      13.935  61.171  99.735  1.00 61.49
ATOM    961  OCT1 THR A 134      14.052  60.565 100.816  1.00 66.36
ATOM    962  OCT2 THR A 134      14.937  61.779  99.291  1.00 63.18
ATOM    963  CB   THR A 134      11.704  62.374  98.968  1.00 56.04
ATOM    964  OG1  THR A 134      12.306  63.614  98.469  1.00 56.23
ATOM    965  CG2  THR A 134      10.869  62.400 100.243  1.00 53.77
ATOM    966  N    GLN A 137      16.953  60.437 100.819  1.00100.00
ATOM    967  CA   GLN A 137      17.845  60.498 102.027  1.00 99.78
ATOM    968  C    GLN A 137      19.036  61.512 102.211  1.00 98.61
ATOM    969  O    GLN A 137      19.386  61.891 103.324  1.00 97.54
ATOM    970  CB   GLN A 137      18.343  59.083 102.397  1.00100.00
ATOM    971  CG   GLN A 137      17.669  58.407 103.615  1.00 99.38
ATOM    972  CD   GLN A 137      18.060  59.017 104.963  1.00 98.64
```

FIG. 28

| ATOM | 973 | OE1 | GLN | A | 137 | 17.484 | 58.784 | 106.009 | 1.00 | 98.03 |
| ATOM | 974 | NE2 | GLN | A | 137 | 19.086 | 59.847 | 104.972 | 1.00 | 100.00 |
| ATOM | 975 | N | ASP | A | 138 | 19.627 | 61.949 | 101.081 | 1.00 | 97.91 |
| ATOM | 976 | CA | ASP | A | 138 | 20.479 | 63.151 | 101.162 | 1.00 | 95.99 |
| ATOM | 977 | C | ASP | A | 138 | 19.761 | 64.494 | 101.063 | 1.00 | 93.86 |
| ATOM | 978 | O | ASP | A | 138 | 18.589 | 64.579 | 100.711 | 1.00 | 92.75 |
| ATOM | 979 | CB | ASP | A | 138 | 21.585 | 63.102 | 100.115 | 1.00 | 97.46 |
| ATOM | 980 | CG | ASP | A | 138 | 22.893 | 62.963 | 100.866 | 1.00 | 100.00 |
| ATOM | 981 | OD1 | ASP | A | 138 | 23.371 | 61.842 | 101.028 | 1.00 | 100.00 |
| ATOM | 982 | OD2 | ASP | A | 138 | 23.432 | 63.969 | 101.333 | 1.00 | 100.00 |
| ATOM | 983 | N | LYS | A | 139 | 20.494 | 65.564 | 101.380 | 1.00 | 92.69 |
| ATOM | 984 | CA | LYS | A | 139 | 19.813 | 66.855 | 101.218 | 1.00 | 91.50 |
| ATOM | 985 | C | LYS | A | 139 | 19.719 | 67.313 | 99.775 | 1.00 | 88.92 |
| ATOM | 986 | O | LYS | A | 139 | 20.557 | 68.082 | 99.308 | 1.00 | 89.47 |
| ATOM | 987 | CB | LYS | A | 139 | 20.464 | 67.987 | 102.010 | 1.00 | 94.21 |
| ATOM | 988 | CG | LYS | A | 139 | 19.574 | 69.246 | 102.020 | 1.00 | 96.82 |
| ATOM | 989 | CD | LYS | A | 139 | 20.362 | 70.569 | 102.123 | 1.00 | 99.43 |
| ATOM | 990 | CE | LYS | A | 139 | 20.785 | 71.241 | 100.793 | 1.00 | 100.00 |
| ATOM | 991 | NZ | LYS | A | 139 | 21.686 | 70.402 | 99.978 | 1.00 | 100.00 |
| ATOM | 992 | N | LEU | A | 140 | 18.654 | 66.828 | 99.114 | 1.00 | 85.87 |
| ATOM | 993 | CA | LEU | A | 140 | 18.426 | 67.018 | 97.660 | 1.00 | 79.60 |
| ATOM | 994 | C | LEU | A | 140 | 18.772 | 68.392 | 97.043 | 1.00 | 75.62 |
| ATOM | 995 | O | LEU | A | 140 | 18.242 | 69.442 | 97.416 | 1.00 | 75.74 |
| ATOM | 996 | CB | LEU | A | 140 | 16.981 | 66.620 | 97.283 | 1.00 | 77.27 |
| ATOM | 997 | CG | LEU | A | 140 | 16.640 | 65.142 | 97.462 | 1.00 | 74.31 |
| ATOM | 998 | CD1 | LEU | A | 140 | 17.569 | 64.263 | 96.645 | 1.00 | 73.21 |
| ATOM | 999 | CD2 | LEU | A | 140 | 15.178 | 64.838 | 97.167 | 1.00 | 73.91 |
| ATOM | 1000 | N | SER | A | 141 | 19.713 | 68.357 | 96.067 | 1.00 | 70.08 |
| ATOM | 1001 | CA | SER | A | 141 | 19.868 | 69.619 | 95.320 | 1.00 | 64.86 |
| ATOM | 1002 | C | SER | A | 141 | 18.713 | 69.941 | 94.396 | 1.00 | 61.18 |
| ATOM | 1003 | O | SER | A | 141 | 18.189 | 69.080 | 93.708 | 1.00 | 61.77 |
| ATOM | 1004 | CB | SER | A | 141 | 21.127 | 69.682 | 94.461 | 1.00 | 64.49 |
| ATOM | 1005 | OG | SER | A | 141 | 21.354 | 71.028 | 94.002 | 1.00 | 66.43 |
| ATOM | 1006 | N | LYS | A | 142 | 18.349 | 71.235 | 94.379 | 1.00 | 57.81 |
| ATOM | 1007 | CA | LYS | A | 142 | 17.238 | 71.661 | 93.493 | 1.00 | 54.35 |
| ATOM | 1008 | C | LYS | A | 142 | 17.498 | 71.829 | 91.964 | 1.00 | 45.94 |
| ATOM | 1009 | O | LYS | A | 142 | 16.615 | 72.091 | 91.202 | 1.00 | 40.89 |
| ATOM | 1010 | CB | LYS | A | 142 | 16.631 | 72.953 | 94.061 | 1.00 | 57.69 |
| ATOM | 1011 | CG | LYS | A | 142 | 17.518 | 74.222 | 93.959 | 1.00 | 62.63 |
| ATOM | 1012 | CD | LYS | A | 142 | 16.625 | 75.420 | 93.545 | 1.00 | 68.07 |
| ATOM | 1013 | CE | LYS | A | 142 | 17.200 | 76.856 | 93.475 | 1.00 | 71.28 |
| ATOM | 1014 | NZ | LYS | A | 142 | 16.136 | 77.844 | 93.162 | 1.00 | 70.88 |
| ATOM | 1015 | N | ASN | A | 143 | 18.772 | 71.719 | 91.611 | 1.00 | 45.99 |
| ATOM | 1016 | CA | ASN | A | 143 | 19.527 | 72.392 | 90.538 | 1.00 | 44.71 |
| ATOM | 1017 | C | ASN | A | 143 | 20.592 | 71.481 | 89.878 | 1.00 | 42.57 |
| ATOM | 1018 | O | ASN | A | 143 | 20.794 | 70.322 | 90.283 | 1.00 | 40.17 |
| ATOM | 1019 | CB | ASN | A | 143 | 20.343 | 73.547 | 91.124 | 1.00 | 50.34 |
| ATOM | 1020 | CG | ASN | A | 143 | 19.624 | 74.818 | 90.876 | 1.00 | 55.19 |
| ATOM | 1021 | OD1 | ASN | A | 143 | 18.441 | 74.944 | 91.098 | 1.00 | 59.21 |
| ATOM | 1022 | ND2 | ASN | A | 143 | 20.366 | 75.786 | 90.389 | 1.00 | 59.88 |
| ATOM | 1023 | N | GLY | A | 144 | 21.265 | 72.084 | 88.819 | 1.00 | 39.72 |
| ATOM | 1024 | CA | GLY | A | 144 | 22.264 | 71.401 | 87.953 | 1.00 | 26.74 |
| ATOM | 1025 | C | GLY | A | 144 | 21.691 | 70.105 | 87.407 | 1.00 | 21.44 |
| ATOM | 1026 | O | GLY | A | 144 | 22.343 | 69.071 | 87.322 | 1.00 | 25.73 |

FIG. 29

| ATOM | 1027 | N   | SER | A | 145 | 20.380 | 70.181 | 87.105 | 1.00 | 19.15 |
| ---- | ---- | --- | --- | - | --- | ------ | ------ | ------ | ---- | ----- |
| ATOM | 1028 | CA  | SER | A | 145 | 19.590 | 69.023 | 86.596 | 1.00 | 20.14 |
| ATOM | 1029 | C   | SER | A | 145 | 20.077 | 68.461 | 85.223 | 1.00 | 20.58 |
| ATOM | 1030 | O   | SER | A | 145 | 20.121 | 67.279 | 84.943 | 1.00 | 21.22 |
| ATOM | 1031 | CB  | SER | A | 145 | 18.171 | 69.499 | 86.338 | 1.00 | 18.89 |
| ATOM | 1032 | OG  | SER | A | 145 | 17.219 | 68.526 | 86.712 | 1.00 | 28.02 |
| ATOM | 1033 | N   | TYR | A | 146 | 20.531 | 69.419 | 84.399 | 1.00 | 22.70 |
| ATOM | 1034 | CA  | TYR | A | 146 | 20.867 | 69.170 | 82.968 | 1.00 | 19.51 |
| ATOM | 1035 | C   | TYR | A | 146 | 22.366 | 69.260 | 82.633 | 1.00 | 16.00 |
| ATOM | 1036 | O   | TYR | A | 146 | 22.930 | 70.339 | 82.736 | 1.00 | 17.85 |
| ATOM | 1037 | CB  | TYR | A | 146 | 20.097 | 70.216 | 82.114 | 1.00 | 18.79 |
| ATOM | 1038 | CG  | TYR | A | 146 | 20.211 | 69.933 | 80.600 | 1.00 | 20.29 |
| ATOM | 1039 | CD1 | TYR | A | 146 | 19.310 | 69.027 | 80.015 | 1.00 | 19.58 |
| ATOM | 1040 | CD2 | TYR | A | 146 | 21.205 | 70.582 | 79.824 | 1.00 | 20.42 |
| ATOM | 1041 | CE1 | TYR | A | 146 | 19.389 | 68.781 | 78.631 | 1.00 | 23.13 |
| ATOM | 1042 | CE2 | TYR | A | 146 | 21.287 | 70.337 | 78.424 | 1.00 | 21.68 |
| ATOM | 1043 | CZ  | TYR | A | 146 | 20.349 | 69.449 | 77.849 | 1.00 | 20.03 |
| ATOM | 1044 | OH  | TYR | A | 146 | 20.320 | 69.236 | 76.483 | 1.00 | 21.40 |
| ATOM | 1045 | N   | PRO | A | 147 | 22.994 | 68.144 | 82.187 | 1.00 | 16.52 |
| ATOM | 1046 | CA  | PRO | A | 147 | 22.385 | 66.793 | 82.188 | 1.00 | 17.87 |
| ATOM | 1047 | C   | PRO | A | 147 | 22.496 | 66.069 | 83.580 | 1.00 | 20.67 |
| ATOM | 1048 | O   | PRO | A | 147 | 23.198 | 66.531 | 84.480 | 1.00 | 22.35 |
| ATOM | 1049 | CB  | PRO | A | 147 | 23.250 | 66.107 | 81.122 | 1.00 | 15.36 |
| ATOM | 1050 | CG  | PRO | A | 147 | 24.649 | 66.716 | 81.297 | 1.00 | 15.06 |
| ATOM | 1051 | CD  | PRO | A | 147 | 24.356 | 68.168 | 81.630 | 1.00 | 16.28 |
| ATOM | 1052 | N   | SER | A | 148 | 21.827 | 64.908 | 83.662 | 1.00 | 18.73 |
| ATOM | 1053 | CA  | SER | A | 148 | 21.951 | 64.019 | 84.823 | 1.00 | 19.51 |
| ATOM | 1054 | C   | SER | A | 148 | 23.269 | 63.281 | 84.930 | 1.00 | 19.93 |
| ATOM | 1055 | O   | SER | A | 148 | 23.601 | 62.439 | 84.108 | 1.00 | 20.09 |
| ATOM | 1056 | CB  | SER | A | 148 | 20.828 | 62.997 | 84.807 | 1.00 | 18.55 |
| ATOM | 1057 | OG  | SER | A | 148 | 20.990 | 61.966 | 85.780 | 1.00 | 19.29 |
| ATOM | 1058 | N   | GLY | A | 149 | 24.036 | 63.618 | 85.972 | 1.00 | 18.26 |
| ATOM | 1059 | CA  | GLY | A | 149 | 25.284 | 62.888 | 86.231 | 1.00 | 16.00 |
| ATOM | 1060 | C   | GLY | A | 149 | 25.096 | 61.411 | 86.577 | 1.00 | 19.38 |
| ATOM | 1061 | O   | GLY | A | 149 | 25.791 | 60.549 | 86.044 | 1.00 | 21.04 |
| ATOM | 1062 | N   | HIS | A | 150 | 24.085 | 61.096 | 87.427 | 1.00 | 20.25 |
| ATOM | 1063 | CA  | HIS | A | 150 | 23.690 | 59.680 | 87.624 | 1.00 | 19.01 |
| ATOM | 1064 | C   | HIS | A | 150 | 23.381 | 58.861 | 86.330 | 1.00 | 19.93 |
| ATOM | 1065 | O   | HIS | A | 150 | 23.833 | 57.725 | 86.145 | 1.00 | 20.78 |
| ATOM | 1066 | CB  | HIS | A | 150 | 22.507 | 59.533 | 88.619 | 1.00 | 18.01 |
| ATOM | 1067 | CG  | HIS | A | 150 | 22.162 | 58.068 | 88.909 | 1.00 | 20.60 |
| ATOM | 1068 | ND1 | HIS | A | 150 | 22.864 | 57.235 | 89.730 | 1.00 | 23.41 |
| ATOM | 1069 | CD2 | HIS | A | 150 | 21.117 | 57.313 | 88.374 | 1.00 | 21.91 |
| ATOM | 1070 | CE1 | HIS | A | 150 | 22.287 | 55.996 | 89.732 | 1.00 | 22.83 |
| ATOM | 1071 | NE2 | HIS | A | 150 | 21.220 | 56.051 | 88.893 | 1.00 | 24.19 |
| ATOM | 1072 | N   | THR | A | 151 | 22.593 | 59.482 | 85.432 | 1.00 | 18.98 |
| ATOM | 1073 | CA  | THR | A | 151 | 22.325 | 58.814 | 84.132 | 1.00 | 17.17 |
| ATOM | 1074 | C   | THR | A | 151 | 23.548 | 58.652 | 83.228 | 1.00 | 13.61 |
| ATOM | 1075 | O   | THR | A | 151 | 23.814 | 57.594 | 82.659 | 1.00 | 17.00 |
| ATOM | 1076 | CB  | THR | A | 151 | 21.270 | 59.590 | 83.407 | 1.00 | 16.57 |
| ATOM | 1077 | OG1 | THR | A | 151 | 20.137 | 59.738 | 84.258 | 1.00 | 18.00 |
| ATOM | 1078 | CG2 | THR | A | 151 | 20.898 | 58.983 | 82.045 | 1.00 | 13.22 |
| ATOM | 1079 | N   | SER | A | 152 | 24.361 | 59.722 | 83.197 | 1.00 | 14.30 |
| ATOM | 1080 | CA  | SER | A | 152 | 25.687 | 59.598 | 82.557 | 1.00 | 15.99 |

FIG. 30

```
ATOM   1081  C    SER A 152      26.575  58.446  83.029  1.00 19.72
ATOM   1082  O    SER A 152      27.086  57.628  82.255  1.00 17.38
ATOM   1083  CB   SER A 152      26.434  60.927  82.644  1.00 12.58
ATOM   1084  OG   SER A 152      27.648  60.861  81.911  1.00 16.08
ATOM   1085  N    ILE A 153      26.662  58.340  84.403  1.00 20.60
ATOM   1086  CA   ILE A 153      27.272  57.121  85.017  1.00 16.15
ATOM   1087  C    ILE A 153      26.622  55.802  84.631  1.00 10.76
ATOM   1088  O    ILE A 153      27.293  54.850  84.262  1.00 14.38
ATOM   1089  CB   ILE A 153      27.384  57.170  86.608  1.00 15.02
ATOM   1090  CG1  ILE A 153      28.187  58.421  86.963  1.00 16.37
ATOM   1091  CG2  ILE A 153      28.154  55.944  87.164  1.00 12.98
ATOM   1092  CD1  ILE A 153      27.870  59.034  88.338  1.00 16.58
ATOM   1093  N    GLY A 154      25.285  55.763  84.720  1.00  9.72
ATOM   1094  CA   GLY A 154      24.662  54.476  84.397  1.00 13.63
ATOM   1095  C    GLY A 154      24.843  54.033  82.910  1.00 16.00
ATOM   1096  O    GLY A 154      25.022  52.866  82.571  1.00 16.37
ATOM   1097  N    TRP A 155      24.801  55.047  82.025  1.00 16.77
ATOM   1098  CA   TRP A 155      24.960  54.747  80.589  1.00 16.73
ATOM   1099  C    TRP A 155      26.378  54.351  80.200  1.00 15.90
ATOM   1100  O    TRP A 155      26.656  53.301  79.628  1.00 18.41
ATOM   1101  CB   TRP A 155      24.442  55.940  79.771  1.00 16.52
ATOM   1102  CG   TRP A 155      24.320  55.475  78.321  1.00 19.11
ATOM   1103  CD1  TRP A 155      25.009  56.015  77.210  1.00 18.94
ATOM   1104  CD2  TRP A 155      23.471  54.426  77.765  1.00 18.98
ATOM   1105  NE1  TRP A 155      24.679  55.352  76.044  1.00 17.77
ATOM   1106  CE2  TRP A 155      23.781  54.322  76.357  1.00 22.22
ATOM   1107  CE3  TRP A 155      22.585  53.486  78.337  1.00 19.43
ATOM   1108  CZ2  TRP A 155      23.084  53.377  75.564  1.00 17.99
ATOM   1109  CZ3  TRP A 155      21.913  52.538  77.537  1.00 19.46
ATOM   1110  CH2  TRP A 155      22.191  52.464  76.158  1.00 17.84
ATOM   1111  N    ALA A 156      27.299  55.209  80.623  1.00 15.37
ATOM   1112  CA   ALA A 156      28.702  54.836  80.515  1.00 14.36
ATOM   1113  C    ALA A 156      29.156  53.503  81.108  1.00 19.46
ATOM   1114  O    ALA A 156      29.895  52.723  80.528  1.00 19.86
ATOM   1115  CB   ALA A 156      29.564  55.918  81.136  1.00 15.83
ATOM   1116  N    THR A 157      28.651  53.207  82.327  1.00 19.95
ATOM   1117  CA   THR A 157      28.820  51.832  82.831  1.00 17.52
ATOM   1118  C    THR A 157      28.177  50.744  81.994  1.00 15.22
ATOM   1119  O    THR A 157      28.825  49.745  81.765  1.00 19.09
ATOM   1120  CB   THR A 157      28.328  51.667  84.291  1.00 14.92
ATOM   1121  OG1  THR A 157      28.932  52.679  85.054  1.00 18.29
ATOM   1122  CG2  THR A 157      28.620  50.327  84.944  1.00 13.21
ATOM   1123  N    ALA A 158      26.930  50.947  81.535  1.00 14.63
ATOM   1124  CA   ALA A 158      26.365  49.936  80.621  1.00 17.10
ATOM   1125  C    ALA A 158      27.213  49.686  79.354  1.00 15.52
ATOM   1126  O    ALA A 158      27.539  48.565  79.025  1.00 16.52
ATOM   1127  CB   ALA A 158      24.942  50.300  80.203  1.00 13.99
ATOM   1128  N    LEU A 159      27.655  50.766  78.705  1.00 17.91
ATOM   1129  CA   LEU A 159      28.613  50.615  77.580  1.00 17.69
ATOM   1130  C    LEU A 159      29.895  49.851  77.846  1.00 19.93
ATOM   1131  O    LEU A 159      30.277  48.954  77.092  1.00 19.21
ATOM   1132  CB   LEU A 159      28.959  51.971  76.939  1.00 14.08
ATOM   1133  CG   LEU A 159      27.744  52.759  76.396  1.00 11.97
ATOM   1134  CD1  LEU A 159      27.045  52.105  75.210  1.00 12.90
```

FIG. 31

```
ATOM   1135  CD2  LEU A 159      28.177  54.158  76.046  1.00 12.40
ATOM   1136  N    VAL A 160      30.547  50.181  79.014  1.00 21.70
ATOM   1137  CA   VAL A 160      31.713  49.315  79.310  1.00 20.85
ATOM   1138  C    VAL A 160      31.429  47.877  79.767  1.00 21.33
ATOM   1139  O    VAL A 160      32.086  46.918  79.409  1.00 20.74
ATOM   1140  CB   VAL A 160      32.574  50.032  80.367  1.00 21.59
ATOM   1141  CG1  VAL A 160      33.518  49.143  81.174  1.00 20.11
ATOM   1142  CG2  VAL A 160      33.299  51.307  79.977  1.00 20.10
ATOM   1143  N    LEU A 161      30.351  47.711  80.542  1.00 21.86
ATOM   1144  CA   LEU A 161      29.850  46.366  80.838  1.00 20.50
ATOM   1145  C    LEU A 161      29.462  45.490  79.613  1.00 23.16
ATOM   1146  O    LEU A 161      29.753  44.294  79.564  1.00 22.89
ATOM   1147  CB   LEU A 161      28.623  46.472  81.733  1.00 18.65
ATOM   1148  CG   LEU A 161      28.685  46.438  83.262  1.00 20.99
ATOM   1149  CD1  LEU A 161      27.473  46.378  84.194  1.00 21.43
ATOM   1150  CD2  LEU A 161      29.729  45.492  83.855  1.00 19.30
ATOM   1151  N    ALA A 162      28.755  46.146  78.648  1.00 21.20
ATOM   1152  CA   ALA A 162      28.384  45.496  77.361  1.00 19.14
ATOM   1153  C    ALA A 162      29.591  44.948  76.586  1.00 17.15
ATOM   1154  O    ALA A 162      29.620  43.812  76.133  1.00 20.85
ATOM   1155  CB   ALA A 162      27.581  46.464  76.500  1.00 17.38
ATOM   1156  N    GLU A 163      30.663  45.745  76.603  1.00 14.74
ATOM   1157  CA   GLU A 163      31.962  45.262  76.118  1.00 17.48
ATOM   1158  C    GLU A 163      32.648  44.080  76.824  1.00 22.07
ATOM   1159  O    GLU A 163      33.271  43.216  76.227  1.00 23.96
ATOM   1160  CB   GLU A 163      32.915  46.448  76.000  1.00 13.52
ATOM   1161  CG   GLU A 163      34.227  46.018  75.359  1.00 13.04
ATOM   1162  CD   GLU A 163      35.240  47.119  75.338  1.00 15.88
ATOM   1163  OE1  GLU A 163      36.427  46.814  75.269  1.00 19.78
ATOM   1164  OE2  GLU A 163      34.873  48.290  75.377  1.00 20.10
ATOM   1165  N    ILE A 164      32.504  44.039  78.153  1.00 20.17
ATOM   1166  CA   ILE A 164      32.996  42.869  78.905  1.00 18.72
ATOM   1167  C    ILE A 164      32.164  41.609  78.757  1.00 17.39
ATOM   1168  O    ILE A 164      32.635  40.481  78.674  1.00 20.44
ATOM   1169  CB   ILE A 164      33.132  43.293  80.382  1.00 20.67
ATOM   1170  CG1  ILE A 164      34.222  44.361  80.452  1.00 18.83
ATOM   1171  CG2  ILE A 164      33.398  42.110  81.345  1.00 20.70
ATOM   1172  CD1  ILE A 164      34.144  45.084  81.793  1.00 21.31
ATOM   1173  N    ASN A 165      30.869  41.846  78.704  1.00 18.41
ATOM   1174  CA   ASN A 165      29.979  40.712  78.524  1.00 21.36
ATOM   1175  C    ASN A 165      28.957  40.867  77.375  1.00 23.74
ATOM   1176  O    ASN A 165      27.753  40.988  77.563  1.00 23.14
ATOM   1177  CB   ASN A 165      29.324  40.404  79.878  1.00 21.69
ATOM   1178  CG   ASN A 165      28.471  39.156  79.861  1.00 25.72
ATOM   1179  OD1  ASN A 165      28.469  38.307  78.967  1.00 29.37
ATOM   1180  ND2  ASN A 165      27.730  39.051  80.951  1.00 27.39
ATOM   1181  N    PRO A 166      29.466  40.814  76.118  1.00 25.93
ATOM   1182  CA   PRO A 166      28.556  40.971  74.957  1.00 26.27
ATOM   1183  C    PRO A 166      27.447  39.924  74.837  1.00 24.06
ATOM   1184  O    PRO A 166      26.361  40.184  74.360  1.00 24.11
ATOM   1185  CB   PRO A 166      29.517  41.040  73.781  1.00 25.15
ATOM   1186  CG   PRO A 166      30.731  40.254  74.255  1.00 27.68
ATOM   1187  CD   PRO A 166      30.849  40.613  75.728  1.00 24.89
ATOM   1188  N    GLN A 167      27.679  38.741  75.385  1.00 25.15
```

FIG. 32

| ATOM | 1189 | CA | GLN | A | 167 | 26.552 | 37.804 | 75.508 | 1.00 | 27.09 |
| ATOM | 1190 | C | GLN | A | 167 | 25.275 | 38.321 | 76.189 | 1.00 | 25.06 |
| ATOM | 1191 | O | GLN | A | 167 | 24.162 | 37.932 | 75.883 | 1.00 | 23.75 |
| ATOM | 1192 | CB | GLN | A | 167 | 27.080 | 36.617 | 76.282 | 1.00 | 35.50 |
| ATOM | 1193 | CG | GLN | A | 167 | 27.386 | 35.380 | 75.468 | 1.00 | 52.12 |
| ATOM | 1194 | CD | GLN | A | 167 | 26.074 | 34.747 | 75.000 | 1.00 | 65.78 |
| ATOM | 1195 | OE1 | GLN | A | 167 | 25.950 | 34.245 | 73.889 | 1.00 | 72.02 |
| ATOM | 1196 | NE2 | GLN | A | 167 | 25.047 | 34.780 | 75.867 | 1.00 | 71.50 |
| ATOM | 1197 | N | ARG | A | 168 | 25.513 | 39.242 | 77.156 | 1.00 | 26.04 |
| ATOM | 1198 | CA | ARG | A | 168 | 24.389 | 39.900 | 77.837 | 1.00 | 25.63 |
| ATOM | 1199 | C | ARG | A | 168 | 24.242 | 41.368 | 77.558 | 1.00 | 23.88 |
| ATOM | 1200 | O | ARG | A | 168 | 23.632 | 42.106 | 78.308 | 1.00 | 24.09 |
| ATOM | 1201 | CB | ARG | A | 168 | 24.452 | 39.638 | 79.337 | 1.00 | 24.63 |
| ATOM | 1202 | CG | ARG | A | 168 | 24.087 | 38.171 | 79.408 | 1.00 | 25.72 |
| ATOM | 1203 | CD | ARG | A | 168 | 23.986 | 37.617 | 80.802 | 1.00 | 33.72 |
| ATOM | 1204 | NE | ARG | A | 168 | 22.970 | 38.302 | 81.587 | 1.00 | 35.38 |
| ATOM | 1205 | CZ | ARG | A | 168 | 21.729 | 37.877 | 81.680 | 1.00 | 35.91 |
| ATOM | 1206 | NH1 | ARG | A | 168 | 20.908 | 38.482 | 82.490 | 1.00 | 34.99 |
| ATOM | 1207 | NH2 | ARG | A | 168 | 21.314 | 36.867 | 80.975 | 1.00 | 39.28 |
| ATOM | 1208 | N | GLN | A | 169 | 24.838 | 41.810 | 76.424 | 1.00 | 23.22 |
| ATOM | 1209 | CA | GLN | A | 169 | 24.820 | 43.228 | 76.080 | 1.00 | 19.99 |
| ATOM | 1210 | C | GLN | A | 169 | 23.441 | 43.850 | 76.067 | 1.00 | 21.38 |
| ATOM | 1211 | O | GLN | A | 169 | 23.216 | 44.969 | 76.492 | 1.00 | 24.60 |
| ATOM | 1212 | CB | GLN | A | 169 | 25.571 | 43.510 | 74.769 | 1.00 | 22.07 |
| ATOM | 1213 | CG | GLN | A | 169 | 24.970 | 42.878 | 73.494 | 1.00 | 20.93 |
| ATOM | 1214 | CD | GLN | A | 169 | 25.716 | 43.287 | 72.207 | 1.00 | 23.42 |
| ATOM | 1215 | OE1 | GLN | A | 169 | 26.680 | 44.055 | 72.202 | 1.00 | 24.82 |
| ATOM | 1216 | NE2 | GLN | A | 169 | 25.186 | 42.738 | 71.109 | 1.00 | 13.86 |
| ATOM | 1217 | N | ASN | A | 170 | 22.455 | 43.089 | 75.600 | 1.00 | 20.48 |
| ATOM | 1218 | CA | ASN | A | 170 | 21.138 | 43.736 | 75.525 | 1.00 | 20.97 |
| ATOM | 1219 | C | ASN | A | 170 | 20.484 | 44.007 | 76.892 | 1.00 | 19.73 |
| ATOM | 1220 | O | ASN | A | 170 | 19.852 | 45.020 | 77.128 | 1.00 | 18.90 |
| ATOM | 1221 | CB | ASN | A | 170 | 20.195 | 42.930 | 74.595 | 1.00 | 24.43 |
| ATOM | 1222 | CG | ASN | A | 170 | 20.763 | 42.881 | 73.153 | 1.00 | 25.82 |
| ATOM | 1223 | OD1 | ASN | A | 170 | 20.842 | 43.862 | 72.440 | 1.00 | 26.22 |
| ATOM | 1224 | ND2 | ASN | A | 170 | 21.197 | 41.709 | 72.734 | 1.00 | 25.47 |
| ATOM | 1225 | N | GLU | A | 171 | 20.680 | 43.042 | 77.790 | 1.00 | 21.27 |
| ATOM | 1226 | CA | GLU | A | 171 | 20.166 | 43.146 | 79.157 | 1.00 | 19.84 |
| ATOM | 1227 | C | GLU | A | 171 | 20.849 | 44.220 | 79.926 | 1.00 | 16.23 |
| ATOM | 1228 | O | GLU | A | 171 | 20.199 | 45.026 | 80.575 | 1.00 | 20.87 |
| ATOM | 1229 | CB | GLU | A | 171 | 20.317 | 41.822 | 79.892 | 1.00 | 20.47 |
| ATOM | 1230 | CG | GLU | A | 171 | 19.412 | 40.750 | 79.312 | 1.00 | 24.15 |
| ATOM | 1231 | CD | GLU | A | 171 | 20.157 | 39.825 | 78.376 | 1.00 | 26.37 |
| ATOM | 1232 | OE1 | GLU | A | 171 | 21.076 | 40.256 | 77.685 | 1.00 | 23.54 |
| ATOM | 1233 | OE2 | GLU | A | 171 | 19.801 | 38.645 | 78.363 | 1.00 | 32.14 |
| ATOM | 1234 | N | ILE | A | 172 | 22.169 | 44.236 | 79.751 | 1.00 | 17.53 |
| ATOM | 1235 | CA | ILE | A | 172 | 23.029 | 45.318 | 80.257 | 1.00 | 16.90 |
| ATOM | 1236 | C | ILE | A | 172 | 22.679 | 46.733 | 79.813 | 1.00 | 20.21 |
| ATOM | 1237 | O | ILE | A | 172 | 22.454 | 47.636 | 80.617 | 1.00 | 18.91 |
| ATOM | 1238 | CB | ILE | A | 172 | 24.507 | 44.992 | 79.956 | 1.00 | 17.00 |
| ATOM | 1239 | CG1 | ILE | A | 172 | 25.000 | 43.685 | 80.613 | 1.00 | 15.78 |
| ATOM | 1240 | CG2 | ILE | A | 172 | 25.426 | 46.163 | 80.300 | 1.00 | 18.13 |
| ATOM | 1241 | CD1 | ILE | A | 172 | 26.426 | 43.320 | 80.163 | 1.00 | 13.83 |
| ATOM | 1242 | N | LEU | A | 173 | 22.575 | 46.909 | 78.468 | 1.00 | 20.75 |

F I G. 3 3

| | | | | | | | | | |
|---|---|---|---|---|---|---|---|---|---|
| ATOM | 1243 | CA | LEU | A | 173 | 22.107 | 48.206 | 77.946 | 1.00 17.70 |
| ATOM | 1244 | C | LEU | A | 173 | 20.699 | 48.622 | 78.396 | 1.00 16.26 |
| ATOM | 1245 | O | LEU | A | 173 | 20.376 | 49.774 | 78.663 | 1.00 18.18 |
| ATOM | 1246 | CB | LEU | A | 173 | 22.176 | 48.201 | 76.419 | 1.00 16.81 |
| ATOM | 1247 | CG | LEU | A | 173 | 23.600 | 48.021 | 75.966 | 1.00 18.73 |
| ATOM | 1248 | CD1 | LEU | A | 173 | 24.410 | 49.282 | 76.138 | 1.00 16.97 |
| ATOM | 1249 | CD2 | LEU | A | 173 | 23.619 | 47.550 | 74.505 | 1.00 23.91 |
| ATOM | 1250 | N | LYS | A | 174 | 19.835 | 47.625 | 78.475 | 1.00 15.86 |
| ATOM | 1251 | CA | LYS | A | 174 | 18.494 | 47.970 | 78.945 | 1.00 19.21 |
| ATOM | 1252 | C | LYS | A | 174 | 18.453 | 48.415 | 80.429 | 1.00 21.86 |
| ATOM | 1253 | O | LYS | A | 174 | 17.800 | 49.404 | 80.737 | 1.00 20.00 |
| ATOM | 1254 | CB | LYS | A | 174 | 17.577 | 46.773 | 78.700 | 1.00 20.19 |
| ATOM | 1255 | CG | LYS | A | 174 | 16.094 | 47.130 | 78.731 | 1.00 27.84 |
| ATOM | 1256 | CD | LYS | A | 174 | 15.799 | 48.368 | 77.858 | 1.00 36.14 |
| ATOM | 1257 | CE | LYS | A | 174 | 14.309 | 48.628 | 77.774 | 1.00 40.56 |
| ATOM | 1258 | NZ | LYS | A | 174 | 13.775 | 48.622 | 79.156 | 1.00 49.45 |
| ATOM | 1259 | N | ARG | A | 175 | 19.250 | 47.698 | 81.286 | 1.00 21.93 |
| ATOM | 1260 | CA | ARG | A | 175 | 19.476 | 48.145 | 82.686 | 1.00 19.65 |
| ATOM | 1261 | C | ARG | A | 175 | 20.037 | 49.561 | 82.807 | 1.00 16.70 |
| ATOM | 1262 | O | ARG | A | 175 | 19.476 | 50.419 | 83.468 | 1.00 18.12 |
| ATOM | 1263 | CB | ARG | A | 175 | 20.345 | 47.126 | 83.467 | 1.00 21.25 |
| ATOM | 1264 | CG | ARG | A | 175 | 20.608 | 47.477 | 84.954 | 1.00 22.00 |
| ATOM | 1265 | CD | ARG | A | 175 | 19.259 | 47.669 | 85.656 | 1.00 25.63 |
| ATOM | 1266 | NE | ARG | A | 175 | 19.435 | 47.923 | 87.095 | 1.00 29.77 |
| ATOM | 1267 | CZ | ARG | A | 175 | 18.601 | 48.672 | 87.834 | 1.00 27.58 |
| ATOM | 1268 | NH1 | ARG | A | 175 | 17.550 | 49.301 | 87.355 | 1.00 24.74 |
| ATOM | 1269 | NH2 | ARG | A | 175 | 18.792 | 48.780 | 89.073 | 1.00 27.45 |
| ATOM | 1270 | N | GLY | A | 176 | 21.122 | 49.800 | 82.048 | 1.00 17.53 |
| ATOM | 1271 | CA | GLY | A | 176 | 21.698 | 51.143 | 81.893 | 1.00 17.18 |
| ATOM | 1272 | C | GLY | A | 176 | 20.679 | 52.214 | 81.552 | 1.00 21.18 |
| ATOM | 1273 | O | GLY | A | 176 | 20.582 | 53.278 | 82.149 | 1.00 21.85 |
| ATOM | 1274 | N | TYR | A | 177 | 19.847 | 51.887 | 80.547 | 1.00 22.48 |
| ATOM | 1275 | CA | TYR | A | 177 | 18.756 | 52.787 | 80.117 | 1.00 20.51 |
| ATOM | 1276 | C | TYR | A | 177 | 17.754 | 53.106 | 81.242 | 1.00 18.92 |
| ATOM | 1277 | O | TYR | A | 177 | 17.406 | 54.246 | 81.542 | 1.00 15.84 |
| ATOM | 1278 | CB | TYR | A | 177 | 18.007 | 52.120 | 78.939 | 1.00 23.76 |
| ATOM | 1279 | CG | TYR | A | 177 | 17.210 | 53.131 | 78.177 | 1.00 24.47 |
| ATOM | 1280 | CD1 | TYR | A | 177 | 15.817 | 53.306 | 78.397 | 1.00 26.61 |
| ATOM | 1281 | CD2 | TYR | A | 177 | 17.941 | 53.869 | 77.236 | 1.00 29.40 |
| ATOM | 1282 | CE1 | TYR | A | 177 | 15.139 | 54.308 | 77.661 | 1.00 29.08 |
| ATOM | 1283 | CE2 | TYR | A | 177 | 17.270 | 54.855 | 76.515 | 1.00 30.70 |
| ATOM | 1284 | CZ | TYR | A | 177 | 15.899 | 55.092 | 76.747 | 1.00 32.01 |
| ATOM | 1285 | OH | TYR | A | 177 | 15.401 | 56.167 | 76.020 | 1.00 41.52 |
| ATOM | 1286 | N | GLU | A | 178 | 17.354 | 52.008 | 81.867 | 1.00 19.45 |
| ATOM | 1287 | CA | GLU | A | 178 | 16.429 | 52.094 | 82.972 | 1.00 22.02 |
| ATOM | 1288 | C | GLU | A | 178 | 16.820 | 52.802 | 84.236 | 1.00 20.09 |
| ATOM | 1289 | O | GLU | A | 178 | 16.001 | 53.492 | 84.805 | 1.00 21.41 |
| ATOM | 1290 | CB | GLU | A | 178 | 16.010 | 50.731 | 83.357 | 1.00 25.45 |
| ATOM | 1291 | CG | GLU | A | 178 | 15.173 | 50.032 | 82.303 | 1.00 34.73 |
| ATOM | 1292 | CD | GLU | A | 178 | 13.893 | 50.810 | 81.951 | 1.00 40.36 |
| ATOM | 1293 | OE1 | GLU | A | 178 | 13.432 | 51.667 | 82.707 | 1.00 33.51 |
| ATOM | 1294 | OE2 | GLU | A | 178 | 13.352 | 50.556 | 80.876 | 1.00 45.77 |
| ATOM | 1295 | N | LEU | A | 179 | 18.090 | 52.695 | 84.609 | 1.00 19.63 |
| ATOM | 1296 | CA | LEU | A | 179 | 18.655 | 53.567 | 85.665 | 1.00 19.10 |

FIG. 34

| ATOM | 1297 | C   | LEU | A | 179 | 18.366 | 55.051 | 85.511 | 1.00 | 20.25 |
|------|------|-----|-----|---|-----|--------|--------|--------|------|-------|
| ATOM | 1298 | O   | LEU | A | 179 | 17.838 | 55.726 | 86.374 | 1.00 | 19.26 |
| ATOM | 1299 | CB  | LEU | A | 179 | 20.178 | 53.361 | 85.813 | 1.00 | 17.45 |
| ATOM | 1300 | CG  | LEU | A | 179 | 20.610 | 52.013 | 86.426 | 1.00 | 18.23 |
| ATOM | 1301 | CD1 | LEU | A | 179 | 20.093 | 51.829 | 87.873 | 1.00 | 16.98 |
| ATOM | 1302 | CD2 | LEU | A | 179 | 22.124 | 51.811 | 86.340 | 1.00 | 16.34 |
| ATOM | 1303 | N   | GLY | A | 180 | 18.647 | 55.545 | 84.290 | 1.00 | 19.84 |
| ATOM | 1304 | CA  | GLY | A | 180 | 18.171 | 56.903 | 83.987 | 1.00 | 15.90 |
| ATOM | 1305 | C   | GLY | A | 180 | 16.655 | 57.072 | 84.027 | 1.00 | 17.05 |
| ATOM | 1306 | O   | GLY | A | 180 | 16.130 | 58.031 | 84.564 | 1.00 | 19.49 |
| ATOM | 1307 | N   | GLN | A | 181 | 15.923 | 56.068 | 83.478 | 1.00 | 18.19 |
| ATOM | 1308 | CA  | GLN | A | 181 | 14.448 | 56.207 | 83.522 | 1.00 | 17.92 |
| ATOM | 1309 | C   | GLN | A | 181 | 13.822 | 56.265 | 84.938 | 1.00 | 18.20 |
| ATOM | 1310 | O   | GLN | A | 181 | 12.903 | 57.008 | 85.258 | 1.00 | 19.66 |
| ATOM | 1311 | CB  | GLN | A | 181 | 13.716 | 55.189 | 82.620 | 1.00 | 15.39 |
| ATOM | 1312 | CG  | GLN | A | 181 | 13.936 | 55.324 | 81.073 | 1.00 | 15.18 |
| ATOM | 1313 | CD  | GLN | A | 181 | 13.823 | 56.763 | 80.634 | 1.00 | 13.30 |
| ATOM | 1314 | OE1 | GLN | A | 181 | 14.769 | 57.400 | 80.176 | 1.00 | 17.23 |
| ATOM | 1315 | NE2 | GLN | A | 181 | 12.626 | 57.300 | 80.812 | 1.00 | 12.82 |
| ATOM | 1316 | N   | SER | A | 182 | 14.440 | 55.497 | 85.821 | 1.00 | 20.03 |
| ATOM | 1317 | CA  | SER | A | 182 | 14.156 | 55.600 | 87.273 | 1.00 | 16.56 |
| ATOM | 1318 | C   | SER | A | 182 | 14.209 | 56.973 | 87.871 | 1.00 | 14.78 |
| ATOM | 1319 | O   | SER | A | 182 | 13.305 | 57.369 | 88.582 | 1.00 | 19.49 |
| ATOM | 1320 | CB  | SER | A | 182 | 15.056 | 54.630 | 88.021 | 1.00 | 15.31 |
| ATOM | 1321 | OG  | SER | A | 182 | 14.563 | 53.332 | 87.714 | 1.00 | 16.70 |
| ATOM | 1322 | N   | ARG | A | 183 | 15.246 | 57.738 | 87.523 | 1.00 | 16.99 |
| ATOM | 1323 | CA  | ARG | A | 183 | 15.289 | 59.169 | 87.858 | 1.00 | 15.54 |
| ATOM | 1324 | C   | ARG | A | 183 | 14.161 | 60.085 | 87.309 | 1.00 | 19.55 |
| ATOM | 1325 | O   | ARG | A | 183 | 13.693 | 61.039 | 87.956 | 1.00 | 17.04 |
| ATOM | 1326 | CB  | ARG | A | 183 | 16.661 | 59.785 | 87.569 | 1.00 | 14.08 |
| ATOM | 1327 | CG  | ARG | A | 183 | 17.811 | 59.024 | 88.265 | 1.00 | 19.49 |
| ATOM | 1328 | CD  | ARG | A | 183 | 17.716 | 59.007 | 89.816 | 1.00 | 21.46 |
| ATOM | 1329 | NE  | ARG | A | 183 | 18.519 | 57.930 | 90.434 | 1.00 | 22.16 |
| ATOM | 1330 | CZ  | ARG | A | 183 | 19.509 | 58.121 | 91.300 | 1.00 | 19.15 |
| ATOM | 1331 | NH1 | ARG | A | 183 | 19.913 | 59.335 | 91.541 | 1.00 | 16.50 |
| ATOM | 1332 | NH2 | ARG | A | 183 | 20.042 | 57.081 | 91.914 | 1.00 | 18.34 |
| ATOM | 1333 | N   | VAL | A | 184 | 13.681 | 59.704 | 86.076 | 1.00 | 21.38 |
| ATOM | 1334 | CA  | VAL | A | 184 | 12.494 | 60.417 | 85.589 | 1.00 | 19.02 |
| ATOM | 1335 | C   | VAL | A | 184 | 11.194 | 60.051 | 86.301 | 1.00 | 16.98 |
| ATOM | 1336 | O   | VAL | A | 184 | 10.468 | 60.913 | 86.800 | 1.00 | 18.45 |
| ATOM | 1337 | CB  | VAL | A | 184 | 12.368 | 60.194 | 84.070 | 1.00 | 19.28 |
| ATOM | 1338 | CG1 | VAL | A | 184 | 11.057 | 60.717 | 83.496 | 1.00 | 17.84 |
| ATOM | 1339 | CG2 | VAL | A | 184 | 13.517 | 60.605 | 83.169 | 1.00 | 15.69 |
| ATOM | 1340 | N   | ILE | A | 185 | 10.977 | 58.734 | 86.408 | 1.00 | 17.32 |
| ATOM | 1341 | CA  | ILE | A | 185 |  9.834 | 58.241 | 87.202 | 1.00 | 21.14 |
| ATOM | 1342 | C   | ILE | A | 185 |  9.790 | 58.797 | 88.672 | 1.00 | 22.77 |
| ATOM | 1343 | O   | ILE | A | 185 |  8.749 | 59.230 | 89.142 | 1.00 | 22.95 |
| ATOM | 1344 | CB  | ILE | A | 185 |  9.810 | 56.695 | 87.193 | 1.00 | 20.65 |
| ATOM | 1345 | CG1 | ILE | A | 185 |  9.555 | 56.195 | 85.758 | 1.00 | 18.43 |
| ATOM | 1346 | CG2 | ILE | A | 185 |  8.776 | 56.133 | 88.202 | 1.00 | 18.29 |
| ATOM | 1347 | CD1 | ILE | A | 185 |  9.914 | 54.734 | 85.494 | 1.00 | 14.60 |
| ATOM | 1348 | N   | CYS | A | 186 | 10.976 | 58.837 | 89.332 | 1.00 | 20.34 |
| ATOM | 1349 | CA  | CYS | A | 186 | 11.005 | 59.262 | 90.745 | 1.00 | 21.26 |
| ATOM | 1350 | C   | CYS | A | 186 | 10.979 | 60.766 | 90.931 | 1.00 | 22.80 |

FIG. 35

```
ATOM   1351  O    CYS A 186      10.775  61.304  92.009  1.00 23.98
ATOM   1352  CB   CYS A 186      12.220  58.669  91.429  1.00 21.60
ATOM   1353  SG   CYS A 186      12.075  58.576  93.237  1.00 25.16
ATOM   1354  N    GLY A 187      11.149  61.494  89.814  1.00 20.34
ATOM   1355  CA   GLY A 187      11.023  62.949  89.981  1.00 13.75
ATOM   1356  C    GLY A 187      12.351  63.676  90.197  1.00 14.55
ATOM   1357  O    GLY A 187      12.436  64.871  90.453  1.00 16.08
ATOM   1358  N    TYR A 188      13.434  62.894  90.072  1.00 14.86
ATOM   1359  CA   TYR A 188      14.736  63.526  90.226  1.00 16.85
ATOM   1360  C    TYR A 188      15.214  64.366  89.046  1.00 20.24
ATOM   1361  O    TYR A 188      15.979  65.318  89.192  1.00 18.42
ATOM   1362  CB   TYR A 188      15.758  62.441  90.479  1.00 21.64
ATOM   1363  CG   TYR A 188      15.683  61.913  91.899  1.00 27.20
ATOM   1364  CD1  TYR A 188      16.748  62.226  92.737  1.00 32.00
ATOM   1365  CD2  TYR A 188      14.604  61.128  92.365  1.00 30.81
ATOM   1366  CE1  TYR A 188      16.727  61.784  94.071  1.00 35.38
ATOM   1367  CE2  TYR A 188      14.570  60.695  93.705  1.00 30.65
ATOM   1368  CZ   TYR A 188      15.624  61.071  94.556  1.00 35.88
ATOM   1369  OH   TYR A 188      15.607  60.787  95.912  1.00 41.39
ATOM   1370  N    HIS A 189      14.751  63.890  87.862  1.00 19.35
ATOM   1371  CA   HIS A 189      15.215  64.475  86.589  1.00 19.83
ATOM   1372  C    HIS A 189      14.108  64.550  85.551  1.00 16.85
ATOM   1373  O    HIS A 189      13.232  63.689  85.533  1.00 18.10
ATOM   1374  CB   HIS A 189      16.360  63.648  86.032  1.00 15.43
ATOM   1375  CG   HIS A 189      17.677  64.142  86.589  1.00 16.05
ATOM   1376  ND1  HIS A 189      18.154  65.384  86.414  1.00 17.24
ATOM   1377  CD2  HIS A 189      18.581  63.433  87.382  1.00 17.58
ATOM   1378  CE1  HIS A 189      19.347  65.503  87.080  1.00 16.38
ATOM   1379  NE2  HIS A 189      19.587  64.304  87.667  1.00 18.68
ATOM   1380  N    TRP A 190      14.183  65.611  84.723  1.00 18.99
ATOM   1381  CA   TRP A 190      13.341  65.719  83.490  1.00 17.22
ATOM   1382  C    TRP A 190      13.768  64.690  82.453  1.00 15.79
ATOM   1383  O    TRP A 190      14.942  64.354  82.416  1.00 15.77
ATOM   1384  CB   TRP A 190      13.502  67.102  82.855  1.00 16.12
ATOM   1385  CG   TRP A 190      13.134  68.178  83.857  1.00 12.39
ATOM   1386  CD1  TRP A 190      14.033  69.073  84.454  1.00 10.88
ATOM   1387  CD2  TRP A 190      11.800  68.581  84.295  1.00 14.35
ATOM   1388  NE1  TRP A 190      13.343  69.989  85.186  1.00 13.77
ATOM   1389  CE2  TRP A 190      11.976  69.731  85.141  1.00 10.71
ATOM   1390  CE3  TRP A 190      10.505  68.036  84.094  1.00 14.68
ATOM   1391  CZ2  TRP A 190      10.845  70.401  85.666  1.00 12.89
ATOM   1392  CZ3  TRP A 190       9.393  68.700  84.672  1.00 16.93
ATOM   1393  CH2  TRP A 190       9.557  69.875  85.441  1.00 12.82
ATOM   1394  N    GLN A 191      12.859  64.188  81.613  1.00 16.92
ATOM   1395  CA   GLN A 191      13.316  63.234  80.569  1.00 17.49
ATOM   1396  C    GLN A 191      14.519  63.720  79.696  1.00 15.64
ATOM   1397  O    GLN A 191      15.508  63.054  79.429  1.00 16.52
ATOM   1398  CB   GLN A 191      12.113  62.829  79.721  1.00 15.28
ATOM   1399  CG   GLN A 191      12.522  61.832  78.632  1.00 17.26
ATOM   1400  CD   GLN A 191      12.860  60.493  79.206  1.00 16.84
ATOM   1401  OE1  GLN A 191      12.086  59.920  79.946  1.00 21.21
ATOM   1402  NE2  GLN A 191      14.027  59.971  78.864  1.00 16.69
ATOM   1403  N    SER A 192      14.448  65.016  79.389  1.00 17.04
ATOM   1404  CA   SER A 192      15.564  65.622  78.666  1.00 15.31
```

FIG. 36

```
ATOM   1405  C    SER A 192      16.899  65.683  79.339  1.00 17.61
ATOM   1406  O    SER A 192      17.937  65.640  78.700  1.00 16.65
ATOM   1407  CB   SER A 192      15.209  67.005  78.211  1.00 15.87
ATOM   1408  OG   SER A 192      14.862  67.833  79.313  1.00 21.12
ATOM   1409  N    ASP A 193      16.886  65.712  80.681  1.00 17.44
ATOM   1410  CA   ASP A 193      18.190  65.648  81.360  1.00 15.23
ATOM   1411  C    ASP A 193      18.889  64.316  81.197  1.00 12.26
ATOM   1412  O    ASP A 193      20.113  64.204  81.054  1.00 14.16
ATOM   1413  CB   ASP A 193      18.036  65.832  82.887  1.00 16.01
ATOM   1414  CG   ASP A 193      17.367  67.116  83.311  1.00 14.57
ATOM   1415  OD1  ASP A 193      17.503  68.180  82.691  1.00 15.89
ATOM   1416  OD2  ASP A 193      16.673  67.038  84.312  1.00 19.14
ATOM   1417  N    VAL A 194      18.025  63.283  81.216  1.00 11.48
ATOM   1418  CA   VAL A 194      18.425  61.882  81.108  1.00 13.18
ATOM   1419  C    VAL A 194      18.851  61.478  79.663  1.00 15.63
ATOM   1420  O    VAL A 194      19.852  60.822  79.387  1.00 15.79
ATOM   1421  CB   VAL A 194      17.210  61.135  81.625  1.00 16.33
ATOM   1422  CG1  VAL A 194      17.152  61.202  83.184  1.00 19.26
ATOM   1423  CG2  VAL A 194      17.079  59.712  81.106  1.00 17.70
ATOM   1424  N    ASP A 195      18.050  61.992  78.728  1.00 16.54
ATOM   1425  CA   ASP A 195      18.488  61.921  77.332  1.00 16.55
ATOM   1426  C    ASP A 195      19.801  62.636  77.029  1.00 14.74
ATOM   1427  O    ASP A 195      20.758  62.076  76.519  1.00 18.92
ATOM   1428  CB   ASP A 195      17.367  62.455  76.477  1.00 15.91
ATOM   1429  CG   ASP A 195      16.139  61.563  76.560  1.00 19.86
ATOM   1430  OD1  ASP A 195      16.153  60.385  76.922  1.00 27.62
ATOM   1431  OD2  ASP A 195      15.090  62.069  76.264  1.00 26.20
ATOM   1432  N    ALA A 196      19.902  63.900  77.450  1.00 15.85
ATOM   1433  CA   ALA A 196      21.203  64.555  77.312  1.00 14.73
ATOM   1434  C    ALA A 196      22.383  63.806  77.932  1.00 18.85
ATOM   1435  O    ALA A 196      23.512  63.751  77.429  1.00 21.06
ATOM   1436  CB   ALA A 196      21.134  65.950  77.904  1.00 13.59
ATOM   1437  N    ALA A 197      22.056  63.177  79.091  1.00 19.14
ATOM   1438  CA   ALA A 197      23.098  62.442  79.808  1.00 17.62
ATOM   1439  C    ALA A 197      23.644  61.202  79.090  1.00 17.71
ATOM   1440  O    ALA A 197      24.851  60.931  79.104  1.00 18.18
ATOM   1441  CB   ALA A 197      22.587  62.002  81.181  1.00 15.91
ATOM   1442  N    ARG A 198      22.711  60.477  78.418  1.00 16.04
ATOM   1443  CA   ARG A 198      23.238  59.409  77.565  1.00 15.41
ATOM   1444  C    ARG A 198      24.179  59.843  76.413  1.00 14.99
ATOM   1445  O    ARG A 198      25.194  59.219  76.113  1.00 17.07
ATOM   1446  CB   ARG A 198      22.136  58.469  77.080  1.00 14.50
ATOM   1447  CG   ARG A 198      21.195  58.043  78.179  1.00 16.67
ATOM   1448  CD   ARG A 198      20.142  57.044  77.730  1.00 19.20
ATOM   1449  NE   ARG A 198      19.280  56.629  78.849  1.00 22.72
ATOM   1450  CZ   ARG A 198      18.003  57.012  79.061  1.00 22.30
ATOM   1451  NH1  ARG A 198      17.412  57.905  78.325  1.00 20.95
ATOM   1452  NH2  ARG A 198      17.292  56.518  80.045  1.00 21.57
ATOM   1453  N    VAL A 199      23.907  61.030  75.842  1.00 17.69
ATOM   1454  CA   VAL A 199      24.961  61.510  74.913  1.00 17.44
ATOM   1455  C    VAL A 199      26.376  61.736  75.457  1.00 18.48
ATOM   1456  O    VAL A 199      27.360  61.145  74.988  1.00 19.25
ATOM   1457  CB   VAL A 199      24.452  62.820  74.284  1.00 15.93
ATOM   1458  CG1  VAL A 199      25.350  63.540  73.279  1.00 11.45
```

FIG. 37

```
ATOM   1459  CG2 VAL A 199      23.072  62.640  73.680  1.00 15.33
ATOM   1460  N   VAL A 200      26.471  62.548  76.550  1.00 18.52
ATOM   1461  CA  VAL A 200      27.822  62.723  77.153  1.00 16.27
ATOM   1462  C   VAL A 200      28.442  61.461  77.794  1.00 14.37
ATOM   1463  O   VAL A 200      29.643  61.247  77.797  1.00 17.25
ATOM   1464  CB  VAL A 200      27.811  63.938  78.100  1.00 16.56
ATOM   1465  CG1 VAL A 200      26.761  63.894  79.246  1.00 13.52
ATOM   1466  CG2 VAL A 200      27.666  65.177  77.226  1.00 17.14
ATOM   1467  N   GLY A 201      27.556  60.570  78.283  1.00 14.98
ATOM   1468  CA  GLY A 201      27.998  59.297  78.836  1.00 13.20
ATOM   1469  C   GLY A 201      28.609  58.377  77.824  1.00 16.81
ATOM   1470  O   GLY A 201      29.588  57.701  78.067  1.00 17.03
ATOM   1471  N   SER A 202      28.034  58.413  76.614  1.00 17.82
ATOM   1472  CA  SER A 202      28.757  57.750  75.509  1.00 16.70
ATOM   1473  C   SER A 202      30.087  58.390  75.104  1.00 13.91
ATOM   1474  O   SER A 202      31.117  57.765  74.939  1.00 18.47
ATOM   1475  CB  SER A 202      27.813  57.511  74.303  1.00 15.94
ATOM   1476  OG  SER A 202      27.634  58.737  73.600  1.00 19.26
ATOM   1477  N   ALA A 203      30.094  59.719  75.030  1.00 14.76
ATOM   1478  CA  ALA A 203      31.333  60.383  74.641  1.00 14.41
ATOM   1479  C   ALA A 203      32.527  60.110  75.563  1.00 17.92
ATOM   1480  O   ALA A 203      33.652  59.803  75.177  1.00 16.36
ATOM   1481  CB  ALA A 203      31.042  61.872  74.572  1.00 13.61
ATOM   1482  N   VAL A 204      32.200  60.126  76.880  1.00 18.27
ATOM   1483  CA  VAL A 204      33.290  59.835  77.823  1.00 16.45
ATOM   1484  C   VAL A 204      33.834  58.394  77.718  1.00 13.88
ATOM   1485  O   VAL A 204      35.015  58.177  77.916  1.00 17.64
ATOM   1486  CB  VAL A 204      32.893  60.245  79.285  1.00 16.63
ATOM   1487  CG1 VAL A 204      34.131  60.323  80.177  1.00 16.51
ATOM   1488  CG2 VAL A 204      31.836  59.301  79.862  1.00 13.53
ATOM   1489  N   VAL A 205      32.971  57.392  77.355  1.00 15.31
ATOM   1490  CA  VAL A 205      33.648  56.100  77.152  1.00 17.30
ATOM   1491  C   VAL A 205      34.636  56.018  75.953  1.00 19.20
ATOM   1492  O   VAL A 205      35.644  55.311  76.002  1.00 19.08
ATOM   1493  CB  VAL A 205      32.563  55.014  77.035  1.00 19.10
ATOM   1494  CG1 VAL A 205      32.812  53.549  76.681  1.00 16.51
ATOM   1495  CG2 VAL A 205      31.797  55.088  78.343  1.00 17.27
ATOM   1496  N   ALA A 206      34.409  56.893  74.934  1.00 21.03
ATOM   1497  CA  ALA A 206      35.452  57.018  73.888  1.00 19.17
ATOM   1498  C   ALA A 206      36.765  57.498  74.469  1.00 19.27
ATOM   1499  O   ALA A 206      37.809  56.868  74.353  1.00 18.59
ATOM   1500  CB  ALA A 206      34.982  57.988  72.809  1.00 16.60
ATOM   1501  N   THR A 207      36.643  58.597  75.234  1.00 20.20
ATOM   1502  CA  THR A 207      37.873  59.078  75.903  1.00 20.52
ATOM   1503  C   THR A 207      38.613  58.126  76.838  1.00 21.84
ATOM   1504  O   THR A 207      39.831  58.030  76.898  1.00 23.45
ATOM   1505  CB  THR A 207      37.659  60.341  76.674  1.00 19.84
ATOM   1506  OG1 THR A 207      36.577  61.100  76.137  1.00 20.11
ATOM   1507  CG2 THR A 207      38.945  61.141  76.710  1.00 21.15
ATOM   1508  N   LEU A 208      37.806  57.345  77.574  1.00 23.89
ATOM   1509  CA  LEU A 208      38.323  56.332  78.510  1.00 22.19
ATOM   1510  C   LEU A 208      39.165  55.285  77.783  1.00 25.28
ATOM   1511  O   LEU A 208      40.232  54.880  78.228  1.00 24.41
ATOM   1512  CB  LEU A 208      37.170  55.700  79.312  1.00 21.93
```

FIG. 38

```
ATOM   1513  CG   LEU A 208      36.238  56.370  80.325  1.00  24.99
ATOM   1514  CD1  LEU A 208      35.117  55.631  81.058  1.00  26.55
ATOM   1515  CD2  LEU A 208      37.303  56.685  81.377  1.00  22.67
ATOM   1516  N    HIS A 209      38.666  54.873  76.588  1.00  24.64
ATOM   1517  CA   HIS A 209      39.495  53.970  75.766  1.00  20.81
ATOM   1518  C    HIS A 209      40.863  54.530  75.277  1.00  19.15
ATOM   1519  O    HIS A 209      41.807  53.872  74.934  1.00  20.30
ATOM   1520  CB   HIS A 209      38.656  53.449  74.595  1.00  16.87
ATOM   1521  CG   HIS A 209      37.588  52.476  74.994  1.00  13.42
ATOM   1522  ND1  HIS A 209      36.335  52.782  75.375  1.00  14.12
ATOM   1523  CD2  HIS A 209      37.686  51.099  74.975  1.00  12.37
ATOM   1524  CE1  HIS A 209      35.653  51.616  75.586  1.00  10.36
ATOM   1525  NE2  HIS A 209      36.493  50.590  75.334  1.00  13.53
ATOM   1526  N    THR A 210      41.035  55.827  75.336  1.00  20.82
ATOM   1527  CA   THR A 210      42.393  56.384  75.116  1.00  21.40
ATOM   1528  C    THR A 210      43.396  56.387  76.298  1.00  26.34
ATOM   1529  O    THR A 210      44.567  56.745  76.188  1.00  27.83
ATOM   1530  CB   THR A 210      42.315  57.836  74.662  1.00  22.02
ATOM   1531  OG1  THR A 210      42.096  58.723  75.795  1.00  25.04
ATOM   1532  CG2  THR A 210      41.307  58.070  73.528  1.00  20.46
ATOM   1533  N    ASN A 211      42.844  56.032  77.482  1.00  26.32
ATOM   1534  CA   ASN A 211      43.544  56.135  78.782  1.00  23.64
ATOM   1535  C    ASN A 211      44.212  54.824  79.204  1.00  20.62
ATOM   1536  O    ASN A 211      43.591  53.785  79.374  1.00  22.28
ATOM   1537  CB   ASN A 211      42.563  56.749  79.827  1.00  24.99
ATOM   1538  CG   ASN A 211      43.226  56.863  81.206  1.00  24.09
ATOM   1539  OD1  ASN A 211      43.320  55.886  81.935  1.00  25.25
ATOM   1540  ND2  ASN A 211      43.689  58.038  81.566  1.00  21.24
ATOM   1541  N    PRO A 212      45.563  54.884  79.353  1.00  22.01
ATOM   1542  CA   PRO A 212      46.337  53.660  79.633  1.00  21.52
ATOM   1543  C    PRO A 212      45.859  52.883  80.848  1.00  22.52
ATOM   1544  O    PRO A 212      45.670  51.673  80.882  1.00  22.12
ATOM   1545  CB   PRO A 212      47.743  54.190  79.845  1.00  22.52
ATOM   1546  CG   PRO A 212      47.805  55.535  79.117  1.00  25.40
ATOM   1547  CD   PRO A 212      46.391  56.076  79.175  1.00  22.01
ATOM   1548  N    ALA A 213      45.626  53.674  81.897  1.00  23.96
ATOM   1549  CA   ALA A 213      45.139  53.025  83.140  1.00  23.57
ATOM   1550  C    ALA A 213      43.797  52.337  83.019  1.00  21.76
ATOM   1551  O    ALA A 213      43.600  51.185  83.403  1.00  24.96
ATOM   1552  CB   ALA A 213      45.039  54.071  84.259  1.00  21.55
ATOM   1553  N    PHE A 214      42.885  53.085  82.373  1.00  19.30
ATOM   1554  CA   PHE A 214      41.617  52.431  82.017  1.00  20.02
ATOM   1555  C    PHE A 214      41.798  51.170  81.197  1.00  20.38
ATOM   1556  O    PHE A 214      41.255  50.120  81.510  1.00  18.82
ATOM   1557  CB   PHE A 214      40.690  53.445  81.314  1.00  23.58
ATOM   1558  CG   PHE A 214      39.367  52.839  80.840  1.00  26.35
ATOM   1559  CD1  PHE A 214      38.249  52.765  81.711  1.00  24.66
ATOM   1560  CD2  PHE A 214      39.262  52.365  79.507  1.00  23.08
ATOM   1561  CE1  PHE A 214      37.032  52.191  81.265  1.00  27.05
ATOM   1562  CE2  PHE A 214      38.052  51.792  79.077  1.00  19.74
ATOM   1563  CZ   PHE A 214      36.951  51.697  79.944  1.00  22.04
ATOM   1564  N    GLN A 215      42.654  51.298  80.149  1.00  22.02
ATOM   1565  CA   GLN A 215      42.904  50.137  79.275  1.00  21.33
ATOM   1566  C    GLN A 215      43.354  48.889  79.995  1.00  21.73
```

F I G. 39

```
ATOM   1567  O    GLN A 215      42.823  47.783  79.875  1.00 21.17
ATOM   1568  CB   GLN A 215      43.970  50.520  78.278  1.00 22.37
ATOM   1569  CG   GLN A 215      43.483  51.517  77.261  1.00 22.30
ATOM   1570  CD   GLN A 215      44.662  52.026  76.479  1.00 28.18
ATOM   1571  OE1  GLN A 215      45.821  51.695  76.664  1.00 32.27
ATOM   1572  NE2  GLN A 215      44.359  52.947  75.605  1.00 28.35
ATOM   1573  N    GLN A 216      44.375  49.154  80.845  1.00 24.60
ATOM   1574  CA   GLN A 216      44.876  48.089  81.718  1.00 25.81
ATOM   1575  C    GLN A 216      43.909  47.530  82.715  1.00 23.07
ATOM   1576  O    GLN A 216      43.822  46.328  82.899  1.00 22.91
ATOM   1577  CB   GLN A 216      46.052  48.544  82.517  1.00 33.78
ATOM   1578  CG   GLN A 216      47.181  49.037  81.631  1.00 49.94
ATOM   1579  CD   GLN A 216      48.161  49.693  82.574  1.00 61.57
ATOM   1580  OE1  GLN A 216      48.354  49.243  83.704  1.00 69.34
ATOM   1581  NE2  GLN A 216      48.737  50.805  82.114  1.00 63.50
ATOM   1582  N    GLN A 217      43.155  48.439  83.377  1.00 22.58
ATOM   1583  CA   GLN A 217      42.099  47.917  84.261  1.00 23.69
ATOM   1584  C    GLN A 217      40.971  47.113  83.590  1.00 24.92
ATOM   1585  O    GLN A 217      40.480  46.102  84.088  1.00 24.09
ATOM   1586  CB   GLN A 217      41.565  49.042  85.189  1.00 23.44
ATOM   1587  CG   GLN A 217      40.720  48.541  86.407  1.00 23.24
ATOM   1588  CD   GLN A 217      41.489  47.589  87.335  1.00 21.58
ATOM   1589  OE1  GLN A 217      42.676  47.749  87.598  1.00 24.82
ATOM   1590  NE2  GLN A 217      40.827  46.516  87.744  1.00 19.85
ATOM   1591  N    LEU A 218      40.628  47.595  82.390  1.00 26.00
ATOM   1592  CA   LEU A 218      39.701  46.859  81.532  1.00 23.47
ATOM   1593  C    LEU A 218      40.195  45.495  81.093  1.00 21.96
ATOM   1594  O    LEU A 218      39.476  44.515  81.209  1.00 22.51
ATOM   1595  CB   LEU A 218      39.309  47.724  80.327  1.00 23.65
ATOM   1596  CG   LEU A 218      38.292  47.073  79.369  1.00 21.04
ATOM   1597  CD1  LEU A 218      38.103  47.980  78.168  1.00 25.30
ATOM   1598  CD2  LEU A 218      36.952  46.736  80.004  1.00 13.22
ATOM   1599  N    GLN A 219      41.451  45.425  80.640  1.00 23.49
ATOM   1600  CA   GLN A 219      42.033  44.079  80.457  1.00 29.37
ATOM   1601  C    GLN A 219      41.880  43.156  81.681  1.00 29.60
ATOM   1602  O    GLN A 219      41.455  42.016  81.569  1.00 29.63
ATOM   1603  CB   GLN A 219      43.544  44.131  80.199  1.00 37.46
ATOM   1604  CG   GLN A 219      44.052  44.703  78.867  1.00 51.74
ATOM   1605  CD   GLN A 219      45.511  45.267  78.911  1.00 60.29
ATOM   1606  OE1  GLN A 219      46.415  44.774  79.568  1.00 65.45
ATOM   1607  NE2  GLN A 219      45.764  46.352  78.161  1.00 60.81
ATOM   1608  N    LYS A 220      42.206  43.722  82.879  1.00 28.28
ATOM   1609  CA   LYS A 220      42.004  42.926  84.111  1.00 26.68
ATOM   1610  C    LYS A 220      40.588  42.446  84.386  1.00 24.54
ATOM   1611  O    LYS A 220      40.347  41.275  84.640  1.00 26.87
ATOM   1612  CB   LYS A 220      42.591  43.631  85.319  1.00 29.93
ATOM   1613  CG   LYS A 220      44.019  43.952  84.934  1.00 36.96
ATOM   1614  CD   LYS A 220      45.015  44.044  86.081  1.00 47.54
ATOM   1615  CE   LYS A 220      44.741  45.121  87.121  1.00 55.28
ATOM   1616  NZ   LYS A 220      44.868  46.456  86.510  1.00 61.92
ATOM   1617  N    ALA A 221      39.630  43.379  84.217  1.00 21.04
ATOM   1618  CA   ALA A 221      38.215  42.960  84.307  1.00 18.69
ATOM   1619  C    ALA A 221      37.761  41.903  83.291  1.00 24.31
ATOM   1620  O    ALA A 221      37.095  40.921  83.598  1.00 26.78
```

FIG. 40

| ATOM | 1621 | CB | ALA | A | 221 | 37.306 | 44.177 | 84.140 | 1.00 | 14.85 |
|---|---|---|---|---|---|---|---|---|---|---|
| ATOM | 1622 | N | LYS | A | 222 | 38.223 | 42.106 | 82.029 | 1.00 | 24.15 |
| ATOM | 1623 | CA | LYS | A | 222 | 38.065 | 41.018 | 81.046 | 1.00 | 23.96 |
| ATOM | 1624 | C | LYS | A | 222 | 38.668 | 39.675 | 81.431 | 1.00 | 22.61 |
| ATOM | 1625 | O | LYS | A | 222 | 38.023 | 38.628 | 81.422 | 1.00 | 21.88 |
| ATOM | 1626 | CB | LYS | A | 222 | 38.591 | 41.444 | 79.659 | 1.00 | 22.92 |
| ATOM | 1627 | CG | LYS | A | 222 | 37.682 | 42.516 | 79.109 | 1.00 | 22.76 |
| ATOM | 1628 | CD | LYS | A | 222 | 38.038 | 42.903 | 77.691 | 1.00 | 22.50 |
| ATOM | 1629 | CE | LYS | A | 222 | 37.050 | 43.918 | 77.109 | 1.00 | 22.07 |
| ATOM | 1630 | NZ | LYS | A | 222 | 37.556 | 44.613 | 75.909 | 1.00 | 21.47 |
| ATOM | 1631 | N | ALA | A | 223 | 39.949 | 39.728 | 81.830 | 1.00 | 22.84 |
| ATOM | 1632 | CA | ALA | A | 223 | 40.533 | 38.472 | 82.353 | 1.00 | 25.17 |
| ATOM | 1633 | C | ALA | A | 223 | 39.812 | 37.842 | 83.543 | 1.00 | 26.19 |
| ATOM | 1634 | O | ALA | A | 223 | 39.534 | 36.652 | 83.573 | 1.00 | 27.99 |
| ATOM | 1635 | CB | ALA | A | 223 | 42.013 | 38.638 | 82.691 | 1.00 | 21.36 |
| ATOM | 1636 | N | GLU | A | 224 | 39.424 | 38.696 | 84.487 | 1.00 | 27.72 |
| ATOM | 1637 | CA | GLU | A | 224 | 38.643 | 38.187 | 85.610 | 1.00 | 27.59 |
| ATOM | 1638 | C | GLU | A | 224 | 37.338 | 37.525 | 85.191 | 1.00 | 28.89 |
| ATOM | 1639 | O | GLU | A | 224 | 36.971 | 36.412 | 85.568 | 1.00 | 28.75 |
| ATOM | 1640 | CB | GLU | A | 224 | 38.476 | 39.348 | 86.606 | 1.00 | 29.18 |
| ATOM | 1641 | CG | GLU | A | 224 | 37.470 | 39.099 | 87.741 | 1.00 | 29.05 |
| ATOM | 1642 | CD | GLU | A | 224 | 37.335 | 40.348 | 88.557 | 1.00 | 29.41 |
| ATOM | 1643 | OE1 | GLU | A | 224 | 36.506 | 41.189 | 88.269 | 1.00 | 28.08 |
| ATOM | 1644 | OE2 | GLU | A | 224 | 38.060 | 40.487 | 89.516 | 1.00 | 31.14 |
| ATOM | 1645 | N | PHE | A | 225 | 36.659 | 38.233 | 84.288 | 1.00 | 29.33 |
| ATOM | 1646 | CA | PHE | A | 225 | 35.398 | 37.699 | 83.770 | 1.00 | 28.70 |
| ATOM | 1647 | C | PHE | A | 225 | 35.551 | 36.354 | 83.061 | 1.00 | 31.53 |
| ATOM | 1648 | O | PHE | A | 225 | 34.802 | 35.399 | 83.222 | 1.00 | 29.17 |
| ATOM | 1649 | CB | PHE | A | 225 | 34.786 | 38.756 | 82.858 | 1.00 | 26.48 |
| ATOM | 1650 | CG | PHE | A | 225 | 33.449 | 38.281 | 82.361 | 1.00 | 25.90 |
| ATOM | 1651 | CD1 | PHE | A | 225 | 32.361 | 38.258 | 83.250 | 1.00 | 28.71 |
| ATOM | 1652 | CD2 | PHE | A | 225 | 33.317 | 37.854 | 81.022 | 1.00 | 28.64 |
| ATOM | 1653 | CE1 | PHE | A | 225 | 31.129 | 37.758 | 82.817 | 1.00 | 29.98 |
| ATOM | 1654 | CE2 | PHE | A | 225 | 32.074 | 37.365 | 80.564 | 1.00 | 28.53 |
| ATOM | 1655 | CZ | PHE | A | 225 | 30.998 | 37.309 | 81.479 | 1.00 | 30.02 |
| ATOM | 1656 | N | ALA | A | 226 | 36.635 | 36.308 | 82.289 | 1.00 | 31.91 |
| ATOM | 1657 | CA | ALA | A | 226 | 36.996 | 35.055 | 81.643 | 1.00 | 36.17 |
| ATOM | 1658 | C | ALA | A | 226 | 37.178 | 33.829 | 82.536 | 1.00 | 40.94 |
| ATOM | 1659 | O | ALA | A | 226 | 36.704 | 32.735 | 82.271 | 1.00 | 41.75 |
| ATOM | 1660 | CB | ALA | A | 226 | 38.284 | 35.261 | 80.877 | 1.00 | 33.81 |
| ATOM | 1661 | N | GLN | A | 227 | 37.883 | 34.081 | 83.647 | 1.00 | 44.91 |
| ATOM | 1662 | CA | GLN | A | 227 | 38.067 | 32.931 | 84.543 | 1.00 | 49.32 |
| ATOM | 1663 | C | GLN | A | 227 | 36.782 | 32.579 | 85.233 | 1.00 | 51.62 |
| ATOM | 1664 | O | GLN | A | 227 | 36.396 | 31.467 | 85.528 | 1.00 | 50.02 |
| ATOM | 1665 | CB | GLN | A | 227 | 39.239 | 33.150 | 85.499 | 1.00 | 50.80 |
| ATOM | 1666 | CG | GLN | A | 227 | 40.441 | 33.937 | 84.900 | 1.00 | 59.92 |
| ATOM | 1667 | CD | GLN | A | 227 | 40.812 | 33.681 | 83.397 | 1.00 | 68.68 |
| ATOM | 1668 | OE1 | GLN | A | 227 | 40.799 | 32.592 | 82.834 | 1.00 | 73.97 |
| ATOM | 1669 | NE2 | GLN | A | 227 | 41.221 | 34.764 | 82.726 | 1.00 | 65.71 |
| ATOM | 1670 | N | HIS | A | 228 | 36.041 | 33.669 | 85.411 | 1.00 | 58.91 |
| ATOM | 1671 | CA | HIS | A | 228 | 34.687 | 33.501 | 85.925 | 1.00 | 65.53 |
| ATOM | 1672 | C | HIS | A | 228 | 33.816 | 32.519 | 85.143 | 1.00 | 68.04 |
| ATOM | 1673 | O | HIS | A | 228 | 33.014 | 31.764 | 85.662 | 1.00 | 67.46 |
| ATOM | 1674 | CB | HIS | A | 228 | 34.091 | 34.903 | 86.045 | 1.00 | 68.11 |

F I G. 4 1

| ATOM | 1675 | CG | HIS | A | 228 | 32.632 | 34.780 | 86.283 | 1.00 | 71.87 |
|---|---|---|---|---|---|---|---|---|---|---|
| ATOM | 1676 | ND1 | HIS | A | 228 | 31.729 | 34.968 | 85.313 | 1.00 | 74.51 |
| ATOM | 1677 | CD2 | HIS | A | 228 | 32.007 | 34.363 | 87.458 | 1.00 | 75.53 |
| ATOM | 1678 | CE1 | HIS | A | 228 | 30.511 | 34.660 | 85.852 | 1.00 | 78.68 |
| ATOM | 1679 | NE2 | HIS | A | 228 | 30.682 | 34.288 | 87.171 | 1.00 | 80.02 |
| ATOM | 1680 | N | GLN | A | 229 | 34.061 | 32.545 | 83.846 | 1.00 | 74.45 |
| ATOM | 1681 | CA | GLN | A | 229 | 33.306 | 31.659 | 82.963 | 1.00 | 81.06 |
| ATOM | 1682 | C | GLN | A | 229 | 33.569 | 30.149 | 83.028 | 1.00 | 85.59 |
| ATOM | 1683 | O | GLN | A | 229 | 33.123 | 29.427 | 82.135 | 1.00 | 86.52 |
| ATOM | 1684 | CB | GLN | A | 229 | 33.477 | 32.181 | 81.530 | 1.00 | 81.47 |
| ATOM | 1685 | CG | GLN | A | 229 | 33.002 | 33.631 | 81.335 | 1.00 | 81.55 |
| ATOM | 1686 | CD | GLN | A | 229 | 31.488 | 33.690 | 81.352 | 1.00 | 83.81 |
| ATOM | 1687 | OE1 | GLN | A | 229 | 30.804 | 33.832 | 82.355 | 1.00 | 82.35 |
| ATOM | 1688 | NE2 | GLN | A | 229 | 30.950 | 33.588 | 80.141 | 1.00 | 86.80 |
| ATOM | 1689 | N | LYS | A | 230 | 34.317 | 29.749 | 84.086 | 1.00 | 91.08 |
| ATOM | 1690 | CA | LYS | A | 230 | 34.965 | 28.444 | 84.325 | 1.00 | 95.45 |
| ATOM | 1691 | CB | LYS | A | 230 | 33.976 | 27.245 | 84.052 | 1.00 | 97.51 |
| ATOM | 1692 | CG | LYS | A | 230 | 34.256 | 26.053 | 83.073 | 1.00 | 98.30 |
| ATOM | 1693 | CD | LYS | A | 230 | 34.035 | 26.121 | 81.534 | 1.00 | 98.30 |
| ATOM | 1694 | CE | LYS | A | 230 | 34.810 | 27.172 | 80.713 | 1.00 | 100.00 |
| ATOM | 1695 | NZ | LYS | A | 230 | 36.244 | 27.239 | 81.067 | 1.00 | 100.00 |
| ATOM | 1696 | C | LYS | A | 230 | 36.409 | 28.279 | 83.743 | 1.00 | 97.06 |
| ATOM | 1697 | OCT1 | LYS | A | 230 | 36.876 | 29.108 | 82.942 | 1.00 | 95.86 |
| ATOM | 1698 | OCT2 | LYS | A | 230 | 37.052 | 27.241 | 83.957 | 1.00 | 99.89 |
| ATOM | 1935 | S | SO4 | S | 231 | 22.561 | 63.872 | 89.148 | 1.00 | 45.29 |
| ATOM | 1936 | O1 | SO4 | S | 231 | 21.748 | 62.858 | 88.279 | 1.00 | 50.45 |
| ATOM | 1937 | O2 | SO4 | S | 231 | 21.648 | 64.707 | 90.036 | 1.00 | 51.74 |
| ATOM | 1938 | O3 | SO4 | S | 231 | 23.551 | 63.095 | 90.035 | 1.00 | 49.75 |
| ATOM | 1939 | O4 | SO4 | S | 231 | 23.260 | 64.912 | 88.285 | 1.00 | 44.08 |
| ATOM | 1 | O | HOH | W | 232 | 10.522 | 63.513 | 85.670 | 1.00 | 17.86 |
| ATOM | 2 | O | HOH | W | 233 | 34.116 | 63.633 | 80.578 | 1.00 | 20.45 |
| ATOM | 3 | O | HOH | W | 234 | 7.928 | 61.775 | 88.229 | 1.00 | 15.62 |
| ATOM | 4 | O | HOH | W | 235 | 10.374 | 64.545 | 82.597 | 1.00 | 14.58 |
| ATOM | 5 | O | HOH | W | 236 | 15.375 | 75.641 | 85.508 | 1.00 | 22.07 |
| ATOM | 6 | O | HOH | W | 237 | 20.773 | 44.507 | 86.785 | 1.00 | 18.67 |
| ATOM | 7 | O | HOH | W | 238 | 32.701 | 49.912 | 75.935 | 1.00 | 15.79 |
| ATOM | 8 | O | HOH | W | 239 | 21.979 | 72.096 | 84.493 | 1.00 | 19.08 |
| ATOM | 9 | O | HOH | W | 240 | 13.158 | 73.905 | 82.705 | 1.00 | 27.34 |
| ATOM | 10 | O | HOH | W | 241 | 14.358 | 71.880 | 73.410 | 1.00 | 26.83 |
| ATOM | 11 | O | HOH | W | 242 | 5.537 | 80.043 | 74.802 | 1.00 | 23.33 |
| ATOM | 12 | O | HOH | W | 243 | 36.136 | 62.604 | 78.407 | 1.00 | 23.19 |
| ATOM | 13 | O | HOH | W | 244 | 30.393 | 53.028 | 87.579 | 1.00 | 19.02 |
| ATOM | 14 | O | HOH | W | 245 | 28.532 | 49.107 | 93.252 | 1.00 | 21.32 |
| ATOM | 15 | O | HOH | W | 246 | 24.657 | 73.146 | 75.882 | 1.00 | 20.92 |
| ATOM | 16 | O | HOH | W | 247 | 10.080 | 55.567 | 81.848 | 1.00 | 33.80 |
| ATOM | 17 | O | HOH | W | 248 | 29.907 | 52.840 | 73.379 | 1.00 | 22.59 |
| ATOM | 18 | O | HOH | W | 249 | 38.583 | 48.054 | 74.575 | 1.00 | 24.10 |
| ATOM | 19 | O | HOH | W | 250 | 29.465 | 68.020 | 86.676 | 1.00 | 32.30 |
| ATOM | 20 | O | HOH | W | 251 | 12.847 | 73.680 | 85.460 | 1.00 | 40.76 |
| ATOM | 21 | O | HOH | W | 252 | 5.516 | 59.770 | 95.129 | 1.00 | 40.84 |
| ATOM | 22 | O | HOH | W | 253 | 42.504 | 47.354 | 77.319 | 1.00 | 30.77 |
| ATOM | 23 | O | HOH | W | 254 | 13.495 | 75.378 | 74.412 | 1.00 | 22.57 |
| ATOM | 24 | O | HOH | W | 255 | 17.100 | 76.564 | 77.737 | 1.00 | 30.00 |
| ATOM | 25 | O | HOH | W | 256 | 33.508 | 40.103 | 102.712 | 1.00 | 26.49 |

FIG. 42

```
ATOM    26  O   HOH W 257     20.825  55.648  81.278  1.00 20.11
ATOM    27  O   HOH W 258     19.730  61.701  89.970  1.00 23.10
ATOM    28  O   HOH W 259      4.363  74.520  80.720  1.00 33.74
ATOM    29  O   HOH W 260     31.490  42.656  98.480  1.00 34.19
ATOM    30  O   HOH W 261      6.696  75.130  78.477  1.00 15.66
ATOM    31  O   HOH W 262     10.667  67.023  75.103  1.00 38.86
ATOM    32  O   HOH W 263      8.252  64.433  92.307  1.00 23.15
ATOM    33  O   HOH W 264     41.924  51.223  74.247  1.00 30.19
ATOM    34  O   HOH W 265      1.437  67.705  89.398  1.00 39.48
ATOM    35  O   HOH W 266      4.055  66.946  91.467  1.00 29.22
ATOM    36  O   HOH W 267      3.092  69.112  84.950  1.00 25.58
ATOM    37  O   HOH W 268      9.537  59.065  79.795  1.00 30.90
ATOM    38  O   HOH W 269      9.306  83.197  79.638  1.00 44.19
ATOM    39  O   HOH W 270     34.786  41.166  75.522  1.00 32.98
ATOM    40  O   HOH W 271     28.084  37.193  84.163  1.00 30.43
ATOM    41  O   HOH W 272     40.742  49.227  76.024  1.00 21.82
ATOM    42  O   HOH W 273     35.074  40.712  85.668  1.00 29.87
ATOM    43  O   HOH W 274     30.318  45.526  96.384  1.00 35.57
ATOM    44  O   HOH W 275     31.493  69.162  80.850  1.00 19.51
ATOM    45  O   HOH W 276     42.914  61.700  76.016  1.00 28.69
ATOM    46  O   HOH W 277     34.422  64.714  92.625  1.00 38.81
ATOM    47  O   HOH W 278     13.405  78.374  80.916  1.00 25.22
ATOM    48  O   HOH W 279     44.634  57.811  84.433  1.00 31.73
ATOM    49  O   HOH W 280     44.303  60.992  82.740  1.00 28.14
ATOM    50  O   HOH W 281     32.596  51.432  73.247  1.00 22.63
ATOM    51  O   HOH W 282     22.182  40.126  75.125  1.00 27.50
ATOM    52  O   HOH W 283     18.482  55.362  89.100  1.00 21.25
ATOM    53  O   HOH W 284     36.960  42.360  74.192  1.00 28.88
ATOM    54  O   HOH W 285     35.881  48.845  94.047  1.00 26.90
ATOM    55  O   HOH W 286     26.212  59.698  94.760  1.00 23.37
ATOM    56  O   HOH W 287     29.246  44.303  73.369  1.00 40.38
ATOM    57  O   HOH W 288     27.356  35.947  80.422  1.00 31.74
ATOM    58  O   HOH W 289     40.482  45.029  76.766  1.00 30.88
ATOM    59  O   HOH W 290     24.864  58.724  91.112  1.00 25.30
ATOM    60  O   HOH W 291     28.560  61.547  91.755  1.00 39.37
ATOM    61  O   HOH W 292     27.888  63.113  90.252  1.00 40.28
ATOM    62  O   HOH W 293     31.069  41.023 103.435  1.00 38.13
ATOM    63  O   HOH W 294      5.144  47.860  86.978  1.00 37.63
ATOM    64  O   HOH W 295     29.373  52.425  90.409  1.00 21.69
ATOM    65  O   HOH W 296     41.571  51.401  87.864  1.00 31.72
ATOM    66  O   HOH W 297     35.633  56.807 101.396  1.00 42.27
ATOM    67  O   HOH W 298     35.257  40.157  78.063  1.00 30.17
ATOM    68  O   HOH W 299     33.734  71.189  79.910  1.00 32.64
ATOM    69  O   HOH W 300     17.659  69.593  75.158  1.00 46.73
ATOM    70  O   HOH W 301     17.005  72.932  72.774  1.00 33.93
ATOM    71  O   HOH W 302     15.769  48.059  85.107  1.00 24.21
ATOM    72  O   HOH W 303     15.023  64.697  75.333  1.00 39.99
ATOM    73  O   HOH W 304     13.546  67.305  74.469  1.00 38.11
ATOM    74  O   HOH W 305     30.044  75.863  82.738  1.00 29.02
ATOM    75  O   HOH W 306      5.253  66.383  98.323  1.00 61.09
ATOM    76  O   HOH W 307     25.914  72.829  89.073  1.00 48.08
ATOM    77  O   HOH W 308     38.474  67.620  76.050  1.00 32.88
ATOM    78  O   HOH W 309     34.101  41.534 100.215  1.00 39.54
ATOM    79  O   HOH W 310     29.974  37.419  76.650  1.00 39.99
```

FIG. 43

```
ATOM    80  O   HOH W 311     17.829  44.406  81.773  1.00 29.29
ATOM    81  O   HOH W 312     17.766  66.478  75.705  1.00 34.51
ATOM    82  O   HOH W 313     35.983  70.225  78.152  1.00 38.85
ATOM    83  O   HOH W 314     18.063  58.644  75.592  1.00 33.24
ATOM    84  O   HOH W 315     17.740  45.824  75.692  1.00 31.29
ATOM    85  O   HOH W 316     21.442  55.668 101.498  1.00 30.06
ATOM    86  O   HOH W 317     30.660  37.639 105.501  1.00 46.34
ATOM    87  O   HOH W 318     28.143  47.582  99.410  1.00 71.00
ATOM    88  O   HOH W 319     11.398  65.394  76.821  1.00 34.86
ATOM    89  O   HOH W 320     31.737  45.760  98.744  1.00 38.11
ATOM    90  O   HOH W 321     16.084  45.559  87.137  1.00 43.68
ATOM    91  O   HOH W 322     36.498  37.962  78.989  1.00 35.45
ATOM    92  O   HOH W 323     41.868  42.172  76.980  1.00 56.04
ATOM    93  O   HOH W 324     44.704  68.004  76.606  1.00 73.28
ATOM    94  O   HOH W 325     30.214  44.935 101.119  1.00 28.63
ATOM    95  O   HOH W 326     43.719  69.244  83.004  1.00 32.20
ATOM    96  O   HOH W 327      7.992  54.768  93.490  1.00 36.05
ATOM    97  O   HOH W 328     11.059  49.604  75.476  1.00 43.80
ATOM    98  O   HOH W 329     17.730  37.202  79.516  1.00 44.41
ATOM    99  O   HOH W 330     14.170  59.796  74.913  1.00 70.26
ATOM   100  O   HOH W 331     28.648  70.326  88.645  1.00 34.35
ATOM   101  O   HOH W 332     16.146  57.197  73.492  1.00 49.27
ATOM   102  O   HOH W 333     11.086  52.502  82.116  1.00 39.47
ATOM   103  O   HOH W 334     15.950  60.744  73.392  1.00 63.16
ATOM   104  O   HOH W 335     23.809  74.443  89.142  1.00 63.73
ATOM   105  O   HOH W 336     43.077  70.945  86.543  1.00 41.77
ATOM   106  O   HOH W 337     44.625  68.578  85.466  1.00 42.53
ATOM   107  O   HOH W 338     38.003  70.941  79.707  1.00 47.97
ATOM   108  O   HOH W 339     42.635  39.826  86.317  1.00 39.90
ATOM   109  O   HOH W 340     28.158  51.028  97.893  1.00 35.28
ATOM   110  O   HOH W 341     34.562  57.666  98.193  1.00 56.42
ATOM   111  O   HOH W 342     23.659  34.535  79.197  1.00 84.39
ATOM   112  O   HOH W 343     10.337  58.458  76.704  1.00 45.85
ATOM   113  O   HOH W 344     32.164  75.101  85.461  1.00 54.21
ATOM   114  O   HOH W 345     32.930  38.410  86.586  1.00 43.15
ATOM   115  O   HOH W 346     32.310  36.987 102.558  1.00 47.71
ATOM   116  O   HOH W 347     11.163  49.101  82.634  1.00 84.37
ATOM   117  O   HOH W 348     34.268  69.634  83.019  1.00 47.39
ATOM   118  O   HOH W 349     31.352  37.085  89.579  1.00 74.88
ATOM   119  O   HOH W 350     29.118  56.986  95.860  1.00 34.59
ATOM   120  O   HOH W 351      1.634  70.786  81.659  1.00 41.89
ATOM   121  O   HOH W 352      2.044  71.714  85.736  1.00 37.84
ATOM   122  O   HOH W 353     16.219  75.511  74.471  1.00 44.53
ATOM   123  O   HOH W 354     24.035  45.705  97.204  1.00 48.11
ATOM   124  O   HOH W 355     17.939  77.382  82.853  1.00 65.65
ATOM   125  O   HOH W 356     12.504  76.991  70.634  1.00 50.43
ATOM   126  O   HOH W 357     16.951  78.295  74.889  1.00 47.02
ATOM   127  O   HOH W 358     15.777  75.404  81.566  1.00 33.68
ATOM   128  O   HOH W 359     37.401  72.376  82.831  1.00 50.52
ATOM   129  O   HOH W 360     14.060  44.359  88.918  1.00 80.84
ATOM   130  O   HOH W 361     32.619  76.123  75.757  1.00 42.84
ATOM   131  O   HOH W 362     21.836  66.226  94.339  1.00 63.40
ATOM   132  O   HOH W 363     16.011  46.526  82.837  1.00 38.42
ATOM   133  O   HOH W 364      7.716  57.886  82.470  1.00 50.22
```

FIG. 44

```
ATOM   134  O   HOH W 365    41.813  72.155  81.960  1.00 76.60
ATOM   135  O   HOH W 366     5.810  63.614  94.440  1.00 41.72
ATOM   136  O   HOH W 367    22.833  66.006  98.308  1.00 65.79
ATOM   137  O   HOH W 368    21.384  36.791  76.692  1.00 59.29
ATOM   138  O   HOH W 369    38.765  52.950  92.219  1.00 27.87
ATOM   139  O   HOH W 370    46.430  68.991  81.609  1.00 70.52
ATOM   140  O   HOH W 371    36.973  69.709  83.153  1.00 33.81
ATOM   141  O   HOH W 372    22.238  43.716  92.825  1.00 44.49
ATOM   142  O   HOH W 373    23.096  80.189  77.308  1.00 50.73
ATOM   143  O   HOH W 374     2.790  53.932  81.478  1.00 50.22
ATOM   144  O   HOH W 375     3.292  64.768  94.055  1.00 46.64
ATOM   145  O   HOH W 376    26.937  79.257  75.755  1.00 47.21
ATOM   146  O   HOH W 377    45.046  50.594  85.873  1.00 46.10
ATOM   147  O   HOH W 378    24.988  68.312  90.158  1.00 39.03
ATOM   148  O   HOH W 379     2.045  61.203  93.643  1.00 49.73
ATOM   149  O   HOH W 380    44.273  56.110  87.700  1.00 46.74
ATOM   150  O   HOH W 381    26.747  76.462  73.043  1.00 50.91
ATOM   151  O   HOH W 382    40.545  70.889  76.918  1.00 68.80
ATOM   152  O   HOH W 383    25.523  80.486  83.807  1.00 67.90
ATOM   153  O   HOH W 384    40.972  36.296  87.372  1.00 66.49
ATOM   154  O   HOH W 385    12.617  56.710  77.567  1.00 44.81
ATOM   155  O   HOH W 386    44.460  48.054  74.082  1.00 41.02
ATOM   156  O   HOH W 387    35.781  73.896  86.117  1.00 38.14
ATOM   157  O   HOH W 388    21.625  80.398  81.815  1.00 47.96
ATOM   158  O   HOH W 389    46.628  56.635  82.977  1.00 50.89
ATOM   159  O   HOH W 390    12.308  51.573  78.083  1.00 64.92
ATOM   160  O   HOH W 391    30.773  39.420  87.798  1.00 55.92
ATOM   161  O   HOH W 392    26.088  65.110  89.923  1.00 44.80
ATOM   162  O   HOH W 393    10.719  70.886  96.928  1.00 48.46
ATOM   163  O   HOH W 394    12.474  47.243  84.457  1.00 53.08
ATOM   164  O   HOH W 395    24.296  71.312  91.828  1.00 48.39
ATOM   165  O   HOH W 396     6.459  50.108  83.133  1.00 57.82
ATOM   166  O   HOH W 397    42.423  66.213  75.196  1.00 34.97
ATOM   167  O   HOH W 398    29.045  53.518 101.769  1.00 46.59
ATOM   168  O   HOH W 399    27.195  39.655 105.406  1.00 41.59
ATOM   169  O   HOH W 400     6.834  56.385  96.211  1.00 45.81
ATOM   170  O   HOH W 401    47.957  50.138  78.280  1.00 43.60
ATOM   171  O   HOH W 402    23.330  36.461  72.787  1.00 54.41
ATOM   172  O   HOH W 403    29.051  79.533  81.900  1.00 78.87
ATOM   173  O   HOH W 404    46.670  55.026  74.340  1.00 68.61
ATOM   174  O   HOH W 405    28.985  78.746  85.840  1.00 75.16
ATOM   175  O   HOH W 406    32.117  68.589  73.365  1.00 42.10
ATOM   176  O   HOH W 407    48.677  52.842  75.727  1.00 66.77
ATOM   177  O   HOH W 408    29.185  36.245  72.017  1.00 75.24
ATOM   178  O   HOH W 409    37.168  67.596  97.670  1.00 38.24
ATOM   179  O   HOH W 410    11.986  77.352  92.370  1.00 35.94
ATOM   180  O   HOH W 411    39.548  63.174  98.280  1.00 39.58
ATOM   181  O   HOH W 412    30.500  79.967  79.292  1.00 62.87
ATOM   182  O   HOH W 413    18.003  41.205  83.764  1.00 64.48
ATOM   183  O   HOH W 414    34.455  37.242  89.080  1.00 52.58
ATOM   184  O   HOH W 415    47.074  60.938  83.746  1.00 66.98
ATOM   185  O   HOH W 416    10.880  54.535  78.559  1.00 45.29
ATOM   186  O   HOH W 417    30.230  76.830  74.341  1.00 71.09
ATOM   187  O   HOH W 418    12.118  81.147  79.341  1.00 49.66
```

FIG. 45

```
ATOM    188  O   HOH W 419      32.095  76.945  80.548  1.00 63.23
ATOM    189  O   HOH W 420      -0.301  68.264  84.539  1.00 48.83
ATOM    190  O   HOH W 421      10.822  64.227 102.313  1.00 81.32
ATOM    191  O   HOH W 422      23.374  42.555 101.170  1.00 42.91
ATOM    192  O   HOH W 423      20.016  59.713  74.793  1.00 38.45
ATOM    193  O   HOH W 424      15.833  78.412  79.495  1.00 56.01
ATOM    194  O   HOH W 425      43.534  35.850  84.957  1.00 63.16
ATOM    195  O   HOH W 426      11.933  68.018  98.874  1.00 52.15
ATOM    196  O   HOH W 427      20.777  37.368  85.962  1.00 57.71
ATOM    197  O   HOH W 428      22.392  36.632  89.560  1.00 68.43
ATOM    198  O   HOH W 429      29.340  37.487 101.980  1.00 74.20
ATOM    199  O   HOH W 430      23.237  39.294  91.878  1.00 74.07
ATOM    200  O   HOH W 431      13.654  75.325  94.697  1.00 73.83
ATOM    201  O   HOH W 432      27.904  38.307  96.631  1.00 57.14
ATOM    202  O   HOH W 433      44.213  59.909  79.188  1.00 37.71
ATOM    203  O   HOH W 434       2.129  75.408  79.755  1.00 64.17
ATOM    204  O   HOH W 435      13.993  43.469  84.483  1.00 59.78
ATOM    205  O   HOH W 436      31.644  55.529  99.951  1.00 58.81
ATOM    206  O   HOH W 437       9.462  82.415  76.470  1.00 48.44
ATOM    207  O   HOH W 438      21.813  58.761  98.061  1.00 60.37
ATOM    208  O   HOH W 439      22.202  59.533  93.382  1.00 43.39
ATOM    209  O   HOH W 440      18.118  43.497  86.455  1.00 46.86
ATOM    210  O   HOH W 441      13.762  54.340 105.466  1.00 57.78
ATOM    211  O   HOH W 442      33.277  73.931  83.853  1.00 56.73
ATOM    212  O   HOH W 443      34.442  68.648  90.744  1.00 27.90
ATOM    213  O   HOH W 444      30.640  67.899  91.831  1.00 53.48
ATOM    214  O   HOH W 445      40.813  44.217  74.058  1.00 53.35
ATOM    215  O   HOH W 446      33.012  71.334  90.213  1.00 53.98
ATOM    216  O   HOH W 447      25.130  57.928 101.293  1.00 38.97
ATOM    217  O   HOH W 448       7.584  82.067  74.163  1.00 26.55
ATOM    218  O   HOH W 449      42.214  40.521  78.980  1.00 37.75
ATOM    219  O   HOH W 450       8.915  57.776 101.115  1.00 50.37
ATOM    220  O   HOH W 451      15.963  42.582  79.699  1.00 71.24
ATOM    221  O   HOH W 452      23.011  77.967  75.363  1.00 64.04
ATOM    222  O   HOH W 453      36.910  35.452  88.469  1.00 70.47
ATOM    223  O   HOH W 454      37.814  55.271  99.966  1.00 54.36
ATOM    224  O   HOH W 455      26.721  58.439  99.230  1.00 86.46
ATOM    225  O   HOH W 456      16.108  40.093  81.126  1.00 98.28
ATOM    226  O   HOH W 457      27.800  35.543  96.536  1.00 63.56
ATOM    227  O   HOH W 458       5.859  51.318  95.801  1.00 68.96
ATOM    228  O   HOH W 459       7.841  51.875  96.622  1.00 64.76
ATOM    229  O   HOH W 460      28.280  66.535  89.122  1.00 73.27
ATOM    230  O   HOH W 461      13.943  46.268  81.680  1.00 56.20
ATOM    231  O   HOH W 462      14.681  69.220  73.344  1.00 83.46
ATOM    232  O   HOH W 463      30.388  71.379  89.815  1.00 60.45
ATOM    233  O   HOH W 464       8.062  56.915  75.809  1.00 59.76
ATOM    234  O   HOH W 465      30.104  41.907 101.688  1.00 61.89
ATOM    235  O   HOH W 466       4.988  49.407  95.471  1.00 61.48
ATOM    236  O   HOH W 467       8.747  53.997  77.187  1.00 79.74
END
```

VARIANT NUCLEOSIDE-5'-PHOSPHATE PRODUCING ENZYME

TECHNICAL FIELD

The present invention relates to mutant nucleoside-5'-phosphate producing enzymes with improved nucleoside-5'-phosphate producing ability, and a method for producing them. The present invention further relates to enzymes useful for the production of the aforementioned enzymes. Furthermore, the present invention relates to methods for producing a nucleoside-5'-phosphate as well as genes coding for the aforementioned mutant enzymes, recombinant DNA containing the genes and microorganisms that harbor the recombinant DNA, which are useful for the production methods. Nucleoside-5'-phosphates are useful as seasonings, drugs, raw materials therefor and so forth. The present invention is based on successful elucidation of the three-dimensional structures of a novel protein, and the three-dimensional structures have expandability that they are not limited to microorganisms.

BACKGROUND ART

As a method for efficiently producing nucleoside-5'-phosphates at a low cost by biochemically phosphorylating nucleosides, there was developed a method of efficiently producing a nucleoside-5'-phosphate without generation of byproducts of nucleoside-2'-phosphate acid and nucleoside-3'-phosphate isomers, which comprises allowing cells of a particular microorganism to act on a nucleoside and a phosphate donor selected from the group consisting of polyphosphoric acid (salt thereof), phenyl phosphate (salt thereof) and carbamyl phosphate under an acidic condition (Japanese Patent Laid-open (Kokai) No. 7-231793/1995).

Then, it was confirmed that the productivity of nucleoside-5'-phosphates can further be improved by obtaining a gene coding for an acid phosphatase from *Escherichia blattae* or *Morganella morganii* and expressing the gene in *Escherichia coli* in a large scale using genetic engineering techniques.

The structure of the acid phosphatase is shown in FIG. 2. That is, FIG. 2 shows alignment of the amino acid sequence of the acid phosphatase derived from *Escherichia blattae* (abbreviated as "EB-AP" hereinafter) with the amino acid sequences of acid phosphatases derived from *Morganella morganii, Salmonella typhimurium* and *Zymomonas mobilis*. The asterisks indicate conserved residues. The regions of the secondary structure are indicated with bars over the aligned sequences. The boxed portions are motives commonly observed in the acid phosphatase family. The motives consist of three domains, 1) KXXXXXXRP (SEQ ID NO: 121), 2) PSGH (SEQ ID NO: 122) and 3) SRXXXXXHXXXD (SEQ ID NO: 123). In these motives, X represents an arbitrary amino acid residue.

Although these acid phosphatases (FIG. 2) have transphosphorylation activity, they suffer from a drawback that their phosphatase activity for decomposing nucleoside-5'-phosphate into a nucleoside is dominant in wild-type strains, and hence accumulated nucleoside-5'-phosphate will be decomposed. Therefore, a large number of mutant enzymes were generated by the random mutagenesis method, and a mutant acid phosphatase having relatively improved transphosphorylation activity compared with phosphatase activity was found among the mutant enzymes. And it was demonstrated that the productivity of nucleoside-5'-phosphate was drastically improved by abundantly expressing a gene coding for the mutant acid phosphatase gene (Japanese Patent Laid-open (Kokai) No. 8-535568/1996).

This mutant acid phosphatase has improved affinity for a nucleoside, and it is thought that the transphosphorylation activity was improved by the enhanced affinity.

It was demonstrated that the aforementioned mutant acid phosphatase derived from *Escherichia blattae* (=G74D/I153T mutant enzyme (mutant enzyme in which 74th Gly is replaced with Asp and 153rd Ile is replaced with Thr, the mutation pattern will be similarly represented hereinafter)) showed weaker transphosphorylation activity compared with a corresponding G72D/I151T mutant enzyme of acid phosphatase derived from *Morganella morganii* (MM-AP), whereas a 10-residue replaced L63Q/A65Q/E66A/N69D/S71A/S72A/G74D/T135K/E136D/I153T mutant enzyme (referred to simply as "10-residue replaced mutant EB-AP" hereinafter), in which 8 amino acid residues were replaced with the amino acids of MM-AP that correspond on the primary structure basis, showed transphosphorylation activity substantially comparable to that of G72D/I151T mutant MM-AP (Japanese Patent Laid-open (Kokai) No. 9-161674/1997).

A method for producing a nucleoside-5'-phosphate has been established by expressing a large amount of the aforementioned G74D/I153T mutant enzyme gene, or the 10-residue replaced mutant enzyme gene in *Escherichia coli* (Japanese Patent Laid-open (Kokai) Nos. 9-37785/1997 and 10-201481/1999). However, a mutant EB-AP with further improved productivity is still desired.

DISCLOSURE OF THE INVENTION

The object of the present invention is to further improve the productivity of nucleoside-5'-phosphate by designing a mutant EB-AP based on the three-dimensional structure of EB-AP.

That is, aspects of the present invention are as follows:

(1) A mutant nucleoside-5'-phosphate producing enzyme with improved nucleoside-5'-phosphate producing ability, which is obtained by modifying a nucleoside-5'-phosphate producing enzyme that has transphosphorylation activity and/or phosphatase activity and has one Lys residue, two Arg residues and two His residues with distances between their Cα's within the ranges shown in FIG. 1 and a space around them allowing a binding of a nucleoside.

(2) The mutant nucleoside-5'-phosphate producing enzyme according to (1), wherein the distances between Cα's of the Lys residue, two Arg residues and two His residues are within the ranges shown in FIG. 1.

(3) The mutant nucleoside-5'-phosphate producing enzyme according to (1), wherein the nucleoside-5'-phosphate producing ability is improved by predicting a binding mode of the enzyme to a nucleoside such as inosine and guanosine and phosphorylated compounds thereof based on the atomic coordinate data obtained by X-ray crystallographic analysis of acid phosphatase derived from *Escherichia blattae*, and substituting, adding or deleting at least one amino acid residue and/or a prosthetic factor etc.

(4) The mutant nucleoside-5'-phosphate producing enzyme according to (1), wherein the enzyme is derived from a bacterium belonging to the genus *Escherichia, Morganella, Providencia, Enterobacter* or *Klebsiella*.

(5) A mutant nucleoside-5'-phosphate producing enzyme with improved nucleoside-5'-phosphate producing ability, which has an amino acid sequence of the acid phosphatase derived from *Escherichia blattae* including modification at one or more of the following positions (Ser72 or residues located within a distance of 10 Å from Ser72): 16, 67–76, 78–79, 96, 99–100, 102–104, 106–108, 149–154, 157, 179 and 183.

(6) A mutant nucleoside-5'-phosphate producing enzyme with improved nucleoside-5'-phosphate producing ability, which has transphosphorylation activity and/or phosphatase activity, and has modification at one or more of positions corresponding to the following positions in the amino acid sequence of the acid phosphatase derived from *Escherichia blattae* (Ser72 of *Escherichia blattae* acid phosphatase or residues located within a distance of 10 Å from Ser72): 16, 67–76, 78–79, 96, 99–100, 102–104, 106–108, 149–154, 157, 179 and 183 in amino acid sequence alignment with the acid phosphatase derived from *Escherichia blattae*.

(7) A mutant nucleoside-5'-phosphate producing enzyme with improved nucleoside-5'-phosphate producing ability, which has transphosphorylation activity and/or phosphatase activity, and has modification at one or more of positions corresponding to the following positions in the amino acid sequence of the acid phosphatase derived from *Escherichia blattae* (Ser72 of *Escherichia* blattae acid phosphatase or residues located within a distance of 10 Å from Ser72): 16, 67–76, 78–79, 96, 99–100, 102–104, 106–108, 149–154, 157, 179 and 183 in alignment with the three-dimensional structure of the acid phosphatase derived from *Escherichia blattae* performed by the threading method.

(8) The mutant nucleoside-5'-phosphate producing enzyme according to (6), wherein the three-dimensional structure of the enzyme is put close to that of an enzyme derived from another organism having transphosphorylation activity higher than that of a wild-type of the enzyme having the transphosphorylation activity and/or phosphatase activity by making modification at one or more positions other than the positions (Ser72 of *Escherichia blattae* acid phosphatase or residues present within a distance of 10 Å from Ser72).

(9) A mutant nucleoside-5'-phosphate producing enzyme with improved nucleoside-5'-phosphate producing ability, which has an amino acid sequence of the acid phosphatase derived from *Escherichia blattae* including modification at one or more of the following positions: 16, 71, 72, 73, 103, 104, 140, 151 and 153.

(10) A mutant nucleoside-5'-phosphate producing enzyme with improved nucleoside-5'-phosphate producing ability, which has transphosphorylation activity and/or phosphatase activity, and has modification at one or more of positions corresponding to the following positions of the amino acid sequence of the acid phosphatase derived from *Escherichia blattae*: 16, 71, 72, 73, 103, 104, 140, 151 and 153 in amino acid sequence alignment with the acid phosphatase derived from *Escherichia blattae*.

(11) A mutant nucleoside-5'-phosphate producing enzyme with improved nucleoside-5'-phosphate producing ability, which has transphosphorylation activity and/or phosphatase activity, and has modification at one or more of positions corresponding to the following positions of the amino acid sequence of the acid phosphatase derived from *Escherichia blattae*: 16, 71, 72, 73, 103, 104, 140, 151 and 153 in alignment with the three-dimensional structure of the acid phosphatase derived from *Escherichia blattae* performed by the threading method.

(12) A mutant nucleoside-5'-phosphate producing enzyme, which has an amino acid sequence of the acid phosphatase derived from *Escherichia blattae* including replacement of the 72nd residue with another amino acid residue.

(13) A mutant nucleoside-5'-phosphate producing enzyme, which has transphosphorylation activity and/or phosphatase activity, and has replacement of a residue corresponding to the 72nd residue of the amino acid sequence of the acid phosphatase derived from *Escherichia blattae* with another amino acid in amino acid sequence alignment with the acid phosphatase derived from *Escherichia blattae*.

(14) A mutant nucleoside-5'-phosphate producing enzyme, which has transphosphorylation activity and/or phosphatase activity, and has replacement of a residue corresponding to the 72nd residue of the amino acid sequence of the acid phosphatase derived from *Escherichia blattae* with another amino acid in alignment with the three-dimensional structure of the acid phosphatase derived from *Escherichia blattae* performed by the threading method.

(15) The mutant nucleoside-5'-phosphate producing enzyme according to (10), wherein the enzyme is derived from *Enterobacter aerogenes*, and the amino acid sequence of the enzyme includes replacement with another amino acid residue of at least one amino acid residue among the 14th leucine residue, the 61st leucine residue, the 63rd alanine residue, the 64th glutamic acid residue, the 67th asparagine residue, the 69th serine residue, the 70th alanine residue, the 71st glycine residue, the 72nd glycine residue, the 101st isoleucine residue, the 102nd glutamic acid residue, the 133rd threonine residue, the 134th glutamic acid residue, the 138th leucine residue, 149th threonine residue and the 151st isoleucine residue.

(16) The mutant nucleoside-5'-phosphate producing enzyme according to (12), wherein the enzyme is derived from *Enterobacter aerogenes*, and the enzyme has any one of following amino acid replacements:

(a) mutation consisting of replacements of the 61st leucine residue with a glutamine residue, the 63rd alanine residue with a glutamine residue, the 64th glutamic acid residue with an alanine residue, the 67th asparagine residue with an aspartic acid residue, the 69th serine residue with an alanine residue, the 70th alanine residue with a valine residue, the 72nd glycine residue with an aspartic acid residue, the 102nd glutamic acid residue with a leucine residue, the 133rd threonine residue with a lysine residue, the 134th glutamic acid residue with an aspartic acid residue, the 149th threonine residue with a serine residue and the 151st isoleucine residue with a serine residue;

(b) mutation consisting of replacements of the 61st leucine residue with a glutamine residue, the 63rd alanine residue with a glutamine residue, the 64th glutamic acid residue with an alanine residue, the 67th asparagine residue with an aspartic acid residue, the 69th serine residue with an alanine residue, the 70th alanine residue with a valine residue, the 72nd glycine residue with an aspartic acid residue, the 133rd threonine residue with a lysine residue, the 134th glutamic acid residue with an aspartic acid residue, the 149th threonine residue with a alanine residue and the 151st isoleucine residue with a serine residue;

(c) mutation consisting of replacements of the 61st leucine residue with a glutamine residue, the 63rd alanine residue with a glutamine residue, the 64th glutamic acid residue with an alanine residue, the 67th asparagine residue with an aspartic acid residue, the 69th serine residue with an alanine residue, the 70th alanine residue with a glutamic acid residue, the 72nd glycine residue with an aspartic acid residue, the 133rd threonine residue with a lysine residue, the 134th glutamic acid residue with an aspartic acid residue, the 149th threonine residue with a glycine residue and the 151st isoleucine residue with a serine residue;

(d) mutation consisting of replacements of the 61st leucine residue with a glutamine residue, the 63rd alanine residue with a glutamine residue, the 64th glutamic acid residue with an alanine residue, the 67th asparagine residue with an aspartic acid residue, the 69th serine residue with an alanine residue, the 70th alanine residue with a lysine residue, the 72nd glycine residue with an aspartic acid residue, the 133rd threonine residue with a lysine residue, the 134th glutamic acid residue with an aspartic acid residue, the 149th threonine residue with a glycine residue and the 151st isoleucine residue with a serine residue; and (e) mutation consisting of replacements of the 61st leucine residue with a glutamine residue, the 63rd alanine residue with a glutamine residue, the 64th glutamic acid residue with an alanine residue, the 67th asparagine residue with an aspartic acid residue, the 69th serine residue with an alanine residue, the 70th alanine residue with a methionine residue, the 72nd glycine residue with an aspartic acid residue, the 102nd glutamic acid residue with a glutamine residue, the 133rd threonine residue with a lysine residue, the 134th glutamic acid residue with an aspartic acid residue, the 149th threonine residue with a serine residue and the 151st isoleucine residue with a serine residue.

(17) A method for producing a mutant nucleoside-5'-phosphate producing enzyme, wherein a mutant enzyme with improved nucleoside-5'-phosphate producing ability is produced by substituting, adding or deleting at least one amino acid residue in the active site of an enzyme having transphosphorylation activity and/or phosphatase activity and/or an amino acid residue located within a distance of 10 Å from the active site, in which the active site is determined based on the three-dimensional structure of the enzyme obtained by X-ray crystallographic analysis of the enzyme or a complex of the enzyme with molybdate.

(18) A method for producing an inhibitor for a phosphatase or transphosphorylation enzyme, which utilizes the atomic coordinates of the acid phosphatase derived from *Escherichia blattae*.

(19) A crystal of an enzyme having transphosphorylation activity and/or phosphatase activity or the complex of the enzyme with molybdate.

(20) A crystal of acid phosphatase derived from *Escherichia blattae*, which has a space group $P6_322$ of a hexagonal system.

(21) A crystal of mutant enzyme acid phosphatase G74D/I153T derived from *Escherichia blattae*, which has a space group $P2_12_12_1$ of a rhombic system.

(22) A crystal of complex of acid phosphatase derived from *Escherichia blattae* and molybdate (reaction intermediate analogue), which has a space group $P3_121$ of a trigonal system.

(23) A gene coding for any one of the enzymes according to any one of (1) to (16).

(24) A recombinant DNA, which contains the gene according to (23).

(25) A microorganism, which contains the gene according to (23) or the recombinant DNA according to (24).

(26) A method for producing a nucleoside-5'-phosphate, which comprises allowing the enzyme according to any one of (1) to (16), a microorganism containing it or the microorganism according to (25) to act on a nucleoside and a phosphate donor to produce nucleoside-5'-phosphate and collecting it.

(27) The method according to (26), wherein the enzyme, the microorganism containing it or the microorganism according to (25) is allowed to act on a nucleoside and a phosphate donor under a condition of pH 3.0–5.5.

The present invention provides a method for producing nucleoside-5'-phosphate using a mutant EB-AP, which is designed based on a binding model of EB-AP with a nucleoside constructed on the basis of the three-dimensional structure of EB-AP.

However, the mutant nucleoside-5'-phosphate producing enzyme of the present invention does not include the G74D/I153T mutant EB-AP, the G72D/I151T mutant MM-AP and the 10-residue replaced mutant EB-AP.

The present invention will be specifically explained hereinafter.

(1) In order to determine the three-dimensional structure of a protein by X-ray crystallography, the protein must be crystallized (details will be described in Examples 1–3). In order to crystallize a protein, many parameters must be determined on the trial and error basis, such as pH, kind of buffer, concentration of buffer, kind of precipitating agent, concentration of precipitating agent, concentrations of additives such as metals, concentration of protein and purity of protein. Therefore, it usually takes several months to several years before obtaining crystals, and there is often a case where crystals cannot be obtained in spite of such great effort. While crystallization is indispensable for the determination of the three-dimensional structure, it is also industrially useful as purification method of proteins to high purity, method for storage of proteins with high density and high protease resistance as well as a process prior to utilization as immobilized enzymes.

(2) By irradiating the produced crystals with an x-ray, diffraction data are collected. A protein crystal is often damaged by X-ray irradiation, and thus suffers from degradation of diffraction ability. For such a case, low temperature measurement recently becomes popular, in which crystals are rapidly cooled to about −173° C. and diffraction data are collected in that state. Upon cooling, it is necessary to devise a solvent composition so that the crystals should not be destroyed and the whole system should be vitrified.

(3) In order to perform crystal structure analysis, phase information is required in addition to the diffraction data.

Since three-dimensional structures of proteins analogous to EB-AP have not been known yet, the problem concerning the phase must be solved by the heavy atom isomorphous replacement method. The heavy atom isomorphous replacement method is a method for obtaining phase information by introducing a metal of a large atomic number such as mercury and platinum into a crystal and utilizing contribution of strong x-ray scattering ability of metal atoms to X-ray diffraction data to obtain phase information. If the three-dimensional structure of wild-type EB-AP is once determined, crystal structures of analogous compounds thereof such as mutant enzymes and reaction intermediate analogues can be determined by the molecule replacement method by using it. The molecule replacement method is a technique for crystal structure determination by using a three-dimensional structure of a protein analogous to the protein of which crystal structure is to be determined, when the three-dimensional structure of the analogous protein is known. For example, if a three-dimensional structure of a wild-type of a certain protein is known, the molecule replacement method can be used for the determination of a crystal structure of a mutant protein or a chemically modified protein thereof.

As for the G74D/I153T mutant EB-AP, its crystal structure is determined for elucidating the molecular mechanism for the enhancement of affinity for a nucleoside by substitution of two amino acids.

As for a reaction intermediate analogue, its crystal structure is determined in order to construct its binding model with a nucleoside. A nucleoside binds to EB-AP to which phosphate group to be donated binds through a covalent bond, i.e., a reaction intermediate, and then converted into a nucleoside-5'-phosphate. Since the reaction intermediate of EB-AP is unstable, its structure cannot be determined. It was considered that, however, since a reaction intermediate analogue to which molybdate binds through a covalent bond instead of phosphate was not hydrolyzed, its structure could be determined. The details will be described in Examples 4, 6, and 7.

(4) On computer graphics (CG), a binding mode model is constructed by fitting a nucleoside to a hollow near the molybdate binding site based on the binding site in the three-dimensional structure of the reaction intermediate analogue (FIG. 3). For the construction of the model, a program such as QUANTA and INSIGHT II of MSI (United States) is utilized.

FIG. 3 is a photograph of the crystal structure of the aforementioned binding mode model.

The details will be described in Examples 5 and 8.

(5) By extensively examining the binding model, a mutation that is considered to increase the affinity for a nucleoside is designed. In order to improve the affinity, it is effective to enhance hydrophobic interaction, electrostatic interaction, hydrogen bond, π—π interaction (interaction of magnetic fields generated by ring currents of aromatic rings) and CH/π interaction (interaction of magnetic field generated by ring current of an aromatic ring and electrons of methyl group).

For example, since it is expected that Ser72 most strongly interacts with a base of nucleoside in the binding mode model, it can be considered that replacement of the residue with Phe, Tyr and Trp enhances the hydrophobic interaction and the π—π interaction, replacement with Val, Ile and Leu enhances the hydrophobic interaction and the CH/π interaction, and replacement with Glu and Asp enhances the electrostatic interaction and the hydrogen bond. Further, the hydrophobic interaction and so forth may also be enhanced by replacement with other amino acids, in particular, replacement with an amino acid having a longer side chain.

It is also expected that replacements of Leu16, Ser71, Ser73 and Glu104 with Phe, Tyr and Trp generate the π—π interaction between the aromatic rings of the replaced amino acid residues and a base of nucleoside. Further, it is expected that replacements of Ile103 or Thr153 with a hydrophilic residue having a longer chain generate a hydrogen bond with the ribose of nucleoside. Furthermore, it is expected that replacement of Thr151 that is present near the nucleoside binding site and buried inside the protein with an amino acid residue having a small side chain such as Ser, Ala and Gly produces a space in the protein so that flexibility of the nucleoside binding site is increased and the binding site can have a conformation more suitable for binding with a nucleoside. Although Leu410 is separated from Ser72 by more than 10 Å, it is located near the phosphate binding site in the three-dimensional structure of a reaction intermediate analogue. Therefore, it is considered that if this residue is replaced, the structure around the phosphate binding site of the reaction intermediate is changed, and as a result, it also influences the structure of the nucleoside binding site and fluctuation thereof. It is expected that if this residue is replaced with more bulky Phe, positively charged Lys or negatively charged Glu, the affinity with a nucleoside may be changed.

The aforementioned mutations are introduced into, for example, the G74D/I153T mutant EB-AP. However, the mutant enzyme to which the mutations are introduced is not limited to the G74D/I153T mutant EB-AP. For example, it is also possible to introduce the mutations into the 10-residue replaced mutant EB-AP.

The details will be described in Example 10.

(6) A plasmid containing a gene coding for a mutant EB-AP is produced. The gene coding for a mutant EB-AP can be obtained by introducing a target mutation into a gene coding for a wild-type EB-AP through site-specific mutagenesis.

The plasmid containing the gene coding for a mutant EB-AP is introduced into *Escherichia coli* JM109 to produce a mutant EB-AP. A Km value, which serves as an index of affinity of the mutant EB-AP for inosine, and transphosphorylation activity to convert inosine into 5'-inosinic acid are measured to evaluate the performance of the mutant EB-AP. It is considered that the production amount of nucleoside-5'-phosphate much depends on the Km value. After pyrophosphoric acid reacts with EB-AP and a phosphate ion dissociates so that a reaction intermediate with the phosphate group covalently bonded to EB-AP is formed, if a water molecule attacks it, the phosphate group will be released (phosphatase reaction). It means that the pyrophosphoric acid was consumed vainly without generating nucleoside-5'-phosphate. On the other hand, if a nucleoside attacks the reaction intermediate, the phosphate group will form a phosphomonoester linkage with the nucleoside, and the generated nucleoside-5'-phosphate will dissociate from EB-AP (transphosphorylation reaction). It means that the pyrophosphoric acid was utilized for the production of nucleoside-5'-phosphate. That is, if water binds to the reaction intermediate, phosphatase activity will be exerted, and if the nucleoside binds to the intermediate, transphosphorylation activity will be exerted. If the affinity of EB-AP for the nucleoside is increased, i.e., if the Km value is decreased, the likelihood of the transphosphorylation reaction will become high. Further, if the hydrophobicity around the phosphate binding site is increased and thus it becomes difficult for water to approach the binding site, the phosphatase activity will become weaker and the transphosphorylation activity will become relatively stronger. Thus, the expression of "nucleoside-5'-phosphate producing ability is improved"used for the present invention may mean either improvement of the transphosphorylation activity or decrease of the phosphatase activity of a mutant acid phosphatase (see WO96/37603), or it may mean the both.

The details will be described in Example 11.

(7) By using *Escherichia coli* JM109 transformed with the plasmid containing a mutant EB-AP gene, in which the Km value is decreased and the transphosphorylation activity is increased, experimental production of 5'-inosinic acid from inosine is performed. The reaction is performed at 30° C. for 45 hours, and the variation with time in the production amount of 5'-inosinic acid is monitored. The details will be described in Example 13.

If mutation sites that decrease Km are found out, a mutant enzyme having improved affinity for a nucleoside and higher productivity can be produced by combining two or more mutations. By repeating the site-specific mutagenesis, two or more mutation sites can be cumulatively introduced. Further, upon introduction of site-specific mutations, if primers having mixed nucleotides as the nucleotides of a portion coding for an amino acid residue for which the mutation is introduced, a library of mutant genes in which a particular encoded amino acid is replaced with all of amino acid residues can be produced. If a mutation is introduced into multiple sites by using primers having mixed nucleotides, a library of mutant genes coding for extremely many kinds of mutant enzymes can be produced. It is also effective to introduce a library constructed as described above into *Escherichia coli*, and select a mutant comprising a combination of amino acid substitutions providing high activity from the expressed library.

Other than EB-AP, an enzyme having an active site similar to that of EB-AP and a space for binding of a nucleoside may potentially be utilized for the production of nucleoside-5'-phosphate. The active site must have amino acid residues indispensable for the activity, and the residues must be configured in a suitable relationship in special positions. In EB-AP, Lys115, Arg122, His150, Arg183 and His189 are indispensable for the activity, and it is possible to define the relationship of special positions with distances between Cα's of these 5 residues. In the present invention, since crystal structures of three kinds of EB-AP, wild-type, G74D/I153T mutant and reaction intermediate analogue, were determined, Cα interatomic distances of the active residues in each structure were measured, and summarized in Table 1. Since the distance distribution for each of the distances shown in Table 1 showed a range of about 1 Å, it was considered that the desired active site could be formed if each distance is in the range of from a distance shorter than the shortest distance by 1 Å (Table 1, lower limit) to a distance longer than the longest distance by 1 Å (Table 1, upper limit). In FIG. 1, positional relationship of the five residues is shown with upper limits and lower limits of the distances between Cα's.

In Example 8, it will be demonstrated that, in MM-AP, which is an analogous enzyme of EB-AP, all the interatomic distances between active residues fall within the ranges defined based on the three-dimensional structure of EB-AP. In that example, although not a wild-type, but the G72D/I151T mutant was exemplified, it is considered that there is not significant difference in the active site structure between a wild-type and a mutant of the same enzyme. This assumption is supported by the fact that the structures of the active sites in a wild-type and the G74D/I153T mutant of EB-AP are basically identical to each other (see Table 1).

TABLE 1

|  |  | Wild-type | G74D/I153T mutant | Reaction intermediate analogue | Lower limit | Upper limit |
|---|---|---|---|---|---|---|
| Lys115 | Arg122 | 11.6 Å | 11.6 Å | 11.4 Å | 10.4 Å | 12.6 Å |
|  | His150 | 12.4 Å | 12.3 Å | 12.8 Å | 11.3 Å | 13.8 Å |
|  | Arg183 | 16.4 Å | 16.3 Å | 15.5 Å | 14.5 Å | 17.4 Å |
|  | His189 | 12.6 Å | 12.1 Å | 11.7 Å | 10.7 Å | 13.6 Å |
| Arg122 | His150 | 13.2 Å | 13.6 Å | 14.2 Å | 12.2 Å | 15.2 Å |
|  | Arg183 | 10.4 Å | 10.5 Å | 10.8 Å | 9.4 Å | 11.8 Å |
|  | His189 | 5.6 Å | 5.5 Å | 5.7 Å | 4.5 Å | 6.7 Å |
| His150 | Arg183 | 8.4 Å | 8.8 Å | 7.7 Å | 6.7 Å | 9.8 Å |
|  | His189 | 9.8 Å | 10.0 Å | 10.0 Å | 8.8 Å | 11.0 Å |
| Arg183 | His189 | 5.5 Å | 5.8 Å | 5.7 Å | 4.5 Å | 6.8 Å |

In order to convert a nucleoside into nucleoside-5'-phosphate by phosphorylation, the presence of the active site that consists of the aforementioned five residues alone is not sufficient, and a nucleoside must be able to bind to a suitable position. In EB-AP, in the neighborhood of phosphate group, a slot-like space suitable for binding of a nucleoside is present on the surface of the molecule [(FIG. 3): it can be displayed on computer graphics (CG) by using the atomic coordinates represented in the appended FIGS. 10–45]. This slot is defined as a space surrounded by four residues of Leu16, Ser72, Glu104 and His189. Even if an enzyme has the active site, the enzyme is unsuitable as a nucleoside-5'-phosphate producing enzyme without a suitable space for binding of a nucleoside.

The mutant nucleoside-5'-phosphate producing enzyme of the present invention can be obtained by modifying an enzyme having the transphosphorylation activity and/or the phosphatase activity, in which the distances between Cα's of five residues of Lys115, Arg122, His150, Arg183 and His189 are within the ranges shown in FIG. 1. However, so long as it has a space for binding of a nucleoside near the aforementioned five residues and has transphosphorylation activity, the distances between Cα's of the five residues may not be within the ranges shown in FIG. 1. Nonetheless, the mutant acid phosphatase to be obtained is preferably has the distances between Cα's of the aforementioned five residues falling within the ranges shown in FIG. 1.

The present invention further provides a mutant EB-AP comprising a replacement of Ser72 with another amino acid, preferably with any one of Phe, Tyr, Trp, Val, Leu, Glu, Asp, Gln, Met, Thr, Arg and Lys, and, in addition, two mutations of G74D and I153T, which are already published as mutations enhancing the nucleoside-5'-phosphate producing ability (henceforth referred to as the "3-residue replaced mutant EB-AP"). Furthermore, the residues present within a distance of 10 Å from Ser72 (residue numbers: 16, 70–71, 73–76, 100, 102–104, 106–108, 115, 148–154, 183) are very likely to interact with a nucleoside, and the present invention also provides a mutant EB-AP comprising one or more replacements of these amino acid residues with one or more other amino acids. The term "replacement (substitution)" used herein include not only an artificial replacement of amino acid residue, but also selection of another acid phosphatase belonging to the same enzyme family as EB-AP and comprising a naturally occurring replacement. However, the present invention is still able to provide a mutant EB-AP containing a mutation point other than the aforementioned amino acid residues.

Further, another acid phosphatase belonging to the same enzyme family as EB-AP may be used for the production of nucleoside-5'-phosphate, if an amino acid mutation homologous to those used for EB-AP is made in that enzyme. As such an acid phosphatase, there can be mentioned those enzymes derived from *Escherichia* bacteria other than *Escherichia blattae*, *Morganella* bacteria other than *Morganella morganii*, *Providencia* bacteria such as *Providencia stuartii*, *Enterobacter* bacteria, *Klebsiella* bacteria such as *Klebsiella planticola* and so forth. However, the amino acid residues of EB-AP do not necessarily correspond to the amino acid residues of the same numbers in other acid phosphatases. For example, Ser72 of EB-AP corresponds to Ala70 in MM-AP. The correspondence of amino acid residues in two different proteins can be determined by alignment of the amino acid sequences (Sequence Alignment) when the identity between the both amino acid sequences is about 20% or more, or alignment of the three-dimensional structure and amino acid sequence (Threading) when the identity between the both amino acid sequences is about 20% or less. The former can be performed with a program of BLAST etc., and the latter can be performed with a program of INSIGHT II etc.

The amino acid sequence alignment of EB-AP and a wild-type acid phosphatase (wild-type EA-AP) derived from Enterobacter aerogenes obtained by using BLAST is described in Example 20 (see FIG. 9). Further, alignment of the amino acid sequences of EB-AP, MM-AP and acid phosphatases derived from Salmonella typhimurium and Zymomonas mobilis is shown in FIG. 2. The sequences of the genes coding for EB-AP, MM-AP, acid phosphatases derived from Salmonella typhimurium and Zymomonas mobilis and EA-AP and amino acid sequences thereof are shown in SEQ ID NOS: 1-10. Among these sequences, EA-AP is of 10-residue replaced mutant, and others are of wild-type. Further, EA-AP is represented as a proprotein containing a signal peptide. In addition, the amino acid sequences of the acid phosphatase derived from Providencia stuartii (GenBank accession X64820) and Klebsiella planticola (GenBank accession E16588) and the nucleotide sequences of the genes coding for them are known.

When acid phosphatase is produced as a precursor protein having a signal peptide and then processed into a mature protein through removal of the signal peptide, alignment is performed for the amino acid sequence of the mature protein.

As for BLAST, a file compatible with a computer to be used can be obtained from the files stored in /blast/executable from the NCBI database managed by the National Library of Medicine, National Institutes of Health (Bethesda, Md. USA) by using an FTP server.

The details about the operation method are described in the installation and procedures packet available on the website for the National Institutes of Health (Bethesda, Md., USA).

While the improvement of nucleoside-5'-phosphate producing ability is often attained by enhancement of affinity for a nucleoside, besides it, it may also be attained by improvement in reaction rate, shift of optimum pH, enhancement of thermal stability etc. The shift of optimum pH can be attained by changing pK of active residues (Protein Engng., 11, 383–388 (1998)). The enhancement of thermal stability can be attained by introduction of proline residues, replacement of residues that show left-handed helical structure with glycine residues (Protein Engng., 6, 85–91 (1993)), filling space in the protein (Biochemistry, 32, 6171–6178 (1993)) and so forth.

Further, the mutant nucleoside-5'-phosphate producing enzyme of the present invention may have mutations of other amino acid residues in addition to the aforementioned mutations, so long as such mutations do not adversely affect the nucleoside-5'-phosphate producing ability. Examples of such mutations include a mutation that enhances temperature stability (refer to Japanese Patent Laid-open (Kokai) No. 10-201481/1998). In addition, a single mutation may exert the effect for improvement of the nucleoside-5'-phosphate producing ability and another effect, for example, for improvement of temperature stability. In any case, an enzyme containing such a mutation falls within the scope of the mutant nucleoside-5'-phosphate producing enzyme of the present invention, so long as its nucleoside-5'-phosphate producing ability is eventually enhanced.

For example, the nucleoside-5'-phosphate producing ability may be enhanced even by replacing a residue that is not Ser72 of EB-AP or is not present within a distance of 10 Å from the Ser72 with another residue. Examples of such a residue include Leu140 for EB-AP and Leu138 for EA-AP.

As described in detail above, the three-dimensional structure is effective for producing a mutant of which affinity for a nucleoside and nucleoside-5'-phosphate producing ability are improved. However, the three-dimensional structure is effective not only in changing the affinity for a nucleoside of an enzyme, but also in changing affinity for a phosphate donor. As disclosed in Japanese Patent Laid-open (Kokai) No. 9-37785/1997, the enzyme can use various phosphoric acid ester compounds such as polyphosphoric acid (salt thereof), phenyl phosphate (salt thereof), acetyl phosphate (salt thereof) and carbamyl phosphate (salt thereof) as a phosphate donor. However, it is also possible to broaden its substrate specificity for the phosphate donor, or improve the utilization factor of phosphate by designing a mutation that increases the affinity for a phosphoric acid ester compound in a manner similar to that for designing a mutation enhancing the affinity for a nucleoside.

BRIEF DESCRIPTION OF THE DRAWINGS

FIG. 1 shows the five amino acid residues serving as the components of the active site having the phosphatase activity or the transphosphorylation activity, and their relationship in special positions as distances between Cα atoms. The identified amino acids are as follows:

Lys: $115^{th}$ residue of SEQ ID NO: 124;

Arg (N-terminus side): $122^{nd}$ residue of SEQ ID NO: 124;

His (N-terminus side): $150^{th}$ residue of SEQ ID NO: 124;

Arg (C-terminus side): $183^{rd}$ residue of SEQ ID NO: 124; and

His (C-terminus side): $189^{th}$ residue of SEQ ID NO: 124.

FIG. 2 shows alignment of the amino acid sequence of EB-AP (Escherichia blattae-acid phosphatase, SEQ ID NO: 2) with the amino acid sequences of the acid phosphatases derived from Morganella morganii (SEQ ID NO: 4), Salmonella typhimurium (SEQ ID NO: 6), and Zymomonas mobilis (SEQ ID NO: 8).

Figure 3:
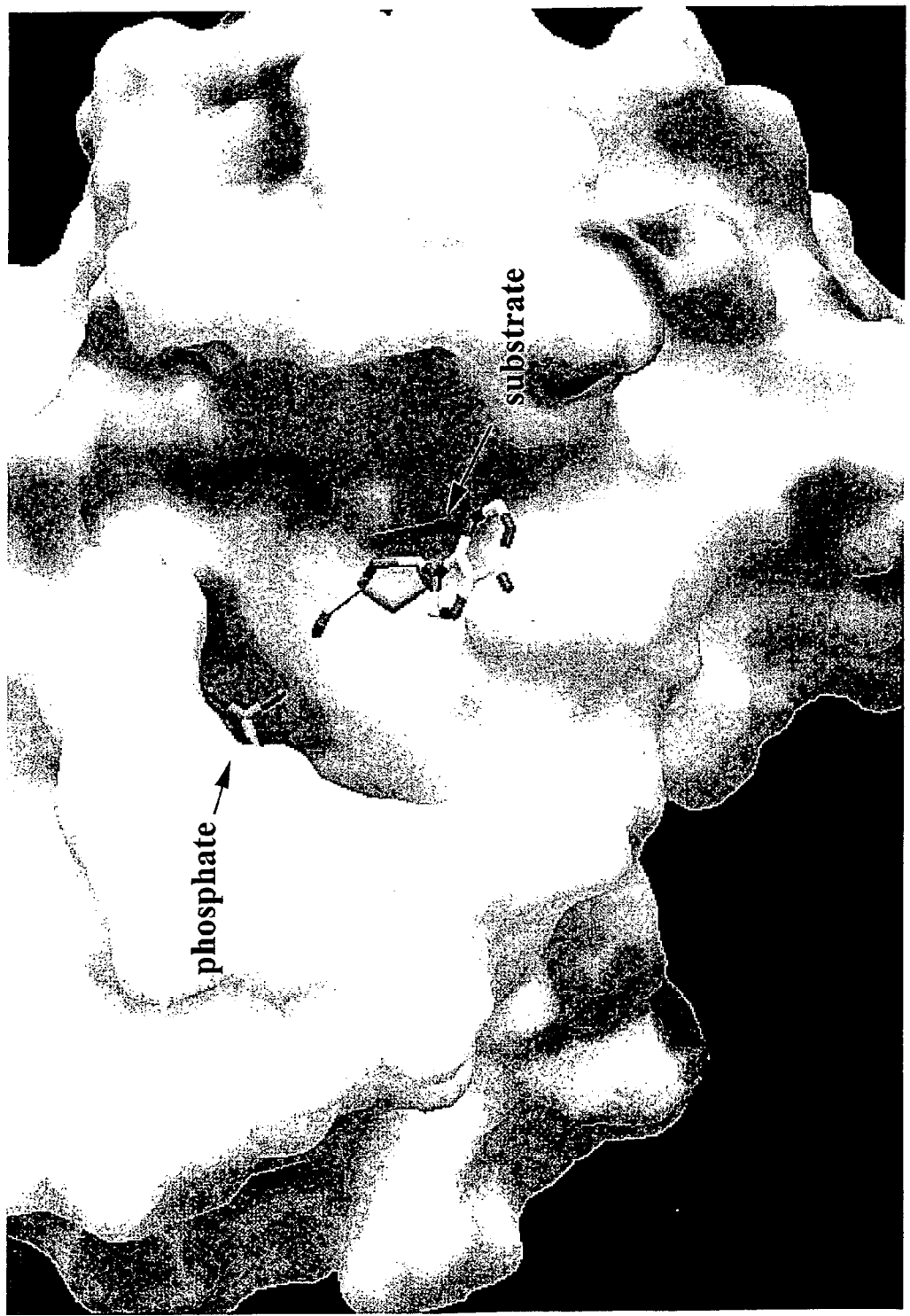

FIG. 3 is a photograph of computer graphics (CG), which represents a crystal structure in a binding mode model of the EB-AP reaction intermediate analogue and inosine.

Figure 4:
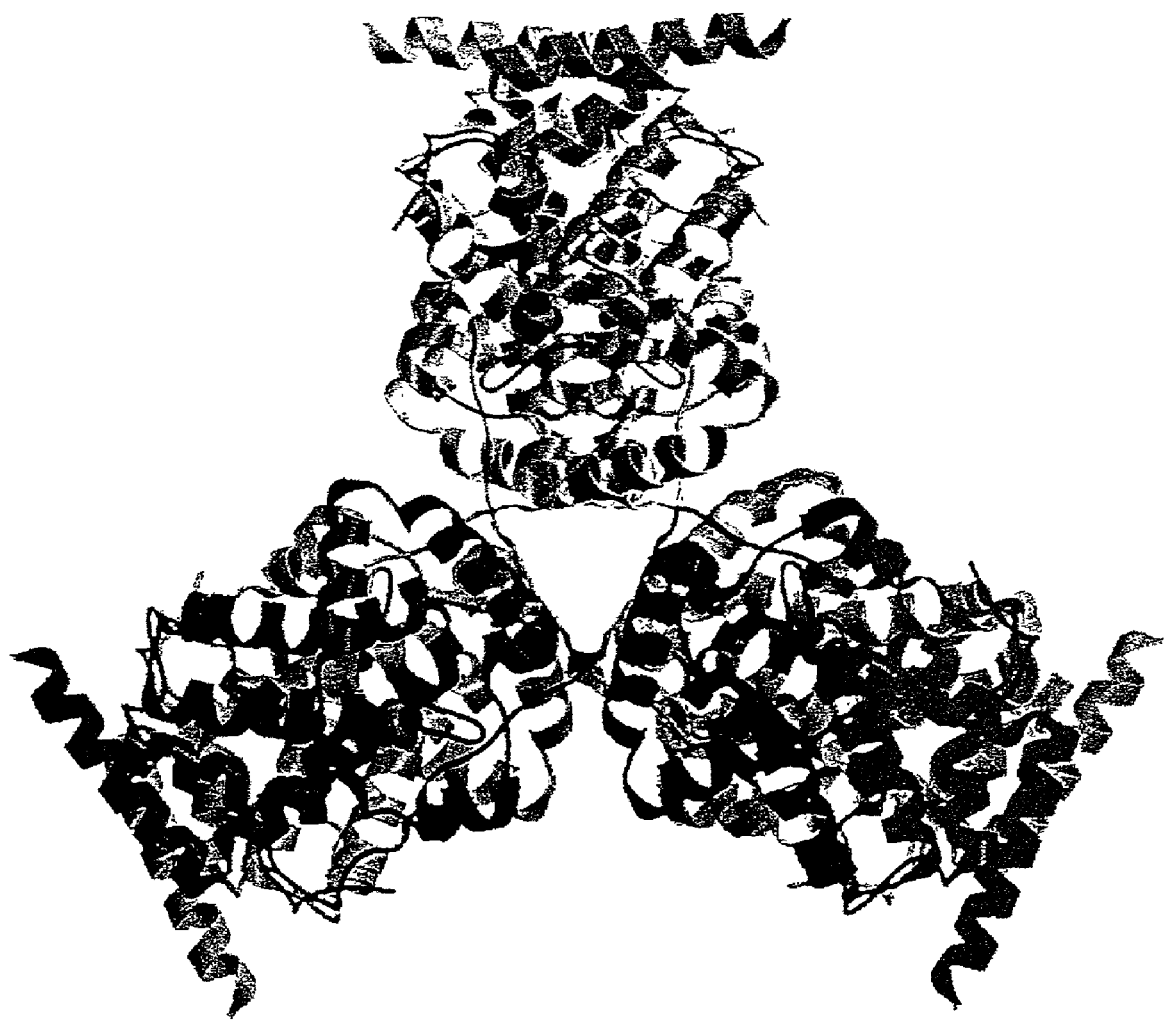

FIG. 4 is a photograph of CG, which shows a crystal structure of the hexamer molecule of EB-AP.

Figure 5:
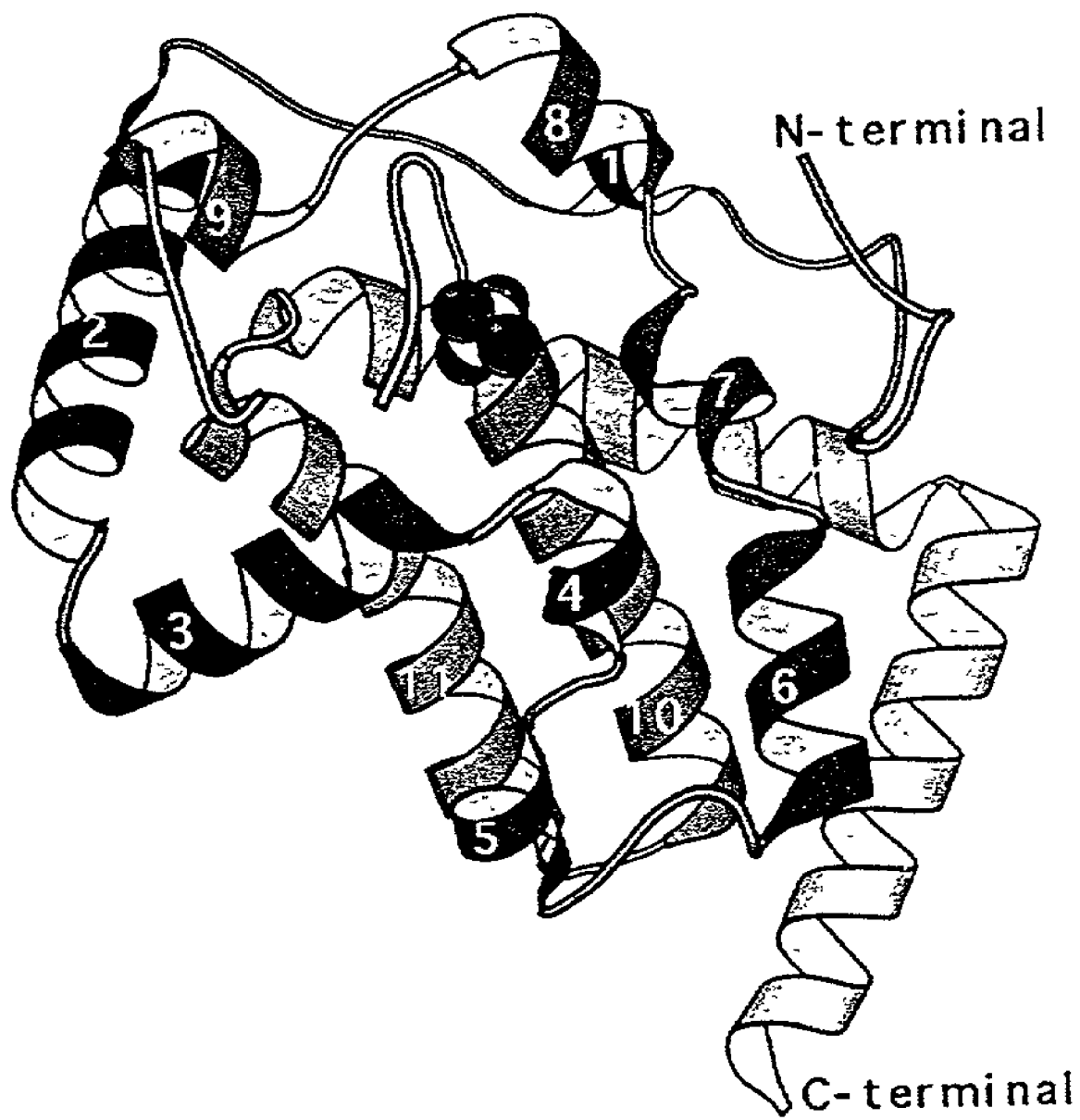

FIG. 5 is a photograph of CG, which shows a crystal structure of a subunit of EB-AP.

Figure 6:
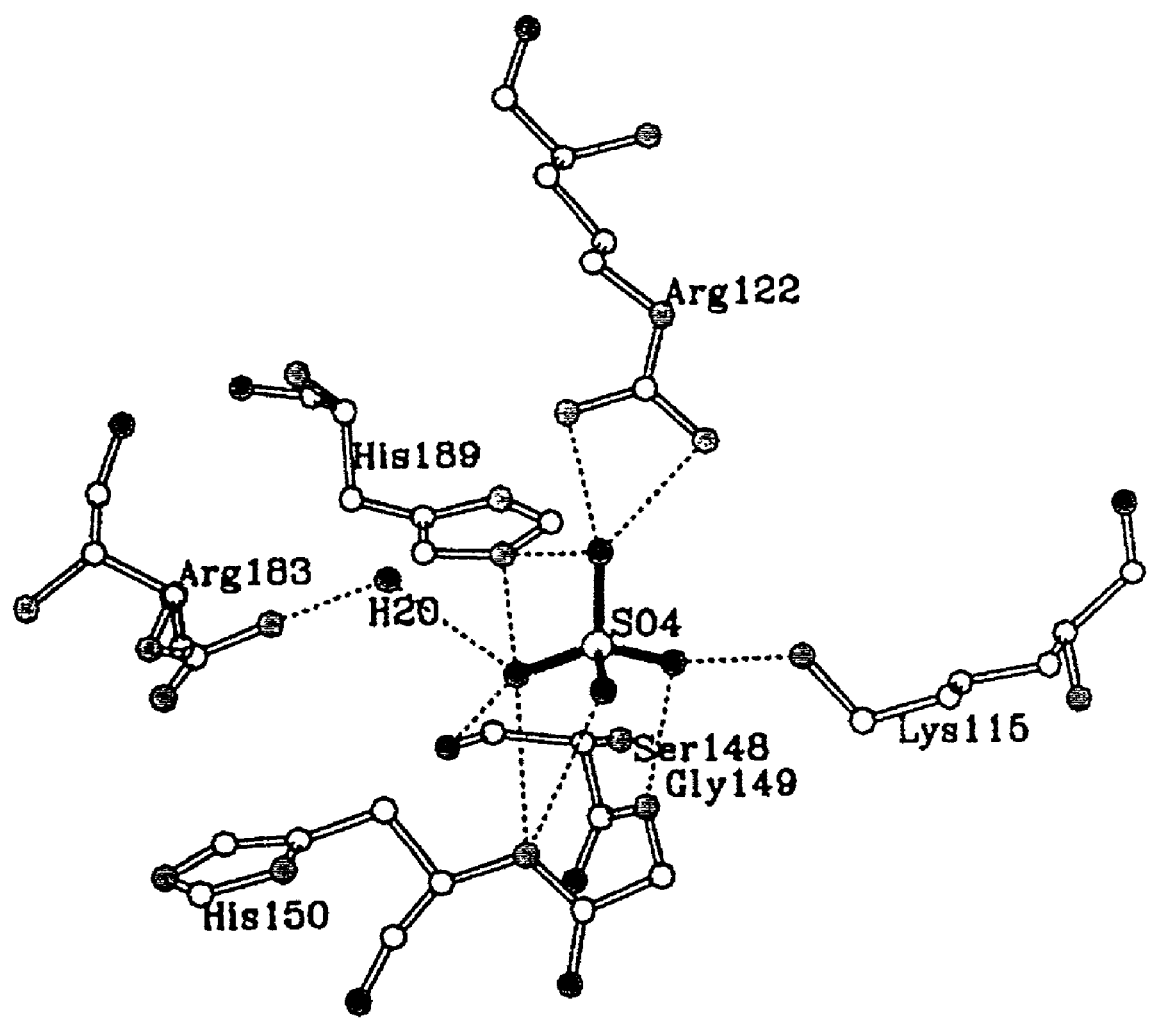

FIG. 6 shows a structure of the active site of EB-AP.

FIG. 7 shows primer sets used for site-directed mutagenesis.

FIG. 8 shows primer sets used for site-directed mutagenesis.

FIG. 9 shows the result of amino acid sequence alignment of EB-AP (SEQ ID NO: 124) and a wild-type acid phosphatase derived from Enterobacter aerogenes (wild-type EA-AP, SEQ ID NO: 125) performed by using the program BLAST.

FIG. 10 shows the crystallographic data (1) for the structure of EB-AP.

FIG. 11 shows the crystallographic data (2) for the structure of EB-AP.

FIG. 12 shows the crystallographic data (3) for the structure of EB-AP.

FIG. 13 shows the crystallographic data (4) for the structure of EB-AP.

FIG. 14 shows the crystallographic data (5) for the structure of EB-AP.

FIG. 15 shows the crystallographic data (6) for the structure of EB-AP.

FIG. 16 shows the crystallographic data (7) for the structure of EB-AP.

FIG. 17 shows the crystallographic data (8) for the structure of EB-AP.

FIG. 18 shows the crystallographic data (9) for the structure of EB-AP.

FIG. 19 shows the crystallographic data (10) for the structure of EB-AP.

FIG. 20 shows the crystallographic data (11) for the structure of EB-AP.

FIG. 21 shows the crystallographic data (12) for the structure of EB-AP.

FIG. 22 shows the crystallographic data (13) for the structure of EB-AP.

FIG. 23 shows the crystallographic data (14) for the structure of EB-AP.

FIG. 24 shows the crystallographic data (15) for the structure of EB-AP.

FIG. 25 shows the crystallographic data (16) for the structure of EB-AP.

FIG. 26 shows the crystallographic data (17) for the structure of EB-AP.

FIG. 27 shows the crystallographic data (18) for the structure of EB-AP.

FIG. 28 shows the crystallographic data (19) for the structure of EB-AP.

FIG. 29 shows the crystallographic data (20) for the structure of EB-AP.

FIG. 30 shows the crystallographic data (21) for the structure of EB-AP.

FIG. 31 shows the crystallographic data (22) for the structure of EB-AP.

FIG. 32 shows the crystallographic data (23) for the structure of EB-AP.

FIG. 33 shows the crystallographic data (24) for the structure of EB-AP.

FIG. 34 shows the crystallographic data (25) for the structure of EB-AP.

FIG. 35 shows the crystallographic data (26) for the structure of EB-AP.

FIG. 36 shows the crystallographic data (27) for the structure of EB-AP.

FIG. 37 shows the crystallographic data (28) for the structure of EB-AP.

FIG. 38 shows the crystallographic data (29) for the structure of EB-AP.

FIG. 39 shows the crystallographic data (30) for the structure of EB-AP.

FIG. 40 shows the crystallographic data (31) for the structure of EB-AP.

FIG. 41 shows the crystallographic data (32) for the structure of EB-AP.

FIG. 42 shows the crystallographic data (33) for the structure of EB-AP.

FIG. 43 shows the crystallographic data (34) for the structure of EB-AP.

FIG. 44 shows the crystallographic data (35) for the structure of EB-AP.

FIG. 45 shows the crystallographic data (36) for the structure of EB-AP.

BEST MODE FOR CARRYING OUT THE INVENTION

Hereafter, the present invention will be explained more specifically with reference to the following examples. However, the present invention is not limited to these examples.

EXAMPLE 1

Crystallization of Wild-Type EB-AP

Crystallization was performed by using vapor diffusion in the hanging drop method. A 20 mM sodium phosphate buffer (pH 8.0) containing the wild-type EB-AP (concentration: 10 mg/ml) and a 100 mM Tris-HCl buffer containing 45% (w/v) of polyethylene glycol 400 in the same amounts (7–10 $\mu$l each) were dropped and mixed on siliconized cover glass, and a well filled with 500 $\mu$l of 100 mM Tris-HCl buffer containing 45% (w/v) of polyethylene glycol 400 was covered with the cover glass so that a drop of the mixed solution should be hung above the well and left stand at 20° C. Crystals appeared within a few days, and they grew up to hexagonal columnar crystals in a measurable size (about 0.3×0.3×1.2 mm) within 1 to 2 weeks. For the X-ray data measurement, the crystals were transferred into 100 mM Tris-HCl buffer (pH 8.0) containing 50% (w/v) polyethylene glycol 400.

Upon handling of these crystals, it was necessary to pay attention to the following points. 1) Since the crystals were very likely to collapse by contacting with a container or tools when crystals were taken out from the droplet, the crystallization scheme of the sitting drop method could not be used (although crystals grew), the hanging drop method described herein was used. 2) Since crystals would degrade during measurement and hence resolution would be gradually reduced if the measurement was performed at room temperature, it was necessary to perform the measurement at a low temperature. The time required for mounting the crystals on a stage was made as short as possible to prevent them from being exposed to air.

Using an X-ray diffraction apparatus, R-AXIS IIc of Rigaku Co., Ltd., X-ray diffraction data were collected and crystallographic parameters were determined. The space group was determined to be $P6_322$ and the cell parameters to be a=b=124.4 Å and c=97.7 Å. Assuming that one subunit having a molecular weight of 25000 is contained in an asymmetric unit, the solvent content of the crystals is determined to be 72%.

EXAMPLE 2

Crystallization of G74D/I153T Mutant EB-AP

Crystallization was performed by using vapor diffusion in the hanging drop method. A 20 mM sodium phosphate buffer (pH 8.0) containing the G74D/I153T mutant EB-AP (concentration: 20 mg/ml) and a 20 mM Tris-HCl buffer containing 38% (w/v) of polyethylene glycol 400 in the same amounts (5 $\mu$l each) were dropped and mixed on siliconized cover glass, and a well filled with 500 $\mu$l of 20 mM Tris-HCl buffer containing 38% (w/v) of polyethylene glycol 400 was covered with the cover glass so that a drop of the mixed solution should be hung above the well and left stand at 20° C. Crystals appeared within a few days, and they grew up to tabular crystals in a measurable size (about 0.7×0.4×0.2 mm) within 1 week. For the X-ray data measurement, the crystals were transferred into 100 mM Tris-HCl buffer (pH 8.0) containing 50% (w/v) polyethylene glycol 400.

Using an X-ray diffraction apparatus, R-AXIS IIc of Rigaku Co., Ltd., X-ray diffraction data were collected and crystallographic parameters were determined. The space group was determined to be $P2_12_12_1$ and the cell parameters to be a=138.0 Å, b=168.3 Å and c=58.2 Å. Assuming that one subunit having a molecular weight of 15000 is contained in an asymmetric unit, the solvent content of the crystals is determined to be 64%.

EXAMPLE 3

Crystallization of Complex of Wild-Type EB-AP and Molybdate (Reaction Intermediate Analogue)

Crystallization was performed by a co-crystallization method by using vapor diffusion in the sitting drop method. A 20 mM sodium phosphate buffer (pH 8.0) containing the wild-type EB-AP (concentration: 10 mg/ml) and a 100 mM Tris-HCl buffer containing 40% (w/v) of polyethylene glycol 400 and 1 mM sodium molybdate in the same amounts (15 μl each) were added dropwise to a hollow of a bridge provided on a well filled with 500 μl of 100 mM Tris-HCl buffer containing 40% (w/v) of polyethylene glycol 400, mixed, and left stand at 20° C. Crystals appeared within a few days, and they grew up to rhomboidal crystals in a measurable size (about 0.3×0.3×0.3 mm) within 1 to 2 weeks. For the X-ray data measurement, the crystals were transferred into 100 mM Tris-HCl buffer (pH 8.0) containing 50% (w/v) polyethylene glycol 400.

Using an X-ray diffraction apparatus, R-AXIS IIc of Rigaku Co., Ltd., X-ray diffraction data were collected and crystallographic parameters were determined. The space group was determined to be $P3_121$ and the cell parameters to be a=b=86.6 Å and c=205.3 Å. Assuming that three subunits having a molecular weight of 25000 is contained in an asymmetric unit, the solvent content of the crystals is determined to be 58%.

EXAMPLE 4

Crystal Structure Analysis of Wild-Type EB-AP

X-ray diffraction data were collected up to the maximum resolution of 1.9 Å. Since the crystals were severely damaged by the irradiation of X-ray at room temperature, they were rapidly cooled to −173° C., and the measurement was performed. Heavy atom derivatives were screened by immersing the crystals into a solution of heavy metal salts. The diffraction data of heavy atom derivative crystals were obtained by using Rigaku R-AXISIIc. Based on a difference Fourier map with respect to the native data, it was found that $K_2PtCl_4$ provided good heavy atom isomorphic crystals. The coordinates of the only one platinum binding site of $K_2PtCl_4$ were obtained by using the program RSPS. These coordinates were further refined by using the program MLPHARE, from which the phase was calculated. By using this phase, five mercury binding sites of the second heavy atom derivative $KHgI_4$-KI were determined. The heavy atom parameters for both of $K_2PtCl_4$ and $KHgI_4$-KI were simultaneously refined by using MLPHARE, and then the phase was improved by performing solvent smoothing and histogram matching by using the program DM. As for $K_2PtCl_4$, anomalous scattering data were also used. The electron density map calculated by using this good phase was very clear, and thus almost all of amino acid residues were finely fitted.

The first model was constructed on an electron density map prepared with 2.8 Å resolution by using the program QUANTA, and structure refinement was performed by using the program X-PLOR. Electron density was not observed for the six residues at the N-terminus, 135 to 136th residues and one residue at the C-terminus, and thus the structure could not be determined uniquely. The final model refined with 1.9 Å resolution (FIG. 4 to FIG. 6) contained 222 residues out of the 231 residues in total, 236 water molecules and one molecule of sulfate ion. The sulfate ion was derived from ammonium sulfate used in the purification process, and was considered to fit to the phosphate binding site of the active center. The crystallographic reliability factor (R factor) determined by using reflections of 8 to 1.9 Å resolution was 21.5%. The average temperature factor was 26 $Å^2$ for protein atoms and 45 $Å^2$ for water molecules. When a Ramachandran plot was prepared by using the program PROCHECK, it was demonstrated that 93% of residues other than glycine located in the most preferred domain and 7% located at next preferred domain. One subunit was contained in an asymmetric unit and a hexamer was formed by the crystallographic symmetries. The atomic coordinates were represented in FIG. 10 to FIG. 45.

FIG. 4 is a CG photograph representing a crystal structure of the hexamer molecule of EB-AP. The flows of a carbon atoms were represented with ribbon models. Further, the sulfate ion marking the active center was represented with a ball model.

FIG. 5 is a CG photograph representing a crystal structure of a subunit of EB-AP. The flows of a carbon atoms were represented with ribbon models. Further, the sulfate ion marking the active center was represented with a ball model.

FIG. 6 shows the structure of the active site of EB-AP. The sulfate ion is represented at the center. The doted lines represent hydrogen bonds.

FIG. 10 shows the crystallographic data (1) for the structure of EB-AP.

FIG. 11 shows the crystallographic data (2) for the structure of EB-AP.

FIG. 12 shows the crystallographic data (3) for the structure of EB-AP.

FIG. 13 shows the crystallographic data (4) for the structure of EB-AP.

FIG. 14 shows the crystallographic data (5) for the structure of EB-AP.

FIG. 15 shows the crystallographic data (6) for the structure of EB-AP.

FIG. 16 shows the crystallographic data (7) for the structure of EB-AP.

FIG. 17 shows the crystallographic data (8) for the structure of EB-AP.

FIG. 18 shows the crystallographic data (9) for the structure of EB-AP.

FIG. 19 shows the crystallographic data (10) for the structure of EB-AP.

FIG. 20 shows the crystallographic data (11) for the structure of EB-AP.

FIG. 21 shows the crystallographic data (12) for the structure of EB-AP.

FIG. 22 shows the crystallographic data (13) for the structure of EB-AP.

FIG. 23 shows the crystallographic data (14) for the structure of EB-AP.

FIG. 24 shows the crystallographic data (15) for the structure of EB-AP.

FIG. 25 shows the crystallographic data (16) for the structure of EB-AP.

FIG. 26 shows the crystallographic data (17) for the structure of EB-AP.

FIG. 27 shows the crystallographic data (18) for the structure of EB-AP.

FIG. 28 shows the crystallographic data (19) for the structure of EB-AP.

FIG. 29 shows the crystallographic data (20) for the structure of EB-AP.

FIG. 30 shows the crystallographic data (21) for the structure of EB-AP.

FIG. 31 shows the crystallographic data (22) for the structure of EB-AP.

FIG. 32 shows the crystallographic data (23) for the structure of EB-AP.

FIG. 33 shows the crystallographic data (24) for the structure of EB-AP.

FIG. 34 shows the crystallographic data (25) for the structure of EB-AP.

FIG. 35 shows the crystallographic data (26) for the structure of EB-AP.

FIG. 36 shows the crystallographic data (27) for the structure of EB-AP.

FIG. 37 shows the crystallographic data (28) for the structure of EB-AP.

FIG. 38 shows the crystallographic data (29) for the structure of EB-AP.

FIG. 39 shows the crystallographic data (30) for the structure of EB-AP.

FIG. 40 shows the crystallographic data (31) for the structure of EB-AP.

FIG. 41 shows the crystallographic data (32) for the structure of EB-AP.

FIG. 42 shows the crystallographic data (33) for the structure of EB-AP.

FIG. 43 shows the crystallographic data (34) for the structure of EB-AP.

FIG. 44 shows the crystallographic data (35) for the structure of EB-AP.

FIG. 45 shows the crystallographic data (36) for the structure of EB-AP.

EXAMPLE 5

Modeling of the Binding Mode of Wild-Type EB-AP and 5'-Inosinic Acid

Since the Km value of inosine for EB-AP exceeds 100 mM, the affinity is not high enough to determine the binding mode by X-ray crystallography. In fact, when compounds serving as an inhibitor of EB-AP such as glucose-6-sulfate and adenosine-thiomonophosphate were soaked into the crystals of wild-type EB-AP and X-ray diffraction data were collected to prepare an electron density map, electron density corresponding to these compounds was not observed. Therefore, it was decided to predict the binding style of 5'-inosinic acid and EB-AP by using computer graphics (so-called docking study). As the program, QUANTA was used. Since a sulfate ion was found at the center of the active site in the crystal structure, the phosphate group of 5'-inosinic acid was superimposed on it. Further, since it was known that mutations of G74D and I153T would reduce the Km value of 5'-inosinic acid for EB-AP, it was judged that 5'-inosinic acid would bind to a position not far from G74 and I153, and decided the position of 5'-inosinic acid. At that time, the position was decided so that the atoms constituting 5'-inosinic acid and the atoms constituting EB-AP should not interfere with each other. In the model constructed as described above, if I153 is changed to Thr, the γ-oxygen atom of the side chain of the threonine introduced by the replacement and 2'-hydroxyl group of the ribose of inosine form a hydrogen bond. Further, when the electrostatic potential of EB-AP was displayed by using the program GRASP, the positively charged inosine base interacted with a negatively charged domain of the surface of the EB-AP molecule, which suggested that a model was reasonable.

EXAMPLE 6

Crystal Structure Analysis of G74D/I153T Mutant EB-AP

The G74D/I153T mutant EB-AP has an increased ratio of the transphosphorylation activity relative to the phosphatase activity, and in connection with this fact, the nucleoside-5'-phosphate producing ability is also improved. It is considered that this is caused by the decrease of the Km value for a nucleoside, i.e., improvement of the affinity for a nucleoside. It was expected that the molecular mechanism for improvement of the affinity for a nucleoside should be elucidated by determining the crystal structure of the mutant EB-AP and comparing it with the crystal structure of wild-type EB-AP.

At room temperature, the X-ray diffraction data were collected to the maximum resolution of 2.4 Å. Estimating from the volume of the unit cell, space group and molecular weight of the enzyme, it was expected that one hexamer molecule is contained in the asymmetric unit. Then, as a model for searching the hexamer structure of wild-type EB-AP, analysis was performed by the molecule replacement method using the program amore. Data of 10-3 Å resolution were used for the rotation search, and data of 10-4 Å resolution were used for the translation search. In the both searches, the correct answer appeared as a top peak. When refinement was performed by considering the molecule as a rigid body, the R factor decreased to 37.3%. Then, structure modification on graphics using QUANTA and structure refinement using X-PLOR were repeated to obtain a model with an R factor of 19.9% at 10-2.4 Å resolution.

When a docking model of 5'-inosinic acid and the G74D/I153T mutant EB-AP was prepared in the same manner as in Example 5, it was expected that the γ-oxygen atom of the side chain of the Thr153 introduced by the replacement would form a hydrogen bond with a hydroxyl group of ribose of inosine. By comparing temperature factors, it was found that the fluctuation of the loop containing Asp74 where another replacement was made was larger in the G74D/I153T mutant EB-AP compared with the wild-type. This loop is expected to interact with the base of inosine, and it is suggested that it becomes more likely to bind to the base due to the larger fluctuation.

EXAMPLE 7

Crystal Structure Analysis of the Complex of Wild-Type EB-AP with Molybdate (Reaction Intermediate Analogue)

In the enzymatic reaction of EB-AP, a phosphoric acid monoester linkage is first cleaved, and the phosphate group forms a covalent bond with an active site residue, His189. The enzyme molecule in this state is called a reaction intermediate. The reaction intermediate is quickly attacked by water or alcohol, and as a result, a phosphate ion dissociates from it. When water attacks, phosphatase activity will be exerted, and when alcohol attacks, the transphosphorylation activity will be exerted. In the both cases, the reaction intermediate is unstable and it is impossible to determine its structure by X-ray crystallography. However, a complex (reaction intermediate analogue) in which molybdate covalently bonds to His189 instead of phosphate is not attacked by water, and thus it exists stably.

In the transphosphorylation reaction, a phosphate acceptor binds to the reaction intermediate to form a phosphoric acid monoester linkage. Therefore, for the purpose of modeling the binding mode with a nucleoside, it is more suitable to use a reaction intermediate structure rather than the structure in free form. In order to perform docking study of the reaction intermediate and a nucleoside, the crystal structure of the reaction intermediate analogue was determined.

At room temperature, the X-ray diffraction data were collected to the maximum resolution of 2.4 Å. Estimating from the volume of unit cell, space group and molecular weight of the enzyme, it was expected that a half of the hexamer, i.e., three subunits, were contained in the asymmetric unit. Therefore, trimer structure in which the subunits were correlated with one another with a three-fold axis was prepared as a model for searching in the molecule replacement method. Data of 10-3 Å resolution were used for the rotation search, and data of 10-4 Å resolution were used for the translation search. In the both searches, the correct answer appeared as a top peak. When refinement was performed by considering the molecule as a rigid body, the R factor decreased to 42.4%. Then, structure modification on graphics using QUANTA and structure refinement using X-PLOR were repeated to obtain a model showing an R factor of 22.3% at 8-2.4 Å resolution. The asymmetric unit contained a half of the hexamer, i.e., three subunits.

EXAMPLE 8

Crystallization and Crystal Structure Analysis of G72D/I151T Mutant Enzyme Derived From Acid Phosphatase of *Morganella morganii* (MM-AP)

Crystallization of G72D/I151T double mutation mutant of MM-AP was performed by using vapor diffusion in the hanging drop method. A solution of the protein (concentration: 40 mg/ml) and a 125 mM citrate buffer (pH 4.8) containing 25% (w/v) of polyethylene glycol 1000, 25 mM ammonium sulfate and 25 mM DTT in the same amounts (5 µl each) were dropped and mixed on siliconized cover glass, and a well filled with 500 pl of 125 mM citrate buffer (pH 4.8) containing 25% (w/v) of polyethylene glycol 1000, 25 mM ammonium sulfate and 25 mM DTT was covered with the cover glass so that a drop of the mixed solution should be hung above the well and left stand at 20° C. Crystals appeared within a few days, and they grew up to a measurable size (about 0.4×0.4×0.3 mm) within 1 week.

Using an X-ray diffraction apparatus, R-AXIS IIc of Rigaku Co., Ltd., X-ray diffraction data were collected to determine crystallographic parameters. The space group was determined to be $P2_12_12_1$ and the cell parameters to be a=90.64 Å, b=119.74 Å and c=136.14 Å. The diffraction data to 2.6 Å resolution data were measured at 100 K on the synchrotron radiation light facility BL-6B at the HIGH ENERGY ACCELERATOR RESEARCH ORGANIZATION, Tsukuba.

Estimating from the volume of unit cell, space group and molecular weight of the enzyme, it was expected that one hexamer molecule was contained in the asymmetric unit. Then, by using the hexamer structure of wild-type EB-AP as a model for searching, the molecule replacement method was performed using the program amore. Data of 10-3 Å resolution were used for the rotation search, and data of 10-4 Å resolution were used for the translation search. In the both searches, the correct answer appeared as a top peak. After refinement was performed by considering the molecule as a rigid body, structure modification on graphics using QUANTA and structure refinement using X-PLOR were repeated to obtain a model with an R factor of 0.197% at 10-2.6 Å resolution.

The distances between Cα atoms of the five active residues shown in FIG. 1 (Lys113, Arg120, His148, Arg181 and His187) are shown in Table 2. It was confirmed that, in MM-AP that is an analogous enzyme of EB-MP, all of the interatomic distances between the active residues fell within the ranges defined based on the three-dimensional structure of EB-AP.

TABLE 2

| | | G72D/I151T mutant MM-AP | Lower limit | Upper limit |
|---|---|---|---|---|
| Lys113 | Arg120 | 11.3Å | 10.4Å | 12.6Å |
| | His148 | 12.6Å | 11.3Å | 13.8Å |
| | Arg181 | 16.3Å | 14.5Å | 17.4Å |
| | His187 | 12.5Å | 10.7Å | 13.6Å |
| Arg120 | His148 | 14.0Å | 12.2Å | 15.2Å |
| | Arg181 | 10.9Å | 9.4Å | 11.8Å |
| | His187 | 6.1Å | 4.5Å | 6.7Å |
| His148 | Arg181 | 8.9Å | 6.7Å | 9.8Å |
| | His187 | 10.2Å | 8.8Å | 11.0Å |
| Arg181 | His187 | 5.4Å | 4.5Å | 6.8Å |

EXAMPLE 9

Modeling of the Binding Mode of EB-AP Reaction Intermediate and Inosine

A binding mode model was constructed on computer graphics by using QUANTA (FIG. 3). Molybdate was replaced with phosphate as it was. Inosine was placed near the nucleoside portion of 5'-inosinic acid in the binding mode model of wild-type EB-AP and 5'-inosinic acid. However, the degree of freedom was of course higher than the docking with 5'-inosinic acid, since an inosine did not have a phosphoric acid monoester linkage. Therefore, fine adjustment of the position of inosine was performed so that inosine should bind to the molecular surface of EB-AP in a more preferred condition to obtain a binding style model. For the subsequent designing of a mutant enzyme, this model was used.

EXAMPLE 10

Design of Mutant EB-AP Aiming at Enhancement of Affinity for Nucleoside

According to the model constructed in Example 8, it was suggested that the side chain of Ser72 might interact with the base of inosine. It was expected that, if this residue was replaced with an aromatic amino acid such as phenylalanine, tyrosine and tryptophan, the π—π interaction would be generated between an aromatic ring and a nucleoside base and thus the affinity of nucleoside for EB-AP would be improved. Similarly, it was expected that, if it was replaced with an amino acid having a branched hydrophobic group in the side chain such as valine, leucine and isoleucine, the CH/π interaction would be generated between the branched hydrophobic group in the side chain and the nucleoside base, or if it was replaced with a negatively charged amino acid such as glutamic acid and an aspartic acid, it would be electrostatically attracted by the positive charge of the nucleoside base, and thus the affinity would be improved. Therefore, in order to further enhance the transphosphorylation activity of the G74D/I153T mutant EB-AP of which transphosphorylation activity was relatively increased compared with the phosphatase activity, S72F, S72Y, S72W, S72V, S72E and S72D mutants of this mutant EB-AP were prepared. In addition, mutants in which S72 was replaced with the other amino acids were also produced. Incidentally, these mutants would become a 3-residue replaced mutant EB-AP.

EXAMPLE 11

Construction of 3-Residue Replaced Mutant of EB-AP in which Ser72 is Replaced with Another Amino Acid In order to construct a mutant EB-AP for expression in *Escherichia coli* JM109, a plasmid pEPI340 containing a gene for G74D/I153T mutant EB-AP was used as a template for site-directed mutagenesis utilizing PCR. The nucleotide sequences of these plasmids pEPI305 and pEPI340 are disclosed in Japanese Patent Laid-open (Kokai) No. 10-201481/1998, paragraph (0143), Table 12. A strain of *Escherichia coli* JM109 harboring the plasmid pEPI305 was designated as AJ13144, and deposited as an international deposition at the National Institute of Bioscience and Human-Technology, Agency of Industrial Science and Technology, Ministry of International Trade and Industry (postal code 305-8566, 1–3, Higashi, 1-chome, Tsukuba-shi, Ibaraki-ken, Japan) on Feb. 23, 1996, and it received an accession number of FERM BP-5423 [refer to the description of the aforementioned patent document, paragraphs (0105) to (0110)].

The mutation was introduced by using Quick Change site-directed mutagenesis kit available from Stratagene, United States, and primers corresponding to each mutant enzyme (FIG. 7, SEQ ID NOS: 11–61) according to the manufacturer's protocol. *Escherichia coli* XL-1 was transformed with the PCR product. The transformed cells were plated on an L agar medium plate containing 100 μl/ml of ampicillin, and incubated at 37° C. for 16 hours. The produced colonies were collected, and cultured overnight in L medium containing 100 μl/ml of ampicillin with shaking. The cells were collected from the medium by centrifugation, and the plasmid was extracted by using FlexiPrep Kit available from Pharmacia (Sweden) according to the manufacturer's protocol. The nucleotide sequences coding for the various 3-residue replaced mutant EB-AP were confirmed by DNA sequence analysis.

The synthesis of the primers shown in FIG. 7 was consigned to Japan BioService Co., Ltd.

EXAMPLE 12

Measurement of Transphosphorylation Activity and Reaction Rate Constants of Mutant EB-AP

*Escherichia coli* JM109 transformed with a plasmid containing a gene for one of various 3-residue replaced mutant EB-AP's was inoculated into 50 ml of L medium containing 100 μl/ml of ampicillin and cultured at 37° C. for 16 hours. The cells were collected by centrifugation from the medium, suspended in 3 ml of 25 mM phosphate buffer (pH 7.0), and disrupted by sonication at 4° C. for 20 minutes. The insoluble fraction in the sonicated suspension was removed by centrifugation to prepare a cell free extract. The expression of each EB-AP 3-residue replaced mutant enzyme was confirmed by SDS-PAGE. The expression amount was about 20% of the total protein.

The transphosphorylation activity of the cell free extract was measured under the following conditions. A reaction mixture (1 ml) containing 2 mM inosine, 100 mM sodium pyrophosphate, 100 mM acetate buffer (pH 4.0) and 100 μl of the cell free extract was incubated at pH 4 and 30° C. for 10 minutes. After 200 μl of 1 N hydrochloric acid was added to stop the reaction, the precipitates were removed by centrifugation, and the produced 5'-inosinic acid was quantified. The transphosphorylation activity of each 3-residue replaced mutant EB-AP was represented with a relative activity, which was a ratio of the amount of 5'-inosinic acid produced by the 3-residue replaced mutant over that produce by the G74D/I153T mutant, to which the third mutation was introduced.

Then, the Km value for inosine in the transphosphorylation reaction by each 3-residue replaced mutant EB-AP was measured under the following conditions. A reaction mixture (1 ml) containing 100 mM sodium pyrophosphate, 100 mM acetate buffer (pH 4.0), 10–100 mM inosine and 100 μl of the cell free extract was incubated at pH 4 and 30° C. for 10 minutes. After 200 μl of 1 N hydrochloric acid was added to stop the reaction, the precipitates were removed by centrifugation, and the produced 5'-inosinic acid was quantified. The Km value was calculated by the Hanes-Woolf plotting. The results are shown in Table 3.

TABLE 3

|  | Km value | Transphosphorylation activity |
|---|---|---|
| S72F/G74D/I153T | 20 mM | 2.80 |
| S72Y/G74D/I153T | 25 mM | 2.04 |
| S72W/G74D/I153T | 30 mM | 1.71 |
| S72D/G74D/I153T | 33 mM | 1.59 |
| S72V/G74D/I153T | 40 mM | 2.46 |
| S72E/G74D/I153T | 40 mM | 3.19 |
| S72M/G74D/I153T | 46 mM | 1.94 |
| S72T/G74D/I153T | 50 mM | 1.91 |
| S72L/G74D/I153T | 57 mM | 2.24 |
| S72R/G74D/I153T | 59 mM | 1.99 |
| S72Q/G74D/I153T | 77 mM | 2.42 |
| S72K/G74D/I153T | 78 mM | 1.53 |
| S72P/G74D/I153T | 109 mM | 1.34 |
| S72A/G74D/I153T | 115 mM | 0.78 |
| S72N/G74D/I153T | 124 mM | 0.43 |
| S72G/G74D/I153T | 137 mM | 0.43 |
| S72H/G74D/I153T | N.D. | N.D. |
| G74D/I153T | 100 mM | 1.00 |
| 10-Residue replaced mutant enzyme | 40 mM | 1.44 |

In Example 10, all of the mutants expected to have improved affinity for inosine due to the π—π interaction, the CH/π interaction and the electrostatic interaction (S72F, S72Y, S72W, S72V, S72E, S72D) showed decreased Km value for inosine compared with that of the G74D/I153T mutant EB-AP, in which Ser72 is unchanged, and thus they showed improved affinity for inosine. Further, they also showed improvement in transphosphorylation activity. In particular, the S72F mutant showed marked improvements in both of the Km value and the transphosphorylation activity. It is estimated that the aromatic ring of phenylalanine and the inosine base caused the π—π interaction in

23 suitable positional relationship, and thus the affinity was improved. The Km values of S72M, S72T, S72R, S72Q and S72K mutants also decreased. It was considered that some preferred interactions such as hydrophobic interaction and formation of hydrogen bonds were caused between these amino acid residues and the nucleoside base. Incidentally, a gene could not be produced for S72I. Further, considering the possibility that the S72C mutation causes an erroneous S—S bond, it was not produced.

5'-Inosinic acid was analyzed by high performance liquid chromatography (HPLC) under the following conditions.

Column: Cosmosil 5C18-AR (4.6×150 mm), produced by Nakarai Tesque

Mobile phase: 5 mM potassium phosphate buffer (pH 2.8)/ methanol= 95/5

Flow rate: 1.0 ml/min

Temperature: room temperature

Detection: UV 245 nm

Example 13

Production of 5'-Inosinic Acid Using *Escherichia coli* JM109 to which S72F/G74D/I153T Mutant EB-AP Gene is Introduced

*Escherichia coli* JM109 transformed with a plasmid containing a gene for G74D/I153T mutant, 10-residue replaced mutant or S72F/G74D/I153T mutant EB-AP was inoculated into 50 ml of L medium containing 100 µg/ml of ampicillin and 1 mM of IPTG, and cultured at 37° C. for 16 hours.

Cells of *Escherichia coli* JM109 introduced with each of the aforementioned mutant EB-AP genes were added at a density of 100 mg/dl in terms of dry cell weight to a solution in an acetate buffer (pH 4.0) containing 12 g/dl of pyrophosphoric acid and 6 g/dl of inosine, and reaction was performed at 30° C. for 24 hours while pH was maintained at 4.0. The results of measurement of the produced amount of 5'-inosinic acid are shown in Table 4. The produced inosinic acid consisted only of 5'-inosinic acid, and 2'-inosinic acid and 3'-inosinic acid byproducts were not observed at all.

In the reaction utilizing *Escherichia coli* JM109 introduced with the plasmid containing the G74D/I153T mutant EB-AP gene, 7.5 g/dl of 5'-inosinic acid was produced and accumulated, but the accumulation did not increase even if the reaction time was prolonged. In the reaction utilizing *Escherichia coli* JM109 introduced with the plasmid containing the 10-residue replaced mutant EB-AP gene, the accumulation was improved, and 12.1 g/dl of 5'-inosinic acid was produced and accumulated. In the reaction utilizing *Escherichia coli* JM109 transformed with the plasmid containing the S72F/G74D/I153T mutant EB-AP gene, which was designed and constructed based on the three-dimensional structure, the productivity was further improved, and 13.2 g/dl of 5'-inosinic acid was produced and accumulated.

TABLE 4

| Introduced mutant enzyme gene | Produced inosinic acid (g/dl) |
| --- | --- |
| G74D/I153T | 7.5 |
| 10-Residue replaced mutant | 12.1 |
| S72F/G74D/I153T | 13.2 |

24

EXAMPLE 14

Measurement of Transphosphorylation Activity and Reaction Rate Constant of 3-Residue Replaced Mutant EB-AP, in which L16W, S71W, S73W, E104F or E104W Mutation is Introduced Since it was considered that the S72F mutation improved the affinity for inosine by the π—π interaction, other amino acid residues that could be expected to cause the π—π interaction with the inosine base by replacement with an aromatic amino acid were searched on computer graphics. As a result, there was suggested possibility that an aromatic ring introduced by L16W, S71W, S73W, E104F and E104W might interact with the inosine base. Therefore, these five kinds of 3-residue replaced mutant EB-AP's were prepared (based on the G74D/I153T mutant EB-AP) by the method described in Example 11 (primers corresponding to each mutant enzyme were shown in FIG. 8A, SEQ ID NOS: 62–76), and their transphosphorylation activity and reaction rate constant were measured by the method described in Example 12. The results are shown in Table 5. Although the transphosphorylation activity decreased in all of the mutant enzymes, the Km value decreased in all of the mutant enzymes and thus it was suggested that the affinity for inosine was improved. Although Leu16 was separated by 10 Å (in terms of the distance between Cα's) from Ser72, which was considered to surely interacts with inosine, it was demonstrated that the interaction with inosine was possible, even if it was separated by such a distance.

The synthesis of the primer sets shown in FIG. 8A was consigned to Japan BioService Co., Ltd.

TABLE 5

| | Km value | Transphosphorylation activity |
| --- | --- | --- |
| L16W/G74D/I153T | 33 mM | 0.21 |
| S71W/G74D/I153T | 75 mM | 0.26 |
| S73W/G74D/I153T | 29 mM | 0.77 |
| E104F/G74D/I153T | 61 mM | 0.65 |
| E104W/G74D/I153T | 67 mM | 0.26 |
| G74D/I153T | 100 mM | 1.00 |
| 10-Residue replaced mutant enzyme | 40 mM | 1.44 |

EXAMPLE 15

Construction of 10-Residue Replaced Mutant EB-AP, in which A72F or A72E Mutation is Introduced, and Measurement of Transphosphorylation Activity and Reaction Rate Constant Thereof The S72F mutation that decreased the Km value in the highest degree and the S72E mutation that enhanced the activity in the highest degree in Example 12 were introduced into the 10-residue replaced mutant EB-AP. Since Ser72 was replaced with Ala in the 10-residue replaced mutant EB-AP, the A72F and A72E mutations were actually introduced. When a wild-type EB-AP is considered as standard, ten residues were replaced in the both. These two kinds of mutants were produced by the method described in Example 11 (primers corresponding to each mutant enzyme are shown in FIG. 8B, SEQ ID NOS: 77–82). As a template for site-directed mutagenesis utilizing PCR, plasmid pEMP370 (Japanese Patent Laid-open (Kokai) No. 9-37785/1997, Example 19) containing a 10-residue replaced mutant EB-AP gene was used. Furthermore, transphosphorylation activity and reaction rate constant were measured by the method described in Example 12. The results are shown in Table 6. The transphosphorylation activity was represented in terms of relative activity, which was a ratio of the amount of 5'-inosinic acid produced by the 3-residue replaced mutant over that produce by the G74D/I153T mutant, to which the third mutation was introduced. In both of the mutant enzymes, the Km value markedly decreased. As for the transphosphorylation activity, it was decreased by the A72F mutation, whereas it was increased by A72E mutation.

TABLE 6

|  | Km value | Transphosphorylation activity |
| --- | --- | --- |
| A72F/10-residue replaced mutant enzyme | 9 mM | 0.11 |
| A72E/10-residue replaced mutant enzyme | 15 mM | 2.30 |
| 10-residue replaced mutant enzyme | 40 mM | 1.44 |

EXAMPLE 16

Production of 5'-Inosinic Acid Utilizing *Escherichia coli* JM109 to which Gene for A72F/10-Residue Replaced Mutant EB-AP or Gene for A72E/10-Residue Replaced Mutant EB-AP is Introduced Experimental production of 5'-inosinic acid was performed by the method described in Example 13 using *Escherichia coli* JM109 transformed with a plasmid containing the genes for A72E/10-residue replaced mutant or A72F/10-residue replaced mutant EB-AP. The results are shown in Table 7. The accumulation amount of 5'-inosinic acid increased in the both mutants.

TABLE 7

| Introduced mutant enzyme gene | Produced inosinic acid (g/dl) |
| --- | --- |
| A72F/10-residue replaced mutant | 13.9 |
| A72E/10-residue replaced mutant | 13.9 |
| 10-residue replaced mutant | 12.1 |

EXAMPLE 17

Construction of Mutant EB-AP, in which I103D and T153N Mutations are Introduced, and Measurement of Transphosphorylation Activity and Reaction Rate Constant The model shown in FIG. 3 suggested that Asp introduced by the I103D mutation caused electrostatic interaction with the inosine base and Asn introduced by the T153N mutation formed a hydrogen bond with a hydroxyl group of ribose. Therefore, I103D/G74D/I153T mutant EB-AP and G74D/I153N mutant EB-AP were produced by introducing these residues into the G74D/I153T mutant EB-AP in a manner described in Example 11 (primers corresponding to each mutant enzyme were shown in FIG. 8C, SEQ ID NOS: 83–88). Further, transphosphorylation activity and reaction rate constant were measured by the method described in Example 12. The results are shown in Table 8. The transphosphorylation activity was represented in terms of relative activity, which was a ratio of the amount of 5'-inosinic acid produced by the 3-residue replaced mutant over that produce by the G74D/I153T mutant, to which the third mutation was introduced. In the both mutants, the transphosphorylation activity decreased, whereas the Km value decreased. Thus, it was demonstrated that the affinity for inosine was improved.

TABLE 8

|  | Km value | Transphosphorylation activity |
| --- | --- | --- |
| I103D/G74D/I153T | 51 mM | 0.09 |
| G74D/I153N | 38 mM | 0.18 |
| G74D/I153T | 100 mM | 1.00 |

EXAMPLE 18

Construction of Mutant EB-AP in which Leu140 is Replaced with Phe, Glu or Lys and Measurement of Transphosphorylation Activity and Reaction Rate Constant Although Leu140 is separated from Ser72 more than 10 Å, it is located at a position immediately adjacent to the phosphate binding site in the three-dimensional structure of the reaction intermediate analogue. Therefore, it was considered that, if this residue was replaced, the structure around the phosphate binding site of the reaction intermediate would be changed, and as a result, the structure and fluctuation of the nucleoside binding site would also be affected. It is expected that, if this residue is replaced with more bulky Phe, positively charged Lys or negatively charged Glu, the affinity for a nucleoside may be changed. It was decided that the mutations should be introduced into the A72E/10-residue replaced enzyme, which showed high transphosphorylation activity in Example 15. These three kinds of mutants were produced by the method described in Example 11 (primers corresponding to each mutant enzyme are shown in FIG. 8D, SEQ ID NOS: 89–97). As a template for site-directed mutagenesis utilizing PCR, a plasmid containing the gene for A72E/10-residue replaced mutant EB-AP was used. Furthermore, transphosphorylation activity and reaction rate constant were measured by the method described in Example 12. The results are shown in Table 9. The transphosphorylation activity was represented in terms of relative activity, which was a ratio of the amount of 5'-inosinic acid produced by the 3-residue replaced mutant over that produce by the G74D/I153T mutant, to which the third mutation was introduced.

TABLE 9

|  | Km value | Transphosphorylation activity |
| --- | --- | --- |
| A72E/L140F/10-residue replaced mutant enzyme | 9 mM | 1.66 |
| A72E/L140K/10-residue replaced mutant enzyme | 78 mM | 0.07 |
| A72E/L140E/10-residue replaced mutant enzyme | 322 mM | 0.16 |

TABLE 9-continued

| | Km value | Transphosphorylation activity |
|---|---|---|
| A72E/10-residue replaced mutant enzyme | 15 mM | 2.30 |

The mutant, in which L140F mutation is introduced, showed decreased Km value. Conversely, L140K and L140E mutations markedly increased Km.

EXAMPLE 19

Purification of Wild-Type Acid Phosphatase Derived from Enterobacter Aerogenes IFO12010 and Determination of N-Terminus Amino Acid Sequence Thereof An acid phosphatase derived from *Enterobacter aerogenes* IFO12010 was purified from cultured cells of *Escherichia coli* JM109/pENP110 described in Japanese Patent Laid-open (Kokai) No. 10-201481/1998, Example 24, and its N-terminus amino acid sequence was determined to determine the amino acid sequence of the mature protein. *Escherichia coli* JM109/pENP110 is a bacterium prepared by introducing an acid phosphatase gene derived from *Enterobacter aerogenes* IFO12010 into *Escherichia coli* JM109 strain, and it produces the acid phosphatase. The amino acid sequence of a precursor protein deduced from the nucleotide sequence of this acid phosphatase gene corresponds to the sequence shown in SEQ ID NO: 10. The amino acid sequence shown in SEQ ID NO: 10 is an amino acid sequence of L61Q/A63Q/E64A/N67D/S69A/G72D/T133K/E134D/I151T mutant EA-AP.

50 ml of the nutrient medium (pH 7.0) containing 1 g/dl of peptone, 0.5 g/dl of yeast extract and 1 g/dl of sodium chloride was put into 500-ml Sakaguchi flask, and sterilized by heating at 120° C. for 20 minutes. One platinum loop of *Escherichia coli* JM109/pENP110 was inoculated into the medium, and cultured at 30° C. for 16 hours with shaking. The cells were collected from the medium by centrifugation, suspended in 100 mL of 100 mM potassium phosphate buffer (pH 7.0), and disrupted by sonication at 4° C. for 20 minutes. The insoluble fraction in the sonicated suspension was removed by centrifugation to prepare a cell free extract. Ammonium sulfate was added to this cell free extract to 30% saturation. After the produced precipitates were removed by centrifugation, ammonium sulfate was further added to the supernatant solution to 60% saturation. The produced precipitates were collected by centrifugation and dissolved in 100 mM potassium phosphate buffer. This crude enzyme solution was dialyzed three times against 500 mL of 100 mM potassium phosphate buffer (pH 7.0), then loaded on a DEAE-Toyopearl 650M column (φ3.0×10.0 cm) equilibrated with 20 mM potassium phosphate buffer (pH 7.0), and washed with 20 mM potassium phosphate buffer (pH 7.0). Since the transphosphorylation activity was found in a passing fraction, that fraction was collected. The fraction was added with ammonium sulfate to 35% saturation, and adsorbed on a Butyl Toyopearl column (+3.0×7.0 cm) equilibrated with 20 mM potassium phosphate buffer (pH 7.0) containing 35% saturated ammonium sulfate. The fraction was eluted with a linear concentration gradient of 35% saturated to 20% saturated potassium phosphate buffer (pH 7.0). The active fractions were collected, dialyzed against 1 L of 10 mM potassium phosphate buffer (pH 6.0), and adsorbed on a CM-Toyopearl column (φ3.0×7.0 cm) equilibrated with 10 mM potassium phosphate buffer (pH 6.0). The fractions were eluted with a linear concentration gradient of potassium phosphate buffer (pH 6.0) containing 0 mM to 300 mM potassium chloride. The active fractions were collected.

As a result of the above procedure, an enzyme exhibiting transphosphorylation activity was finally purified by about five times from the cell free extract at a recovery ratio of about 16%. This enzyme preparation was confirmed to be uniform by SDS-polyacrylamide gel electrophoresis.

This purified enzyme was adsorbed on a DITC membrane (produced by Milligen/Biosearch), and the amino acid sequence of its N-terminus was determined by using Prose-quencer 6625 (produced by Milligen/Biosearch). As a result, the amino acid sequence of the five residues at the N-terminus was determined, which is shown in SEQ ID NO: 98. Since the N-terminus of the purified enzyme was started from the 21st leucine residue (amino acid number 1) of the sequence of SEQ ID NO: 10, it was considered that the amino acid sequence shown in SEQ ID NO: 10 was a sequence of a precursor protein, and the peptide from the 1st methionine residue (amino acid number 20) to the 20th alanine residue (amino acid number 1) was removed after translation. Based on this result, it was considered that the amino acid sequence of the mature protein corresponded to the sequence of the amino acid numbers 1–228 of the sequence shown in SEQ ID NO: 10.

EXAMPLE 20

Construction of Gene for Mutant Enzyme of Acid Phosphatase Derived from Enterobacter aerogenes (EA-AP) and Production of 5'-Inosinic Acid Using Escherichia coli JM109 to which that Gene is Introduced It was decided that a mutation homologous to the three mutations of S72F/G74D/I153T, which enhanced the transphosphorylation activity for inosine in EB-AP, was introduced into EA-AP. The result of alignment of the amino acid sequences of EB-AP and EA-AP (wild-type) performed by using the program BLAST is shown in FIG. 9. It was demonstrated that Ser72/Gly74/Ile153 of EB-AP corresponded to Ala70/Gly72/Ile151 in EA-AP. Therefore, A70F/G72D/I151T mutant EA-AP was produced by the method described in Example 11. 5'-Inosinic acid was produced from inosine by using *Escherichia coli* JM109 transformed with a plasmid containing the mutant enzyme gene by the method described in Example 13. The results are shown in Table 10. The A70F/G72D/I151T mutant EA-AP showed 5'-inosinic acid producing ability comparable to that of the S72F/G74D/I153T mutant EB-AP.

TABLE 10

| Introduced mutant enzyme gene | Produced inosinic acid (g/dl) |
|---|---|
| EA-AP A72F/G74D/I153T | 13.1 |
| EB-AP S72F/G74D/I153T | 13.2 |

FIG. 9 shows the result of amino acid sequence alignment of EB-AP and the acid phosphatase derived from *Enterobacter aerogenes* (EA-AP) performed by using the program BLAST. The upper row indicates EB-AP and the lower row indicates EA-AP. In the middle row, if the residues of the both are identical, the name of the residue is indicated, and if they are analogous even though they are not identical, + is indicated. The position of the 72nd residue (Ser72) of EB-AP was indicated with [72]. The corresponding residue in EA-AP is Ala70.

EXAMPLE 21

High Expression of Enzyme Caused by Modification of Promoter Sequence in Novel Mutant Acid Phosphatase Gene Derived from *Enterobacter* Aeroagenes IFO12010

A site-specific mutation was introduced by a genetic engineering technique into the promoter sequence segment of the gene coding for the mutant acid phosphatase derived from *Enterobacter aerogenes* IFO12010 to construct a gene coding for a mutant acid phosphatase exhibiting increased enzyme expression amount. As a gene for introducing a mutation, a plasmid pENP170 that contained a mutant EA-AP gene coding for L61Q/A63Q/E64A/N67D/S69A/G72D/T133K/E134D/I151T mutant EA-AP was used. pENP170 was prepared as follows.

From a plasmid pENP110 containing the gene coding for a wild-type acid phosphatase derived from *Enterobacter aerogenes* IFO12010 obtained by the method described in Japanese Patent Laid-open (Kokai) No. 10-201481/1998, Example 24, a DNA fragment having a size of 1.6 kbp and containing a gene coding for the wild-type acid phosphatase was excised with restriction enzymes SalI and KpnI, and ligated to pUC19 (product produced by Takara Shuzo Co. Ltd.) digested with SalI and KpnI. This plasmid was designated as pENP120. The following mutations were introduced into pENP120 by site-specific mutagenesis to obtain pENP170. The nucleotide sequence of the SalI-KpnI 1.6 kbp DNA fragment in pENP170 was a sequence shown in SEQ ID NO: 9.

72Gly (GGC)->Asp (G*AC)
151Ile (ATC)->Thr (A*CC)
61Leu (CTG)->Gln (C*AG)
63Ala (GCT)->Gln (*C*A*G)
64Glu (GAA)->Ala (G*CA)
67Asn (AAC)->Asp (*GAC)
69Ser (AGC)->Ala (*G*CC)
133Thr (ACC)->Lys (A*A*A)
134Glu (GAG)->Asp (GA*C)

The mutations were introduced into the promoter sequence segment of the mutant EA-AP gene contained in pENP170 by using Quick Change site-directed mutagenesis kit produced by Stratagene. The mutation was introduced according to the protocol of Stratagene by using oligonucleotides for introduction of mutation, MUT170 (SEQ ID NO: 99) and MUT171 (SEQ ID NO: 100), which were synthesized by using a DNA synthesizer (Model 394 produced by Applied Biosystem), and pENP170 as a template.

*Escherichia coli* JM109 (produced by Takara Shuzo) was transformed with the obtained plasmid DNA in a conventional manner. The cells were plated on L agar medium containing 100 µg/ml of ampicillin to obtain transformants. A plasmid was prepared from the transformants by the alkali lysis method, and their nucleotide sequence was determined to confirm that the target nucleotides were replaced. The determination of the nucleotide sequences was performed according to the method of Sanger et al. (J. Mol. Biol., 143, 161 (1980)) using Taq DyeDeoxy Terminator Cycle Sequencing Kit (produced by Applied Biochemical).

As described above, a mutant gene was constructed, in which the nucleotide sequence of −10 region of the deduced promoter sequence located upstream from the coding region of the deduced acid phosphatase derived from *Enterobacter aerogenes* IFO12010 was changed from AAAAAT to TATAAT, which was the same as lac promoter of *Escherichia coli*. The plasmid containing this mutant gene was designated as pENP180.

*Escherichia coli* JM109/pENP170 and *Escherichia coli* JM109/pENP180 introduced with the gene of which −10 region of the promoter sequence was modified were each inoculated to 50 ml of L medium containing 100 µg/ml of ampicillin and 50 ml of L medium containing 100 µg/ml of ampicillin added with 1 mM of IPTG, respectively, and cultured at 37° C. for 16 hours. The cells were collected by centrifugation from each medium of each strain, and washed once with physiological saline. The cells of each culture was added in an amount of 100 mg/dl in terms of dry cell weight to a solution containing 15 g/dl of pyrophosphoric acid and 8 g/dl of inosine dissolved in 100 mM acetate buffer (pH 4.0), and allowed to react at 30° C. for 1 hour while pH was maintained at 4.0. The amounts of the produced 5'-inosinic acid are shown in Table 11.

Inosine and 5'-inosinic acid were analyzed by high performance liquid chromatography (HPLC) under the following conditions.

Column: Cosmosil 5C18-AR (4.6×150 mm, produced by Nakarai Tesque)
Mobile phase: 5 mM potassium phosphate buffer (pH 2.8)/methanol=95/5
Flow rate: 1.0 ml/min
Temperature: room temperature
Detection: UV 245 nm

*Escherichia coli* JM109/pENP170 showed low activity with no addition of IPTG, whereas *Escherichia coli* JM109/pENP180 showed high activity even with no addition of IPTG. Further, *Escherichia coli* JM109/pENP180 showed further higher activity with addition of IPTG. Thus, the effectiveness of the modification of the promoter region was demonstrated.

TABLE 11

| Strain | IPTG | Produced 5'-inosinic acid (g/dl) |
|---|---|---|
| *Escherichia coli* JM109/pENP170 | Not added | 0.73 |
| | Addition of 1 mM | 3.09 |
| *Escherichia coli* JM109/PENP180 | Not added | 2.86 |
| | Addition of 1 mM | 3.37 |

EXAMPLE 22

Construction of Gene Coding for Novel Mutant Acid Phosphatase Derived from *Enterobacter Aerogenes* IFO01210 Showing Improved Affinity for Nucleoside A site specific mutation was introduced into the mutant acid phosphatase gene derived form *Enterobacter aerogenes* IFO12010 constructed in Example 21 by a genetic engineering technique to prepare a gene coding for a mutant acid phosphatase of which affinity for a nucleoside, in particular, guanosine, was improved. As the replacements of amino acid residues, a combination of the amino acid residue replacements identified to contribute to the enhancement of the affinity based on the three-dimensional structure analysis of the *Escherichia blattae* enzyme was introduced.

The mutations were introduced into the plasmid DNA by using Quick Change site-directed mutagenesis kit produced by Stratagene. Twenty kinds of oligonucleotides (Table 12) for introduction of mutation from MUT180 (SEQ ID NO: 101) to MUT521 (SEQ ID NO: 120) were synthesized by using a DNA synthesizer (Model 394 produced by Applied Biosystem). The mutations were introduced according to the protocol of Stratagene by using pENP170 as the first template and MUT180 and MUT181 as oligonucleotides for introduction of mutation.

*Escherichia coli* JM109 (produced by Takara Shuzo) was transformed with each obtained plasmid DNA in a conventional manner. The cells were plated on L agar medium containing 100 μg/ml of ampicillin to obtain transformants. A plasmid was prepared from the transformants by the alkali lysis method, and the nucleotide sequence was determined to confirm that the target nucleotide was replaced. The determination of the nucleotide sequence was performed according to the method of Sanger et al. (J. Mol. Biol., 143, 161 (1980)) using Taq DyeDeoxy Terminator Cycle Sequencing Kit (produced by Applied Biochemical). As described above, a gene coding for a mutant acid phosphatase was constructed, in which 153rd threonine residue (ACC) was replaced with a serine residue (TCC), and a plasmid containing this mutant gene was designated as pENP200.

By using a plasmid introduced with a mutation as a new template, the same procedure was repeated to cumulatively introduce site-specific mutations. Plasmids were prepared from the transformants by the alkali lysis method, and their nucleotide sequences were determined to confirm that the target nucleotides were replaced. The prepared mutant enzyme genes coding for mutant acid phosphatases and the mutation sites thereof are shown in Table 13. The amino acid residues of the mutation sites represents the amino acid residues in the amino acid sequence shown in SEQ ID NO: 10.

*Escherichia coli* JM109/pENP180, *Escherichia coli* JM109/pENP320, *Escherichia coli* JM109/pENP340, *Escherichia coli* JM109/pENP410, *Escherichia coli* JM109/pENP510 and *Escherichia coli* JM109/pENP520, which were introduced with a plasmid containing each mutant acid phosphatase gene, were each inoculated to 50 ml of L medium containing 100 pg/ml of ampicillin and 1 mM of IPTG, and cultured at 37° C. for 16 hours. The cells were suspended in 50 mL of 100 mM potassium phosphate buffer (pH 7.0), and disrupted by sonication at 4° C. for 20 minutes. The cells were collected from each medium by centrifugation, and washed once with physiological saline. The insoluble fraction in the sonicated suspension was removed by centrifugation to prepare a cell free extract. Km values for inosine and guanosine in the transphosphorylation reaction were measured by using each cell free extract.

The measurement of the transphosphorylation activity for a nucleoside was performed under the following conditions by using inosine and guanosine as substrates. The reaction was performed in a reaction mixture (1 ml) containing various concentrations of inosine or guanosine, 100 μmol/ml of sodium pyrophosphate, 100 μmol/ml of sodium acetate buffer solution (pH 4.0) and each enzyme at pH 4.0 and 30° C. for 10 minutes. After the reaction was stopped by adding 200 μl of 2 N hydrochloric acid, the precipitates were removed by centrifugation, and 5'-inosinic acid or 5'guanylic acid produced by the transphosphorylation reaction was quantified. Inosine, guanosine, 5'inosinic acid and 5'-guanylic acid were analyzed by high performance liquid chromatography (HPLC) under the same conditions as Example 21.

The transphosphorylation activity was measured by changing the concentration of inosine or guanosine in the reaction conditions using the aforementioned composition, and rate constants of inosine and guanosine in the transphosphorylation reaction were determined by Hanes-Woolf plot (Biochem. J., 26, 1406 (1932)). The results are shown in Table 14. As for the Km values of the mutant enzymes produced in the examples, the Km values for guanosine markedly decreased, and thus it was revealed that the affinity for guanosine was improved. Moreover, the Km values for inosine were also markedly reduced in the four kinds of mutant enzymes other than the mutant enzyme encoded by pENP520.

TABLE 13

| Plasmid | Plasmid introduced with mutation | Primer used for introduction of mutation | Mutation point and amino acid replacement |
|---|---|---|---|
| PENP180 | | | 61L(CTG) → Q(CAG) |
| | | | 63A(GCT) → Q(CAG) |
| | | | 64E(GAA) → A(GCA) |
| | | | 67N(AAC) → D(GAC) |
| | | | 69S(AGC) → A(GCC) |
| | | | 72G(GGC) → D(GAC) |
| | | | 133T(ACC) → K(AAA) |
| | | | 134E(GAG) → D(GAC) |
| | | | 151I(ATC) → T(ACC) |
| pENP200 | pENP130 | MUT180, MUT181 | 61L(CTG) → Q(CAG) |
| | | | 63A(GCT) → Q(CAG) |
| | | | 64E(GAA) → A(GCA) |
| | | | 67N(AAC) → D(GAC) |
| | | | 69S(AGC) → A(GCC) |
| | | | 72G(GGC) → D(GAC) |
| | | | 133T(ACC) → K(AAA) |
| | | | 134E(GAG) → D(GAC) |
| | | | 151T(ACC) → S(TCC) |
| pENP300 | pENP200 | MUT300, MUT301 | 61L(CTG) → Q(CAG) |
| | | | 63A(GCT) → Q(CAG) |
| | | | 64E(GAA) → A(GCA) |
| | | | 67N(AAC) → D(GAC) |
| | | | 69S(AGC) → A(GCC) |
| | | | 72G(GGC) → D(GAC) |
| | | | 133T(ACC) → K(AAA) |
| | | | 134E(GAG) → D(GAC) |
| | | | 151I(ATC) → T(ACC) |
| | | | 149T(ACC) → S(TCC) |
| | | | 151T(ACC) → S(TCC) |
| pENP310 | pENP300 | MUT310, MUT311 | 61L(CTG) → Q(CAG) |
| | | | 63A(GCT) → Q(CAG) |
| | | | 64E(GAA) → A(GCA) |
| | | | 67N(AAC) → D(GAC) |
| | | | 69S(AGC) → A(GCC) |
| | | | 70A(GCC) → V(GTT) |
| | | | 72G(GGC) → D(GAC) |
| | | | 133T(ACC) → K(AAA) |
| | | | 134E(GAG) → D(GAC) |
| | | | 151I(ATC) → T(ACC) |
| | | | 149T(ACC) → S(TCC) |
| | | | 151T(ACC) → S(TCC) |
| pENP320 | pENP310 | MUT320, MUT321 | 61L(CTG) → Q(CAG) |
| | | | 63A(GCT) → Q(CAG) |
| | | | 64E(GAA) → A(GCA) |
| | | | 67N(AAC) → D(GAC) |
| | | | 69S(AGC) → A(GCC) |
| | | | 70A(GCC) → V(GTT) |
| | | | 72G(GGC) → D(GAC) |
| | | | 102E(GAG) → L(CTG) |
| | | | 133T(ACC) → K(AAA) |
| | | | 134E(GAG) → D(GAC) |
| | | | 149T(ACC) → S(TCC) |
| | | | 151T(ACC) → S(TCC) |

TABLE 13-continued

| Plasmid | Plasmid introduced with mutation | Primer used for introduction of mutation | Mutation point and amino acid replacement |
|---|---|---|---|
| pENP330 | pENP300 | MUT330, MUT331 | 61L(CTG) → Q(CAG)<br>63A(GCT) → Q(CAG)<br>64E(GAA) → A(GCA)<br>67N(AAC) → D(GAC)<br>69S(AGC) → A(GCC)<br>70A(GCC) → M(ATG)<br>72G(GGC) → D(GAC)<br>133T(ACC) → K(AAA)<br>134E(GAG) → D(GAC)<br>149T(ACC) → S(TCC)<br>151T(ACC) → S(TCC) |
| pENP340 | pENP330 | MUT340, MUT341 | 61L(CTG) → Q(CAG)<br>63A(GCT) → Q(CAG)<br>64E(GAA) → A(GCA)<br>67N(AAC) → D(GAC)<br>69S(AGC) → A(GCC)<br>70A(GCC) → V(GTT)<br>72G(GGC) → D(GAC)<br>102E(GAG) → Q(CAG)<br>133T(ACC) → K(AAA)<br>134E(GAG) → D(GAC)<br>149T(ACC) → S(TCC)<br>151T(ACC) → S(TCC) |
| pENP400 | pENP200 | MUT400, MUT401 | 61L(CTG) → Q(CAG)<br>63A(GCT) → Q(CAG)<br>64E(GAA) → A(GCA)<br>67N(AAC) → D(GAC)<br>69S(AGC) → A(GCC)<br>72G(GGC) → D(GAC)<br>133T(ACC) → K(AAA)<br>134E(GAG) → D(GAC)<br>149T(ACC) → A(GCT)<br>151T(ACC) → S(TCC) |
| pENP410 | pENP400 | MUT310, MUT311 | 61L(CTG) → Q(CAG)<br>63A(GCT) → Q(CAG)<br>64E(GAA) → A(GCA)<br>67N(AAC) → D(GAC)<br>69S(AGC) → A(GCC)<br>70A(GCC) → V(GTT)<br>72G(GGC) → D(GAC)<br>133T(ACC) → K(AAA)<br>134E(GAG) → D(GAC)<br>149T(ACC) → A(GCT)<br>151T(ACC) → S(TCC) |
| pENP500 | pENP200 | MUT500, MUT501 | 61L(CTG) → Q(CAG)<br>63A(GCT) → Q(CAG)<br>64E(GAA) → A(GCA)<br>67N(AAC) → D(GAC)<br>69S(AGC) → A(GCC)<br>72G(GGC) → D(GAC)<br>133T(ACC) → K(AAA)<br>134E(GAG) → D(GAC)<br>149T(ACC) → G(GGC)<br>151T(ACC) → S(TCC) |
| pENP510 | pENP500 | MUT510, MUT511 | 61L(CTG) → Q(CAG)<br>63A(GCT) → Q(CAG)<br>64E(GAA) → A(GCA)<br>67N(AAC) → D(GAC)<br>69S(AGC) → A(GCC)<br>70A(GCC) → E(GAA)<br>72G(GGC) → D(GAC)<br>133T(ACC) → K(AAA)<br>134E(GAG) → D(GAC)<br>149T(ACC) → G(GGC)<br>151T(ACC) → S(TCC) |
| pENP520 | pENP500 | MUT520, MUT521 | 61L(CTG) → Q(CAG)<br>63A(GCT) → Q(CAG)<br>64E(GAA) → A(GCA)<br>67N(AAC) → D(GAC)<br>69S(AGC) → A(GCC)<br>70A(GCC) → K(AAA)<br>72G(GGC) → D(GAC)<br>133T(ACC) → K(AAA)<br>134E(GAG) → D(GAC)<br>149T(ACC) → G(GGC)<br>151T(ACC) → S(TCC) |

TABLE 14

| | Km value for inosine (mM) | Relative activity when inosine is used as substrate | Km value for guanosine (mM) | Relative activity when guanosine is used as substrate |
|---|---|---|---|---|
| pENP180 | 40 | 1.0 | 40 | 1.0 |
| pENP320 | 19 | 1.9 | 4.6 | 1.5 |
| pENP340 | 19 | 1.4 | 5.1 | 1.3 |
| pENP410 | 18 | 1.0 | 4.9 | 0.70 |
| pENP510 | 17 | 0.55 | 4.0 | 0.39 |
| pENP520 | 46 | 0.63 | 4.4 | 0.21 |

EXAMPLE 23

Transphosphorylation Reaction of Guanosine by *E. coli* Transformed with a Plasmid Containing Gene for Novel Mutant Acid Phosphatase Derived from *Enterobacter Aerogenes* IFO12010 Having Improved Affinity for Guanosine

*Escherichia coli* JM109/pENP180, *Escherichia coli* JM109/pENP320, *Escherichia coli* JM109/pENP340, *Escherichia coli* JM109/pENP410, *Escherichia coli* JM109/pENP510 and *Escherichia coli* JM109/pENP520, which were transformed with a plasmid containing each mutant acid phosphatase gene, were inoculated to 50 ml of L medium containing 100 μg/ml of ampicillin and 1 mM of IPTG, and cultured at 37° C. for 16 hours.

10 g/dl of pyrophosphoric acid and guanosine crystals were made into slurry in water, and subjected grinding treatment by a grinding mill (DYNO-MILL produced by WAB, Switzerland). 6.6 g/dl of the obtained guanosine was dissolved in 100 mM acetate buffer (pH 4.5), added with cells of each strain in an amount of 100 mg/dl in terms of dry cell weight, and allowed to react at 35° C. for 12 hours while pH was maintained at 4.5. The amounts of produced 5'-guanylic acid are shown in Table 15. As shown in the table, all of the strains introduced with a mutant enzyme showed improved productivity compared with the parent strain, *Escherichia coli* JM109/pENP180, and produced and accumulated 5'-guanylic acid with high yield.

TABLE 15

| Strain | Produced 5'-guanylic acid (g/dl) |
|---|---|
| *Escherichia coli* JM109/pENP180 | 9.90 |
| *Escherichia coli* JM109/pENP320 | 10.4 |
| *Escherichia coli* JM109/pENP340 | 10.2 |
| *Escherichia coli* JM109/pENP410 | 11.1 |
| *Escherichia coli* JM109/pENP510 | 11.0 |
| *Escherichia coli* JM109/pENP520 | 10.5 |

INDUSTRIAL APPLICABILITY

As explained above in detail, the present invention provides mutant nucleoside-5'-phosphate producing enzymes of which nucleoside-5'-phosphate producing ability is improved, and methods for producing them. The present invention further provides genes coding for the aforementioned mutant enzymes, recombinant DNA containing the genes and microorganisms that harbor the recombinant DNA, which are useful for a method for producing nucleoside-5'-phosphate.

Further, novel three-dimensional structures of proteins were successfully elucidated by X-ray crystallography techniques.

The mutant nucleoside-5'-phosphate producing enzymes of the present invention can be used for the production of nucleoside-5'-phosphates useful as seasonings, drugs, raw materials therefor and so forth.

What is claimed is:

1. An isolated mutant acid phosphatase with improved nucleoside-5'-phosphate producing ability relative to the wild type enzyme, wherein the enzyme has the amino acid sequence of SEQ ID NO: 125 wherein said amino acid sequence contains substitution of at least one amino acid residue selected from the group consisting of Leu-14, Leu-61, Ala-63, Glu-64, Asn-67, Ser-69, Ala-70, Gly-71, Gly-72, Ile-101, Glu-102, Thr-133, Glu-134, Leu-138, Thr-149, and Ile-151.

2. A gene coding for a mutant acid phosphatase according to claim 1.

3. A recombinant DNA, which contains the gene according to claim 2.

4. A microorganism comprising the recombinant DNA according to claim 3.

5. A method for producing a nucleoside-5' phosphate, which comprises:
reacting a nucleoside and a phosphate donor in the presence of a microorganism according to claim 4 to produce nucleoside-5'-phosphate and collecting the nucleoside-5'-phosphate,
wherein said phosphate donor is a phosphoric acid ester compound, or a salt thereof, selected from the group consisting of polyphosphoric acid, phenyl phosphate, acetyl phosphate, and carbamyl phosphate.

6. The method according to claim 5, wherein said reacting is at a pH ranging from 3.0–5.5.

7. A microorganism comprising the gene according to claim 2.

8. A method for producing a nucleoside-5'-phosphate, which comprises:
reacting a nucleoside and a phosphate donor in the presence of a microorganism according to claim 7 to produce nucleoside-5'-phosphate and collecting the nucleoside-5'-phosphate,
wherein said phosphate donor is a phosphoric acid ester compound, or a salt thereof, selected from the group consisting of polyphosphoric acid, phenyl phosphate, acetyl phosphate, and carbamyl phosphate.

9. The method according to claim 8, wherein said reacting is at a pH ranging from 3.0–5.5.

10. A method for producing a nucleoside-5'-phosphate, which comprises:
reacting a nucleoside and a phosphate donor in the presence of a mutant acid phosphatase according to claim 1 to produce nucleoside-5'-phosphate and collecting the nucleoside-5'-phosphate,
wherein said phosphate donor is a phosphoric acid ester compound, or a salt thereof, selected from the group consisting of polyphosphoric acid, phenyl phosphate, acetyl phosphate, and carbonyl phosphate.

11. The method according to claim 10, wherein said reacting is at a pH ranging from 3.0–5.5.

12. An isolated mutant acid phosphatase having an amino acid sequence of SEQ ID NO: 125 which contains a series of replacements, wherein said replacements are selected from the group consisting of:

(a) Leu-61 with a glutamine residue, Ala-63 with a glutamine residue, Glu-64 with an alanine residue, Asn-67 with an aspartic acid residue, Ser-69 with an alanine residue, Ala-70 with a valine residue, Gly-72 with an aspartic acid residue, Glu-102 with a leucine residue, Thr-133 with a lysine residue, Glu-134 with an aspartic acid residue, Thr-149 with a serine residue and Ile-151 with a serine residue;

(b) replacements of Leu-61 with a glutamine residue, Ala-63 with a glutamine residue, Glu-64 with an alanine residue, Asn-67 with an aspartic acid residue, Ser-69 with an alanine residue, Ala-70 with a valine residue, Gly-72 with an aspartic acid residue, Thr-133 with a lysine residue, Glu-134 with an aspartic acid residue, Thr-149 with a alanine residue and Ile-151 with a serine residue;

(c) replacements of Leu-61 with a glutamine residue, Ala-63 with a glutamine residue, Glu-64 with an alanine residue, Asn-67 with an aspartic acid residue, Ser-69 with an alanine residue, Ala-70 with a glutamic acid residue, Gly-72 with an aspartic acid residue, Thr-133 with a lysine residue, Glu-134 with an aspartic acid residue, Thr-149 with a glycine residue and Ile-151 with a serine residue;

(d) replacements of Leu-61 with a glutamine residue, Ala-63 with a glutamine residue, Glu-64 with an alanine residue, Asn-67 with an aspartic acid residue, Ser-69 with an alanine residue, Ala-70 with a lysine residue, Gly-72 with an aspartic acid residue, Thr-133 with a lysine residue, Glu-134 with an aspartic acid residue, Thr-149 with a glycine residue and Ile-151 with a serine residue; and (e) replacements of Leu-61 with a glutamine residue, Ala-63 with a glutamine residue, Glu-64 with an alanine residue, Asn-67 with an aspartic acid residue, Ser-69 with an alanine residue, Ala-70 with a methionine residue, Gly-72 with an aspartic acid residue, Glu-102 with a glutamine residue, Thr-133 with a lysine residue, Glu-134 with an aspartic acid residue, Thr-149 with a serine residue and Ile-151 with a serine residue.

13. A method for producing a nucleoside-5'-phosphate, which comprises:
reacting a nucleoside and a phosphate donor in the presence of a mutant acid phosphatase according to claim 12 to produce nucleoside-5'-phosphate and collecting the nucleoside-5'-phosphate,
wherein said phosphate donor is a phosphoric acid ester compound, or a salt thereof, selected from the group consisting of polyphosphoric acid, phenyl phosphate, acetyl phosphate, and carbamyl phosphate.

14. The method according to claim 13, wherein said reacting is at a pH ranging from 3.0–5.5.

15. A gene coding for a mutant acid phosphatase according to claim 12.

16. A microorganism comprising the gene according to claim 15.

17. A method for producing a nucleoside-5'-phosphate, which comprises:
reacting a nucleoside and a phosphate donor in the presence of a microorganism according to claim 16 to produce nucleoside-5'-phosphate and collecting the nucleoside-5'-phosphate,
wherein said phosphate donor is a phosphoric acid ester compound, or a salt thereof, selected from the group consisting of polyphosphoric acid, phenyl phosphate, acetyl phosphate, and carbamyl phosphate.

18. The method according to claim 17, wherein said reacting is at a pH ranging from 3.0–5.5.

19. A recombinant DNA, which contains the gene according to claim 15.

20. A microorganism comprising the recombinant DNA according to claim 19.

21. A method for producing a nucleoside-5'-phosphate, which comprises:
reacting a nucleoside and a phosphate donor in the presence of a microorganism according to claim 20 to produce nucleoside-5'-phosphate and collecting the nucleoside-5'-phosphate,
wherein said phosphate donor is a phosphoric acid ester compound, or a salt thereof, selected from the group consisting of polyphosphoric acid, phenyl phosphate, acetyl phosphate, and carbonyl phosphate.

22. The method according to claim 21, wherein said reacting is at a pH ranging from 3.0–5.5.

23. A crystal of an acid phosphatase having an amino acid sequence of SEQ ID NO: 124, which has a space group $P6_322$ of a hexagonal system.

24. A crystal of a mutant enzyme acid phosphatase having an amino acid sequence of SEQ ID NO: 124, wherein the Gly-74 is replaced with an aspartic acid residue and Ile-153 is replaced with a serine residue, which has a space group $P2_12_12_1$ of a rhombic system.

25. A crystal of complex of an acid phosphatase having an amino acid sequence of SEQ ID NO: 124 and molybdate, which has a space group $P3_121$ of a trigonal system.

* * * * *

SEQUENCE LISTING

```
<160> NUMBER OF SEQ ID NOS: 125

<210> SEQ ID NO 1
<211> LENGTH: 1225
<212> TYPE: DNA
<213> ORGANISM: Escherichia blattae
<220> FEATURE:
<221> NAME/KEY: CDS
<222> LOCATION: (331)..(1077)

<400> SEQUENCE: 1
ctgcaggcga aaggcaatgt ggtggccggt gagacggcac tctacgagat taaggataag      60
taactatcca ttattacagg taacagcatt gctcctgagt gtgatgtcat acctgagcgg     120
cgcgggggtt ccccgggccg cttttttta tggggctgcg gtgaggagcg ttatctgctg     180
gccctgtttg tgcaacaaac gcttttattg tgtaattttt gtgacgtata tcaggttttt     240
aagcaccctg tggcgctcat actggcaacc tgttgatatt aagcaacact cttcactcac     300
ggaattaaca cgcacagtaa aggtatacgc atg aaa aaa cgt gtt ctg gca gtt     354
                                  Met Lys Lys Arg Val Leu Ala Val
                                   1               5 tgt ttt gcc gca ttg ttc tct tct cag gcc ctg gcg ctg gtc gct acc      402
Cys Phe Ala Ala Leu Phe Ser Ser Gln Ala Leu Ala Leu Val Ala Thr
         10                  15                  20 ggc aac gac act acc acg aaa ccg gat ctc tac tac ctc aag aac agt      450
Gly Asn Asp Thr Thr Thr Lys Pro Asp Leu Tyr Tyr Leu Lys Asn Ser
 25                  30                  35                  40 gaa gcc att aac agc ctg gcg ctg ttg ccg cca cca ccg gcg gtg ggc      498
Glu Ala Ile Asn Ser Leu Ala Leu Leu Pro Pro Pro Pro Ala Val Gly
                 45                  50                  55 tcc att gcg ttt ctc aac gat cag gcc atg tat gaa cag ggg cgc ctg      546
Ser Ile Ala Phe Leu Asn Asp Gln Ala Met Tyr Glu Gln Gly Arg Leu
             60                  65                  70 ctg cgc aac acc gaa cgc ggt aag ctg gcg gcg gaa gat gca aac ctg      594
Leu Arg Asn Thr Glu Arg Gly Lys Leu Ala Ala Glu Asp Ala Asn Leu
         75                  80                  85 agc agt ggc ggg gtg gcg aat gct ttc tcc ggc gcg ttt ggt agc ccg      642
Ser Ser Gly Gly Val Ala Asn Ala Phe Ser Gly Ala Phe Gly Ser Pro
 90                  95                 100 atc acc gaa aaa gac gcc ccg gcg ctg cat aaa tta ctg acc aat atg      690
Ile Thr Glu Lys Asp Ala Pro Ala Leu His Lys Leu Leu Thr Asn Met
105                 110                 115                 120 att gag gac gcc ggg gat ctg gcg acc cgc agc gcg aaa gat cac tat      738
Ile Glu Asp Ala Gly Asp Leu Ala Thr Arg Ser Ala Lys Asp His Tyr
                125                 130                 135 atg cgc att cgt ccg ttc gcg ttt tat ggg gtc tct acc tgt aat acc      786
Met Arg Ile Arg Pro Phe Ala Phe Tyr Gly Val Ser Thr Cys Asn Thr
            140                 145                 150
```

```
acc gag cag gac aaa ctg tcc aaa aat ggc tct tat ccg tcc ggg cat    834
Thr Glu Gln Asp Lys Leu Ser Lys Asn Gly Ser Tyr Pro Ser Gly His
        155                 160                 165 acc tct atc ggc tgg gct act gcg ctg gtg ctg gca gag atc aac cct    882
Thr Ser Ile Gly Trp Ala Thr Ala Leu Val Leu Ala Glu Ile Asn Pro
    170                 175                 180 cag cgc cag aac gag atc ctg aaa cgc ggt tat gag ctg ggc cag agc    930
Gln Arg Gln Asn Glu Ile Leu Lys Arg Gly Tyr Glu Leu Gly Gln Ser
185                 190                 195                 200 cgg gtg att tgc ggc tac cac tgg cag agt gat gtg gat gcc gcg cgg    978
Arg Val Ile Cys Gly Tyr His Trp Gln Ser Asp Val Asp Ala Ala Arg
            205                 210                 215 gta gtg gga tct gcc gtt gtg gcg acc ctg cat acc aac ccg gcg ttc   1026
Val Val Gly Ser Ala Val Val Ala Thr Leu His Thr Asn Pro Ala Phe
                220                 225                 230 cag cag cag ttg cag aaa gcg aag gcc gaa ttc gcc cag cat cag aag   1074
Gln Gln Gln Leu Gln Lys Ala Lys Ala Glu Phe Ala Gln His Gln Lys
            235                 240                 245 aaa taatcctgac taccgccttg ccttgcaggg cggtagtggt ttccactggc         1127
Lys cccgattcgc tattcccaca gtaataatga cggtatatga ttttgtgcaa cgaaaaggtt  1187
gtgtcacgcc acagcttata agatcatgtg ccgttaac                          1225

<210> SEQ ID NO 2
<211> LENGTH: 249
<212> TYPE: PRT
<213> ORGANISM: Escherichia blattae

<400> SEQUENCE: 2

Met Lys Lys Arg Val Leu Ala Val Cys Phe Ala Ala Leu Phe Ser Ser
1               5                   10                  15

Gln Ala Leu Ala Leu Val Ala Thr Gly Asn Asp Thr Thr Thr Lys Pro
            20                  25                  30

Asp Leu Tyr Tyr Leu Lys Asn Ser Glu Ala Ile Asn Ser Leu Ala Leu
        35                  40                  45

Leu Pro Pro Pro Pro Ala Val Gly Ser Ile Ala Phe Leu Asn Asp Gln
    50                  55                  60

Ala Met Tyr Glu Gln Gly Arg Leu Leu Arg Asn Thr Glu Arg Gly Lys
65                  70                  75                  80

Leu Ala Ala Glu Asp Ala Asn Leu Ser Ser Gly Gly Val Ala Asn Ala
                85                  90                  95

Phe Ser Gly Ala Phe Gly Ser Pro Ile Thr Glu Lys Asp Ala Pro Ala
            100                 105                 110

Leu His Lys Leu Leu Thr Asn Met Ile Glu Asp Ala Gly Asp Leu Ala
        115                 120                 125

Thr Arg Ser Ala Lys Asp His Tyr Met Arg Ile Arg Pro Phe Ala Phe
    130                 135                 140

Tyr Gly Val Ser Thr Cys Asn Thr Thr Glu Gln Asp Lys Leu Ser Lys
145                 150                 155                 160

Asn Gly Ser Tyr Pro Ser Gly His Thr Ser Ile Gly Trp Ala Thr Ala
                165                 170                 175

Leu Val Leu Ala Glu Ile Asn Pro Gln Arg Gln Asn Glu Ile Leu Lys
            180                 185                 190

Arg Gly Tyr Glu Leu Gly Gln Ser Arg Val Ile Cys Gly Tyr His Trp
        195                 200                 205
```

```
Gln Ser Asp Val Asp Ala Ala Arg Val Val Gly Ser Ala Val Val Ala
        210             215                 220
Thr Leu His Thr Asn Pro Ala Phe Gln Gln Gln Leu Gln Lys Ala Lys
225                 230                 235                 240
Ala Glu Phe Ala Gln His Gln Lys Lys
                245

<210> SEQ ID NO 3
<211> LENGTH: 1344
<212> TYPE: DNA
<213> ORGANISM: Morganella morganii
<220> FEATURE:
<221> NAME/KEY: CDS
<222> LOCATION: (316)..(1062)

<400> SEQUENCE: 3
gaattccgga aaatttcatt cattttaatt gttaagaata tgctggcaaa aacaaaaccc      60
aatgctttat attttcttat aatatctgtg tgttatcttt ttcaatacta tcggtcaggt     120
cttatttatc cgttcgttaa caaaagccat gctgtttctg tcaaattatc tgaaaatcat     180
catcaaaaat acttacctgt cttccgtctg tttcgtcaca ctttttttgaa agagttaaca    240 tcaatttgca tctctccgcc ctacactggc agacaggttt ctgagtaata ctgttgtatc     300
tgataaggag atgtc atg aag aag aat att atc gcc ggt tgt ctg ttc tca     351
                Met Lys Lys Asn Ile Ile Ala Gly Cys Leu Phe Ser
                 1               5                  10 ctg ttt tcc ctt tcc gcg ctg gcc gcg atc ccg gcg ggc aac gat gcc    399
Leu Phe Ser Leu Ser Ala Leu Ala Ala Ile Pro Ala Gly Asn Asp Ala
         15                  20                  25 acc acc aag ccg gat tta tat tat ctg aaa aat gaa cag gct atc gac    447
Thr Thr Lys Pro Asp Leu Tyr Tyr Leu Lys Asn Glu Gln Ala Ile Asp
 30                  35                  40 agc ctg aaa ctg tta ccg cca ccg ccg gaa gtc ggc agt att cag ttt    495
Ser Leu Lys Leu Leu Pro Pro Pro Pro Glu Val Gly Ser Ile Gln Phe
45                  50                  55                  60 tta aat gat cag gca atg tat gag aaa ggc cgt atg ctg cgc aat acc    543
Leu Asn Asp Gln Ala Met Tyr Glu Lys Gly Arg Met Leu Arg Asn Thr
                 65                  70                  75 gag cgc gga aaa cag gca cag gca gat gct gac ctg gcc gca ggg ggt    591
Glu Arg Gly Lys Gln Ala Gln Ala Asp Ala Asp Leu Ala Ala Gly Gly
             80                  85                  90 gtg gca acc gca ttt tca ggg gca ttc ggc tat ccg ata acc gaa aaa    639
Val Ala Thr Ala Phe Ser Gly Ala Phe Gly Tyr Pro Ile Thr Glu Lys
         95                 100                 105 gac tct ccg gag ctg tat aaa ctg ctg acc aat atg att gag gat gcc    687
Asp Ser Pro Glu Leu Tyr Lys Leu Leu Thr Asn Met Ile Glu Asp Ala
    110                 115                 120 ggt gat ctt gcc acc cgc tcc gcc aaa gaa cat tac atg cgc atc cgg    735
Gly Asp Leu Ala Thr Arg Ser Ala Lys Glu His Tyr Met Arg Ile Arg
125                 130                 135                 140 ccg ttt gcg ttt tac ggc aca gaa acc tgt aat acc aaa gat cag aaa    783
Pro Phe Ala Phe Tyr Gly Thr Glu Thr Cys Asn Thr Lys Asp Gln Lys
                145                 150                 155 aaa ctc tcc acc aac gga tct tac ccg tca ggt cat acg tct atc ggc    831
Lys Leu Ser Thr Asn Gly Ser Tyr Pro Ser Gly His Thr Ser Ile Gly
            160                 165                 170 tgg gca acc gca ctg gtg ctg gcg gaa gtg aac ccg gca aat cag gat    879
Trp Ala Thr Ala Leu Val Leu Ala Glu Val Asn Pro Ala Asn Gln Asp
        175                 180                 185 gcg att ctg gaa cgg ggt tat cag ctc gga cag agc cgg gtg att tgc    927
```

-continued

| | | | | | | | | | | | | |
|---|---|---|---|---|---|---|---|---|---|---|---|---|
| Ala | Ile | Leu | Glu | Arg | Gly | Tyr | Gln | Leu | Gly | Gln | Ser | Arg | Val | Ile | Cys |
| | | 190 | | | | 195 | | | | 200 | | | |

```
ggc tat cac tgg cag agt gat gtg gat gcc gcg cgg att gtc ggt tca     975
Gly Tyr His Trp Gln Ser Asp Val Asp Ala Ala Arg Ile Val Gly Ser
205             210                 215                 220 gcc gct gtc gcg aca tta cat tcc gat ccg gca ttt cag gcg cag tta    1023
Ala Ala Val Ala Thr Leu His Ser Asp Pro Ala Phe Gln Ala Gln Leu
                225                 230                 235 gcg aaa gcc aaa cag gaa ttt gca caa aaa tca cag aaa taaaagcagt     1072
Ala Lys Ala Lys Gln Glu Phe Ala Gln Lys Ser Gln Lys
            240                 245 gatatctggt cagggcagtg caatatctgc cctgaaatcc ctgtttattc ccacatccag  1132
cggtcttccc gatcccagcc ttttgttttc atgcagctgt agaaatagcg gttgcggctg  1192
tcttcattca catccatcac ataactttcc gttaccggtg tctgctcttt gtaggttttg  1252
ctgttaccgc agtcatcgtc ttttttgcag cgtttctcca catcccgcat cacactgcgc  1312
tgagcaactt cattttttcac cggataaagc tt                              1344
```

<210> SEQ ID NO 4
<211> LENGTH: 249
<212> TYPE: PRT
<213> ORGANISM: Morganella morganii

<400> SEQUENCE: 4

Met Lys Lys Asn Ile Ile Ala Gly Cys Leu Phe Ser Leu Phe Ser Leu
1               5                   10                  15

Ser Ala Leu Ala Ala Ile Pro Ala Gly Asn Asp Ala Thr Thr Lys Pro
                20                  25                  30

Asp Leu Tyr Tyr Leu Lys Asn Glu Gln Ala Ile Asp Ser Leu Lys Leu
            35                  40                  45

Leu Pro Pro Pro Glu Val Gly Ser Ile Gln Phe Leu Asn Asp Gln
        50                  55                  60

Ala Met Tyr Glu Lys Gly Arg Met Leu Arg Asn Thr Glu Arg Gly Lys
65                  70                  75                  80

Gln Ala Gln Ala Asp Ala Asp Leu Ala Ala Gly Val Ala Thr Ala
                85                  90                  95

Phe Ser Gly Ala Phe Gly Tyr Pro Ile Thr Glu Lys Asp Ser Pro Glu
            100                 105                 110

Leu Tyr Lys Leu Leu Thr Asn Met Ile Glu Asp Ala Gly Asp Leu Ala
        115                 120                 125

Thr Arg Ser Ala Lys Glu His Tyr Met Arg Ile Arg Pro Phe Ala Phe
130                 135                 140

Tyr Gly Thr Glu Thr Cys Asn Thr Lys Asp Gln Lys Lys Leu Ser Thr
145                 150                 155                 160

Asn Gly Ser Tyr Pro Ser Gly His Thr Ser Ile Gly Trp Ala Thr Ala
                165                 170                 175

Leu Val Leu Ala Glu Val Asn Pro Ala Asn Gln Asp Ala Ile Leu Glu
            180                 185                 190

Arg Gly Tyr Gln Leu Gly Gln Ser Arg Val Ile Cys Gly Tyr His Trp
        195                 200                 205

Gln Ser Asp Val Asp Ala Ala Arg Ile Val Gly Ser Ala Ala Val Ala
210                 215                 220

Thr Leu His Ser Asp Pro Ala Phe Gln Ala Gln Leu Ala Lys Ala Lys
225                 230                 235                 240

Gln Glu Phe Ala Gln Lys Ser Gln Lys
                245

```
<210> SEQ ID NO 5
<211> LENGTH: 991
<212> TYPE: DNA
<213> ORGANISM: Salmonella typhimurium
<220> FEATURE:
<221> NAME/KEY: CDS
<222> LOCATION: (132)..(827)

<400> SEQUENCE: 5
cagtccggta tggacagacg ataatgccag gcgcagcgtc ctgcttttt acctgtatgt      60 tgaataacca ttgcaataaa tcattatagg attacatctg tttattattg cctgatccgg    120
agtgagtctt t atg aaa agt cgt tat tta gta ttt ttt cta cca ctg atc     170
            Met Lys Ser Arg Tyr Leu Val Phe Phe Leu Pro Leu Ile
              1               5                  10 gta gct aaa tat aca tca gca gaa aca gtg caa ccc ttt cat tct cct      218
Val Ala Lys Tyr Thr Ser Ala Glu Thr Val Gln Pro Phe His Ser Pro
         15                  20                  25 gaa gaa tca gtg aac agt cag ttc tac tta cca cca ccg cca ggt aat      266
Glu Glu Ser Val Asn Ser Gln Phe Tyr Leu Pro Pro Pro Pro Gly Asn
 30                  35                  40                  45 gat gat ccg gct tac cgc tat gat aag gag gct tat ttt aag ggc tat      314
Asp Asp Pro Ala Tyr Arg Tyr Asp Lys Glu Ala Tyr Phe Lys Gly Tyr
                 50                  55                  60 gcg ata aag ggt tcc ccg cga tgg aaa caa gct gct gag gat gca gat      362
Ala Ile Lys Gly Ser Pro Arg Trp Lys Gln Ala Ala Glu Asp Ala Asp
             65                  70                  75 gta agc gtg gaa aat ata gcc aga ata ttc tcg cca gta gtg ggt gct      410
Val Ser Val Glu Asn Ile Ala Arg Ile Phe Ser Pro Val Val Gly Ala
         80                  85                  90 aaa att aac ccc aaa gat acg cca gaa acc tgg aat atg tta aag aat      458
Lys Ile Asn Pro Lys Asp Thr Pro Glu Thr Trp Asn Met Leu Lys Asn
     95                 100                 105 ctt ctg aca atg ggc ggc tac tac gct act gct tcg gca aaa aaa tat      506
Leu Leu Thr Met Gly Gly Tyr Tyr Ala Thr Ala Ser Ala Lys Lys Tyr
110                 115                 120                 125 tat atg cgt acc cgc ccc ttt gtc tta ttt aat cat tcc acc tgc cgt      554
Tyr Met Arg Thr Arg Pro Phe Val Leu Phe Asn His Ser Thr Cys Arg
                130                 135                 140 cct gaa gat gag aat act ttg cga aaa aat ggc tct tac cct tcc ggg      602
Pro Glu Asp Glu Asn Thr Leu Arg Lys Asn Gly Ser Tyr Pro Ser Gly
            145                 150                 155 cat act gct tat ggt aca ctt ctg gca tta gta tta tcc gag gcc aga      650
His Thr Ala Tyr Gly Thr Leu Leu Ala Leu Val Leu Ser Glu Ala Arg
        160                 165                 170 ccg gaa cgc gcg cag gag ctc gcc aga cgc gga tgg gag ttc ggg caa      698
Pro Glu Arg Ala Gln Glu Leu Ala Arg Arg Gly Trp Glu Phe Gly Gln
    175                 180                 185 agc aga gtg ata tgc ggt gct cac tgg caa agc gat gtt gat gct ggc      746
Ser Arg Val Ile Cys Gly Ala His Trp Gln Ser Asp Val Asp Ala Gly
190                 195                 200                 205 cgt tat gtg gga gca gta gag ttt gca aga ctg caa aca atc ccg gct      794
Arg Tyr Val Gly Ala Val Glu Phe Ala Arg Leu Gln Thr Ile Pro Ala
                210                 215                 220 ttt cag aag tca ctg gca aaa tcc gtg agg agc tgaacgacaa aaataattta   847
Phe Gln Lys Ser Leu Ala Lys Ser Val Arg Ser
            225                 230 ttgagtaaag aagatcaccc caaacttaat tactgaaggt gaaagtcttc ccgcaaactg    907
```

```
gccacagcaa atgaaaggaa gtgcaactgc gtaggggcgg ccgggcgtgg agaatgcctt    967
tggtttcccc gattcgcatg aatt                                           991
```

<210> SEQ ID NO 6
<211> LENGTH: 232
<212> TYPE: PRT
<213> ORGANISM: Salmonella typhimurium

<400> SEQUENCE: 6

```
Met Lys Ser Arg Tyr Leu Val Phe Phe Leu Pro Leu Ile Val Ala Lys
1               5                   10                  15

Tyr Thr Ser Ala Glu Thr Val Gln Pro Phe His Ser Pro Glu Ser
            20                  25                  30

Val Asn Ser Gln Phe Tyr Leu Pro Pro Pro Gly Asn Asp Asp Pro
        35                  40                  45

Ala Tyr Arg Tyr Asp Lys Glu Ala Tyr Phe Lys Gly Tyr Ala Ile Lys
    50                  55                  60

Gly Ser Pro Arg Trp Lys Gln Ala Ala Glu Asp Ala Asp Val Ser Val
65                  70                  75                  80

Glu Asn Ile Ala Arg Ile Phe Ser Pro Val Val Gly Ala Lys Ile Asn
                85                  90                  95

Pro Lys Asp Thr Pro Glu Thr Trp Asn Met Leu Lys Asn Leu Leu Thr
            100                 105                 110

Met Gly Gly Tyr Tyr Ala Thr Ala Ser Ala Lys Lys Tyr Tyr Met Arg
        115                 120                 125

Thr Arg Pro Phe Val Leu Phe Asn His Ser Thr Cys Arg Pro Glu Asp
    130                 135                 140

Glu Asn Thr Leu Arg Lys Asn Gly Ser Tyr Pro Ser Gly His Thr Ala
145                 150                 155                 160

Tyr Gly Thr Leu Leu Ala Leu Val Leu Ser Glu Ala Arg Pro Glu Arg
                165                 170                 175

Ala Gln Glu Leu Ala Arg Arg Gly Trp Glu Phe Gly Gln Ser Arg Val
            180                 185                 190

Ile Cys Gly Ala His Trp Gln Ser Asp Val Asp Ala Gly Arg Tyr Val
        195                 200                 205

Gly Ala Val Glu Phe Ala Arg Leu Gln Thr Ile Pro Ala Phe Gln Lys
    210                 215                 220

Ser Leu Ala Lys Ser Val Arg Ser
225                 230
```

<210> SEQ ID NO 7
<211> LENGTH: 1335
<212> TYPE: DNA
<213> ORGANISM: Zymomonas mobilis
<220> FEATURE:
<221> NAME/KEY: CDS
<222> LOCATION: (317)..(1108)

<400> SEQUENCE: 7

```
gtgccttata tcacgggggg atcagtctgc ggcaattggt ggcatggcac gcgctacggc    60
acgccggaag gcttcatggt cgtcaaagtc gaaaagggta agtcattcc gcattacgaa    120 agctatggct tccacacgat agacccgcgc aacacataat tgtcttatta tagccacatg    180 atattttat attacaattt taaactaaaa ttaagaatta aattcttgaa ataaaggttt    240
ttttattaaa aggataggaa atgtcgtgaa atcggcattt tctatccata ttatataaca    300
agggaagact gacgac atg ata aaa gtc ccg cgg ttc atc tgt atg atc gcg    352
```

```
              Met Ile Lys Val Pro Arg Phe Ile Cys Met Ile Ala
                1               5                  10 ctt aca tcc ggc gtt ctg gca agc ggc ctt tct caa agc gtt tca gct      400
Leu Thr Ser Gly Val Leu Ala Ser Gly Leu Ser Gln Ser Val Ser Ala
        15              20              25 cat aca gaa aaa agt gaa ccc tcc tcg act tat cat ttc cac agc gat      448
His Thr Glu Lys Ser Glu Pro Ser Ser Thr Tyr His Phe His Ser Asp
    30              35              40 ccc ctt ctt tac ctt gcg ccc cca ccc act tcc ggc agt cca tta cag      496
Pro Leu Leu Tyr Leu Ala Pro Pro Pro Thr Ser Gly Ser Pro Leu Gln
45              50              55              60 gcg cat gat gat caa acc ttt aac agc acc aga caa tta aaa ggt agc      544
Ala His Asp Asp Gln Thr Phe Asn Ser Thr Arg Gln Leu Lys Gly Ser
                65              70              75 acg cgc tgg gca ttg gca act caa gat gcc gat ctt cat ctc gct tca      592
Thr Arg Trp Ala Leu Ala Thr Gln Asp Ala Asp Leu His Leu Ala Ser
            80              85              90 gtt ctc aaa gac tat gcc tgc gcc gca gga atg aat ctc gat att gcg      640
Val Leu Lys Asp Tyr Ala Cys Ala Ala Gly Met Asn Leu Asp Ile Ala
        95              100             105 caa tta ccg cat ctt gcc aat ttg att aaa cgc gca ctt cgc acc gaa      688
Gln Leu Pro His Leu Ala Asn Leu Ile Lys Arg Ala Leu Arg Thr Glu
    110             115             120 tat gac gat att ggc aga gcc aaa aat aac tgg aat cgc aaa cga cct      736
Tyr Asp Asp Ile Gly Arg Ala Lys Asn Asn Trp Asn Arg Lys Arg Pro
125             130             135             140 ttt gtg gat acc gat caa ccc atc tgc acg gaa aaa gat cgc gaa ggt      784
Phe Val Asp Thr Asp Gln Pro Ile Cys Thr Glu Lys Asp Arg Glu Gly
                145             150             155 ctg gga aaa caa ggc tcc tat cct tca ggt cat acg act atc ggt tgg      832
Leu Gly Lys Gln Gly Ser Tyr Pro Ser Gly His Thr Thr Ile Gly Trp
            160             165             170 agc gtt gcg ctc att ctg gct gaa ttg atc ccc gat cat gcg gcg aat      880
Ser Val Ala Leu Ile Leu Ala Glu Leu Ile Pro Asp His Ala Ala Asn
        175             180             185 att ttg cag cgt ggc caa att ttt gga acc agc cgg att gtc tgc ggc      928
Ile Leu Gln Arg Gly Gln Ile Phe Gly Thr Ser Arg Ile Val Cys Gly
    190             195             200 gcc cat tgg ttc agc gat gtg cag gca ggc tat atc atg gca tcg ggc      976
Ala His Trp Phe Ser Asp Val Gln Ala Gly Tyr Ile Met Ala Ser Gly
205             210             215             220 gaa att gca gct tta cat ggg gat gcc gat ttc gcc cga gat atg gaa     1024
Glu Ile Ala Ala Leu His Gly Asp Ala Asp Phe Arg Arg Asp Met Glu
                225             230             235 tta gct cgg aaa gaa tta gaa aag gca cgc aca tca gcg cac acg cca     1072
Leu Ala Arg Lys Glu Leu Glu Lys Ala Arg Thr Ser Ala His Thr Pro
            240             245             250 gac gat ctt cta tgc aag att gaa caa agc gct cgc taaattcaat          1118
Asp Asp Leu Leu Cys Lys Ile Glu Gln Ser Ala Arg
        255             260 caagtattat ttcaacaagg ggaaagattg cttgctgtaa tttttggata tcaaacaggc   1178
gaaaaaatga aagagcgcac gctctttcaa aggcaattcg atttagtccg gtggcattct   1238
cacgccacaa accaaatcat aaataaccgc ctctttccg ccagataact gcaaaattat    1298
agaataccga cagctggaat atcgtcactt ttcctag                            1335

<210> SEQ ID NO 8
<211> LENGTH: 264
<212> TYPE: PRT
```

<213> ORGANISM: Zymomonas mobilis

<400> SEQUENCE: 8

```
Met Ile Lys Val Pro Arg Phe Ile Cys Met Ile Ala Leu Thr Ser Gly
1               5                   10                  15
Val Leu Ala Ser Gly Leu Ser Gln Ser Val Ser Ala His Thr Glu Lys
            20                  25                  30
Ser Glu Pro Ser Ser Thr Tyr His Phe His Ser Asp Pro Leu Leu Tyr
        35                  40                  45
Leu Ala Pro Pro Thr Ser Gly Ser Pro Leu Gln Ala His Asp Asp
    50                  55                  60
Gln Thr Phe Asn Ser Thr Arg Gln Leu Lys Gly Ser Thr Arg Trp Ala
65                  70                  75                  80
Leu Ala Thr Gln Asp Ala Asp Leu His Leu Ala Ser Val Leu Lys Asp
                85                  90                  95
Tyr Ala Cys Ala Ala Gly Met Asn Leu Asp Ile Ala Gln Leu Pro His
            100                 105                 110
Leu Ala Asn Leu Ile Lys Arg Ala Leu Arg Thr Glu Tyr Asp Asp Ile
        115                 120                 125
Gly Arg Ala Lys Asn Asn Trp Asn Arg Lys Arg Pro Phe Val Asp Thr
    130                 135                 140
Asp Gln Pro Ile Cys Thr Glu Lys Asp Arg Glu Gly Leu Gly Lys Gln
145                 150                 155                 160
Gly Ser Tyr Pro Ser Gly His Thr Thr Ile Gly Trp Ser Val Ala Leu
                165                 170                 175
Ile Leu Ala Glu Leu Ile Pro Asp His Ala Ala Asn Ile Leu Gln Arg
            180                 185                 190
Gly Gln Ile Phe Gly Thr Ser Arg Ile Val Cys Gly Ala His Trp Phe
        195                 200                 205
Ser Asp Val Gln Ala Gly Tyr Ile Met Ala Ser Gly Glu Ile Ala Ala
    210                 215                 220
Leu His Gly Asp Ala Asp Phe Arg Arg Asp Met Glu Leu Ala Arg Lys
225                 230                 235                 240
Glu Leu Glu Lys Ala Arg Thr Ser Ala His Thr Pro Asp Asp Leu Leu
                245                 250                 255
Cys Lys Ile Glu Gln Ser Ala Arg
            260
```

```
<210> SEQ ID NO 9
<211> LENGTH: 1650
<212> TYPE: DNA
<213> ORGANISM: Enterobacter aerogenes
<220> FEATURE:
<221> NAME/KEY: CDS
<222> LOCATION: (344)..(1087)
<220> FEATURE:
<221> NAME/KEY: sig_peptide
<222> LOCATION: (344)..(403)
<220> FEATURE:
<221> NAME/KEY: mat_peptide
<222> LOCATION: (404)..()
```

<400> SEQUENCE: 9

| | | | |
|---|---|---|---|
| gtcgacaaac ttcgcctgct cgctatgcag aatggtttcc agcactttag gggaaatttt | 60 |
| acaaccgcaa ccggctccgt ggctgtattg cgttaaacga atagcttgct cgctcatgga | 120 |
| catctcctgt cattgcaatc ccgctatggt agcgcccaaa cggcaaggtg ataagtgcga | 180 |
| cagtccgaaa tcgcgagtgg ttgctcatta agcagacaaa tatgcgtttt tgcgataccg | 240 |

```
aacaattttt tcaatgtgat tttaactttt acttacagat gacaaaaatg tgactaaaaa      300
caaaaccatt gttctggaca tataacaccg taaggaaatg tag atg aaa aag cgc       355
                                             Met Lys Lys Arg
                                             -20 gtt ctc gcc ctc tgc ctc gcc agc ctg ttt tcc gtt aac gct ttc gcg      403
Val Leu Ala Leu Cys Leu Ala Ser Leu Phe Ser Val Asn Ala Phe Ala
    -15             -10              -5                   -1 ctg gtc cct gcc ggc aat gat gca acc acc aaa ccg gat ctc tat tat      451
Leu Val Pro Ala Gly Asn Asp Ala Thr Thr Lys Pro Asp Leu Tyr Tyr
 1           5                   10                  15 ctg aaa aat gca cag gcc atc gat agt ctg gcg ctg ttg ccg ccg ccg      499
Leu Lys Asn Ala Gln Ala Ile Asp Ser Leu Ala Leu Leu Pro Pro Pro
         20                  25                  30 ccg gaa gtt ggc agc atc gca ttt tta aac gat cag gcg atg tat gag      547
Pro Glu Val Gly Ser Ile Ala Phe Leu Asn Asp Gln Ala Met Tyr Glu
         35                  40                  45 aaa gga cgg ctg ttg cgc aat acc gaa cgt ggc aag cag gcg cag gca      595
Lys Gly Arg Leu Leu Arg Asn Thr Glu Arg Gly Lys Gln Ala Gln Ala
         50                  55                  60 gat gct gac ctg gcc gcc ggc gac gtc gcg aat gcc ttc tcc agc gct      643
Asp Ala Asp Leu Ala Ala Gly Asp Val Ala Asn Ala Phe Ser Ser Ala
65              70                  75                  80 ttt ggt tcg ccc atc acc gaa aaa gac gcg ccg cag tta cat aag ctg      691
Phe Gly Ser Pro Ile Thr Glu Lys Asp Ala Pro Gln Leu His Lys Leu
                 85                  90                  95 ctg aca aat atg att gag gat gcc ggc gat ctg gcc acc cgc agc gcg      739
Leu Thr Asn Met Ile Glu Asp Ala Gly Asp Leu Ala Thr Arg Ser Ala
             100                 105                 110 aaa gag aaa tat atg cgc att cgc ccg ttt gcg ttc tac ggc gtt tca      787
Lys Glu Lys Tyr Met Arg Ile Arg Pro Phe Ala Phe Tyr Gly Val Ser
             115                 120                 125 acc tgt aac act aaa gac cag gac aag ctg tcg aaa aac gga tct tac      835
Thr Cys Asn Thr Lys Asp Gln Asp Lys Leu Ser Lys Asn Gly Ser Tyr
        130                 135                 140 cct tcc ggc cat acc tct acc ggt tgg gca acc gcg ctg gta ctg gcg      883
Pro Ser Gly His Thr Ser Thr Gly Trp Ala Thr Ala Leu Val Leu Ala
145             150                 155                 160 gag atc aat ccg cag cgg caa aac gaa att ctc aaa cgc ggc tat gaa      931
Glu Ile Asn Pro Gln Arg Gln Asn Glu Ile Leu Lys Arg Gly Tyr Glu
            165                 170                 175 ttg ggc gaa agc cgg gtt atc tgc ggc tat cat tgg cag agc gat gtc      979
Leu Gly Glu Ser Arg Val Ile Cys Gly Tyr His Trp Gln Ser Asp Val
            180                 185                 190 gat gcg gcg cgg ata gtc ggc tcg gcg gtg gtg gcg acc ctg cat acc      1027
Asp Ala Ala Arg Ile Val Gly Ser Ala Val Val Ala Thr Leu His Thr
            195                 200                 205 aac ccg gcc ttc caa cag cag ttg cag aaa gca aag gat gaa ttc gcc      1075
Asn Pro Ala Phe Gln Gln Gln Leu Gln Lys Ala Lys Asp Glu Phe Ala
        210                 215                 220 aaa acg cag aag taacgtcatc gccgttgaac tcccggaggc ggcgcttaac           1127
Lys Thr Gln Lys
225 gcgccttctc cgggctacta atcgcacag cgctgtagcc ccgtaagcg ccagcgccac       1187 cggggatttt gagatagcca gcaccagtag tttcagccag cgtgatgaat acattaacgg    1247 caggccgcat gagtcgtaga tactgttatc ggtttgcaac ttttttaagg ttttttcccg    1307 gaggcggcgc gctgcgcctt ctccgggcta ctaaatcgca cagcgctgta gccccggtaa    1367
```

```
gcggcagcgc caccgggggt aacaagcgca gattcagaag cgcgtgacga acggcgcggt    1427
atccgggcgc gtaaacatgg ttgatgcttt taactgcggc gtgccaaggt agaggaaacc    1487
gacaattttg tcctgttcgc ggcagccaaa gccttcgcgg acaaccggac tctcggttaa    1547
cgcaccgata cgccagatac cgttatagcc ctgcgccact gcggccattt gcatcgccat    1607
caccgcacat cccgcggaca tctcctgttc ccacagcggt acc                      1650
```

<210> SEQ ID NO 10
<211> LENGTH: 248
<212> TYPE: PRT
<213> ORGANISM: Enterobacter aerogenes

<400> SEQUENCE: 10

```
Met Lys Lys Arg Val Leu Ala Leu Cys Leu Ala Ser Leu Phe Ser Val
-20             -15                 -10                  -5

Asn Ala Phe Ala Leu Val Pro Ala Gly Asn Asp Ala Thr Thr Lys Pro
         -1   1                   5                  10

Asp Leu Tyr Tyr Leu Lys Asn Ala Gln Ala Ile Asp Ser Leu Ala Leu
             15                  20                  25

Leu Pro Pro Pro Glu Val Gly Ser Ile Ala Phe Leu Asn Asp Gln
     30                  35                  40

Ala Met Tyr Glu Lys Gly Arg Leu Leu Arg Asn Thr Glu Arg Gly Lys
 45                  50                  55                  60

Gln Ala Gln Ala Asp Ala Asp Leu Ala Ala Gly Asp Val Ala Asn Ala
                 65                  70                  75

Phe Ser Ser Ala Phe Gly Ser Pro Ile Thr Glu Lys Asp Ala Pro Gln
                 80                  85                  90

Leu His Lys Leu Leu Thr Asn Met Ile Glu Asp Ala Gly Asp Leu Ala
                 95                 100                 105

Thr Arg Ser Ala Lys Glu Lys Tyr Met Arg Ile Arg Pro Phe Ala Phe
    110                 115                 120

Tyr Gly Val Ser Thr Cys Asn Thr Lys Asp Gln Asp Lys Leu Ser Lys
125                 130                 135                 140

Asn Gly Ser Tyr Pro Ser Gly His Thr Ser Thr Gly Trp Ala Thr Ala
                145                 150                 155

Leu Val Leu Ala Glu Ile Asn Pro Gln Arg Gln Asn Glu Ile Leu Lys
                160                 165                 170

Arg Gly Tyr Glu Leu Gly Glu Ser Arg Val Ile Cys Gly Tyr His Trp
    175                 180                 185

Gln Ser Asp Val Asp Ala Ala Arg Ile Val Gly Ser Ala Val Val Ala
    190                 195                 200

Thr Leu His Thr Asn Pro Ala Phe Gln Gln Leu Gln Lys Ala Lys
205                 210                 215                 220

Asp Glu Phe Ala Lys Thr Gln Lys
                225
```

<210> SEQ ID NO 11
<211> LENGTH: 25
<212> TYPE: DNA
<213> ORGANISM: Artificial Sequence
<220> FEATURE:
<223> OTHER INFORMATION: Synthetic DNA

<400> SEQUENCE: 11

```
caaacctgag ctttggcgat gtggc                                            25
```

```
<210> SEQ ID NO 12
<211> LENGTH: 25
<212> TYPE: DNA
<213> ORGANISM: Artificial Sequence
<220> FEATURE:
<223> OTHER INFORMATION: Synthetic DNA

<400> SEQUENCE: 12
gtttggactc gaaaccgcta caccg                                             25

<210> SEQ ID NO 13
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 13

Asn Leu Ser Phe Gly Asp Val
1               5

<210> SEQ ID NO 14
<211> LENGTH: 25
<212> TYPE: DNA
<213> ORGANISM: Artificial Sequence
<220> FEATURE:
<223> OTHER INFORMATION: Synthetic DNA

<400> SEQUENCE: 14
caaacctgag ctacggcgat gtggc                                             25

<210> SEQ ID NO 15
<211> LENGTH: 25
<212> TYPE: DNA
<213> ORGANISM: Artificial Sequence
<220> FEATURE:
<223> OTHER INFORMATION: Synthetic DNA

<400> SEQUENCE: 15
gtttggactc gatgccgcta caccg                                             25

<210> SEQ ID NO 16
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 16

Asn Leu Ser Tyr Gly Asp Val
1               5

<210> SEQ ID NO 17
<211> LENGTH: 25
<212> TYPE: DNA
<213> ORGANISM: Artificial Sequence
<220> FEATURE:
<223> OTHER INFORMATION: Synthetic DNA

<400> SEQUENCE: 17
caaacctgag ctggggcgat gtggc                                             25

<210> SEQ ID NO 18
<211> LENGTH: 25
<212> TYPE: DNA
```

```
<213> ORGANISM: Artificial Sequence
<220> FEATURE:
<223> OTHER INFORMATION: Synthetic DNA

<400> SEQUENCE: 18
gtttggactc gaccccgcta caccg                                    25

<210> SEQ ID NO 19
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 19

Asn Leu Ser Trp Gly Asp Val
1               5

<210> SEQ ID NO 20
<211> LENGTH: 25
<212> TYPE: DNA
<213> ORGANISM: Artificial Sequence
<220> FEATURE:
<223> OTHER INFORMATION: Synthetic DNA

<400> SEQUENCE: 20
caaacctgag cgacggcgat gtggc                                    25

<210> SEQ ID NO 21
<211> LENGTH: 25
<212> TYPE: DNA
<213> ORGANISM: Artificial Sequence
<220> FEATURE:
<223> OTHER INFORMATION: Synthetic DNA

<400> SEQUENCE: 21
gtttggactc gctgccgcta caccg                                    25

<210> SEQ ID NO 22
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 22

Asn Leu Ser Asp Gly Asp Val
1               5

<210> SEQ ID NO 23
<211> LENGTH: 25
<212> TYPE: DNA
<213> ORGANISM: Artificial Sequence
<220> FEATURE:
<223> OTHER INFORMATION: Sythetic DNA

<400> SEQUENCE: 23
caaacctgag cgttggcgat gtggc                                    25

<210> SEQ ID NO 24
<211> LENGTH: 25
<212> TYPE: DNA
<213> ORGANISM: Artificial Sequence
<220> FEATURE:
<223> OTHER INFORMATION: Synthetic DNA
```

```
<400> SEQUENCE: 24
gtttggactc gcaaccgcta caccg                                           25

<210> SEQ ID NO 25
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 25

Asn Leu Ser Val Gly Asp Val
1               5

<210> SEQ ID NO 26
<211> LENGTH: 25
<212> TYPE: DNA
<213> ORGANISM: Artificial Sequence
<220> FEATURE:
<223> OTHER INFORMATION: Synthetic DNA

<400> SEQUENCE: 26
caaacctgag cgaaggcgat gtggc                                           25

<210> SEQ ID NO 27
<211> LENGTH: 25
<212> TYPE: DNA
<213> ORGANISM: Artificial Sequence
<220> FEATURE:
<223> OTHER INFORMATION: Synthetic DNA

<400> SEQUENCE: 27
gtttggactc gcttccgcta caccg                                           25

<210> SEQ ID NO 28
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 28

Asn Leu Ser Glu Gly Asp Val
1               5

<210> SEQ ID NO 29
<211> LENGTH: 25
<212> TYPE: DNA
<213> ORGANISM: Artificial Sequence
<220> FEATURE:
<223> OTHER INFORMATION: Synthetic DNA

<400> SEQUENCE: 29
caaacctgag catgggcgat gtggc                                           25

<210> SEQ ID NO 30
<211> LENGTH: 25
<212> TYPE: DNA
<213> ORGANISM: Artificial Sequence
<220> FEATURE:
<223> OTHER INFORMATION: Synthetic DNA

<400> SEQUENCE: 30
```
gtttggactc gtacccgcta caccg 25

<210> SEQ ID NO 31
<211> LENGTH: 7
<212> TYPE: PRT
<213> ORGANISM: Artificial Sequence
<220> FEATURE:
<223> OTHER INFORMATION: Internal peptide of Escherichia blattae acid phosphatase with mutation

<400> SEQUENCE: 31

Asn Leu Ser Met Gly Asp Val
1               5

<210> SEQ ID NO 32
<211> LENGTH: 25
<212> TYPE: DNA
<213> ORGANISM: Artificial Sequence
<220> FEATURE:
<223> OTHER INFORMATION: Synthetic DNA

<400> SEQUENCE: 32
caaacctgag caccggcgat gtggc 25

<210> SEQ ID NO 33
<211> LENGTH: 25
<212> TYPE: DNA
<213> ORGANISM: Artificial Sequence
<220> FEATURE:
<223> OTHER INFORMATION: Synthetic DNA

<400> SEQUENCE: 33
gtttggactc gtggccgcta caccg 25

<210> SEQ ID NO 34
<211> LENGTH: 7
<212> TYPE: PRT
<213> ORGANISM: Artificial Sequence
<220> FEATURE:
<223> OTHER INFORMATION: Internal peptide of Escherichia blattae acid phosphatase with mutation

<400> SEQUENCE: 34

Asn Leu Ser Arg Gly Asp Val
1               5

<210> SEQ ID NO 35
<211> LENGTH: 25
<212> TYPE: DNA
<213> ORGANISM: Artificial Sequence
<220> FEATURE:
<223> OTHER INFORMATION: Synthetic DNA

<400> SEQUENCE: 35
caaacctgag cctgggcgat gtggc 25

<210> SEQ ID NO 36
<211> LENGTH: 25
<212> TYPE: DNA
<213> ORGANISM: Artificial Sequence
<220> FEATURE:
<223> OTHER INFORMATION: Synthetic DNA

<400> SEQUENCE: 36
gtttggactc ggacccgcta caccg 25

```
<210> SEQ ID NO 37
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 37

Asn Leu Ser Leu Gly Asp Val
1               5

<210> SEQ ID NO 38
<211> LENGTH: 25
<212> TYPE: DNA
<213> ORGANISM: Artificial Sequence
<220> FEATURE:
<223> OTHER INFORMATION: Synthetic DNA

<400> SEQUENCE: 38
caaacctgag ccgtggcgat gtggc                                              25

<210> SEQ ID NO 39
<211> LENGTH: 25
<212> TYPE: DNA
<213> ORGANISM: Artificial Sequence
<220> FEATURE:
<223> OTHER INFORMATION: Synthetic DNA

<400> SEQUENCE: 39
gtttggactc ggcaccgcta caccg                                              25

<210> SEQ ID NO 40
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 40

Asn Leu Ser Arg Gly Asp Val
1               5

<210> SEQ ID NO 41
<211> LENGTH: 25
<212> TYPE: DNA
<213> ORGANISM: Artificial Sequence
<220> FEATURE:
<223> OTHER INFORMATION: Synthetic DNA

<400> SEQUENCE: 41
caaacctgag ccagggcgat gtggc                                              25

<210> SEQ ID NO 42
<211> LENGTH: 25
<212> TYPE: DNA
<213> ORGANISM: Artificial Sequence
<220> FEATURE:
<223> OTHER INFORMATION: Synthetic DNA

<400> SEQUENCE: 42
gtttggactc ggtcccgcta caccg                                              25

<210> SEQ ID NO 43
<211> LENGTH: 7
<212> TYPE: PRT
```

-continued

<213> ORGANISM: Artificial Sequence
<220> FEATURE:
<223> OTHER INFORMATION: Internal peptide of Escherichia blattae acid
      phosphatase with mutation

<400> SEQUENCE: 43

Asn Leu Ser Gln Gly Asp Val
1               5

<210> SEQ ID NO 44
<211> LENGTH: 25
<212> TYPE: DNA
<213> ORGANISM: Artificial Sequence
<220> FEATURE:
<223> OTHER INFORMATION: Synthetic DNA

<400> SEQUENCE: 44
caaacctgag caaaggcgat gtggc                                             25

<210> SEQ ID NO 45
<211> LENGTH: 25
<212> TYPE: DNA
<213> ORGANISM: Artificial Sequence
<220> FEATURE:
<223> OTHER INFORMATION: Synthetic DNA

<400> SEQUENCE: 45
gtttggactc gtttccgcta caccg                                             25

<210> SEQ ID NO 46
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 46

Asn Leu Ser Lys Gly Asp Val
1               5

<210> SEQ ID NO 47
<211> LENGTH: 25
<212> TYPE: DNA
<213> ORGANISM: Artificial Sequence
<220> FEATURE:
<223> OTHER INFORMATION: Synthetic DNA

<400> SEQUENCE: 47
caaacctgag cccggcgat gtggc                                              25

<210> SEQ ID NO 48
<211> LENGTH: 25
<212> TYPE: DNA
<213> ORGANISM: Artificial Sequence
<220> FEATURE:
<223> OTHER INFORMATION: Synthetic DNA

<400> SEQUENCE: 48
gtttggactc gggcccgcta caccg                                             25

<210> SEQ ID NO 49
<211> LENGTH: 7
<212> TYPE: PRT
<213> ORGANISM: Artificial Sequence
<220> FEATURE:
<223> OTHER INFORMATION: Internal peptide of Escherichia blattae acid phosphatase with mutation

<400> SEQUENCE: 49

Asn Leu Ser Pro Gly Asp Val
1               5

<210> SEQ ID NO 50
<211> LENGTH: 25
<212> TYPE: DNA
<213> ORGANISM: Artificial Sequence
<220> FEATURE:
<223> OTHER INFORMATION: Synthetic DNA

<400> SEQUENCE: 50
caaacctgag cgcgggcgat gtggc                                          25

<210> SEQ ID NO 51
<211> LENGTH: 25
<212> TYPE: DNA
<213> ORGANISM: Artificial Sequence
<220> FEATURE:
<223> OTHER INFORMATION: Synthetic DNA

<400> SEQUENCE: 51
gtttggactc gcgcccgcta caccg                                          25

<210> SEQ ID NO 52
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 52

Asn Leu Ser Ala Gly Asp Val
1               5

<210> SEQ ID NO 53
<211> LENGTH: 25
<212> TYPE: DNA
<213> ORGANISM: Artificial Sequence
<220> FEATURE:
<223> OTHER INFORMATION: Synthetic DNA

<400> SEQUENCE: 53
caaacctgag caacggcgat gtggc                                          25

<210> SEQ ID NO 54
<211> LENGTH: 25
<212> TYPE: DNA
<213> ORGANISM: Artificial Sequence
<220> FEATURE:
<223> OTHER INFORMATION: Synthetic DNA

<400> SEQUENCE: 54
gtttggactc gttgccgcta caccg                                          25

<210> SEQ ID NO 55
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 55

```
Asn Leu Ser Asn Gly Asp Val
1               5
```

<210> SEQ ID NO 56
<211> LENGTH: 25
<212> TYPE: DNA
<213> ORGANISM: Artificial Sequence
<220> FEATURE:
<223> OTHER INFORMATION: Synthetic DNA

<400> SEQUENCE: 56
caaacctgag cggtggcgat gtggc                                    25

<210> SEQ ID NO 57
<211> LENGTH: 25
<212> TYPE: DNA
<213> ORGANISM: Artificial Sequence
<220> FEATURE:
<223> OTHER INFORMATION: Synthetic DNA

<400> SEQUENCE: 57
gtttggactc gccaccgcta caccg                                    25

<210> SEQ ID NO 58
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 58

```
Asn Leu Ser Gly Gly Asp Val
1               5
```

<210> SEQ ID NO 59
<211> LENGTH: 25
<212> TYPE: DNA
<213> ORGANISM: Artificial Sequence
<220> FEATURE:
<223> OTHER INFORMATION: Synthetic DNA

<400> SEQUENCE: 59
caaacctgag ccacggcgat gtggc                                    25

<210> SEQ ID NO 60
<211> LENGTH: 25
<212> TYPE: DNA
<213> ORGANISM: Artificial Sequence
<220> FEATURE:
<223> OTHER INFORMATION: Synthetic DNA

<400> SEQUENCE: 60
gtttggactc ggtgccgcta caccg                                    25

<210> SEQ ID NO 61
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 61

```
Asn Leu Ser His Gly Asp Val
1               5
```

```
<210> SEQ ID NO 62
<211> LENGTH: 25
<212> TYPE: DNA
<213> ORGANISM: Artificial Sequence
<220> FEATURE:
<223> OTHER INFORMATION: Synthetic DNA

<400> SEQUENCE: 62
cgaaaccgga ttggtactac ctcaa                                              25

<210> SEQ ID NO 63
<211> LENGTH: 25
<212> TYPE: DNA
<213> ORGANISM: Artificial Sequence
<220> FEATURE:
<223> OTHER INFORMATION: Synthetic DNA

<400> SEQUENCE: 63
gctttggcct aaccatgatg gagtt                                              25

<210> SEQ ID NO 64
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 64

Lys Pro Asp Trp Tyr Tyr Leu
1               5

<210> SEQ ID NO 65
<211> LENGTH: 25
<212> TYPE: DNA
<213> ORGANISM: Artificial Sequence
<220> FEATURE:
<223> OTHER INFORMATION: Synthetic DNA

<400> SEQUENCE: 65
atgcaaacct gtggagtggc gatgt                                              25

<210> SEQ ID NO 66
<211> LENGTH: 25
<212> TYPE: DNA
<213> ORGANISM: Artificial Sequence
<220> FEATURE:
<223> OTHER INFORMATION: Synthetic DNA

<400> SEQUENCE: 66
tacgtttgga cacctcaccg ctaca                                              25

<210> SEQ ID NO 67
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 67

Ala Asn Leu Trp Ser Gly Asp
1               5

<210> SEQ ID NO 68
```

```
<211> LENGTH: 25
<212> TYPE: DNA
<213> ORGANISM: Artificial Sequence
<220> FEATURE:
<223> OTHER INFORMATION: Synthetic DNA

<400> SEQUENCE: 68
acctgagcag ttgggatgtg gcgaa                                               25

<210> SEQ ID NO 69
<211> LENGTH: 25
<212> TYPE: DNA
<213> ORGANISM: Artificial Sequence
<220> FEATURE:
<223> OTHER INFORMATION: Synthetic DNA

<400> SEQUENCE: 69
tggactcgtc aaccctacac cgctt                                              25

<210> SEQ ID NO 70
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 70

Leu Ser Ser Trp Asp Val Ala
1               5

<210> SEQ ID NO 71
<211> LENGTH: 25
<212> TYPE: DNA
<213> ORGANISM: Artificial Sequence
<220> FEATURE:
<223> OTHER INFORMATION: Synthetic DNA

<400> SEQUENCE: 71
ccaatatgat ttttgacgcc gggga                                              25

<210> SEQ ID NO 72
<211> LENGTH: 25
<212> TYPE: DNA
<213> ORGANISM: Artificial Sequence
<220> FEATURE:
<223> OTHER INFORMATION: Synthetic DNA

<400> SEQUENCE: 72
ggttatacta aaaactgcgg ccccct                                             25

<210> SEQ ID NO 73
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 73

Asn Met Ile Phe Asp Ala Gly
1               5

<210> SEQ ID NO 74
<211> LENGTH: 25
<212> TYPE: DNA
<213> ORGANISM: Artificial Sequence
```

```
<220> FEATURE:
<223> OTHER INFORMATION: Synthetic DNA

<400> SEQUENCE: 74
ccaatatgat tgggacgcc gggga                                           25

<210> SEQ ID NO 75
<211> LENGTH: 25
<212> TYPE: DNA
<213> ORGANISM: Artificial Sequence
<220> FEATURE:
<223> OTHER INFORMATION: Synthetic DNA

<400> SEQUENCE: 75
ggttatacta aaccctgcgg cccct                                          25

<210> SEQ ID NO 76
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 76

Asn Met Ile Trp Asp Ala Gly
1               5

<210> SEQ ID NO 77
<211> LENGTH: 25
<212> TYPE: DNA
<213> ORGANISM: Artificial Sequence
<220> FEATURE:
<223> OTHER INFORMATION: Synthetic DNA

<400> SEQUENCE: 77
cagacctggc ctttggcgat gtggc                                          25

<210> SEQ ID NO 78
<211> LENGTH: 25
<212> TYPE: DNA
<213> ORGANISM: Artificial Sequence
<220> FEATURE:
<223> OTHER INFORMATION: Synthetic DNA

<400> SEQUENCE: 78
gtctggaccg gaaaccgcta caccg                                          25

<210> SEQ ID NO 79
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 79

Asp Leu Ala Phe Gly Asp Val
1               5

<210> SEQ ID NO 80
<211> LENGTH: 25
<212> TYPE: DNA
<213> ORGANISM: Artificial Sequence
<220> FEATURE:
<223> OTHER INFORMATION: Synthetic DNA
```

<400> SEQUENCE: 80
cagacctggc cgaaggcgat gtggc                                             25

<210> SEQ ID NO 81
<211> LENGTH: 25
<212> TYPE: DNA
<213> ORGANISM: Artificial Sequence
<220> FEATURE:
<223> OTHER INFORMATION: Synthetic DNA

<400> SEQUENCE: 81
gtctggaccg gcttccgcta caccg                                             25

<210> SEQ ID NO 82
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 82

Asp Leu Ala Glu Gly Asp Val
1               5

<210> SEQ ID NO 83
<211> LENGTH: 25
<212> TYPE: DNA
<213> ORGANISM: Artificial Sequence
<220> FEATURE:
<223> OTHER INFORMATION: Synthetic DNA

<400> SEQUENCE: 83
tgaccaatat ggacgaggac gccgg                                             25

<210> SEQ ID NO 84
<211> LENGTH: 25
<212> TYPE: DNA
<213> ORGANISM: Artificial Sequence
<220> FEATURE:
<223> OTHER INFORMATION: Synthetic DNA

<400> SEQUENCE: 84
actggttata cctgctcctg cggcc                                             25

<210> SEQ ID NO 85
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 85

Thr Asn Met Asp Glu Asp Ala
1               5

<210> SEQ ID NO 86
<211> LENGTH: 25
<212> TYPE: DNA
<213> ORGANISM: Artificial Sequence
<220> FEATURE:
<223> OTHER INFORMATION: Synthetic DNA

<400> SEQUENCE: 86
ggcatacctc taacggctgg gctac                                             25

```
<210> SEQ ID NO 87
<211> LENGTH: 25
<212> TYPE: DNA
<213> ORGANISM: Artificial Sequence
<220> FEATURE:
<223> OTHER INFORMATION: Synthetic DNA

<400> SEQUENCE: 87
ccgtatggag attgccgacc cgatg                              25

<210> SEQ ID NO 88
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 88

His Thr Ser Asn Gly Trp Ala
1               5

<210> SEQ ID NO 89
<211> LENGTH: 25
<212> TYPE: DNA
<213> ORGANISM: Artificial Sequence
<220> FEATURE:
<223> OTHER INFORMATION: Synthetic DNA

<400> SEQUENCE: 89
accaggacaa attctccaaa aatgg                              25

<210> SEQ ID NO 90
<211> LENGTH: 25
<212> TYPE: DNA
<213> ORGANISM: Artificial Sequence
<220> FEATURE:
<223> OTHER INFORMATION: Synthetic DNA

<400> SEQUENCE: 90
tggtcctgtt taagaggttt ttacc                              25

<210> SEQ ID NO 91
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 91

Gln Asp Lys Phe Ser Lys Asn
1               5

<210> SEQ ID NO 92
<211> LENGTH: 25
<212> TYPE: DNA
<213> ORGANISM: Artificial Sequence
<220> FEATURE:
<223> OTHER INFORMATION: Synthetic DNA

<400> SEQUENCE: 92
accaggacaa aaaatccaaa aatgg                              25

<210> SEQ ID NO 93
```

```
<211> LENGTH: 25
<212> TYPE: DNA
<213> ORGANISM: Artificial Sequence
<220> FEATURE:
<223> OTHER INFORMATION: Synthetic DNA

<400> SEQUENCE: 93
tggtcctgtt ttttaggttt ttacc                                              25

<210> SEQ ID NO 94
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 94

Gln Asp Lys Lys Ser Lys Asn
1               5

<210> SEQ ID NO 95
<211> LENGTH: 25
<212> TYPE: DNA
<213> ORGANISM: Artificial Sequence
<220> FEATURE:
<223> OTHER INFORMATION: Synthetic DNA

<400> SEQUENCE: 95
accaggacaa agaatccaaa aatgg                                              25

<210> SEQ ID NO 96
<211> LENGTH: 25
<212> TYPE: DNA
<213> ORGANISM: Artificial Sequence
<220> FEATURE:
<223> OTHER INFORMATION: Synthetic DNA

<400> SEQUENCE: 96
tggtcctgtt tcttaggttt ttacc                                              25

<210> SEQ ID NO 97
<211> LENGTH: 7
<212> TYPE: PRT
<213> ORGANISM: Artificial Sequence
<220> FEATURE:
<223> OTHER INFORMATION: Internal peptide of Escherichia blattae acid
      phosphatase with mutation

<400> SEQUENCE: 97

Gln Asp Lys Glu Ser Lys Asn
1               5

<210> SEQ ID NO 98
<211> LENGTH: 5
<212> TYPE: PRT
<213> ORGANISM: Enterobacter aerogenes

<400> SEQUENCE: 98

Leu Val Pro Ala Gly
1               5

<210> SEQ ID NO 99
<211> LENGTH: 30
<212> TYPE: DNA
<213> ORGANISM: Artificial Sequence
<220> FEATURE:
```

<223> OTHER INFORMATION: Synthetic DNA

<400> SEQUENCE: 99
cttacagatg actataatgt gactaaaaac　　　　　　　　　　　　　　　　　　30

<210> SEQ ID NO 100
<211> LENGTH: 30
<212> TYPE: DNA
<213> ORGANISM: Artificial Sequence
<220> FEATURE:
<223> OTHER INFORMATION: Synthetic DNA

<400> SEQUENCE: 100
gtttttagtc acattatagt catctgtaag　　　　　　　　　　　　　　　　　　30

<210> SEQ ID NO 101
<211> LENGTH: 33
<212> TYPE: DNA
<213> ORGANISM: Artificial Sequence
<220> FEATURE:
<223> OTHER INFORMATION: Synthetic DNA

<400> SEQUENCE: 101
tctaccggtt gggcatccgc gctggtactg gcg　　　　　　　　　　　　　　　　33

<210> SEQ ID NO 102
<211> LENGTH: 33
<212> TYPE: DNA
<213> ORGANISM: Artificial Sequence
<220> FEATURE:
<223> OTHER INFORMATION: Synthetic DNA

<400> SEQUENCE: 102
cgccagtacc agcgcggatg cccaaccggt aga　　　　　　　　　　　　　　　　33

<210> SEQ ID NO 103
<211> LENGTH: 33
<212> TYPE: DNA
<213> ORGANISM: Artificial Sequence
<220> FEATURE:
<223> OTHER INFORMATION: Synthetic DNA

<400> SEQUENCE: 103
tccggccata cctcttccgg ttgggcatcc gcg　　　　　　　　　　　　　　　　33

<210> SEQ ID NO 104
<211> LENGTH: 33
<212> TYPE: DNA
<213> ORGANISM: Artificial Sequence
<220> FEATURE:
<223> OTHER INFORMATION: Synthetic DNA

<400> SEQUENCE: 104
cgcggatgcc caaccggaag aggtatggcc gga　　　　　　　　　　　　　　　　33

<210> SEQ ID NO 105
<211> LENGTH: 33
<212> TYPE: DNA
<213> ORGANISM: Artificial Sequence
<220> FEATURE:
<223> OTHER INFORMATION: Synthetic DNA

<400> SEQUENCE: 105
gatgctgacc tggccgttgg cgacgtcgcg aat　　　　　　　　　　　　　　　　33

<210> SEQ ID NO 106
<211> LENGTH: 33
<212> TYPE: DNA
<213> ORGANISM: Artificial Sequence
<220> FEATURE:
<223> OTHER INFORMATION: Synthetic DNA

<400> SEQUENCE: 106
attcgcgacg tcgccaacgg ccaggtcagc atc         33

<210> SEQ ID NO 107
<211> LENGTH: 33
<212> TYPE: DNA
<213> ORGANISM: Artificial Sequence
<220> FEATURE:
<223> OTHER INFORMATION: Synthetic DNA

<400> SEQUENCE: 107
ctgacaaata tgattctgga tgccggcgat ctg         33

<210> SEQ ID NO 108
<211> LENGTH: 33
<212> TYPE: DNA
<213> ORGANISM: Artificial Sequence
<220> FEATURE:
<223> OTHER INFORMATION: Synthetic DNA

<400> SEQUENCE: 108
cagatcgccg gcatccagaa tcatatttgt cag         33

<210> SEQ ID NO 109
<211> LENGTH: 33
<212> TYPE: DNA
<213> ORGANISM: Artificial Sequence
<220> FEATURE:
<223> OTHER INFORMATION: Synthetic DNA

<400> SEQUENCE: 109
gatgctgacc tggccatggg cgacgtcgcg aat         33

<210> SEQ ID NO 110
<211> LENGTH: 33
<212> TYPE: DNA
<213> ORGANISM: Artificial Sequence
<220> FEATURE:
<223> OTHER INFORMATION: Synthetic DNA

<400> SEQUENCE: 110
attcgcgacg tcgcccatgg ccaggtcagc atc         33

<210> SEQ ID NO 111
<211> LENGTH: 33
<212> TYPE: DNA
<213> ORGANISM: Artificial Sequence
<220> FEATURE:
<223> OTHER INFORMATION: Synthetic DNA

<400> SEQUENCE: 111
ctgacaaata tgattcagga tgccggcgat ctg         33

<210> SEQ ID NO 112
<211> LENGTH: 33
<212> TYPE: DNA
<213> ORGANISM: Artificial Sequence
<220> FEATURE:
<223> OTHER INFORMATION: Synthetic DNA

```
<400> SEQUENCE: 112
cagatcgccg gcatcctgaa tcatatttgt cag                                    33

<210> SEQ ID NO 113
<211> LENGTH: 33
<212> TYPE: DNA
<213> ORGANISM: Artificial Sequence
<220> FEATURE:
<223> OTHER INFORMATION: Synthetic DNA

<400> SEQUENCE: 113
tccggccata cctctgctgg ttgggcatcc gcg                                    33

<210> SEQ ID NO 114
<211> LENGTH: 33
<212> TYPE: DNA
<213> ORGANISM: Artificial Sequence
<220> FEATURE:
<223> OTHER INFORMATION: Synthetic DNA

<400> SEQUENCE: 114
cgcggatgcc caaccagcag aggtatggcc gga                                    33

<210> SEQ ID NO 115
<211> LENGTH: 33
<212> TYPE: DNA
<213> ORGANISM: Artificial Sequence
<220> FEATURE:
<223> OTHER INFORMATION: Synthetic DNA

<400> SEQUENCE: 115
tccggccata cctctggcgg ttgggcatcc gcg                                    33

<210> SEQ ID NO 116
<211> LENGTH: 33
<212> TYPE: DNA
<213> ORGANISM: Artificial Sequence
<220> FEATURE:
<223> OTHER INFORMATION: Synthetic DNA

<400> SEQUENCE: 116
cgcggatgcc caaccgccag aggtatggcc gga                                    33

<210> SEQ ID NO 117
<211> LENGTH: 33
<212> TYPE: DNA
<213> ORGANISM: Artificial Sequence
<220> FEATURE:
<223> OTHER INFORMATION: Synthetic DNA

<400> SEQUENCE: 117
gatgctgacc tggccgaagg cgacgtcgcg aat                                    33

<210> SEQ ID NO 118
<211> LENGTH: 33
<212> TYPE: DNA
<213> ORGANISM: Artificial Sequence
<220> FEATURE:
<223> OTHER INFORMATION: Synthetic DNA

<400> SEQUENCE: 118
attcgcgacg tcgccttcgg ccaggtcagc atc                                    33

<210> SEQ ID NO 119
<211> LENGTH: 33
```

```
<212> TYPE: DNA
<213> ORGANISM: Artificial Sequence
<220> FEATURE:
<223> OTHER INFORMATION: Synthetic DNA

<400> SEQUENCE: 119
gatgctgacc tggccaaagg cgacgtcgcg aat                                33

<210> SEQ ID NO 120
<211> LENGTH: 33
<212> TYPE: DNA
<213> ORGANISM: Artificial Sequence
<220> FEATURE:
<223> OTHER INFORMATION: Synthetic DNA

<400> SEQUENCE: 120
attcgcgacg tcgcctttgg ccaggtcagc atc                                33

<210> SEQ ID NO 121
<211> LENGTH: 9
<212> TYPE: PRT
<213> ORGANISM: Artificial Sequence
<220> FEATURE:
<223> OTHER INFORMATION: acid phosphatase motif
<220> FEATURE:
<221> NAME/KEY: MISC_FEATURE
<222> LOCATION: (2)..(7)
<223> OTHER INFORMATION: Xaa = any amino acid

<400> SEQUENCE: 121

Lys Xaa Xaa Xaa Xaa Xaa Xaa Arg Pro
1               5

<210> SEQ ID NO 122
<211> LENGTH: 4
<212> TYPE: PRT
<213> ORGANISM: Artificial Sequence
<220> FEATURE:
<223> OTHER INFORMATION: acid phosphatase motif

<400> SEQUENCE: 122

Pro Ser Gly His
1

<210> SEQ ID NO 123
<211> LENGTH: 12
<212> TYPE: PRT
<213> ORGANISM: Artificial Sequence
<220> FEATURE:
<223> OTHER INFORMATION: acid phosphatase motif
<220> FEATURE:
<221> NAME/KEY: MISC_FEATURE
<222> LOCATION: (3)..(7)
<223> OTHER INFORMATION: Xaa = any amino acid
<220> FEATURE:
<221> NAME/KEY: MISC_FEATURE
<222> LOCATION: (9)..(11)
<223> OTHER INFORMATION: Xaa = any amino acid

<400> SEQUENCE: 123

Ser Arg Xaa Xaa Xaa Xaa Xaa His Xaa Xaa Xaa Asp
1               5                   10

<210> SEQ ID NO 124
<211> LENGTH: 231
<212> TYPE: PRT
<213> ORGANISM: Escherichia blattae

<400> SEQUENCE: 124
```

```
Leu Ala Leu Val Ala Thr Gly Asn Asp Thr Thr Lys Pro Asp Leu
1               5                   10                  15

Tyr Tyr Leu Lys Asn Ser Glu Ala Ile Asn Ser Leu Ala Leu Leu Pro
                20                  25                  30

Pro Pro Pro Ala Val Gly Ser Ile Ala Phe Leu Asn Asp Gln Ala Met
            35                  40                  45

Tyr Glu Gln Gly Arg Leu Leu Arg Asn Thr Glu Arg Gly Lys Leu Ala
        50                  55                  60

Ala Glu Asp Ala Asn Leu Ser Ser Gly Gly Val Ala Asn Ala Phe Ser
65                  70                  75                  80

Gly Ala Phe Gly Ser Pro Ile Thr Glu Lys Asp Ala Pro Ala Leu His
                85                  90                  95

Lys Leu Leu Thr Asn Met Ile Glu Asp Ala Gly Asp Leu Ala Thr Arg
                100                 105                 110

Ser Ala Lys Asp His Tyr Met Arg Ile Arg Pro Phe Ala Phe Tyr Gly
            115                 120                 125

Val Ser Thr Cys Asn Thr Thr Glu Gln Asp Lys Leu Ser Lys Asn Gly
130                 135                 140

Ser Tyr Pro Ser Gly His Thr Ser Ile Gly Trp Ala Thr Ala Leu Val
145                 150                 155                 160

Leu Ala Glu Ile Asn Pro Gln Arg Gln Asn Glu Ile Leu Lys Arg Gly
                165                 170                 175

Tyr Glu Leu Gly Gln Ser Arg Val Ile Cys Gly Tyr His Trp Gln Ser
            180                 185                 190

Asp Val Asp Ala Ala Arg Val Val Gly Ser Ala Val Val Ala Thr Leu
            195                 200                 205

His Thr Asn Pro Ala Phe Gln Gln Leu Gln Lys Ala Lys Ala Glu
    210                 215                 220

Phe Ala Gln His Gln Lys Lys
225                 230

<210> SEQ ID NO 125
<211> LENGTH: 228
<212> TYPE: PRT
<213> ORGANISM: Enterobacter aerogenes

<400> SEQUENCE: 125

Leu Val Pro Ala Gly Asn Asp Ala Thr Thr Lys Pro Asp Leu Tyr Tyr
1               5                   10                  15

Leu Lys Asn Ala Gln Ala Ile Asp Ser Leu Ala Leu Leu Pro Pro Pro
                20                  25                  30

Pro Glu Val Gly Ser Ile Ala Phe Leu Asn Asp Gln Ala Met Tyr Glu
            35                  40                  45

Lys Gly Arg Leu Leu Arg Asn Thr Glu Arg Gly Lys Leu Ala Ala Glu
        50                  55                  60

Asp Ala Asn Leu Ser Ala Gly Gly Val Ala Asn Ala Phe Ser Ser Ala
65                  70                  75                  80

Phe Gly Ser Pro Ile Thr Glu Lys Asp Ala Pro Gln Leu His Lys Leu
                85                  90                  95

Leu Thr Asn Met Ile Glu Asp Ala Gly Asp Leu Ala Thr Arg Ser Ala
                100                 105                 110

Lys Glu Lys Tyr Met Arg Ile Arg Pro Phe Ala Phe Tyr Gly Val Ser
            115                 120                 125

Thr Cys Asn Thr Thr Glu Gln Asp Lys Leu Ser Lys Asn Gly Ser Tyr
```

```
                  130                 135                 140
Pro Ser Gly His Thr Ser Ile Gly Trp Ala Thr Ala Leu Val Leu Ala
145                 150                 155                 160

Glu Ile Asn Pro Gln Arg Gln Asn Glu Ile Leu Lys Arg Gly Tyr Glu
                165                 170                 175

Leu Gly Glu Ser Arg Val Ile Cys Gly Tyr His Trp Gln Ser Asp Val
                180                 185                 190

Asp Ala Ala Arg Ile Val Gly Ser Ala Val Val Ala Thr Leu His Thr
                195                 200                 205

Asn Pro Ala Phe Gln Gln Gln Leu Gln Lys Ala Lys Asp Glu Phe Ala
    210                 215                 220

Lys Thr Gln Lys
225
```